US009920357B2

(12) United States Patent
Youngquist et al.

(10) Patent No.: US 9,920,357 B2
(45) Date of Patent: Mar. 20, 2018

(54) SYSTEMS AND METHODS FOR IDENTIFYING COSMETIC AGENTS FOR HAIR/SCALP CARE COMPOSITIONS

(71) Applicant: The Procter & Gamble Company, Cincinnati, OH (US)

(72) Inventors: Robert Scott Youngquist, Mason, OH (US); Jun Xu, Mason, OH (US); Robert Lloyd Binder, Montgomery, OH (US); Ping Hu, Mason, OH (US); Teresa Dicolandrea, Wyoming, OH (US); Thomas Larry Dawson, Hamilton, OH (US); Brian Wilson Howard, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1119 days.

(21) Appl. No.: 13/911,698

(22) Filed: Jun. 6, 2013

(65) Prior Publication Data
US 2013/0331342 A1    Dec. 12, 2013

Related U.S. Application Data

(60) Provisional application No. 61/656,218, filed on Jun. 6, 2012.

(51) Int. Cl.
| G01N 33/48 | (2006.01) |
| C12Q 1/68 | (2018.01) |
| G06F 19/18 | (2011.01) |
| G06F 19/20 | (2011.01) |

(52) U.S. Cl.
CPC ........... *C12Q 1/6837* (2013.01); *G06F 19/18* (2013.01); *G06F 19/20* (2013.01)

(58) Field of Classification Search
CPC .................................................. G06F 19/18
USPC .......................................................... 702/19
See application file for complete search history.

(56) References Cited

U.S. PATENT DOCUMENTS

| 2,694,668 A | 11/1954 | Fricke |
| 2,809,971 A | 10/1957 | Bernstein et al. |
| 2,826,551 A | 3/1958 | Geen |
| 3,152,046 A | 10/1964 | Kapral |
| 3,236,733 A | 2/1966 | Karsten et al. |
| 3,694,668 A | 9/1972 | Foerster |
| 3,753,196 A | 8/1973 | Kurtz et al. |
| 3,755,560 A | 8/1973 | Dickert et al. |
| 3,761,418 A | 9/1973 | Parran, Jr. |
| 3,964,500 A | 6/1976 | Drakoff |
| 4,089,945 A | 5/1978 | Brinkman et al. |
| 4,323,683 A | 4/1982 | Bolich, Jr. et al. |
| 4,345,080 A | 8/1982 | Bolich, Jr. |
| 4,364,837 A | 12/1982 | Pader |
| 4,379,753 A | 4/1983 | Bolich, Jr. |
| 4,421,769 A | 12/1983 | Dixon et al. |
| 4,470,982 A | 9/1984 | Winkler |
| 4,677,120 A | 6/1987 | Parish et al. |
| 4,741,855 A | 5/1988 | Grote et al. |
| 4,885,107 A | 12/1989 | Wetzel |
| 4,885,311 A | 12/1989 | Parish et al. |
| 4,967,341 A | 10/1990 | Yamamoto et al. |
| 5,049,584 A | 9/1991 | Purcell et al. |
| 5,104,646 A | 4/1992 | Bolich, Jr. et al. |
| 5,106,609 A | 4/1992 | Bolich, Jr. et al. |
| 5,124,356 A | 6/1992 | Purcell et al. |
| RE34,075 E | 9/1992 | Purcell et al. |
| 5,297,279 A | 3/1994 | Bannon et al. |
| RE34,584 E | 4/1994 | Grote et al. |
| 5,624,666 A | 4/1997 | Coffindaffer et al. |
| D391,162 S | 2/1998 | Kokenge |
| 6,451,300 B1 | 9/2002 | Dunlop et al. |
| 6,641,848 B1 | 11/2003 | Bonte et al. |
| 6,872,401 B2 | 3/2005 | Seyler et al. |
| 6,974,569 B2 | 12/2005 | Dunlop et al. |
| 7,001,594 B1 | 2/2006 | Peffly et al. |
| D516,436 S | 3/2006 | Campbell et al. |
| 7,101,889 B2 | 9/2006 | Kaczvinsky, Jr. et al. |
| D535,191 S | 1/2007 | Corker |
| D542,660 S | 5/2007 | Thomas et al. |
| D547,193 S | 7/2007 | Blasko et al. |
| D547,661 S | 7/2007 | Blasko et al. |
| D558,591 S | 1/2008 | Blasko et al. |
| D563,221 S | 3/2008 | Ashiwa et al. |
| D570,707 S | 6/2008 | Blasko et al. |

(Continued)

FOREIGN PATENT DOCUMENTS

| CN | 101152138 A | 4/2008 |
| FR | 2811226 A1 | 1/2002 |

(Continued)

OTHER PUBLICATIONS

Aden et al. "Proteomic Analysis of Scleroderma Lesional Skin Reveals Activated Wound Healing Phenotype, of Epidermal Cell Layer", Oct. 1, 2008 Rheumatology 47: 1754-1760.*
Golub et al. "Molecular Classification of Cancer: Class Discovery and Class Prediction by Gene Expression Monitoring", 1999 Science 286: 531-537.*
U.S. Appl. No. 13/966,418, filed Aug. 14, 2013, Kevin John Mills et al.
Aden et al, "Proteomic analysis of scleroderma lesional skin reveals activated wound healing phenotype of epidermal cell layer," Rheumatology 2008; 47: 1754-1760.
Blumenberg, "DNA Microarrays in Dermatology and Skin Biology," OMICS: A Journal of Integrative Biology, Oct. 2006, 10(3): Abstract.
Golub et al, "Molecular classification of cancer: class discovery and class prediction by gene expression monitoring," Science, Oct. 15, 1999; 286 (5439): 531-7.

(Continued)

*Primary Examiner* — Jerry Lin
(74) *Attorney, Agent, or Firm* — Dinsmore & Shohl LLP

(57) ABSTRACT

Provided are methods and systems for determining functional relationships between a cosmetic agent and a hair biology condition of interest. Also provided are methods and systems for identifying cosmetic agents that affect a hair biology condition, as well as the use of agents identified by such methods and systems for the preparation of cosmetic compositions, personal care products, or both.

43 Claims, 9 Drawing Sheets

(56) References Cited

U.S. PATENT DOCUMENTS

| | | |
|---|---|---|
| 7,436,987 B2 | 10/2008 | Takano et al. |
| 7,531,497 B2 | 5/2009 | Midha et al. |
| 7,585,827 B2 | 9/2009 | Geary et al. |
| 7,653,491 B2 | 1/2010 | Schadt et al. |
| 7,654,420 B2 | 2/2010 | Honda et al. |
| 7,704,932 B2 | 4/2010 | Evans et al. |
| 7,709,015 B2 | 5/2010 | Masuda et al. |
| 7,727,516 B2 | 6/2010 | Botchkareva et al. |
| 7,772,214 B2 | 8/2010 | Vatter et al. |
| 7,815,948 B2 | 10/2010 | Paufique |
| 7,890,267 B2 | 2/2011 | Glinsky |
| 8,106,037 B2 | 1/2012 | Rubin et al. |
| 8,324,447 B2 | 12/2012 | Goldstein et al. |
| 8,535,738 B2 | 9/2013 | Collins et al. |
| 8,831,271 B2 | 9/2014 | Sese et al. |
| 9,434,993 B2 | 9/2016 | Binder et al. |
| 2002/0012927 A1 | 1/2002 | Burmer et al. |
| 2002/0044953 A1 | 4/2002 | Michelet et al. |
| 2002/0169562 A1 | 11/2002 | Stephanopoulos et al. |
| 2003/0088437 A1 | 5/2003 | Iobst et al. |
| 2003/0149347 A1 | 8/2003 | Kauffmann et al. |
| 2003/0170739 A1 | 9/2003 | Iobst et al. |
| 2003/0223951 A1 | 12/2003 | Geary et al. |
| 2004/0142335 A1 | 7/2004 | Petersohn et al. |
| 2005/0009015 A1 | 1/2005 | Ji et al. |
| 2005/0170378 A1 | 8/2005 | Yakhini et al. |
| 2007/0040306 A1 | 2/2007 | Morel et al. |
| 2007/0154425 A1* | 7/2007 | Potin ............... A61K 8/64 424/62 |
| 2007/0155772 A1 | 7/2007 | Ide et al. |
| 2007/0184012 A1 | 8/2007 | Perrier et al. |
| 2007/0205226 A1 | 9/2007 | Honda et al. |
| 2008/0280844 A1 | 11/2008 | Lessnick |
| 2008/0312199 A1 | 12/2008 | Glinsky |
| 2009/0011709 A1 | 1/2009 | Akasaka et al. |
| 2009/0017080 A1 | 1/2009 | Tanner et al. |
| 2009/0036415 A1 | 2/2009 | Rubin et al. |
| 2009/0064349 A1 | 3/2009 | Goldstein et al. |
| 2009/0098538 A1 | 4/2009 | Glinsky |
| 2009/0170715 A1 | 7/2009 | Glinsky |
| 2009/0186951 A1 | 7/2009 | Brody et al. |
| 2009/0220488 A1* | 9/2009 | Gardner ............... C07K 16/18 514/1.1 |
| 2009/0298113 A1 | 12/2009 | Vielhaber et al. |
| 2010/0047361 A1 | 2/2010 | Perrier et al. |
| 2010/0093611 A1 | 4/2010 | Horrigan et al. |
| 2010/0113585 A1 | 5/2010 | Falkowski |
| 2010/0189669 A1 | 7/2010 | Hakozaki |
| 2010/0203043 A1 | 8/2010 | Ree et al. |
| 2010/0256001 A1 | 10/2010 | Niculescu et al. |
| 2010/0273676 A1 | 10/2010 | Naar et al. |
| 2010/0285001 A1 | 11/2010 | Land et al. |
| 2010/0292085 A1 | 11/2010 | Lum et al. |
| 2010/0298329 A1 | 11/2010 | Shaw et al. |
| 2011/0010100 A1 | 1/2011 | Li et al. |
| 2011/0015869 A1 | 1/2011 | Watters et al. |
| 2011/0045998 A1 | 2/2011 | Niculescu et al. |
| 2011/0092695 A1 | 4/2011 | Chen et al. |
| 2011/0098188 A1 | 4/2011 | Niculescu et al. |
| 2011/0150775 A1 | 6/2011 | Slonim et al. |
| 2011/0150798 A1 | 6/2011 | Bacus |
| 2011/0160080 A1 | 6/2011 | Chang |
| 2011/0217701 A1 | 9/2011 | Carter et al. |
| 2011/0251087 A1 | 10/2011 | Glinsky |
| 2011/0263693 A1 | 10/2011 | Vinson-Hieronymus et al. |
| 2011/0269852 A1 | 11/2011 | McDaniel |
| 2012/0116081 A1 | 5/2012 | Shieh et al. |
| 2012/0149773 A1 | 6/2012 | Park et al. |
| 2012/0258074 A1 | 10/2012 | Mills et al. |
| 2012/0283112 A1 | 11/2012 | Binder et al. |
| 2013/0165470 A1 | 6/2013 | Isfort et al. |
| 2013/0170739 A1 | 7/2013 | Hosoi |
| 2013/0189381 A1 | 7/2013 | Dal Farra et al. |
| 2013/0217589 A1 | 8/2013 | Xu et al. |
| 2013/0259816 A1 | 10/2013 | Hakozaki et al. |
| 2013/0261006 A1 | 10/2013 | Hakozaki et al. |
| 2013/0261007 A1 | 10/2013 | Hakozaki et al. |
| 2013/0261024 A1 | 10/2013 | Hakozaki et al. |
| 2013/0309217 A1 | 11/2013 | Schmidt |
| 2013/0331342 A1 | 12/2013 | Youngquist et al. |
| 2013/0337087 A1 | 12/2013 | Finlay et al. |
| 2015/0125559 A1 | 5/2015 | Osorio et al. |
| 2015/0232945 A1 | 8/2015 | Brody et al. |
| 2015/0292018 A1 | 10/2015 | Binder et al. |
| 2017/0140097 A1 | 5/2017 | Xu et al. |

FOREIGN PATENT DOCUMENTS

| | | |
|---|---|---|
| FR | 2925331 A1 | 6/2009 |
| GB | 849433 A | 9/1960 |
| JP | 2008245558 A | 10/2008 |
| JP | 2010096748 A | 4/2010 |
| JP | 2010099015 A | 5/2010 |
| JP | 2010172240 A | 8/2010 |
| JP | 2011019414 A | 2/2011 |
| JP | 2011122959 A | 6/2011 |
| JP | 2014502843 A | 2/2014 |
| KR | 10-2013-0058107 | 6/2013 |
| KR | 10-2013-0125969 | 11/2013 |
| WO | 01091700 A2 | 12/2001 |
| WO | 2002090934 A2 | 11/2002 |
| WO | 03100557 A2 | 12/2003 |
| WO | 2004080380 A2 | 9/2004 |
| WO | 2005040416 A1 | 5/2005 |
| WO | 2007077257 A2 | 7/2007 |
| WO | 2007111899 A2 | 10/2007 |
| WO | 2007114896 A2 | 10/2007 |
| WO | 2007117466 A2 | 10/2007 |
| WO | 2008021483 A2 | 2/2008 |
| WO | 2008086182 A2 | 7/2008 |
| WO | 2008086452 A2 | 7/2008 |
| WO | 2008124428 A1 | 10/2008 |
| WO | 2009102957 A2 | 8/2009 |
| WO | 2009135915 A1 | 11/2009 |
| WO | 2009155009 A1 | 12/2009 |
| WO | 2010041678 A1 | 4/2010 |
| WO | 2010060055 A1 | 5/2010 |
| WO | 2010062372 A2 | 6/2010 |
| WO | 2010068794 A2 | 6/2010 |
| WO | 2010093564 A1 | 8/2010 |
| WO | 2011007337 A2 | 1/2011 |
| WO | 2011028819 A1 | 3/2011 |
| WO | 2011041912 A1 | 4/2011 |
| WO | 2011041914 A1 | 4/2011 |
| WO | 2011075032 A2 | 6/2011 |
| WO | 2011103449 A2 | 8/2011 |
| WO | 2011127150 A2 | 10/2011 |
| WO | 2011133538 A1 | 10/2011 |
| WO | 2011146768 A1 | 11/2011 |
| WO | 2012011904 A1 | 1/2012 |
| WO | 2012116081 A3 | 8/2012 |
| WO | 2012135651 A1 | 10/2012 |
| WO | 2014028568 A1 | 2/2014 |
| WO | 2014028569 A1 | 2/2014 |
| WO | 2014028572 A3 | 2/2014 |

OTHER PUBLICATIONS

Ishimatsu-Tsuji et al, "Idnetification of novel hair-growth inducers by means of connectivity mapping," The Faseb Journal, 24, 1789-1496 (2010).
Lamb et al, "The Connectivity Map: Using Gene-Expression Signatures to Connect Small Molecules, Genes, and Disease," Science, vol. 313 Sep. 29, 2006.
Lamore et al, "The topical antimicrobial zinc pyrithione is a heat shock response inducer that causes DNA damage and PARP-dependent energy crisis in human skin cells," Cell Stress and Chaperones (2010) 15:309-322.
Niacinamide Research Update, P&G Beauty, 2011, pp. 1-6.
Palchaudhuri et al, "Transcript Profiling and RNA Interference as Tools to Identify Small Molecule Mechanisms and Therapeutic Potential," ACS Chem Biol. Jan. 21, 2011; 6(1): 21-33.
Office Actions for U.S. Appl. No. 13/402,102; P&G Case 12002M; Binder et al; dated Feb. 22, 2012.

(56) References Cited

OTHER PUBLICATIONS

Office Actions for U.S. Appl. No. 14/749,717; P&G Case 12002MD; Binder et al; dated Jun. 25, 2015.
Office Actions for U.S. Appl. No. 14/749,779; P&G Case 12002MD2; Binder et al; dated Jun. 25, 2015.
Office Actions for U.S. Appl. No. 13/851,858; P&G case 12359M; Hakozaki et al; dated Mar. 27, 2013.
Office Actions for U.S. Appl. No. 13/851,873; P&G case 12359M3; Hakozaki et al; dated Mar. 27, 2013.
Office Actions for U.S. Appl. No. 13/851,864; P&G case 12359M2; Hakozaki et al; dated Mar. 27, 2013.
Office Actions for U.S. Appl. No. 13/851,886; P&G case 12359M4; Hakozaki et al; dated Mar. 27, 2013.
Office Actions for U.S. Appl. No. 13/437,042; Mills et al, filed Apr. 2, 2012.
Office Actions for U.S. Appl. No. 14/472,716; Osorio et al, filed Aug. 29, 2014.
Office Actions for U.S. Appl. No. 15/419,112; Xu et al, filed Jan. 30, 2017.
Office Actions for U.S. Appl. No. 13/502,461; Takahashi et al, filed Apr. 17, 2012.
Office Actions for U.S. Appl. No. 13/966,418; Mills et al, filed Aug. 14, 2013.
Genomics of Skin Aging: Practical Applications; J Drugs Dermatol, 2009 8 Supplement, S1-S18.
Zoe Diane Draelos, Clinical Situations Conducive to Proactive Skin Health and Anti-Aging Improvement; Journal of Investigative Dermatology Symposium Proceedings, 2008, 13, 25-27.
Jens-Michael Jensen et al, Acid and Neutral Sphingomyelinase, ceramide synthase, and acid ceramidase activities in cutaneous aging, Experimental Dermatology, 2005, 14: 609-618.
Ragna Pels et al, Blobetasol Propionate—Where, When, Why?; Drugs of Today 2008, 44(7): 547-557.
Geuranne Tjabringa et al, "Development and Validation of Human Psoriatic Skin Equivalents," The American Journal of Pathology, vol. 173, No. 3, Sep. 2008.
Ivana Arsic et al, Preparation of Novel Apigenin-Enriched, Liposomal and Non-Liposomal, Anti-inflammatory Topical Formulations as Substitutes for Corticosteroid Therapy, PhytoTherapy Research 25: 228-233 (2011).
Zuzana Hegyi et al, Vitamin D Analog Calcipotriol Suppresses the Th17 Cytokine-Induced Proinflammatory S100 "Alarmins" Psoriasin (S100A7) and Koebnerisin (S100A15) in Psoriasis, Journal of Investigative Dermatology, 2012, 132, 1416-1424.
Donald L. Bissett et al, Genomic expression changes induced by topical N-acetylgluocsamine in skin equivalent cultures in vitro, Journal of Cosmetic Dermatology, Sep. 7, 2007, 6, 232-238.
Timothy R. Hughes et al, Functional Discovery via a Compendium of Expression Profiles, Cell, vol. 102, 109-126, Jul. 7, 2000.
Ganesh Chandra Jagetia et al, Genotoxic effect of hydroquinone on the cultured mouse spleenocytes, Toxicology Letters 121 (2001) 15-20.
E. Raynaud et al, Depigmentation for cosmetic purposes: prevalence and side-effects in a female population in Senegal, Ann Dermatol Venereol, Jun.-Jul. 2001; 128 (6-7): 720-4.
G. Sivapirabu et al, Topical nicotinamide modulates cellular energy metabolism and provides broad-spectrum protection against ultraviolet radiation-induced immunosuppression in humans, British Journal of Dermatology, 2009, 161, 1357-1364.
Aravind Subramanian et al, Gene set enrichment analyss: a knowledge-based approach for interpreting genome-wide expression profiles, PNAS, Oct. 25, 2005, vol. 102, No. 43, 15545-15550.
22nd World Congress of Dermatology, May 24-29, 2011, Seoul, Korea.
Robyn M. Smith et al, The effect of a high-protein, low glycemic-load diet versus a conventional, high glycemic-load diet on biochemical parameters associated with acne vulgaris: a randomized, investigator-masked, controlled trial, American Academy of Dermatology, Apr. 20, 2007, 247-256.
Reza Mobini et al, A module-based analytical strategy to identify novel disease-associated genes shows an inhibitory role for interleukin 7 receptor in allergic inflammation, BMC Systems Biology, 2009, 3:19.
H. Kluken et al, Atopic eczema/dermatitis syndrome—a genetically complex disease. New advances in discovering the genetic contribution, Allergy 2003: 58: 5-12.
Michael J. Cork et al, Epidermal Barrier Dysfunction in Atopic Dermatitis, Journal of Investigative Dermatology, 2009, vol. 129.
Hajime Kimata, Enhancement of Allergic Skin Wheal Responses by Microwave Radiation from Mobile Phones in Patients with Atopic Eczema/Dermatitis Syndrome, Int Arch Allergy Immunol 2002; 129: 348-350.
Till Krech et al, Characterization of AKT Independent effects of the synthetic AKT inhibitors SH-5 and SH-6 using an integrated approach combining transcriptomic profiling and signaling pathway perturbations, BMC Cancer 2010, 10:287.
Meiping Chang et al, Evaluation of Phenyoxybenzamine in the CFA model of pain following gene expression studies and connectivity mapping, Molecular Pain 2010, 6:56.
Jurjen W. Westra et al, Construction of a computable cell proliferation network focused on non-diseased lung cells, BMC Systems Biology, 2011, 5:105.
Shiek SSJ Ahmed et al, Systems biological approach on neurological disoreders: a novel molecular connectivity to aging and psychiatric diseases, BMC systems Biology 2011, 5:6.
Jiannis Ragoussis and Gareth Elvidge, Affymetrix GeneChip System: moving from research to the clinic, Expert Rev. Mol. Diagn. 6(2); 145-152 (2006).
Joao Pedro de Magalhaes, Ageing research in the post-genome era: new technologies for an old problem, Mar. 20, 2013.
B. A. Gilchrest and M. Yaar, Ageing and Photoageing of the skin: observations at the cellular and molecular level, British Journal of Dermatology, 1992, 127, Supplement 41, 25-30.
S.B. Hassan, Alpha terpineol: a potential anticancer agent which acts through suppressing, Anticancer Res 2010, (6), 1911-9.
H. Aoki et al, Gene expression profiling analysis of solar lentigo in relation to immunohistochemical characteristics, British Journal of Dermatology 2007, 156, 1214-1223.
Todd C. Mockler, Joseph R. Ecker, Applications of DNA tiling arrays for whole-genome analysis, Genomics 85 (2005) 1-15.
Nirmala Bhogal et al, Toxicity testing: creating a revolution based on new technologies, Trends in Biotechnology, vol. 23, No. 6, Jun. 2005.
DC Hassane et al, Chemical Genomic screening reveals synergism between pathenolide and inhibitors, Blood 2010, Dec. 23, 2016 (26) 5983-90.
Takaomi Sanda et al, Interconnecting molecular pathways in the pathogenesis and drug sensitivity of T-cell acute lymphoblastic leukemia, Blood, Mar. 4, 2010: 115(9): 1735-1745.
Alexander Lachmann et al, ChEA: transcription factor regulation inferred from integrating genome-wide ChIP-X experiments, Bioinformatics, vol. 26, No. 19, 2001, 2438-2444.
J. Gheeya, Expression profiling identifies epoxy anthraquinone derivative as a DNA topoisomerase inhibitor, Cancer Lett Jul. 1, 2010, 293(1): 124-131.
Y. Hong, A 'Metastasis-prone' signature for early-stage mismatch-repair proficient sporadic colorectal cancer patients and its implications for possible therapeutics, Clin Exp Metastasis Feb. 2010; 27(2): 83-90.
Christos C. Zouboulis; Evgenia Makrantonaki, Clinical Aspects and molecular diagnostics of skin aging, Clinics in Dermatology (2011) 20, 3-14.
Justin Lamb, The Connectivity Map: a new tool for biomedical research, Perspectives, www.nature.com/reviews/cancer; 54, Jan. 2007, vol. 7.
Xiangqin Cui and Gary A. Churchill, Statistical tests for differential expression in cDNA microarray experiments, Genome Biology 2003, 4:210.
Lee Ding-Dar et al, Retinoid-Responsive Transcriptional Changes in Epidermal Keratinocytes, Published online in Wiley InterScience, Apr. 22, 2009.

(56) References Cited

OTHER PUBLICATIONS

Frank F. Bier et al, DNA Microarrays, Adv Biochem Engin/Biotechnol (2008) 109: 433-453.
Douglas A. Plager et al, Early cutaneous gene transcription changes in adult atopic dermatitis and potential clinical implications, Experimental Dermatology, 2007; 16: 28-36.
Ij Wang et al, Environmental risk factors for early infantile atopic dermatitis, Pediatr Allergy Immunol, 2007: 18: 441-447.
Andre Fujita et al, Multivariate gene expression analysis reveals functional connectivity changes between normal/tumoral prostates, BMC Systems Biology, 2008, 2: 106.
Nishit R. Trivedi, Gene Array Expression Profiling in Acne Lesions Reveals Marked Upregulation of Genes Involved in Inflammation and Matrix Remodeling, Journal of Investigative Dermatology, 2006, 126, 1071-1079.
William R. Swindell et al, Genome-Wide Expression Profiling of Five Mouse Models Identifies Similarities and Differences with Human Psoriasis, PLoS One 6(4): e18266.doi: 10.1371/journal.pone.0018266, published Apr. 4, 2011.
Rajan P. Nair et al, Genome-wide scan reveals association of psoriasis with IL-23 and NF-κb pathways, Nature Genetics, vol. 41, No. 2, Feb. 2009, 199-204.
Emma Guttman-Yassky et al, Major differences in inflammatory dendritic cells and their products distinguish atopic dermatitis from psoriasis, J Allergy Clin Immunol, vol. 119, No. 5, 2007, 1210-1217.
SB Rho et al, A gene signature-based approach identifies thioridazine as an inhibitor of phosphatidylinositol-3'-kinase(PI3K)/AKT pathway in ovarian cancer cells, Gynecol Oncol Jan. 1, 2011, 121-127.
T. Hakozaki et al, The effect of niacinamide on reducing cutaneous pigmentation and suppression of melanosome transfer, British Journal of Dermatology, 2002; 147: 20-31.
Heitham T. Hassoun et al, Ischemic acute kidney injury induces a distant organ functional and genomic response distinguishable from bilateral nephrectomy, Am J Physiol Renal Physiol 293: F30-F40, 2007.
Jian-Bing Fan et al, Illumina Universal Bead Arrays, Methods in Enzymology, vol. 410, 2006, 57-73.
M. Olsson et al, Increased Expression of Aquaporin 3 in Atopic Eczema, Allergy 2006: 61: 1132-1137.
W. Evan Johnson and Cheng Li; Adjusting batch effects in microarray expression data using empirical Bayes methods, Biostat (2007) 8 (1): 118-127.
Hee Young Kang et al, Transcriptional Profiling Shows Altered Expression of Wnt Pathway- and Lipid Metabolism-Related Genes as Well as Melanogenesis-Related Genes in Melasma, Journal of Investigative Dermatology (2011) 131, 1692-1700.
Kathy Kerr et al, Epidermal changes associated with symptomatic resolution of dandruff: biomarkers of scalp health, American Academy of Dermatology 67th Annual Meeting, Mar. 6-10, 2009, San Francisco, CA.
Steven D. Kunkel et I, mRNA Expressin Signatures of Human Skeletal Muscle Atrophy Identify a Natural Compound that Increases Muscle Mass, Cell Metab. Jun. 8, 2011; 13(6): 627-638.
Hyun-Kyung Choi et al, Labisia pumila extract protects skin cells from photoaging caused by UVB irradiation, Journal of Bioscience and Bioengineering, vol. 109, No. 3, 291-296, 2010.
Jorg D. Hoheisel, Microarray technology: beyond transcript profiling and genotype analysis, www.nature.com/reviews/genetics, Mar. 2006, vol. 7, 200-210.
Johanna Mihaly et al, Decreased retinoid concentration and retinoid signalling pathways in human atopic dermatitis, Experimental Dermatology, 20, 326-330, 2011.

K. J. Mills et al, Dandruff/seborrhoeic dermatitis is characterized by an inflammatory genomic signature and possible immune dysfunction: transcriptional analysis of the condition and treatment effects of zinc pyrithione, British Journal of Dermatology, 2012, 166 (Suppl 2), 33-40.
T.E. Wood et al, Selective Inhibition of histone deacetylases sensitizes malignant cells to death receptor ligands, Mol Cancer Ther Jan. 9, 2010 (1) 246-56.
Luciana Lorena Molinero et al, Up-regulated expression of MICA and proinflammatory cytokines in skin biopsies from patients with seborrhoeic dermatitis, Clinical Immunology 106 (2003) 50-54.
Klaus-Robert Muller et al, An Introduction to Kernel-Based Learning Algorithms, IEEE Transactions of Neural Networks, vol. 12, No. 2, Mar. 2001, 181-201.
P. Nenoff et al, The Antifungal Activity of a Coal Tar Gel on Malassezia furfur in vitro, Dermatology, 1995: (9): 311-314.
Jay O. Boyle et al, Effects of Cigarette Smoke on the Human Oral Mucosal Transcriptome, Cancer Prey Res (Phila.), Mar. 2010; 3(3): 266-278.
Michael Zimmer et al, The Connectivity Map links Iron Response Protein-1 (IRP1)-mediated inhibition of HIF2a translation to the anti-inflammatory 15-deoxy-$\Delta$12, 14-Prostaglandin J2, Cancer Res. Apr. 15, 2010; 70(8): 3071-3079.
GS Coombs et al, Modulation of Wnt/β-catenin signaling and proliferation by a ferrous iron chelator with therapeutic efficacy in genetically engineered mouse models of cancer, Oncogene (2012) 31, 213-225.
Gary J. Fisher et al, Pathophysiology of Premature Skin Aging Induced by Ultraviolet Light, The New England Journal of Medicine, vol. 337, No. 20, 1419-142, Nov. 13, 1997.
Harneet Ranu et al, Periorbital Hyperpigmentation in Asians: An Epidemiologic Study and a Proposed Classification, Dermatol Surg 2011; 37: 1297-1303.
U. Scherf et al, A gene expression database for the molecular pharmacology of cancer, Abstract, http://www.ncbi.nlm.nih.gov/pubmed/10700175, Jul. 30, 2013.
Skin Conditions and Related Need for Medical Care Among Persons 1-74 Years, United States, 1971-1974, Data from the National Health Survey, Series 11, No. 212, DHEW Publication No. (PHS) 79-1660, Nov. 1978.
J. L. Smalley et al, Application of connectivity mapping in predictive toxicology based on gene-expression similarity, Toxicology Feb. 9, 2010; 268 (3): 143-6.
Gregory Stephanopoulos et al, Mapping Physiological states from microarray expression measurements; Bioinformatics, vol. 18, No. 8, 2002, 1054-1063.
Cheri Millikin et al, Topical N-acetyl gluosamine and niacinamide affect pigmentation-relevant gene expression in in vitro genomics experimentation, J Am Acad Dermatol, Feb. 2007, AB169.
Michele Verschoore et al, Determination of Melanin and Hemaglobin in the Skin of Idiopathic Cutaneous Hyperchromia of the Orbital Region (ICHOR): a Study of Indian Patients, J Cutan Aesthet Surg. Jul.-Sep. 2012; 5 (3): 176-182.
S. Vertuani et al, Determination of antioxidant efficacy of cosmetic formulations of non-invasive measurements, Skin Research and Technology 2003; 9: 245-253.
Rachel E. B. Watson et al, A Short-Term Screening Protocol, Using Fibrillin-1 as a Reporter Molecule, for Photoaging Repair Agents, The Society for Investigative Deratology, Inc. 2001, 672-678.
Yumiko Ishimatsu-Tsuji et al, Identification of novel hair-growth inducers by means of connectivity mapping, The FASEB Journal 24, 1489-1496 (2010).
Zhihua Zhang, Regularized Discriminant Analysis, Ridge Regression and Beyond, Journal of Machine Learning Research 11 (2010), 2199-2228.

\* cited by examiner

compromises are therefore required"

SYSTEMS AND METHODS FOR IDENTIFYING COSMETIC AGENTS FOR HAIR/SCALP CARE COMPOSITIONS

CROSS REFERENCE TO RELATED APPLICATIONS

This application claims benefit to U.S. Provisional Application Ser. No. 61/656,218 filed Jun. 6, 2012, which is incorporated by reference herein in its entirety.

BACKGROUND

Connectivity mapping is a well-known hypothesis generating and testing tool having successful application in the fields of operations research, computer networking and telecommunications. The undertaking and completion of the Human Genome Project, and the parallel development of very high throughput high-density DNA microarray technologies enabling rapid and simultaneous quantization of cellular mRNA expression levels, resulted in the generation of an enormous genetic database. At the same time, the search for new pharmaceutical actives via in silico methods such as molecular modeling and docking studies stimulated the generation of vast libraries of potential small molecule actives. The amount of information linking disease to genetic profile, genetic profile to drugs, and disease to drugs grew exponentially, and application of connectivity mapping as a hypothesis testing tool in the medicinal sciences ripened.

The general notion that functionality could be accurately determined for previously uncharacterized genes, and that potential targets of drug agents could be identified by mapping connections in a data base of gene expression profiles for drug-treated cells, was spearheaded in 2000 with publication of a seminal paper by T. R. Hughes et al. ["Functional discovery via a compendium of expression profiles" *Cell* 102, 109-126 (2000)], followed shortly thereafter with the launch of The Connectivity Map (C-map Project by Justin Lamb and researchers at MIT ("Connectivity Map: Gene Expression Signatures to Connect Small Molecules, Genes, and Disease", *Science*, Vol. 313, 2006.) In 2006, Lamb's group began publishing a detailed synopsis of the mechanics of C-map construction and installments of the reference collection of gene expression profiles used to create the first generation C-map and the initiation of an ongoing large scale community C-map project.

The basic paradigm of predicting novel relationships between disease, disease phenotype, and drugs employed to modify the disease phenotype, by comparison to known relationships has been practiced for centuries as an intuitive science by medical clinicians. Modern connectivity mapping, with its rigorous mathematical underpinnings and aided by modern computational power, has resulted in confirmed medical successes with identification of new agents for the treatment of various diseases including cancer. Nonetheless, certain limiting presumptions challenge application of C-map with respect to diseases of polygenic origin or syndromic conditions characterized by diverse and often apparently unrelated cellular phenotypic manifestations. According to Lamb, the challenge to constructing a useful C-map is in the selection of input reference data which permit generation of clinically salient and useful output upon query. For the drug-related C-map of Lamb, strong associations comprise the reference associations, and strong associations are the desired output identified as hits.

Noting the benefit of high-throughput, high density profiling platforms which permit automated amplification, labeling hybridization and scanning of 96 samples in parallel a day, Lamb nonetheless cautioned: "[e]ven this much firepower is insufficient to enable the analysis of every one of the estimated 200 different cell types exposed to every known perturbagen at every possible concentration for every possible duration . . . compromises are therefore required" (page 54, column 3, last paragraph). Hence, Lamb confined his C-map to data from a very small number of established cell lines. This leads to heightened potential for in vitro to in vivo mismatch, and limits information to the context of a particular cell line. Selection of cell line, therefore, may be critical to the utility of a resulting C-map.

Lamb stresses that particular difficulty is encountered if reference connections are extremely sensitive and at the same time difficult to detect (weak), and Lamb adopted compromises aimed at minimizing numerous, diffuse associations. Since the regulatory scheme for drug products requires high degrees of specificity between a purported drug agent and disease state, and modulation of disease by impacting a single protein with a minimum of tangential associations is desired in development of pharmaceutical actives, the Lamb C-map is well-suited for screening for potential pharmaceutical agents despite the Lamb compromises.

The connectivity mapping protocols of Lamb would not be predicted, therefore, to have utility for hypothesis testing/ generating in the field of cosmetics. Cosmetic formulators seek agents or compositions of agents capable of modulating multiple targets and having effects across complex phenotypes and conditions. Further, the phenotypic impact of a cosmetic agent must be relatively low by definition, so that the agent avoids being subject to the regulatory scheme for pharmaceutical actives. Nonetheless, the impact must be perceptible to the consumer and preferably empirically confirmable by scientific methods. Gene transcription/expression profiles for cosmetic conditions are generally diffuse, comprising many genes with low to moderate fold differentials. Cosmetic agents, therefore, provide more diverse and less acute effects on cellular phenotype and generate the sort of associations expressly taught by Lamb as unsuitable for generating connectivity maps useful for confident hypothesis testing.

The present inventors surprisingly discovered that useful connectivity maps could be developed from cosmetic active—cellular phenotype—gene expression data associations in particular with respect to hair care cosmetics. Specifically, certain aspects of the present invention are based on the surprising discovery that selection of human cells such as fibroblasts, keratinocytes, melanocytes or dermal papilla cells are relevant cell lines and that data from such cells has resulted in construction of connectivity maps useful for hypothesis generating and testing relating to cosmetic agents in treatment of specific hair biology conditions such the appearance of gray hair, chronogenetic alopecia, senile alopecia, androgenetic alopecia, loss of hair diameter or hair breakage/fragile hair; for example, BJ fibroblasts are a better cell line than tert-keratinocytes for the identification of Monoamine Oxidase B (MAOB) inhibitors to improve hair growth. Melanocytes are cells of a better cell line for evaluating material to delay the appearance of gray hair, while a combination of cells appeared most suitable for other specific hair biology conditions. For example, a set of biological signatures were generated and combined from different cell lines and clinical data was generated from samples with multiple cell types to capture different aspect for hair growth and healthy fiber quality. Therefore, it could not be accurately predicted that data from one cell type (such as a fibroblast cell or a keratinocyte cell), or any combination thereof, could be used to construct a connectivity map effective for generating and testing hypotheses relating to cosmetic actives and genes associated with a specific hair biology condition.

Hair is a complex, multi-layered and dynamic system that provides a protective covering from elements and acts to disperse products from glands in acting as an interactive boundary between an organism and the environment. It is also vitally important to both individual health and self image. For example, a significant industry has developed to assist individuals with conditions of hair loss (alopecia) as well as to deal with excessive hair growth. In fact, a large array of hair conditions and disorders have been characterized and include alopecia, androgenic alopecia, alopecia greata, permanent alopecia, anagen growth state disorders, anagen effluvium, bulb disorders, bulge disorders, catagen and regression disorders, club hair, hirsutism, hypertrichosis, lanugo hair, miniaturization, telogen disorders, telogen effluvium, terminal hair, and vellus hair as non-limiting examples. FIG. 1 illustrates basic hair anatomy.

Due to the complexity of hair and its interaction with skin, a basic discussion of each is herein included. This discussion is necessary as various treatments of hair biology conditions include application of products or methods related to the hair itself or to the skin surrounding the hair or parts of the hair. For example, various hair treatments include methods and uses of products such as Rogaine®, Propecia®, hair transplants, hair electrolysis, and laser hair removal.

Though the intricacies of hair growth disorders is complex and requires additional research and breakthroughs, basic hair anatomy is well known, and has been previously described. For example a review of hair biology has been written by Ralf Paus and George Cotsarelis (see among other places, Paus R and Cotsarelis G. The Biology of Hair Follicles (Review Article). Mechanisms of Disease, Vol. 341 (7), 1999, pp. 491-497).

A hair contains a hair shaft that extends primarily out from the human skin surface, and having a distal portion recessing into the epidermis of the skin. Outlining the anatomy simplistically, within the skin is the hair follicle, bulb, and papilla. The hair shaft contains keratin. Within the skin, blood vessels nourish cells in the hair bulb and cellular materials including hormones can be transferred via such networks of the vasculature. Hair color is also controlled largely by pigment cells producing melanin in the hair follicle.

More generally, hair follicles cover the vast majority of the body surface. There are approximately 5 million hair follicles on the body with 100,000 on the scalp, with a density of up to roughly 300 to 500 hairs per square centimeter on the scalp. The great significance of the hair follicle requires an outlining of additional follicle details. The hair follicle can be divided anatomically into multiple parts, including the bulb consisting of the dermal papilla and matrix, the suprabulbar area from the matrix to the insertion of the arrector pili muscle, the isthmus that extends from the insertion of the arrector pili muscle to the sebaceous gland, and the infundibulum that extends from the sebaceous gland to the follicular orifice. The lower portion of the hair follicle consists of multiple portions: the dermal papilla, matrix, hair shaft (consisting from inward to outward the medulla, cortex, and cuticle), inner root sheath (IRS) consisting of the inner root sheath cuticle, Huxley's layer, Henle's layer, and the outer root sheath. The base of the follicle is invaginated by the dermal papilla, which has a capillary loop that passes through the papilla. Signal transduction and communication between the dermal papilla and the matrix cells influence how long and how thick the hair shaft will grow. The melanocytes within the matrix also produce the pigment in the hair shaft.

As indicated earlier, the hair shaft contains keratin. As for the hair medulla, this is only partially keratinized and therefore appears amorphous and may not always be present. The hair cortex cells lose their nuclei during their upward growth and do not contain any keratohyaline or trichohyaline granules. The keratin of the cortex is hard in contrast to the IRS and epidermis, which are soft. The cuticle is firmly anchored to the IRS cuticle. The cuticle of the IRS consists of a single layer of flattened overlapping cells that point downward and interlock tightly with the upward angled cells of the hair shaft cuticle. Huxley's layer is composed of two cell layers, whereas the outer Henle's layer is only one cell thick. Just before the isthmus, the IRS becomes fully keratinized but disintegrates at the level of the isthmus. Although the IRS is not present in the emerging hair shaft, the IRS serves as a strong scaffold in the lower portion of the hair follicle.

Returning once again to the hair follicle, the hair follicle is significant in hair development and cycling of hair follicles involves three main stages, including anagen, catagen, and telogen. The anagen phase is known as the growth phase, and a hair can spend several years in this phase. The catagen phase is a transitional phase occurring over a few weeks, with hair growth slowing and the follicle shrinking. The telogen phase is a resting phase where, over months, hair growth stops and the old hair detaches from the follicle; a new hair begins the growth phase and pushes the old hair out.

As indicated, an intricate relationship exists between hair and skin. Regarding the skin, the skin comprises three principal layers, the epidermis, the dermis, and a layer of subcutaneous fat. The majority of cells in the epidermis are keratinocytes that produce a family of proteins called keratins. Keratins contribute to the strength of the epidermis. The epidermis itself may be divided into multiple layers with the outermost layer referred to as the stratum corneum, and the innermost layer referred to as the basal layer. All epidermal cells originate from the basal layer and undergo a process known as differentiation as they gradually displace outward to the stratum corneum, where they fuse into squamous sheets and are eventually shed. In healthy, normal skin, the rate of production equals the rate of shedding (desquamation).

The differentiating epidermal cells form distinct though naturally blended layers. As the cells displace outward, they flatten and become joined by spiny processes forming the stratum spinosum, or spinous layer. The cells manufacture specialized fats called sphingolipids, and begin to express keratins associated with terminal differentiation. As keratin is produced, it is incorporated into the cellular matrix, strengthening the skin and providing structural support to the outer layers. As the cells migrate further outward and develop characteristic granules that contain proteins which contribute to the aggregation of keratins; they now form part of the granular layer. Cells lose their nuclei in the outer part of this layer, and the granules release their contents contributing to cornification. Vesicles containing lipids discharge into the spaces between the cells, creating a barrier structure that has been suggested to function like bricks (cells) and mortar (lipids). As the cells rise into the outermost layer of the epidermis—the stratum corneum, sometimes called the horny layer or the cornified layer—they take the form of flattened discs, tightly packed together. These flattened cells, called corneocytes, are effectively dead. The lipids of the epidermis play an important role in maintaining skin health, as they help the stratum corneum to regulate water loss while providing a virtually impermeable hydrophobic barrier to the environment. Fully mature keratinocytes function to protect the skin from UV light damage, and help effectuate immune responses to environmental stimuli.

The dermis, which lies just beneath the epidermis, is composed largely of the protein collagen. Most of the collagen is organized in bundles which run horizontally through the dermis and which are buried in a jelly-like material called the ground substance. Collagen accounts for up to 75% of the weight of the dermis, and is responsible for the resilience and elasticity of skin. The collagen bundles are held together by elastic fibers running through the dermis. The fibers are comprised of a protein called elastin, and make up less than 5% of the weight of the dermis. Fibroblasts function to synthesize collagen and the dermis ground substance, including components glycoproteins and glycosaminoglycans such as hyaluronic acid (which is able to bind water). The junction between the epidermis and the dermis is not straight but undulates—more markedly so in some areas of the body than others. A series of finger-like structures called rete pegs project up from the dermis, and similar structures project down from the epidermis. These projections increase the area of contact between the layers of skin, and help to prevent the epidermis from being sheared off. As skin ages, the projections get smaller and flatter. Networks of tiny blood vessels run through the rete pegs, bringing nutrients, vitamins and oxygen to the epidermis, although the epidermis itself is avascular and nourished by diffusion from the rete pegs. The dermis also contains the pilobaceous units comprising hair follicles and sebaceous glands, apocrine and eccrine sweat glands, lymphatic vessels, nerves, and various sensory structures, including the mechano-sensing Pacinian and Meissner's corpuscles.

Beneath the dermis lies the hypodermis, which comprises subcutaneous fat that cushions the dermis from underlying tissues such as muscle and bones. The fat is contained in adipose cells embedded in a connective tissue matrix. This layer may also house the hair follicles when they are in the growing phase.

Thus, skin is a multilayered complex organ comprising a wide variety of cellular types and structures, including epidermal and dermal connective tissue with blood and lymphatic vessels, the pilosebaceous units, glands, nerves, various sensory structures, the hypodermal adipose tissue, and the elastic fascia beneath the hypodermis. In turn, these structures are composed of a number of different cell types including keratinocytes, melanocytes, neuroendocrine Merkel cells, sebocytes, fibroblasts, endothelial cells, pericytes, neurons, adipocytes, myocytes and resident immunocytes including Langerhans cells, other dendritic cells, T cells and mast cells. Two of the main cell lineages in the skin are epithelial cells, which in general form the linings of the body and the parenchyma of many organs and glands, and mesenchymal cells, which form connective tissue, blood vessels and muscle. Dermal fibroblasts are mesenchymal cells, and keratinocytes are epithelial cells, which comprise most of the structure of the epidermis.

Thus hair and skin are intricate components that work in a complex manner to regulate hair health. As stated, there are a significant number of hair disorders, and there are many hair care products available to consumers which are directed to improving the health and/or physical appearance of hair.

Despite current treatments, an ongoing need exists to identify cosmetic agents that can provide new or improved benefits to hair. There is also a need to identify additional cosmetic agents that provide similar or improved benefits as compared to existing products but which are easier to formulate, produce, and/or market.

Successful identification of hair-related cosmetic agents has proven to be difficult due to the multi-cellular, multi-factorial processes that occur in and around hair. In addition, many desirable cosmetic agents may comprise a mixture of compounds with effects and interactions that may not be fully understood. This is often the case with a botanical or other natural extract that may affect many cellular/pathways. An additional challenge for cosmetic formulators is that cosmetics must be very safe and adverse effects generally are not acceptable. Further, while much is known about hair biology, there is much that is still poorly understood or unknown. Conventional in vitro studies of biological responses to potential cosmetic agents involve testing hundreds or thousands of potential agents in various cell types before an agent that gives the desired result can be identified and moved into a next stage of testing. However, such studies can be hindered by the complex or weakly detectable responses typically induced and/or caused by cosmetic agents. Such weak responses arise, in part, due to the great number of genes and gene products involved, and cosmetic agents may affect multiple genes in multiple ways. Moreover, the degree of bioactivity of cosmetic agents may differ for each gene and be difficult to quantify.

The value of a connectivity map approach to discover functional connections among cosmetic phenotypes of hair biology, gene expression perturbation, and cosmetic agent action is counter-indicated by the progenitors of the drug-based C-map. The relevant phenotypes are very complex, the gene expression perturbations are numerous and weak, and cosmetic agent action is likewise diffuse and by definition, relatively weak. It has thus far been unclear whether statistically valid data could be generated from cosmetic C-maps and whether a cell line existed to provide salient or detectable cosmetic data.

Surprisingly, the present inventors have provided a C-map approach that is generalizable and biologically relevant for identification of potential cosmetic actives, and demonstrate that the C-map concept is viable by (as a non-limiting example) use of benchmark cosmetic actives to query the reference data and by identification of new cosmetic actives.

SUMMARY

Accordingly, the present invention provides novel methods and systems useful for generating potential new actives for the treatment of hair biology conditions. In particular, by careful selection of cell type, and by generation of a reference collection of gene-expression profiles for known cosmetic actives, the present inventors were surprisingly able to create a connectivity map useful for testing and generating hypotheses about cosmetic actives and cosmetic conditions. The present investigators confirmed the validity of connectivity mapping as a tool for identifying cosmetic agents efficacious in specific hair biology conditions. Potentially efficacious cosmetic agents were identified using gene expression signatures derived from clinical as well as through in vitro experiments of simple cell culture systems.

The present inventors discovered that it is possible to derive unique hair biology-relevant gene expression signatures for use in a connectivity map. The present inventors have also surprisingly discovered methods that utilize a plurality of unique hair biology-relevant gene expression signatures in a connectivity map to identify useful cosmetic hair care agents.

Embodiments herein described broadly include methods and systems for determining relationships between a hair biology condition of interest and one or more cosmetic agents, one or more genes associated with the hair biology condition, and one or more cells associated with the hair biology condition. Such methods may be used to identify cosmetic agents without detailed knowledge of the mechanisms of biological processes associated with a hair biology condition of interest, all of the genes associated with such a condition, or the cell types associated with such a condition.

According to one embodiment of the invention, herein described is a method for constructing a data architecture for use in identifying connections between perturbagens and genes associated with one or more hair biology conditions, comprising: (a) providing a gene expression profile for a control human fibroblast or keratinocyte cell; (b) generating a gene expression profile for a human fibroblast or keratinocyte cell exposed to at least one perturbagen; (c) identifying genes differentially expressed in response to the at least one perturbagen by comparing the gene expression profiles of (a) and (b); (d) creating an ordered list comprising identifiers representing the differentially expressed genes, wherein the identifiers are ordered according to the differential expression of the genes; (e) storing the ordered list as a fibroblast or keratinocyte instance on at least one computer readable medium; and (f) constructing a data architecture of stored fibroblast or keratinocyte instances by repeating (a) through (e), wherein the at least one perturbagen of step (a) is different for each fibroblast or keratinocyte instance.

Specific embodiments herein described include a method for formulating a hair care composition by identifying connections between perturbagens and genes associated with one or more hair biology conditions, comprising: (a) accessing a plurality of instances stored on at least one computer readable medium, wherein each instance is associated with a perturbagen and a hair-related cell type and wherein each instance comprises an ordered list comprising a plurality of identifiers representing a plurality of up-regulated and a plurality of down regulated genes; (b) accessing at least one hair biology-related gene expression signature stored on the at least one computer readable medium, wherein the at least one hair biology-related gene expression signature comprises one or more lists comprising a plurality of identifiers representing a plurality of up-regulated genes and a plurality of down-regulated genes associated with a hair biology-related condition; (c) comparing the at least one hair biology-related gene expression signature to the plurality of the instances, wherein the comparison comprises comparing each identifier in the one or more gene expression signature lists with the position of the same identifier in the ordered lists for each of the plurality of instances; (d) assigning a connectivity score to each of the plurality of instances; and (e) formulating a hair care composition comprising a dermatologically acceptable carrier and at least one perturbagen, wherein the connectivity score of the instance associated with the at least one perturbagen has a negative correlation.

In yet more specific embodiments, described herein is a method for generating a gene expression signature for use in identifying connections between perturbagens and genes associated with one or more hair biology conditions, comprising: (a) providing a gene expression profile for a reference sample of human hair-related cells; (b) generating a gene expression profile for at least one sample of human hair-related cells from a subject exhibiting at least one hair biology condition, (c) comparing the expression profiles of (a) and (b) to determine a gene expression signature comprising a set of genes differentially expressed in (a) and (b); (d) assigning an identifier to each gene constituting the gene expression signature and ordering the identifiers according to the direction of differential expression to create one or more gene expression signature lists; (e) storing the one or more gene expression signature lists on at least one computer readable medium.

In other specific embodiments herein described, is a system for identifying connections between perturbagens and genes associated with one or more hair biology conditions, comprising: (a) at least one computer readable medium having stored thereon a plurality of instances, and at least one hair biology-relevant gene expression signature, wherein the instances and the gene expression signature are derived from a human dermal fibroblast cell, wherein each instance comprises an instance list of rank-ordered identifiers of differentially expressed genes, and wherein the at least one hair biology-relevant gene expression signature comprises one or more gene expression signature lists of identifiers representing differentially expressed genes associated with a hair biology condition; (b) a programmable computer comprising computer-readable instructions that cause the programmable computer to execute one or more of the following: (i) accessing the plurality of instances and the at least one hair biology-relevant gene expression signature stored on the computer readable medium; (ii) comparing the at least one hair biology-relevant gene expression signature to the plurality of the instances, wherein the comparison comprises comparing each identifier in the gene expression signature list with the position of the same identifier in the instance list for each of the plurality of instances; and (iii) assigning a connectivity score to each of the plurality of instances.

In yet additional specific embodiments herein described, is a gene expression signature consisting of genes selected from the genes set forth in Tables C and D.

In yet additional specific embodiments herein described, is a gene expression signature consisting of genes selected from the genes set forth in Tables E and F.

Additional specific embodiments herein described include a computer readable medium, comprising: a data architecture comprising a digital file stored in a spreadsheet file format, a word processing file format, or a database file format suitable to be read by a respective spreadsheet, word processing, or database computer program, the first digital file comprising data arranged to provide one or more gene expression signature lists comprising a plurality of identifiers when read by the respective spreadsheet, word processing, or database computer program; and wherein each identifier is selected from the group consisting of a microarray probe set ID, a human gene name, a human gene symbol, and combinations thereof representing a gene set forth in any of Tables A-R and T-U, wherein each of the one or more gene expression signature lists comprises between about 50 and about 600 identifiers.

Additional specific embodiments herein described include a method for constructing a data architecture for use in identifying connections between perturbens and genes associated with improving hair biology, comprising: (a) providing a gene expression profile for a control human cell, wherein the control cell is from a human cell line selected from the group consisting of fibroblast, keratinocyte, melanocyte, and dermal papilla cell lines; (b) generating a gene expression profile for a human cell exposed to at least one perturbagen, wherein the cell is selected from the same cell line as the control cell; (c) identifying genes differentially expressed in response to at least one perturbagen by comparing the gene expression profiles of (a) and (b); (d) creating an ordered list comprising identifiers representing the differentially expressed genes, wherein the identifiers are ordered according to the differential expression of the genes; (e) storing the ordered list as an instance on at least one computer readable medium, wherein the instance is a fibroblast, keratinocyte, melanocyte, or dermal papilla instance according to the selection in (a); and (f) constructing a data architecture of stored instances by repeating (a) through (e), wherein the at least one perturben of step (b) is different qualitatively or quantitatively for each instance.

Additional specific embodiments herein described include a method for constructing a data architecture for use in identifying connections between perturbagens and genes associated with one or more hair biology conditions, comprising: (a) providing a gene expression profile for a control human keratinocyte cell; (b) generating a gene expression profile for a human keratinocyte cell exposed to at least one perturbagen; (c) identifying genes differentially expressed in response to the at least one perturbagen by comparing the gene expression profiles of (a) and (b); (d) creating an ordered list comprising identifiers representing the differentially expressed genes, wherein the identifiers are ordered according to the differential expression of the genes; (e) storing the ordered list as a keratinocyte instance on at least one computer readable medium; and (f) constructing a data architecture of stored keratinocyte instances by repeating (a) through (e), wherein the at least one perturbagen of step (a) is different for each keratinocyte instance.

These and additional objects, embodiments, and aspects of the invention will become apparent by reference to the Figures and Detailed Description below.

DETAILED DESCRIPTION

Figure 1:
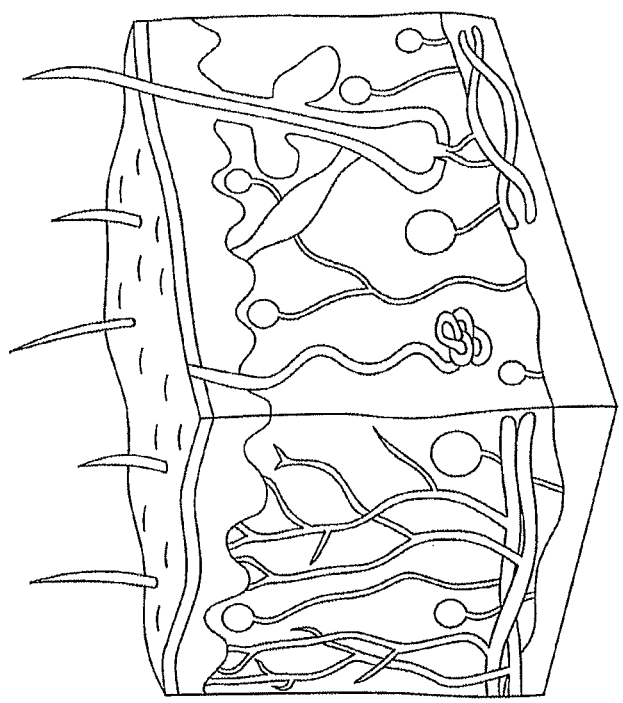
FIG. 1 is a schematic illustration of basic hair anatomy.

Embodiments of the present invention will now be described. Embodiments of this invention may, however, be provided in different forms and should not be construed as limited to the embodiments set forth herein. Rather, these embodiments are provided so that this disclosure will be thorough and complete, and to fully convey the scope of specific embodiments of the invention to those skilled in the art.

Unless otherwise defined, all technical and scientific terms used herein have the same meaning as commonly understood by one of ordinary skill in the art to which this invention pertains. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

As used interchangeably herein, the terms "connectivity map" and "C-map" refer broadly to devices, systems, articles of manufacture, and methodologies for identifying relationships between cellular phenotypes or cosmetic conditions, gene expression, and perturbagens, such as cosmetic actives.

As used herein, the term "cosmetic agent" means any substance, as well any component thereof, intended to be rubbed, poured, sprinkled, sprayed, introduced into, or otherwise applied to a mammalian body or any part thereof for purposes of cleansing, beautifying, promoting attractiveness, altering the appearance, or combinations thereof. Cosmetic agents may include substances that are Generally Recognized as Safe (GRAS) by the US Food and Drug Administration, food additives, and materials used in non-cosmetic consumer products including over-the-counter medications. In some embodiments, cosmetic agents may be incorporated in a cosmetic composition comprising a carrier suitable for topical application. A cosmetic agent includes, but is not limited to, (i) chemicals, compounds, small or large molecules, extracts, formulations, or combinations thereof that are known to induce or cause at least one effect (positive or negative) on hair; (ii) chemicals, compounds, small molecules, extracts, formulations, or combinations thereof that are known to induce or cause at least one effect (positive or negative) on hair and are discovered, using the provided methods and systems, to induce or cause at least one previously unknown effect (positive or negative) on the hair; and (iii) chemicals, compounds, small molecules, extracts, formulations, or combinations thereof that are not known have an effect on skin tissue and are discovered, using the provided methods and systems, to induce or cause an effect on hair.

Some examples of cosmetic agents or cosmetically actionable materials can be found in the PubChem database associated with the National Institutes of Health, USA; the Ingredient Database of the Personal Care Products Council; and the 2010 International Cosmetic Ingredient Dictionary and Handbook, 13$^{th}$ Edition, published by The Personal Care Products Council; the EU Cosmetic Ingredients and Substances list; the Japan Cosmetic Ingredients List; the Personal Care Products Council, the SkinDeep database; the FDA Approved Excipients List; the FDA OTC List; the Japan Quasi Drug List; the US FDA Everything Added to Food database; EU Food Additive list; Japan Existing Food Additives, Flavor GRAS list; US FDA Select Committee on GRAS Substances; US Household Products Database; the Global New Products Database (GNPD) Personal Care, Health Care, Food/Drink/Pet and Household database; and from suppliers of cosmetic ingredients and botanicals.

Other non-limiting examples of cosmetic agents include botanicals (which may be derived from one or more of a root, stem bark, leaf, seed or fruit of a plant). Some botanicals may be extracted from a plant biomass (e.g., root, stem, bark, leaf, etc.) using one more solvents. Botanicals may comprise a complex mixture of compounds and lack a distinct active ingredient. Another category of cosmetic agents are vitamin compounds and derivatives and combinations thereof, such as a vitamin B3 compound, a vitamin B5 compound, a vitamin B6 compound, a vitamin B9 compound, a vitamin A compound, a vitamin C compound, a vitamin E compound, and derivatives and combinations thereof (e.g., retinol, retinyl esters, niacinamide, folic acid, panthenol, ascorbic acid, tocopherol, and tocopherol acetate). Other non-limiting examples of cosmetic agents include sugar amines, phytosterols, hexamidine, hydroxy acids, ceramides, amino acids, and polyols.

The terms "gene expression signature," "gene-expression signature," and "hair biology-related gene expression signature" refer to a rationally derived list, or plurality of lists, of genes representative of a hair biology condition or a hair biology agent. In specific contexts, the hair biology agent may be a benchmark hair biology agent or a potential hair biology agent. Thus, the gene expression signature may serve as a proxy for a phenotype of interest for a hair-related cell type or types. A gene expression signature may comprise genes whose expression, relative to a normal or control state, is increased (up-regulated), whose expression is decreased (down-regulated), and combinations thereof. Generally, a gene expression signature for a modified cellular phenotype may be described as a set of genes differentially expressed in the modified cellular phenotype over the cellular phenotype. A gene expression signature can be derived from various sources of data, including but not limited to, from in vitro testing, in vivo testing and combinations thereof. In some embodiments, a gene expression signature may comprise a first list representative of a plurality of up-regulated genes of the condition of interest and a second list representative of a plurality of down-regulated genes of the condition of interest.

As used herein, the term "benchmark hair biology agent" refers to any chemical, compound, small or large molecule, extract, formulation, or combinations thereof that is known to induce or cause a superior effect (positive or negative) on hair-related cell types. Non-limiting examples of positive benchmark hair biology agents include Minoxidil, Latanoprost, ZPT (zinc pyrithione), ATRA (all trans retinoic acid), a combination of caffeine and Niacinamide and Panthenol, adenosine, apigenin, Finasteride, Cyclosporin A (CSP A), FK506, Bimatoprost, Spironolactone or Cyproterone acetate, RU58841, carnitine tartrate, Aminexil, 6-Benzylaminopurine, melatonin, carpronium chloride, MG132, NEOSH101, AS101, Roxithromycin. Non-limiting negative benchmarks hair biology agents include Vaniqa® (Eflornithine, a drug used to slow the growth of unwanted hair on the face in women, usually around the lips or under the chin.), as well as DHT (Dihydrotestosterone or 5α-Dihydrotestosterone, the primary contributing factor in male pattern baldness).

As used herein, "hair biology condition" is a state of the hair existence capable of improvement; in various non-limiting embodiments this could include pathologies or disorders to which study or application of formulations are aimed to alter that state. Non-limiting examples include dandruff, alopecia, unwanted hair loss, unwanted hair growth, hair thinning, loss of hair diameter, premature hair graying, hair fragility, curl or lack of curl.

As used herein, "hair-related cells" or "hair related cell types" refer to cells or types of cells that are either directly part of a hair (such as a cell shaft), or that are intricately associated with the hair such as to be necessary for homeostatic hair conditions or that involve hair growth. Non-limiting examples of hair related cell types include dermal papilla cells, keratinocytes including inner and outer root sheath cells, dermal fibroblasts, melanocytes, hair/skin stem cells. Induced pluripotent stem cells (IPSC) can be induced in specific embodiments described herein into "hair-related cells" In specific, non-limiting examples, induced pluripotent stem cells (IPSC) can be induced into a human cell or human cell line selected from the group consisting of dermal papilla cells, keratinocytes including inner and outer root sheath cells, dermal fibroblasts, melanocytes, hair/skin stem cells.

As used herein, the term "query" refers to data that is used as an input to a Connectivity Map and against which a plurality of instances are compared. A query may include a gene expression signature associated with one or both of a hair biology condition and a benchmark hair biology agent.

The term "instance," as used herein, refers to data from a gene expression profiling experiment in which hair-related cell types are dosed with a perturbagen. In some embodiments, the data comprises a list of identifiers representing the genes that are part of the gene expression profiling experiment. The identifiers may include gene names, gene symbols, microarray probe set IDs, or any other identifier. In some embodiments, an instance may comprise data from a microarray experiment and comprises a list of probe set IDs of the microarray ordered by their extent of differential expression relative to a control. The data may also comprise metadata, including but not limited to data relating to one or more of the perturbagen, the gene expression profiling test conditions, cells of the hair-related cell types, and the microarray.

The term "keratinous tissue," as used herein, refers to keratin-containing layers disposed as the outermost protective covering of mammals which includes, but is not limited to, skin, hair, nails, cuticles, horns, claws, beaks, and hooves. With respect to skin, the term refers to one or all of the dermal, hypodermal, and epidermal layers, which includes, in part, keratinous tissue.

The term "perturbagen," as used herein, means anything used as a challenge in a gene expression profiling experiment to generate gene expression data for use with embodiments of the present invention. In some embodiments, the perturbagen is applied to fibroblast and/or keratinocyte cells and the gene expression data derived from the gene expression profiling experiment may be stored as an instance in a data architecture. Any substance, chemical, compound, active, natural product, extract, drug [e.g. Sigma-Aldrich LOPAC (Library of Pharmacologically Active Compounds) collection], small molecule, and combinations thereof used as to generate gene expression data can be a perturbagen. A perturbagen can also be any other stimulus used to generate differential gene expression data. For example, a perturbagen may also be UV radiation, heat, osmotic stress, pH, a microbe, a virus, and small interfering RNA. A perturbagen may be, but is not required to be, any cosmetic agent.

The term "dermatologically acceptable," as used herein, means that the compositions or components described are suitable for use in contact with human skin tissue without undue toxicity, incompatibility, instability, allergic response, and the like.

As used herein, the term "computer readable medium" refers to any electronic storage medium and includes but is not limited to any volatile, nonvolatile, removable, and non-removable media implemented in any method or technology for storage of information such as computer readable instructions, data and data structures, digital files, software programs and applications, or other digital information. Computer readable media includes, but are not limited to, application-specific integrated circuit (ASIC), a compact disk (CD), a digital versatile disk (DVD), a random access memory (RAM), a synchronous RAM (SRAM), a dynamic RAM (DRAM), a synchronous DRAM (SDRAM), double data rate SDRAM (DDR SDRAM), a direct RAM bus RAM (DRRAM), a read only memory (ROM), a programmable read only memory (PROM), an electronically erasable programmable read only memory (EEPROM), a disk, a carrier wave, and a memory stick. Examples of volatile memory include, but are not limited to, random access memory (RAM), synchronous RAM (SRAM), dynamic RAM (DRAM), synchronous DRAM (SDRAM), double data rate SDRAM (DDR SDRAM), and direct RAM bus RAM (DRRAM). Examples of non-volatile memory include, but are not limited to, read only memory (ROM), programmable read only memory (PROM), erasable programmable read only memory (EPROM), and electrically erasable programmable read only memory (EEPROM). A memory can store processes and/or data. Still other computer readable media include any suitable disk media, including but not limited to, magnetic disk drives, floppy disk drives, tape drives, Zip drives, flash memory cards, memory sticks, compact disk ROM (CD-ROM), CD recordable drive (CD-R drive), CD rewriteable drive (CD-RW drive), and digital versatile ROM drive (DVD ROM).

As used herein, the terms "software" and "software application" refer to one or more computer readable and/or executable instructions that cause a computing device or other electronic device to perform functions, actions, and/or behave in a desired manner. The instructions may be embodied in one or more various forms like routines, algorithms, modules, libraries, methods, and/or programs. Software may be implemented in a variety of executable and/or loadable forms and can be located in one computer component and/or distributed between two or more communicating, co-operating, and/or parallel processing computer components and thus can be loaded and/or executed in serial, parallel, and other manners. Software can be stored on one or more computer readable medium and may implement, in whole or part, the methods and functionalities of the present invention.

As used herein, the term "connectivity score" refers to a derived value representing the degree to which an instance correlates to a query.

As used herein, the term "data architecture" refers generally to one or more digital data structures comprising an organized collection of data. In some embodiments, the digital data structures can be stored as a digital file (e.g., a spreadsheet file, a text file, a word processing file, a database file, etc.) on a computer readable medium. In some embodiments, the data architecture is provided in the form of a database that may be managed by a database management system (DBMS) that is be used to access, organize, and select data (e.g., instances and gene expression signatures) stored in a database.

As used herein, the terms "gene expression profiling" and "gene expression profiling experiment" refer to the measurement of the expression of multiple genes in a biological sample using any suitable profiling technology. For example, the mRNA expression of thousands of genes may be determined using microarray techniques. Other emerging technologies that may be used include RNA-Seq or whole transcriptome sequencing using NextGen sequencing techniques.

As used herein, the term "microarray" refers broadly to any ordered array of nucleic acids, oligonucleotides, proteins, small molecules, large molecules, and/or combinations thereof on a substrate that enables gene expression profiling of a biological sample. Non-limiting examples of microarrays are available from Affymetrix, Inc.; Agilent Technologies, Inc.; Ilumina, Inc.; GE Healthcare, Inc.; Applied Biosystems, Inc.; Beckman Coulter, Inc.; etc.

Unless otherwise indicated, all numbers expressing quantities of ingredients, properties such as molecular weight, reaction conditions, and so forth as used in the specification and claims are to be understood as being modified in all instances by the term "about." Additionally, the disclosure of any ranges in the specification and claims are to be understood as including the range itself and also anything subsumed therein, as well as endpoints. All numeric ranges are inclusive of narrower ranges; delineated upper and lower range limits are interchangeable to create further ranges not explicitly delineated. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

In accordance with one aspect of specific embodiments of the present invention, provided are devices, systems and methods for implementing a connectivity map utilizing one or more query signatures associated with a hair biology condition. The query signatures may be derived in variety of ways. In some embodiments, the query signatures may be gene expression signatures derived from gene expression profiling biopsies of a hair sample of interest compared to a control. The gene expression profiling can be carried out using any suitable technology, including but not limited to microarray analysis or NextGen sequencing. Query signatures may be used singularly or in combination.

In accordance with another aspect of specific embodiments of the present invention, provided are devices, systems, and methods for implementing a connectivity map utilizing one or more instances derived from a perturbagen, such as a cosmetic agent, exposed to a fibroblast (e.g., BJ fibroblasts) and/or keratinocyte cell line. Instances from more complex cell culture systems may also be used, such as organotypic cultures containing both keratinocytes and fibroblasts and optionally other cell types such as melanocytes or cells from cultured ex vivo samples such as follicles or hair bearing skin. Instances from a plurality of cell lines may be used with the present invention.

In accordance with yet another aspect of specific embodiments of the present invention, provided are devices, systems and methods for identification of relationships between a hair biology-related query signature and a plurality of instances. For example, it may be possible to ascertain perturbagens that give rise to a statistically significant activity on a statistically significant number of genes associated with a hair condition of interest, leading to the identification of new cosmetic agents for treating a hair condition or new uses of known cosmetic agents.

As indicated previously, additional specific embodiments herein described include a computer readable medium, comprising: a data architecture comprising a digital file stored in a spreadsheet file format, a word processing file format, or a database file format suitable to be read by a respective spreadsheet, word processing, or database computer program, the first digital file comprising data arranged to provide one or more gene expression signature lists comprising a plurality of identifiers when read by the respective spreadsheet, word processing, or database computer program; and wherein each identifier is selected from the group consisting of a microarray probe set ID, a human gene name, a human gene symbol, and combinations thereof representing a gene set forth in any of Tables A-R and T-U, wherein each of the one or more gene expression signature lists comprises between about 50 and about 600 identifiers. Tables A-R and T-U are herein provided below:

TABLE A

Follicular miniaturization Gene Studies to Generate the Matrix; Down Genes (up_box_reverse)Bald_nonBald_down

| Affy ID | Gene Symbol | Title |
|---|---|---|
| 203893_at | TAF9 | taf9 rna polymerase ii, tata box binding protein (tbp)-associated factor, 32 kda |
| 209744_x_at | ITCH | itchy e3 ubiquitin protein ligase homolog (mouse) |
| 33307_at | RRP7A | ribosomal rna processing 7 homolog a (s. cerevisiae) |
| 206226_at | HRG | histidine-rich glycoprotein |
| 219913_s_at | CRNKL1 | crooked neck pre-mrna splicing factor-like 1 (drosophila) |
| 210193_at | MOBP | myelin-associated oligodendrocyte basic protein |
| 208515_at | HIST1H2BM | histone cluster 1, h2bm |
| 204128_s_at | RFC3 | replication factor c (activator 1) 3, 38 kda |
| 213997_at | FAM189A1 | family with sequence similarity 189, member a1 |
| 208555_x_at | CST2 | cystatin sa |
| 204343_at | ABCA3 | atp-binding cassette, sub-family a (abc1), member 3 |
| 208564_at | KCNA2 | potassium voltage-gated channel, shaker-related subfamily, member 2 |
| 215168_at | TIMM17A | translocase of inner mitochondrial membrane 17 homolog a (yeast) |
| 214593_at | PIAS2 | protein inhibitor of activated stat, 2 |
| 217329_x_at | — | — |
| 218447_at | C16ORF61 | chromosome 16 open reading frame 61 |
| 222171_s_at | PKNOX2 | pbx/knotted 1 homeobox 2 |
| 208828_at | POLE3 | polymerase (dna directed), epsilon 3 (p17 subunit) |
| 204226_at | STAU2 | staufen, rna binding protein, homolog 2 (drosophila) |
| 219918_s_at | ASPM | asp (abnormal spindle) homolog, microcephaly associated (drosophila) |
| 207895_at | NAALADL1 | n-acetylated alpha-linked acidic dipeptidase-like 1 |
| 221304_at | UGT1A7 | udp glucuronosyltransferase 1 family, polypeptide a10 /// udp glucuronosyltransferase 1 family, polypeptide a7 /// udp glucuronosyltransferase 1 family, polypeptide a8 |
| 219607_s_at | MS4A4A | membrane-spanning 4-domains, subfamily a, member 4 |
| 218806_s_at | VAV3 | vav 3 guanine nucleotide exchange factor |
| 207909_x_at | DAZ1 | deleted in azoospermia 1 /// deleted in azoospermia 2 /// deleted in azoospermia 3 /// deleted in azoospermia 4 |
| 209432_s_at | CREB3 | camp responsive element binding protein 3 |
| 201673_s_at | GYS1 | glycogen synthase 1 (muscle) |
| 210710_at | AGGF1 | angiogenic factor with g patch and fha domains 1 |
| 215438_x_at | GSPT1 | g1 to s phase transition 1 |
| 205705_at | ANKRD26 | ankyrin repeat domain 26 |
| 206300_s_at | PTHLH | parathyroid hormone-like hormone |
| 220891_at | C4ORF23 | chromosome 4 open reading frame 23 |
| 200807_s_at | HSPD1 | heat shock 60 kda protein 1 (chaperonin) |
| 219960_s_at | UCHL5 | ubiquitin carboxyl-terminal hydrolase 15 |
| 216935_at | C1ORF46 | chromosome 1 open reading frame 46 |
| 210744_s_at | IL5RA | interleukin 5 receptor, alpha |
| 203235_at | THOP1 | thimet oligopeptidase 1 |
| 204458_at | PLA2G15 | phospholipase a2, group xv |
| 210293_s_at | SEC23B | sec23 homolog b (s. cerevisiae) |
| 209481_at | SNRK | snf related kinase |
| 207810_at | F13B | coagulation factor xiii, b polypeptide |
| 209363_s_at | MED21 | mediator complex subunit 21 |
| 202233_s_at | UQCRH | ubiquinol-cytochrome c reductase hinge protein |
| 212192_at | KCTD12 | potassium channel tetramerisation domain containing 12 |
| 218854_at | DSE | dermatan sulfate epimerase |
| 209144_s_at | CBFA2T2 | core-binding factor, runt domain, alpha subunit 2; translocated to, 2 |
| 215270_at | LFNG | lfng o-fucosylpeptide 3-beta-n-acetylglucosaminyltransferase |
| 211782_at | IDS | iduronate 2-sulfatase |
| 204813_at | MAPK10 | mitogen-activated protein kinase 10 |
| 201884_at | CEACAM5 | carcinoembryonic antigen-related cell adhesion molecule 5 |
| 217919_s_at | MRPL42 | mitochondrial ribosomal protein 142 |
| 220833_at | — | — |
| 206355_at | GNAL | guanine nucleotide binding protein (g protein), alpha activating activity polypeptide, olfactory type |
| 204870_s_at | PCSK2 | proprotein convertase subtilisin/kexin type 2 |
| 212922_s_at | SMYD2 | set and mynd domain containing 2 |

TABLE A-continued

Follicular miniaturization Gene Studies to Generate the Matrix; Down Genes (up_box_reverse)Bald_nonBald_down

| Affy ID | Gene Symbol | Title |
|---|---|---|
| 201457_x_at | BUB3 | budding uninhibited by benzimidazoles 3 homolog (yeast) |
| 218252_at | CKAP2 | cytoskeleton associated protein 2 |
| 220952_s_at | PLEKHA5 | pleckstrin homology domain containing, family a member 5 |
| 203896_s_at | PLCB4 | phospholipase c, beta 4 |
| 206815_at | SPAG8 | sperm associated antigen 8 |
| 219847_at | HDAC11 | histone deacetylase 11 |
| 208298_at | EVI5 | ecotropic viral integration site 5 |
| 206277_at | P2RY2 | purinergic receptor p2y, g-protein coupled, 2 |
| 207874_s_at | CFHR4 | complement factor h-related 4 |
| 36830_at | MIPEP | mitochondrial intermediate peptidase |
| 211021_s_at | RGS14 | regulator of g-protein signaling 14 |
| 211169_s_at | PPP1R3A | protein phosphatase 1, regulatory (inhibitor) subunit 3a |
| 218882_s_at | WDR3 | wd repeat domain 3 |
| 203224_at | RFK | riboflavin kinase |
| 210346_s_at | CLK4 | cdc-like kinase 4 |
| 208957_at | ERP44 | endoplasmic reticulum protein 44 |
| 218802_at | CCDC109B | coiled-coil domain containing 109b |
| 211550_at | EGFR | epidermal growth factor receptor |
| 207255_at | LEPR | leptin receptor |
| 210834_s_at | PTGER3 | prostaglandin e receptor 3 (subtype ep3) |
| 201524_x_at | UBE2N | ubiquitin-conjugating enzyme e2n (ubc13 homolog, yeast) |
| 212170_at | RBM12 | rna binding motif protein 12 |
| 215303_at | DCLK1 | doublecortin-like kinase 1 |
| 211258_s_at | TGFA | transforming growth factor, alpha |
| 203455_s_at | SAT1 | spermidine/spermine n1-acetyltransferase 1 |
| 214660_at | ITGA1 | integrin, alpha 1 |
| 206540_at | GLB1L | galactosidase, beta 1-like |
| 206691_s_at | PDIA2 | protein disulfide isomerase family a, member 2 |
| 221095_s_at | KCNE2 | potassium voltage-gated channel, isk-related family, member 2 |
| 206664_at | SI | sucrase-isomaltase (alpha-glucosidase) |
| 213262_at | SACS | spastic ataxia of charlevoix-saguenay (sacsin) |
| 203371_s_at | NDUFB3 | nadh dehydrogenase (ubiquinone) 1 beta subcomplex, 3, 12 kda |
| 221935_s_at | C3ORF64 | chromosome 3 open reading frame 64 |
| 206101_at | ECM2 | extracellular matrix protein 2, female organ and adipocyte specific |
| 208526_at | OR2F1 | olfactory receptor, family 2, subfamily f, member 1 |
| 221540_x_at | GTF2H2 | general transcription factor iih, polypeptide 2, 44 kda /// general transcription factor iih, polypeptide 2b /// general transcription factor iih, polypeptide 2c /// general transcription factor iih, polypeptide 2d |
| 203132_at | RB1 | retinoblastoma 1 |
| 209016_s_at | KRT7 | keratin 7 |
| 201014_s_at | PAICS | phosphoribosylaminoimidazole carboxylase, phosphoribosylaminoimidazole succinocarboxamide synthetase |
| 207578_s_at | HTR4 | 5-hydroxytryptamine (serotonin) receptor 4 |
| 203361_s_at | MYCBP | c-myc binding protein |
| 213225_at | PPM1B | protein phosphatase, mg2+/mn2+ dependent, 1b |
| 207090_x_at | ZFP30 | zinc finger protein 30 homolog (mouse) |
| 202584_at | NFX1 | nuclear transcription factor, x-box binding 1 |
| 203536_s_at | CIAO1 | cytosolic iron-sulfur protein assembly 1 |
| 207206_s_at | ALOX12 | arachidonate 12-lipoxygenase |
| 201030_x_at | LDHB | lactate dehydrogenase b |
| 203730_s_at | ZKSCAN5 | zinc finger with krab and scan domains 5 |
| 212185_x_at | MT2A | metallothionein 2a |
| 211257_x_at | ZNF638 | zinc finger protein 638 |
| 202904_s_at | LSM5 | lsm5 homolog, u6 small nuclear rna associated (s. cerevisiae) |
| 213159_at | PCNX | pecanex homolog (drosophila) |
| 216587_s_at | FZD8 | frizzled homolog 8 (drosophila) |
| 201326_at | CCT6A | chaperonin containing tcp1, subunit 6a (zeta 1) |
| 210951_x_at | RAB27A | rab27a, member ras oncogene family |
| 215172_at | PTPN20A | protein tyrosine phosphatase, non-receptor type 20a /// protein tyrosine phosphatase, non-receptor type 20b |
| 206064_s_at | PPIL2 | peptidylprolyl isomerase (cyclophilin)-like 2 |
| 204384_at | GOLGA2 | golgin a2 |
| 208076_at | HIST1H4D | histone cluster 1, h4d |
| 219654_at | PTPLA | protein tyrosine phosphatase-like (proline instead of catalytic arginine), member a |

TABLE A-continued

Follicular miniaturization Gene Studies to Generate the Matrix; Down Genes (up_box_reverse)Bald_nonBald_down

| Affy ID | Gene Symbol | Title |
| --- | --- | --- |
| 201182_s_at | CHD4 | chromodomain helicase dna binding protein 4 |
| 220822_at | — | — |
| 214576_at | KRT36 | keratin 36 |
| 203757_s_at | CEACAM6 | carcinoembryonic antigen-related cell adhesion molecule 6 (non-specific cross reacting antigen) |
| 202543_s_at | GMFB | glia maturation factor, beta |
| 208581_x_at | MT1X | metallothionein 1x |
| 203960_s_at | HSPB11 | heat shock protein family b (small), member 11 |
| 200903_s_at | AHCY | adenosylhomocysteinase |
| 210179_at | KCNJ13 | potassium inwardly-rectifying channel, subfamily j, member 13 |
| 203399_x_at | PSG3 | pregnancy specific beta-l-glycoprotein 3 |
| 220059_at | STAP1 | signal transducing adaptor family member 1 |
| 215227_x_at | ACP1 | acid phosphatase 1, soluble |
| 200961_at | SEPHS2 | selenophosphate synthetase 2 |
| 213310_at | EIF2C2 | eukaryotic translation initiation factor 2c, 2 |
| 210524_x_at | — | — |
| 214151_s_at | CCPG1 | cell cycle progression 1 |
| 214162_at | LOC284244 | hypothetical protein loc284244 |
| 208126_s_at | CYP2C18 | cytochrome p450, family 2, subfamily c, polypeptide 18 |
| 217406_at | — | — |
| 200873_s_at | CCT8 | chaperonin containing tcp1, subunit 8 (theta) |
| 209524_at | HDGFRP3 | hepatoma-derived growth factor, related protein 3 |
| 210592_s_at | SAT1 | spermidine/spermine n1-acetyltransferase 1 |
| 209160_at | AKR1C3 | aldo-keto reductase family 1, member c3 (3-alpha hydroxysteroid dehydrogenase, type ii) |
| 202370_s_at | CBFB | core-binding factor, beta subunit |
| 213263_s_at | PCBP2 | poly(rc) binding protein 2 |
| 206941_x_at | SEMA3E | sema domain, immunoglobulin domain (ig), short basic domain, secreted, (semaphorin) 3e |
| 208059_at | CCR8 | chemokine (c-c motif) receptor 8 |
| 218817_at | SPCS3 | signal peptidase complex subunit 3 homolog (s. cerevisiae) |
| 216585_at | — | — |
| 202674_s_at | LMO7 | lim domain 7 |
| 202744_at | SLC20A2 | solute carrier family 20 (phosphate transporter), member 2 |
| 44065_at | C12ORF52 | chromosome 12 open reading frame 52 |
| 220339_s_at | TPSG1 | tryptase gamma 1 |
| 206245_s_at | IVNS1ABP | influenza virus ns 1a binding protein |
| 42361_g_at | CCHCR1 | coiled-coil alpha-helical rod protein 1 |
| 204326_x_at | MT1X | metallothionein 1x |
| 217165_x_at | MT1F | metallothionein 1f |
| 215418_at | PARVA | parvin, alpha |
| 219450_at | C4ORF19 | chromosome 4 open reading frame 19 |
| 208351_s_at | MAPK1 | mitogen-activated protein kinase 1 |
| 206533_at | CHRNA5 | cholinergic receptor, nicotinic, alpha 5 |
| 220334_at | RGS17 | regulator of g-protein signaling 17 |
| 219480_at | SNAP | snail homolog 1 (drosophila) |
| 211576_s_at | SLC19A1 | solute carrier family 19 (folate transporter), member 1 |
| 206072_at | UCN | urocortin |
| 202282_at | HSD17B10 | hydroxysteroid (17-beta) dehydrogenase 10 |
| 204621_s_at | NR4A2 | nuclear receptor subfamily 4, group a, member 2 |
| 206948_at | NEU3 | sialidase 3 (membrane sialidase) |
| 220123_at | SLC35F5 | solute carrier family 35, member f5 |
| 219584_at | PLA1A | phospholipase a1 member a |
| 219438_at | NKAIN1 | na+/k+ transporting atpase interacting 1 |
| 221758_at | ARMC6 | armadillo repeat containing 6 |
| 213564_x_at | LDHB | lactate dehydrogenase b |
| 218488_at | EIF2B3 | eukaryotic translation initiation factor 2b, subunit 3 gamma, 58 kda |
| 208103_s_at | ANP32E | acidic (leucine-rich) nuclear phosphoprotein 32 family, member e |
| 222317_at | PDE3B | phosphodiesterase 3b, cgmp-inhibited |
| 202620_s_at | PLOD2 | procollagen-lysine, 2-oxoglutarate 5-dioxygenase 2 |
| 207912_s_at | DAZ1 | deleted in azoospermia 1 /// deleted in azoospermia 2 /// deleted in azoospermia 3 /// deleted in azoospermia 4 |
| 219463_at | C20ORF103 | chromosome 20 open reading frame 103 |
| 206376_at | SLC6A15 | solute carrier family 6 (neutral amino acid transporter), member 15 |
| 216614_at | — | — |
| 212907_at | SLC30A1 | solute carrier family 30 (zinc transporter), member 1 |
| 217478_s_at | HLA-DMA | major histocompatibility complex, class ii, dm alpha |
| 203532_x_at | CUL5 | cullin 5 |
| 210543_s_at | PRKDC | protein kinase, dna-activated, catalytic polypeptide |

TABLE A-continued

Follicular miniaturization Gene Studies to Generate the Matrix; Down Genes
(up_box_reverse)Bald_nonBald_down

| Affy ID | Gene Symbol | Title |
| --- | --- | --- |
| 202088_at | SLC39A6 | solute carrier family 39 (zinc transporter), member 6 |
| 219176_at | C2ORF47 | chromosome 2 open reading frame 47 |
| 208844_at | VDAC3 | voltage-dependent anion channel 3 |
| 204444_at | KIF11 | kinesin family member 11 |
| 210913_at | CDH2O | cadherin 20, type 2 |
| 206343_s_at | NRG1 | neuregulin 1 |
| 206488_s_at | CD36 | cd36 molecule (thrombospondin receptor) |
| 213224_s_at | NCRNA00081 | non-protein coding rna 81 |
| 204944_at | PTPRG | protein tyrosine phosphatase, receptor type, g |
| 209955_s_at | FAP | fibroblast activation protein, alpha |
| 202883_s_at | PPP2R1B | protein phosphatase 2, regulatory subunit a, beta |
| 202638_s_at | ICAM1 | intercellular adhesion molecule 1 |
| 213251_at | SMARCA5 | swi/snf related, matrix associated, actin dependent regulator of chromatin, subfamily a, member 5 |
| 205362_s_at | PFDN4 | prefoldin subunit 4 |
| 209001_s_at | ANAPC13 | anaphase promoting complex subunit 13 |
| 210519_s_at | NQ01 | nad(p)h dehydrogenase, quinone 1 |
| 218239_s_at | GTPBP4 | gtp binding protein 4 |
| 216259_at | — | — |
| 207926_at | GP5 | glycoprotein v (platelet) |
| 209683_at | FAM49A | family with sequence similarity 49, member a |

TABLE B

Follicular miniaturization Gene Studies to Generate the Matrix; Up Genes (Down_Box_reverse)
Bald_nonBald up

| Affy ID | Gene Symbol | Title |
| --- | --- | --- |
| 214406_s_at | SLC7A4 | solute carrier family 7 (cationic amino acid transporter, y+ system), member 4 |
| 213848_at | DUSP7 | dual specificity phosphatase 7 |
| 207530_s_at | CDKN2B | cyclin-dependent kinase inhibitor 2b (p15, inhibits cdk4) |
| 210244_at | CAMP | cathelicidin antimicrobial peptide |
| 208165_s_at | PRSS16 | protease, serine, 16 (thymus) |
| 219432_at | EVC | ellis van creveld syndrome |
| 219382_at | SERTAD3 | serta domain containing 3 |
| 200666_s_at | DNAJB1 | dnaj (hsp40) homolog, subfamily b, member 1 |
| 201310_s_at | C5ORF13 | chromosome 5 open reading frame 13 |
| 212062_at | ATP9A | atpase, class ii, type 9a |
| 201910_at | FARP1 | ferm, rhogef (arhgef) and pleckstrin domain protein 1 (chondrocyte-derived) |
| 213579_s_at | EP300 | e1a binding protein p300 |
| 208725_at | EIF2S2 | eukaryotic translation initiation factor 2, subunit 2 beta, 38 kda |
| 203085_s_at | TGFB1 | transforming growth factor, beta 1 |
| 218364_at | LRRFIP2 | leucine rich repeat (in flii) interacting protein 2 |
| 91826_at | EPS8L1 | eps8-like 1 |
| 211066_x_at | PCDHGA1 | protocadherin gamma subfamily a, 1 /// protocadherin gamma subfamily a, 10 /// protocadherin gamma subfamily a, 11 /// protocadherin gamma subfamily a, 12 /// protocadherin gamma subfamily a, 2 /// protocadherin gamma subfamily a, 3 /// protocadherin gamma subfamily a, 4 /// protocadherin gamma subfamily a, 5 /// protocadherin gamma subfamily a, 6 /// protocadherin gamma subfamily a, 7 /// protocadherin gamma subfamily a, 8 /// protocadherin gamma subfamily a, 9 /// protocadherin gamma subfamily b, 1 /// protocadherin gamma subfamily b, 2 /// protocadherin gamma subfamily b, 3 /// protocadherin gamma subfamily b, 4 /// protocadherin gamma subfamily b, 5 /// protocadherin gamma subfamily b, 6 /// protocadherin gamma subfamily b, 7 /// protocadherin gamma subfamily c, 3 /// protocadherin gamma subfamily c, 4 /// protocadherin gamma subfamily c, 5 |
| 201271_s_at | RALY | rna binding protein, autoantigenic (hnrnp-associated with lethal yellow homolog (mouse)) |
| 201681_s_at | DLG5 | discs, large homolog 5 (*drosophila*) |

TABLE B-continued

Follicular miniaturization Gene Studies to Generate the Matrix; Up Genes (Down_Box_reverse)
Bald_nonBald up

| Affy ID | Gene Symbol | Title |
|---|---|---|
| 211889_x_at | CEACAM1 | carcinoembryonic antigen-related cell adhesion molecule 1 (biliary glycoprotein) |
| 207364_at | TEX28 | testis expressed 28 |
| 207163_s_at | AKT1 | v-akt murine thymoma viral oncogene homolog 1 |
| 212159_x_at | AP2A2 | adaptor-related protein complex 2, alpha 2 subunit |
| 212400_at | FAM102A | family with sequence similarity 102, member a |
| 218062_x_at | CDC42EP4 | cdc42 effector protein (rho gtpase binding) 4 |
| 48580_at | CXXC1 | cxxc finger protein 1 |
| 205460_at | NPAS2 | neuronal pas domain protein 2 |
| 210617_at | PHEX | phosphate regulating endopeptidase homolog, x-linked |
| 202123_s_at | ABL1 | c-abl oncogene 1, non-receptor tyrosine kinase |
| 220241_at | TMCO3 | transmembrane and coiled-coil domains 3 |
| 221725_at | WASF2 | was protein family, member 2 |
| 221972_s_at | SDF4 | stromal cell derived factor 4 |
| 221655_x_at | EPS8L1 | eps8-like 1 |
| 215061_at | METTL10 | methyltransferase like 10 |
| 208132_x_at | BAT2 | hla-b associated transcript 2 |
| 202449_s_at | RXRA | retinoid x receptor, alpha |
| 206339_at | CARTPT | cart prepropeptide |
| 216627_s_at | B4GALT1 | udp-gal:betaglcnac beta 1,4-galactosyltransferase, polypeptide 1 |
| 200759_x_at | NFE2L1 | nuclear factor (erythroid-derived 2)-like 1 |
| 218613_at | PSD3 | pleckstrin and sec7 domain containing 3 |
| 202267_at | LAMC2 | laminin, gamma 2 |
| 221134_at | ANGPT4 | angiopoietin 4 |
| 201383_s_at | NBR1 | neighbor of brca1 gene 1 |
| 214302_x_at | GJC2 | gap junction protein, gamma 2, 47 kda |
| 213462_at | NPAS2 | neuronal pas domain protein 2 |
| 222198_at | — | — |
| 214191_at | ICA1 | islet cell autoantigen 1, 69 kda |
| 219439_at | C1GALT1 | core 1 synthase, glycoprotein-n-acetylgalactosamine 3-beta-galactosyltransferase, 1 |
| 201620_at | MBTPS1 | membrane-bound transcription factor peptidase, site 1 |
| 213458_at | FAM149B1 | family with sequence similarity 149, member b1 |
| 212564_at | KCTD2 | potassium channel tetramerisation domain containing 2 |
| 206337_at | CCR7 | chemokine (c-c motif) receptor 7 |
| 215867_x_at | CA12 | carbonic anhydrase xii |
| 216542_x_at | IGHM | immunoglobulin heavy constant alpha 1 /// immunoglobulin heavy constant gamma 1 (g1m marker) /// immunoglobulin heavy constant mu |
| 217253_at | SH3BP2 | sh3-domain binding protein 2 |
| 209221_s_at | OSBPL2 | oxysterol binding protein-like 2 |
| 37860_at | ZNF337 | zinc finger protein 337 |
| 219853_at | FKRP | fukutin related protein |
| 218275_at | SLC25A10 | solute carrier family 25 (mitochondrial carrier; dicarboxylate transporter), member 10 |
| 217992_s_at | EFHD2 | ef-hand domain family, member d2 |
| 201465_s_at | JUN | jun proto-oncogene |
| 212488_at | COL5A1 | collagen, type v, alpha 1 |
| 209035_at | MDK | midkine (neurite growth-promoting factor 2) |
| 212427_at | KIAA0368 | kiaa0368 |
| 201904_s_at | CTDSPL | ctd (carboxy-terminal domain, rna polymerase ii, polypeptide a) small phosphatase-like |
| 204193_at | CHKB | choline kinase beta |
| 210583_at | POLDIP3 | polymerase (dna-directed), delta interacting protein 3 |
| 209866_s_at | LPHN3 | latrophilin 3 |
| 217042_at | RDH11 | retinol dehydrogenase 11 (all-trans/9-cis/11-cis) |
| 218696_at | EIF2AK3 | eukaryotic translation initiation factor 2-alpha kinase 3 |
| 213089_at | LOC100272216 | hypothetical loc100272216 |
| 207339_s_at | LTB | lymphotoxin beta (tnf superfamily, member 3) |
| 206279_at | PRKY | protein kinase, y-linked |
| 209333_at | ULK1 | unc-51-like kinase 1 (*c. elegans*) |
| 202307_s_at | TAP1 | transporter 1, atp-binding cassette, sub-family b (mdr/tap) |
| 220804_s_at | TP73 | tumor protein p73 |
| 214680_at | NTRK2 | neurotrophic tyrosine kinase, receptor, type 2 |
| 216700_at | TRIO | triple functional domain (ptprf interacting) |
| 211087_x_at | MAPK14 | mitogen-activated protein kinase 14 |
| 213502_x_at | LOC91316 | glucuronidase, beta/immunoglobulin lambda-like polypeptide 1 pseudogene |
| 212923_s_at | C6ORF145 | chromosome 6 open reading frame 145 |
| 209331_s_at | MAX | myc associated factor x |
| 213509_x_at | CES2 | carboxylesterase 2 |

TABLE B-continued

Follicular miniaturization Gene Studies to Generate the Matrix; Up Genes (Down_Box_reverse)
Bald_nonBald up

| Affy ID | Gene Symbol | Title |
| --- | --- | --- |
| 217049_x_at | PCDH11Y | protocadherin 11 y-linked |
| 203705_s_at | FZD7 | frizzled homolog 7 (*drosophila*) |
| 203729_at | EMP3 | epithelial membrane protein 3 |
| 202978_s_at | CREBZF | creb/atf bzip transcription factor |
| 219226_at | CDK12 | cyclin-dependent kinase 12 |
| 214557_at | PTTG2 | pituitary tumor-transforming 2 |
| 202454_s_at | ERBB3 | v-erb-b2 erythroblastic leukemia viral oncogene homolog 3 (avian) |
| 212319_at | SGSM2 | small g protein signaling modulator 2 |
| 218699_at | RAB7L1 | rab7, member ras oncogene family-like 1 |
| 219503_s_at | TMEM40 | transmembrane protein 40 |
| 35626_at | SGSH | n-sulfoglucosamine sulfohydrolase |
| 36920_at | MTM1 | myotubularin 1 |
| 214239_x_at | PCGF2 | polycomb group ring finger 2 |
| 203642_s_at | COBLL1 | cobl-like 1 |
| 204425_at | ARHGAP4 | rho gtpase activating protein 4 |
| 207963_at | C6ORF54 | chromosome 6 open reading frame 54 |
| 203313_s_at | TGIF1 | tgfb-induced factor homeobox 1 |
| 200764_s_at | CTNNA1 | catenin (cadherin-associated protein), alpha 1, 102 kda |
| 205329_s_at | SNX4 | sorting nexin 4 |
| 213686_at | VPS13A | vacuolar protein sorting 13 homolog a (*s. cerevisiae*) |
| 219460_s_at | TMEM127 | transmembrane protein 127 |
| 207254_at | SLC15A1 | solute carrier family 15 (oligopeptide transporter), member 1 |
| 205781_at | C16ORF7 | chromosome 16 open reading frame 7 |
| 220945_x_at | MANSC1 | mansc domain containing 1 |
| 208551_at | HIST1H4G | histone cluster 1, h4g |
| 202748_at | GBP2 | guanylate binding protein 2, interferon-inducible |
| 217126_at | — | — |
| 202948_at | IL1R1 | interleukin 1 receptor, type i |
| 213455_at | FAM114A1 | family with sequence similarity 114, member a1 |
| 36865_at | ANGEL1 | angel homolog 1 (*drosophila*) |
| 214320_x_at | CYP2A6 | cytochrome p450, family 2, subfamily a, polypeptide 6 |
| 220080_at | FBXL8 | f-box and leucine-rich repeat protein 8 |
| 218742_at | NARFL | nuclear prelamin a recognition factor-like |
| 218803_at | CHFR | checkpoint with forkhead and ring finger domains |
| 200879_s_at | EPAS1 | endothelial pas domain protein 1 |
| 201782_s_at | AIP | aryl hydrocarbon receptor interacting protein |
| 207951_at | CSN2 | casein beta |
| 203385_at | DGKA | diacylglycerol kinase, alpha 80 kda |
| 203315_at | NCK2 | nck adaptor protein 2 |
| 221132_at | CLDN18 | claudin 18 |
| 208256_at | EFNA2 | ephrin-a2 |
| 212089_at | LMNA | lamin a/c |
| 211226_at | GALR2 | galanin receptor 2 |
| 209867_s_at | LPHN3 | latrophilin 3 |
| 214670_at | ZKSCAN1 | zinc finger with krab and scan domains 1 |
| 206402_s_at | NPFF | neuropeptide ff-amide peptide precursor |
| 209321_s_at | ADCY3 | adenylate cyclase 3 |
| 219427_at | FAT4 | fat tumor suppressor homolog 4 (*drosophila*) |
| 207496_at | MS4A2 | membrane-spanning 4-domains, subfamily a, member 2 (fc fragment of ige, high affinity i, receptor for; beta polypeptide) |
| 205447_s_at | MAP3K12 | mitogen-activated protein kinase kinase kinase 12 |
| 212045_at | GLG1 | golgi glycoprotein 1 |
| 209454_s_at | TEAD3 | tea domain family member 3 |
| 210047_at | SLC11A2 | solute carrier family 11 (proton-coupled divalent metal ion transporters), member 2 |
| 206113_s_at | RAB5A | rab5a, member ras oncogene family |
| 215598_at | TTC12 | tetratricopeptide repeat domain 12 |
| 220237_at | ATG3 | atg3 autophagy related 3 homolog (*s. cerevisiae*) |
| 216107_at | LOC100129503 | hypothetical loc100129503 |
| 214613_at | GPR3 | g protein-coupled receptor 3 |
| 207188_at | CDK3 | cyclin-dependent kinase 3 |
| 222121_at | ARHGEF26 | rho guanine nucleotide exchange factor (gef) 26 |
| 222170_at | — | — |
| 216579_at | GJB4 | gap junction protein, beta 4, 30.3 kda |
| 205986_at | AATK | apoptosis-associated tyrosine kinase |
| 203795_s_at | BCL7A | b-cell cll/lymphoma 7a |
| 212598_at | WDFY3 | wd repeat and fyve domain containing 3 |
| 209890_at | TSPAN5 | tetraspanin 5 |
| 220408_x_at | FAM48A | family with sequence similarity 48, member a |
| 207196_s_at | TNIP1 | tnfaip3 interacting protein 1 |

TABLE B-continued

Follicular miniaturization Gene Studies to Generate the Matrix; Up Genes (Down_Box_reverse)
Bald_nonBald up

| Affy ID | Gene Symbol | Title |
|---|---|---|
| 214882_s_at | SRSF2 | serine/arginine-rich splicing factor 2 |
| 210363_s_at | SCN2B | sodium channel, voltage-gated, type ii, beta |
| 200784_s_at | LRP1 | low density lipoprotein receptor-related protein 1 |
| 214900_at | ZKSCAN1 | zinc finger with krab and scan domains 1 |
| 217237_at | — | — |
| 208786_s_at | MAP1LC3B | microtubule-associated protein 1 light chain 3 beta |
| 216417_x_at | HOXB9 | homeobox b9 |
| 211105_s_at | NFATC1 | nuclear factor of activated t-cells, cytoplasmic, calcineurin-dependent 1 |
| 214343_s_at | ATXN7L1 | ataxin 7-like 1 |
| 222175_at | MED15 | mediator complex subunit 15 |
| 219938_s_at | PSTPIP2 | proline-serine-threonine phosphatase interacting protein 2 |
| 201719_s_at | EPB41L2 | erythrocyte membrane protein band 4.1-like 2 |
| 217187_at | MUC5AC | mucin 5ac, oligomeric mucus/gel-forming |
| 208991_at | STAT3 | signal transducer and activator of transcription 3 (acute-phase response factor) |
| 207280_at | RNF185 | ring finger protein 185 |
| 207159_x_at | CRTC1 | creb regulated transcription coactivator 1 |
| 200707_at | PRKCSH | protein kinase c substrate 80k-h |
| 209329_x_at | HIGD2A | hig1 hypoxia inducible domain family, member 2a |
| 200789_at | ECH1 | enoyl coa hydratase 1, peroxisomal |
| 218899_s_at | BAALC | brain and acute leukemia, cytoplasmic |
| 203995_s_at | C21ORF2 | chromosome 21 open reading frame 2 |
| 215370_at | — | — |
| 214099_s_at | PDE4DIP | phosphodiesterase 4d interacting protein |
| 212026_s_at | EXOC7 | exocyst complex component 7 |
| 212202_s_at | TMEM87A | transmembrane protein 87a |
| 204734_at | KRT15 | keratin 15 |
| 222126_at | AGFG2 | arfgap with fg repeats 2 |
| 216514_at | — | — |
| 210280_at | MPZ | myelin protein zero |
| 220025_at | TBR1 | t-box, brain, 1 |
| 213381_at | C10ORF72 | chromosome 10 open reading frame 72 |
| 204547_at | RAB40B | rab40b, member ras oncogene family |
| 218284_at | SMAD3 | smad family member 3 |
| 211434_s_at | CCRL2 | chemokine (c-c motif) receptor-like 2 |
| 215782_at | RAB40AL | rab40a, member ras oncogene family-like |
| 206138_s_at | PI4KB | phosphatidylinositol 4-kinase, catalytic, beta |
| 213146_at | KDM6B | lysine (k)-specific demethylase 6b |
| 215243_s_at | GJB3 | gap junction protein, beta 3, 31 kda |
| 209079_x_at | PCDHGA1 | protocadherin gamma subfamily a, 1 /// protocadherin gamma subfamily a, 10 /// protocadherin gamma subfamily a, 11 /// protocadherin gamma subfamily a, 12 /// protocadherin gamma subfamily a, 2 /// protocadherin gamma subfamily a, 3 /// protocadherin gamma subfamily a, 4 /// protocadherin gamma subfamily a, 5 /// protocadherin gamma subfamily a, 6 /// protocadherin gamma subfamily a, 7 /// protocadherin gamma subfamily a, 8 /// protocadherin gamma subfamily a, 9 /// protocadherin gamma subfamily b, 1 /// protocadherin gamma subfamily b, 2 /// protocadherin gamma subfamily b, 3 /// protocadherin gamma subfamily b, 4 /// protocadherin gamma subfamily b, 5 /// protocadherin gamma subfamily b, 6 /// protocadherin gamma subfamily b, 7 /// protocadherin gamma subfamily c, 3 /// protocadherin gamma subfamily c, 4 /// protocadherin gamma subfamily c, 5 |
| 208759_at | NCSTN | nicastrin |
| 209747_at | TGFB3 | transforming growth factor, beta 3 |
| 208425_s_at | TANC2 | tetratricopeptide repeat, ankyrin repeat and coiled-coil containing 2 |
| 221266_s_at | TM7SF4 | transmembrane 7 superfamily member 4 |
| 216821_at | KRT8 | keratin 8 |
| 213135_at | TIAM1 | t-cell lymphoma invasion and metastasis 1 |
| 216285_at | DGCR14 | digeorge syndrome critical region gene 14 |
| 209276_s_at | GLRX | glutaredoxin (thioltransferase) |
| 205490_x_at | GJB3 | gap junction protein, beta 3, 31 kda |
| 209835_x_at | CD44 | cd44 molecule (indian blood group) |

TABLE C

Increasing Hair Diameter Gene Studies to Generate the Matrix; Down Genes

Dragon_Pol_R12_NR12_anova4_DOWN

| Affy ID | Gene Symbol | Title |
|---|---|---|
| 212630_at | EXOC3 | exocyst complex component 3 |
| 217704_x_at | SUZ12P | suppressor of zeste 12 homolog pseudogene |
| 210419_at | BARX2 | barx homeobox 2 |
| 212058_at | SR140 | u2-associated sr140 protein |
| 205802_at | TRPC1 | transient receptor potential cation channel, subfamily c, member 1 |
| 206316_s_at | KNTC1 | kinetochore associated 1 |
| 214023_x_at | TUBB2B | tubulin, beta 2b |
| 58696_at | EXOSC4 | exosome component 4 |
| 212455_at | YTHDC1 | yth domain containing 1 |
| 213630_at | NACAD | nac alpha domain containing |
| 201962_s_at | RNF41 | ring finger protein 41 |
| 221973_at | LOC100506076 | hypothetical loc100506076 /// hypothetical loc100506123 |
| 217419_x_at | AGRN | agrin |
| 203938_s_at | TAF1C | tata box binding protein (tbp)-associated factor, rna polymerase i, c, 110 kda |
| 218558_s_at | MRPL39 | mitochondrial ribosomal protein 139 |
| 217954_s_at | PHF3 | phd finger protein 3 |
| 217690_at | LOC100505523 | hypothetical loc100505523 |
| 214436_at | FBXL2 | f-box and leucine-rich repeat protein 2 |
| 218256_s_at | NUP54 | nucleoporin 54 kda |
| 211168_s_at | UPF1 | upf1 regulator of nonsense transcripts homolog (yeast) |
| 200685_at | SRSF11 | serine/arginine-rich splicing factor 11 |
| 213971_s_at | SUZ12 | polycomb protein suz12-like /// suppressor of zeste 12 homolog (*drosophila*) /// suppressor of zeste 12 homolog pseudogene |
| 202137_s_at | ZMYND11 | zinc finger, mynd domain containing 11 |
| 213117_at | KLHL9 | kelch-like 9 (*drosophila*) |
| 212608_s_at | — | — |
| 204531_s_at | BRCA1 | breast cancer 1, early onset |
| 219944_at | CLIP4 | cap-gly domain containing linker protein family, member 4 |
| 215123_at | NPIPL3 | nuclear pore complex interacting protein-like 3 |
| 218371_s_at | PSPC1 | paraspeckle component 1 |
| 222140_s_at | GPR89A | g protein-coupled receptor 89a /// g protein-coupled receptor 89b /// g protein-coupled receptor 89c |
| 215296_at | CDC42BPA | cdc42 binding protein kinase alpha (dmpk-like) |
| 201651_s_at | PACSIN2 | protein kinase c and casein kinase substrate in neurons 2 |
| 222136_x_at | ZNF43 | zinc finger protein 43 |
| 212394_at | KIAA0090 | kiaa0090 |
| 207010_at | GABRB1 | gamma-aminobutyric acid (gaba) a receptor, beta 1 |
| 214093_s_at | FUBP1 | far upstream element (fuse) binding protein 1 |
| 209759_s_at | DCI | dodecenoyl-coa isomerase |
| 212060_at | SR140 | u2-associated sr140 protein |
| 201924_at | AFF1 | af4/fmr2 family, member 1 |
| 212779_at | KIAA1109 | kiaa1109 |
| 212061_at | SR140 | u2-associated sr140 protein |
| 219525_at | SLC47A1 | solute carrier family 47, member 1 |
| 213716_s_at | SECTM1 | secreted and transmembrane 1 |
| 205251_at | PER2 | period homolog 2 (*drosophila*) |
| 40446_at | PHF1 | phd finger protein 1 |
| 204347_at | AK4 | adenylate kinase 4 |
| 210306_at | L3MBTL1 | l(3)mbt-like 1 (*drosophila*) |
| 203250_at | RBM16 | rna binding motif protein 16 |
| 213686_at | VPS13A | vacuolar protein sorting 13 homolog a (*s. cerevisiae*) |
| 212147_at | SMG5 | smg-5 homolog, nonsense mediated mrna decay factor (*c. elegans*) |
| 219368_at | NAP1L2 | nucleosome assembly protein 1-like 2 |
| 218286_s_at | RNF7 | ring finger protein 7 |
| 222138_s_at | WDR13 | wd repeat domain 13 |
| 204451_at | FZD1 | frizzled homolog 1 (*drosophila*) |
| 207078_at | MED6 | mediator complex subunit 6 |
| 209499_x_at | TNFSF13 | tnfsf12-tnfsf13 readthrough /// tumor necrosis factor (ligand) superfamily, member 13 |
| 202606_s_at | TLK1 | tousled-like kinase 1 |
| 213883_s_at | TM2D1 | tm2 domain containing 1 |
| 53071_s_at | C17ORF101 | chromosome 17 open reading frame 101 |
| 203301_s_at | DMTF1 | cyclin d binding myb-like transcription factor 1 |

TABLE C-continued

Increasing Hair Diameter Gene Studies to Generate the Matrix; Down Genes

Dragon_Pol_R12_NR12_anova4_DOWN

| Affy ID | Gene Symbol | Title |
| --- | --- | --- |
| 219750_at | TMEM144 | transmembrane protein 144 |
| 201456_s_at | BUB3 | budding uninhibited by benzimidazoles 3 homolog (yeast) |
| 218756_s_at | DHRS11 | dehydrogenase/reductase (sdr family) member 11 |
| 203729_at | EMP3 | epithelial membrane protein 3 |
| 206011_at | CASP1 | caspase 1, apoptosis-related cysteine peptidase (interleukin 1, beta, convertase) |
| 213704_at | RABGGTB | rab geranylgeranyltransferase, beta subunit |
| 205910_s_at | CEL | carboxyl ester lipase (bile salt-stimulated lipase) /// bile salt-activated lipase-like |
| 213103_at | STARD13 | star-related lipid transfer (start) domain containing 13 |
| 217830_s_at | NSFL1C | nsfl1 (p97) cofactor (p47) |
| 204989_s_at | ITGB4 | integrin, beta 4 |
| 202980_s_at | SIAH1 | seven in absentia homolog 1 (*drosophila*) |
| 222201_s_at | CASP8AP2 | caspase 8 associated protein 2 |
| 204176_at | KLHL20 | kelch-like 20 (*drosophila*) |
| 210994_x_at | TRIM23 | tripartite motif-containing 23 |
| 204350_s_at | MED7 | mediator complex subunit 7 |
| 211703_s_at | TM2D1 | tm2 domain containing 1 |
| 203818_s_at | SF3A3 | splicing factor 3a, subunit 3, 60 kda |
| 219297_at | WDR44 | wd repeat domain 44 |
| 202701_at | BMP1 | bone morphogenetic protein 1 |
| 203038_at | PTPRK | protein tyrosine phosphatase, receptor type, k |
| 204793_at | GPRASP1 | g protein-coupled receptor associated sorting protein 1 |
| 208612_at | PDIA3 | protein disulfide isomerase family a, member 3 |
| 204849_at | TCFL5 | transcription factor-like 5 (basic helix-loop-helix) |
| 216450_x_at | HSP90B1 | heat shock protein 90 kda beta (grp94), member 1 |
| 221559_s_at | MIS12 | mis12, mind kinetochore complex component, homolog (*s. pombe*) |
| 206015_s_at | FOXJ3 | forkhead box j3 |
| 203084_at | TGFB1 | transforming growth factor, beta 1 |
| 202393_s_at | KLF10 | kruppel-like factor 10 |
| 210342_s_at | TPO | thyroid peroxidase |
| 203146_s_at | GABBR1 | gamma-aminobutyric acid (gaba) b receptor, 1 |
| 220823_at | LOC729164 | hcg1732469 |
| 213897_s_at | MRPL23 | mitochondrial ribosomal protein l23 |
| 201613_s_at | AP1G2 | adaptor-related protein complex 1, gamma 2 subunit |
| 206417_at | CNGA1 | cyclic nucleotide gated channel alpha 1 |
| 215314_at | — | — |
| 211182_x_at | RUNX1 | runt-related transcription factor 1 |
| 207451_at | NKX2-8 | nk2 homeobox 8 |
| 222273_at | PAPOLG | poly(a) polymerase gamma |
| 220587_s_at | MLST8 | mtor associated protein, lst8 homolog (*s. cerevisiae*) |
| 214742_at | AZI1 | 5-azacytidine induced 1 |
| 203690_at | TUBGCP3 | tubulin, gamma complex associated protein 3 |
| 201449_at | TIA1 | tia1 cytotoxic granule-associated rna binding protein |
| 205684_s_at | DENND4C | denn/madd domain containing 4c |
| 219200_at | FASTKD3 | fast kinase domains 3 |
| 201130_s_at | CDH1 | cadherin 1, type 1, e-cadherin (epithelial) |
| 218337_at | FAM160B2 | family with sequence similarity 160, member b2 |
| 202512_s_at | ATG5 | atg5 autophagy related 5 homolog (*s. cerevisiae*) |
| 212300_at | TXLNA | taxilin alpha |
| 210100_s_at | ABCA2 | atp-binding cassette, sub-family a (abc1), member 2 |
| 206857_s_at | FKBP1B | fk506 binding protein 1b, 12.6 kda |
| 213449_at | POP1 | processing of precursor 1, ribonuclease p/mrp subunit (*s. cerevisiae*) |
| 38710_at | OTUB1 | otu domain, ubiquitin aldehyde binding 1 |
| 220030_at | STYK1 | serine/threonine/tyrosine kinase 1 |
| 201178_at | FBXO7 | f-box protein 7 |
| 213359_at | HNRNPD | heterogeneous nuclear ribonucleoprotein d (au-rich element rna binding protein 1, 37 kda) |
| 202973_x_at | FAM13A | family with sequence similarity 13, member a |
| 222371_at | — | — |
| 212199_at | MRFAP1L1 | morf4 family associated protein 1-like 1 |
| 201011_at | RPN1 | ribophorin i |
| 211626_x_at | ERG | v-ets erythroblastosis virus e26 oncogene homolog (avian) |

TABLE C-continued

Increasing Hair Diameter Gene Studies to Generate the Matrix; Down Genes

Dragon_Pol_R12_
NR12_anova4_DOWN

| Affy ID | Gene Symbol | Title |
| --- | --- | --- |
| 212927_at | SMC5 | structural maintenance of chromosomes 5 |
| 213363_at | CA5BP | carbonic anhydrase vb pseudogene |
| 204442_x_at | LTBP4 | latent transforming growth factor beta binding protein 4 |
| 212254_s_at | DST | dystonin |
| 217818_s_at | ARPC4 | actin related protein 2/3 complex, subunit 4, 20 kda |
| 220968_s_at | TSPAN9 | tetraspanin 9 |
| 214985_at | EXT1 | exostosin 1 |
| 208975_s_at | KPNB1 | karyopherin (importin) beta 1 |
| 202607_at | NDST1 | n-deacetylase/n-sulfotransferase (heparan glucosaminyl) 1 |
| 203083_at | THBS2 | thrombospondin 2 |
| 212360_at | AMPD2 | adenosine monophosphate deaminase 2 |
| 207465_at | LOC100127886 | hypothetical loc100127886 |
| 204435_at | NUPL1 | nucleoporin like 1 |
| 200069_at | SART3 | squamous cell carcinoma antigen recognized by t cells 3 |
| 213500_at | — | — |
| 221927_s_at | ABHD11 | abhydrolase domain containing 11 |
| 209356_x_at | EFEMP2 | egf-containing fibulin-like extracellular matrix protein 2 |
| 215324_at | SEMA3D | sema domain, immunoglobulin domain (ig), short basic domain, secreted, (semaphorin) 3d |
| 205618_at | PRRG1 | proline rich gla (g-carboxyglutamic acid) 1 |
| 212285_s_at | AGRN | agrin |
| 200792_at | XRCC6 | x-ray repair complementing defective repair in chinese hamster cells 6 |
| 211929_at | HNRNPA3 | heterogeneous nuclear ribonucleoprotein a3 |
| 217833_at | SYNCRIP | synaptotagmin binding, cytoplasmic rna interacting protein |
| 201203_s_at | RRBP1 | ribosome binding protein 1 homolog 180 kda (dog) |
| 215204_at | — | — |
| 202020_s_at | LANCL1 | lanc lantibiotic synthetase component c-like 1 (bacterial) |
| 218784_s_at | C6ORF64 | chromosome 6 open reading frame 64 |
| 216026_s_at | POLE | polymerase (dna directed), epsilon |
| 201700_at | CCND3 | cyclin d3 |
| 216005_at | TNC | tenascin c |
| 209414_at | FZR1 | fizzy/cell division cycle 20 related 1 (*drosophila*) |
| 218093_s_at | ANKRD10 | ankyrin repeat domain 10 |
| 202552_s_at | CRIM1 | cysteine rich transmembrane bmp regulator 1 (chordin-like) |
| 218389_s_at | APH1A | anterior pharynx defective 1 homolog a (*c. elegans*) |
| 221135_s_at | ASTE1 | asteroid homolog 1 (*drosophila*) |
| 32723_at | CSTF1 | cleavage stimulation factor, 3' pre-rna, subunit 1, 50 kda |
| 204484_at | PIK3C2B | phosphoinositide-3-kinase, class 2, beta polypeptide |
| 212164_at | TMEM183A | transmembrane protein 183a |
| 219317_at | POLI | polymerase (dna directed) iota |
| 212418_at | ELF1 | e74-like factor 1 (ets domain transcription factor) |
| 216902_s_at | RRN3 | rrn3 rna polymerase i transcription factor homolog (*s. cerevisiae*) /// rna polymerase i transcription factor homolog (*s. cerevisiae*) pseudogene 1 /// rna polymerase i transcription factor homolog (*s. cerevisiae*) pseudogene 2 |
| 203242_s_at | PDLIM5 | pdz and lim domain 5 |
| 213727_x_at | MPPE1 | metallophosphoesterase 1 |
| 216109_at | MED13L | mediator complex subunit 13-like |
| 202495_at | TBCC | tubulin folding cofactor c |
| 209377_s_at | HMGN3 | high mobility group nucleosomal binding domain 3 |
| 214353_at | — | — |
| 217897_at | FXYD6 | fxyd domain containing ion transport regulator 6 |
| 221696_s_at | STYK1 | serine/threonine/tyrosine kinase 1 |
| 212408_at | TOR1AIP1 | torsin a interacting protein 1 |
| 205498_at | GHR | growth hormone receptor |
| 203527_s_at | APC | adenomatous polyposis coli |
| 203136_at | RABAC1 | rab acceptor 1 (prenylated) |
| 202128_at | KIAA0317 | kiaa0317 |
| 201813_s_at | TBC1D5 | tbc1 domain family, member 5 |
| 212918_at | RECQL | recq protein-like (dna helicase q1-like) |

TABLE C-continued

Increasing Hair Diameter Gene Studies to Generate the Matrix; Down Genes

Dragon_Pol_R12_NR12_anova4_DOWN

| Affy ID | Gene Symbol | Title |
|---|---|---|
| 212031_at | RBM25 | rna binding motif protein 25 |
| 213532_at | ADAM17 | adam metallopeptidase domain 17 |
| 213694_at | RSBN1 | round spermatid basic protein 1 |
| 213459_at | RPL37A | ribosomal protein l37a |
| 203881_s_at | DMD | dystrophin |
| 216983_s_at | ZNF224 | zinc finger protein 224 |
| 218459_at | TOR3A | torsin family 3, member a |
| 211382_s_at | TACC2 | transforming, acidic coiled-coil containing protein 2 |
| 212337_at | TUG1 | taurine upregulated 1 (non-protein coding) |
| 211386_at | MGC12488 | hypothetical protein mgc12488 |
| 209272_at | NAB1 | ngfi-a binding protein 1 (egr1 binding protein 1) |
| 220939_s_at | DPP8 | dipeptidyl-peptidase 8 |
| 200759_x_at | NFE2L1 | nuclear factor (erythroid-derived 2)-like 1 |
| 208675_s_at | DDOST | dolichyl-diphosphooligosaccharide--protein glycosyltransferase |
| 204854_at | LEPREL2 | leprecan-like 2 |
| 207786_at | CYP2R1 | cytochrome p450, family 2, subfamily r, polypeptide 1 |
| 212292_at | SLC7A1 | solute carrier family 7 (cationic amino acid transporter, y+ system), member 1 |
| 217980_s_at | MRPL16 | mitochondrial ribosomal protein l16 |
| 208807_s_at | CHD3 | chromodomain helicase dna binding protein 3 |
| 210947_s_at | MSH3 | muts homolog 3 (*e. coli*) |
| 201237_at | CAPZA2 | capping protein (actin filament) muscle z-line, alpha 2 |
| 201696_at | SRSF4 | serine/arginine-rich splicing factor 4 |
| 203487_s_at | ARMC8 | armadillo repeat containing 8 |
| 210619_s_at | HYAL1 | hyaluronoglucosaminidase 1 |

TABLE D

Increasing Hair Diameter Gene Studies to Generate the Matrix; Up Genes

Dragon_Pol_R12_NR12_anova4_UP

| Affy ID | Gene Symbol | Title |
|---|---|---|
| 206585_at | MKRN3 | makorin ring finger protein 3 |
| 39318_at | TCL1A | t-cell leukemia/lymphoma 1a |
| 217275_at | TSSK2 | testis-specific serine kinase 2 |
| 212527_at | PPPDE2 | pppde peptidase domain containing 2 |
| 213312_at | C6ORF162 | chromosome 6 open reading frame 162 |
| 209856_x_at | ABI2 | abl-interactor 2 |
| 213404_s_at | RHEB | ras homolog enriched in brain |
| 207354_at | CCL16 | chemokine (c-c motif) ligand 16 |
| 215423_at | — | — |
| 208387_s_at | MMP24 | matrix metallopeptidase 24 (membrane-inserted) |
| 216036_x_at | WDTC1 | wd and tetratricopeptide repeats 1 |
| 207929_at | GRPR | gastrin-releasing peptide receptor |
| 209831_x_at | DNASE2 | deoxyribonuclease ii, lysosomal |
| 205624_at | CPA3 | carboxypeptidase a3 (mast cell) |
| 219227_at | CCNJL | cyclin j-like |
| 211226_at | GALR2 | galanin receptor 2 |
| 206890_at | IL12RB1 | interleukin 12 receptor, beta 1 |
| 220295_x_at | DEPDC1 | dep domain containing 1 |
| 208781_x_at | SNX3 | sorting nexin 3 |
| 210501_x_at | EIF3K | eukaryotic translation initiation factor 3, subunit k |
| 210948_s_at | LEF1 | lymphoid enhancer-binding factor 1 |
| 32540_at | — | — |
| 211228_s_at | RAD17 | rad17 homolog (*s. pombe*) |
| 209697_at | — | — |
| 215806_x_at | TARP | tcr gamma alternate reading frame protein /// t cell receptor gamma constant 2 |
| 210406_s_at | RAB6A | rab6a, member ras oncogene family /// rab6c, member ras oncogene family |
| 201176_s_at | ARCN1 | archain 1 |
| 202459_s_at | LPIN2 | lipin 2 |
| 209479_at | CCDC28A | coiled-coil domain containing 28a |
| 205946_at | VIPR2 | vasoactive intestinal peptide receptor 2 |

TABLE D-continued

Increasing Hair Diameter Gene Studies to Generate the Matrix; Up Genes

Dragon_Pol_R12_NR12_anova4_UP

| Affy ID | Gene Symbol | Title |
| --- | --- | --- |
| 211875_x_at | PCDHGA10 | protocadherin gamma subfamily a, 10 |
| 209211_at | KLF5 | kruppel-like factor 5 (intestinal) |
| 214901_at | ZNF8 | zinc finger protein 8 |
| 214307_at | HGD | homogentisate 1,2-dioxygenase |
| 206732_at | SLITRK3 | slit and ntrk-like family, member 3 |
| 201846_s_at | RYBP | ring1 and yy1 binding protein |
| 214699_x_at | WIPI2 | wd repeat domain, phosphoinositide interacting 2 |
| 215639_at | SH2D3C | sh2 domain containing 3c |
| 217330_at | DISC1 | disrupted in schizophrenia 1 |
| 220768_s_at | CSNK1G3 | casein kinase 1, gamma 3 |
| 217219_at | LOC26102 | hypothetical loc26102 |
| 215368_at | NEB | nebulin |
| 214556_at | SSTR4 | somatostatin receptor 4 |
| 211062_s_at | CPZ | carboxypeptidase z /// g protein-coupled receptor 78 |
| 213678_at | TMEM151B | transmembrane protein 151b |
| 202970_at | DYRK2 | dual-specificity tyrosine-(y)-phosphorylation regulated kinase 2 |
| 208292_at | BMP10 | bone morphogenetic protein 10 |
| 220953_s_at | MTMR12 | myotubularin related protein 12 |
| 205323_s_at | MTF1 | metal-regulatory transcription factor 1 |
| 207964_x_at | IFNA4 | interferon, alpha 4 |
| 208255_s_at | FKBP8 | fk506 binding protein 8, 38 kda |
| 218240_at | NKIRAS2 | nfkb inhibitor interacting ras-like 2 |
| 210067_at | AQP4 | aquaporin 4 |
| 211106_at | — | — |
| 214213_x_at | LMNA | lamin a/c |
| 206588_at | DAZL | deleted in azoospermia-like |
| 202884_s_at | PPP2R1B | protein phosphatase 2, regulatory subunit a, beta |
| 221717_at | — | — |
| 210358_x_at | GATA2 | gata binding protein 2 |
| 219931_s_at | KLHL12 | kelch-like 12 (drosophila) |
| 220102_at | FOXL2 | forkhead box 12 |
| 206443_at | RORB | rar-related orphan receptor b |
| 208560_at | KCNA10 | potassium voltage-gated channel, shaker-related subfamily, member 10 |
| 216452_at | TRPM3 | transient receptor potential cation channel, subfamily m, member 3 |
| 221630_s_at | DDX4 | dead (asp-glu-ala-asp) box polypeptide 4 |
| 202366_at | ACADS | acyl-coa dehydrogenase, c-2 to c-3 short chain |
| 206458_s_at | WNT2B | wingless-type mmtv integration site family, member 2b |
| 217052_x_at | — | — |
| 212874_at | APOE | apolipoprotein e |
| 206135_at | ST18 | suppression of tumorigenicity 18 (breast carcinoma) (zinc finger protein) |
| 222220_s_at | TSNAXIP1 | translin-associated factor x interacting protein 1 |
| 214728_x_at | SMARCA4 | swi/snf related, matrix associated, actin dependent regulator of chromatin, subfamily a, member 4 |
| 208203_x_at | KIR2DS5 | killer cell immunoglobulin-like receptor, two domains, short cytoplasmic tail, 5 |
| 205435_s_at | AAK1 | ap2 associated kinase 1 |
| 204533_at | CXCL10 | chemokine (c-x-c motif) ligand 10 |
| 211388_s_at | — | — |
| 218861_at | RNF25 | ring finger protein 25 |
| 214233_at | GGA2 | golgi-associated, gamma adaptin ear containing, arf binding protein 2 |
| 217169_at | IGHM | immunoglobulin heavy constant alpha 1 /// immunoglobulin heavy constant gamma 1 (g1m marker) /// immunoglobulin heavy constant mu |
| 214013_s_at | TBC1D1 | tbc1 (tre-2/usp6, bub2, cdc16) domain family, member 1 |
| 220389_at | CCDC81 | coiled-coil domain containing 81 |
| 202871_at | TRAF4 | tnf receptor-associated factor 4 |
| 209058_at | EDF1 | endothelial differentiation-related factor 1 |
| 214399_s_at | KRT4 | keratin 4 |
| 218865_at | MOSC1 | moco sulphurase c-terminal domain containing 1 |
| 212951_at | GPR116 | g protein-coupled receptor 116 |
| 214893_x_at | HCN2 | hyperpolarization activated cyclic nucleotide-gated potassium channel 2 |
| 222329_x_at | — | — |
| 218373_at | AKTIP | akt interacting protein |
| 204756_at | MAP2K5 | mitogen-activated protein kinase kinase 5 |
| 219315_s_at | TMEM204 | transmembrane protein 204 |

TABLE D-continued

Increasing Hair Diameter Gene Studies to Generate the Matrix; Up Genes

Dragon_Pol_R12_NR12_anova4_UP

| Affy ID | Gene Symbol | Title |
|---|---|---|
| 220285_at | FAM108B1 | family with sequence similarity 108, member b1 |
| 216150_at | — | — |
| 216990_at | GART | phosphoribosylglycinamide formyltransferase, phosphoribosylglycinamide synthetase, phosphoribosylaminoimidazole synthetase |
| 216944_s_at | ITPR1 | inositol 1,4,5-triphosphate receptor, type 1 |
| 219745_at | TMEM180 | transmembrane protein 180 |
| 206218_at | MAGEB2 | melanoma antigen family b, 2 |
| 202247_s_at | MTA1 | metastasis associated 1 |
| 215490_at | C1ORF69 | chromosome 1 open reading frame 69 |
| 215684_s_at | ASCC2 | activating signal cointegrator 1 complex subunit 2 |
| 202511_s_at | ATG5 | atg5 autophagy related 5 homolog (*s. cerevisiae*) |
| 205009_at | TFF1 | trefoil factor 1 |
| 207918_s_at | TSPY1 | testis specific protein, y-linked 1 /// testis specific protein, y-linked 3 /// testis specific protein, y-linked 4 /// testis specific protein, y-linked 8 |
| 216510_x_at | IGHM | immunoglobulin heavy constant alpha 1 /// immunoglobulin heavy constant gamma 1 (g1m marker) /// immunoglobulin heavy constant mu /// immunoglobulin heavy variable 3-23 /// immunoglobulin heavy variable 4-31 |
| 219813_at | LATS1 | lats, large tumor suppressor, homolog 1 (*drosophila*) |
| 202260_s_at | STXBP1 | syntaxin binding protein 1 |
| 207027_at | HGFAC | hgf activator |
| 215471_s_at | MAP7 | microtubule-associated protein 7 |
| 204527_at | MYO5A | myosin va (heavy chain 12, myoxin) |
| 218814_s_at | TMEM206 | transmembrane protein 206 |
| 216073_at | ANKRD34C | ankyrin repeat domain 34c |
| 217786_at | PRMT5 | protein arginine methyltransferase 5 |
| 221149_at | GPR77 | g protein-coupled receptor 77 |
| 209373_at | MALL | mal, t-cell differentiation protein-like |
| 215167_at | MED14 | mediator complex subunit 14 |
| 202874_s_at | ATP6V1C1 | atpase, h+ transporting, lysosomal 42 kda, v1 subunit c1 |
| 207581_s_at | MAGEB4 | melanoma antigen family b, 4 |
| 210517_s_at | AKAP12 | a kinase (prka) anchor protein 12 |
| 216213_at | NEK1 | nima (never in mitosis gene a)-related kinase 1 |
| 218673_s_at | ATG7 | atg7 autophagy related 7 homolog (*s. cerevisiae*) |
| 215873_x_at | ABCC10 | atp-binding cassette, sub-family c (cftr/mrp), member 10 |
| 217637_at | — | — |
| 217117_x_at | MUC3A | mucin 3a, cell surface associated |
| 211393_at | PATZ1 | poz (btb) and at hook containing zinc finger 1 |
| 208429_x_at | HNF4A | hepatocyte nuclear factor 4, alpha |
| 209520_s_at | NCBP1 | nuclear cap binding protein subunit 1, 80 kda |
| 219434_at | TREM1 | triggering receptor expressed on myeloid cells 1 |
| 211600_at | PTPRO | protein tyrosine phosphatase, receptor type, o |
| 206851_at | RNASE3 | ribonuclease, rnase a family, 3 |
| 216852_x_at | IGL@ | immunoglobulin lambda locus |
| 220256_s_at | OXCT2 | 3-oxoacid coa transferase 2 |
| 206947_at | B3GALT5 | udp-gal:betaglcnac beta 1,3-galactosyltransferase, polypeptide 5 |
| 216556_x_at | — | — |
| 204867_at | GCHFR | gtp cyclohydrolase i feedback regulator |
| 212889_x_at | GADD45GIP1 | growth arrest and dna-damage-inducible, gamma interacting protein 1 |
| 211248_s_at | CHRD | chordin |
| 213144_at | GOSR2 | golgi snap receptor complex member 2 |
| 209728_at | HLA-DRB4 | major histocompatibility complex, class ii, dr beta 4 /// hla class ii histocompatibility antigen, dr beta 4 chain-like |
| 212193_s_at | LARP1 | la ribonucleoprotein domain family, member 1 |
| 220048_at | EDAR | ectodysplasin a receptor |
| 209139_s_at | PRKRA | protein kinase, interferon-inducible double stranded rna dependent activator |
| 211300_s_at | TP53 | tumor protein p53 |
| 209937_at | TM4SF4 | transmembrane 4 l six family member 4 |
| 212032_s_at | PTOV1 | prostate tumor overexpressed 1 |
| 210919_at | PHLPP1 | ph domain and leucine rich repeat protein phosphatase 1 |
| 211469_s_at | CXCR6 | chemokine (c-x-c motif) receptor 6 |
| 220452_x_at | — | — |
| 221197_s_at | CHAT | choline o-acetyltransferase |
| 211026_s_at | MGLL | monoglyceride lipase |

TABLE D-continued

Increasing Hair Diameter Gene Studies to Generate the Matrix; Up Genes

Dragon_Pol_R12_NR12_anova4_UP

| Affy ID | Gene Symbol | Title |
| --- | --- | --- |
| 218245_at | TSKU | tsukushi small leucine rich proteoglycan homolog (*xenopus laevis*) |
| 201435_s_at | EIF4E | eukaryotic translation initiation factor 4e |
| 203738_at | C5ORF22 | chromosome 5 open reading frame 22 |
| 220457_at | SAMD4B | sterile alpha motif domain containing 4b |
| 221809_at | RANBP10 | ran binding protein 10 |
| 205348_s_at | DYNC1I1 | dynein, cytoplasmic 1, intermediate chain 1 |
| 218929_at | CDKN2AIP | cdkn2a interacting protein |
| 221620_s_at | APOO | apolipoprotein o |
| 204223_at | PRELP | proline/arginine-rich end leucine-rich repeat protein |
| 211232_x_at | GLP1R | glucagon-like peptide 1 receptor |
| 215755_at | — | — |
| 201767_s_at | ELAC2 | elac homolog 2 (*e. coli*) |
| 220886_at | GABRQ | gamma-aminobutyric acid (gaba) receptor, theta |
| 210923_at | SLC1A7 | solute carrier family 1 (glutamate transporter), member 7 |
| 221164_x_at | CHST5 | carbohydrate (n-acetylglucosamine 6-o) sulfotransferase 5 |
| 218345_at | TMEM176A | transmembrane protein 176a |
| 215396_at | GPR98 | g protein-coupled receptor 98 |
| 206217_at | EDA | ectodysplasin a |
| 219046_s_at | PKNOX2 | pbx/knotted 1 homeobox 2 |
| 205230_at | RPH3A | rabphilin 3a homolog (mouse) |
| 204744_s_at | IARS | isoleucyl-trna synthetase |
| 205682_x_at | APOM | apolipoprotein m |
| 207123_s_at | MATN4 | matrilin 4 |
| 219896_at | CALY | calcyon neuron-specific vesicular protein |
| 217404_s_at | COL2A1 | collagen, type ii, alpha 1 |
| 207426_s_at | TNFSF4 | tumor necrosis factor (ligand) superfamily, member 4 |
| 215727_x_at | — | — |
| 204747_at | IFIT3 | interferon-induced protein with tetratricopeptide repeats 3 |
| 206708_at | FOXN2 | forkhead box n2 |
| 212894_at | SUPV3L1 | suppressor of var1, 3-like 1 (*s. cerevisiae*) |
| 221239_s_at | FCRL2 | fc receptor-like 2 |
| 206726_at | HPGDS | hematopoietic prostaglandin d synthase |
| 207209_at | CETN1 | centrin, ef-hand protein, 1 |
| 218089_at | C20ORF4 | chromosome 20 open reading frame 4 |
| 221720_s_at | — | — |
| 208209_s_at | C4BPB | complement component 4 binding protein, beta |
| 203826_s_at | PITPNM1 | phosphatidylinositol transfer protein, membrane-associated 1 |
| 216301_at | LOC100287927 | hypothetical loc100287927 |
| 213228_at | PDE8B | phosphodiesterase 8b |
| 222208_s_at | POLR2J4 | polymerase (rna) ii (dna directed) polypeptide j4, pseudogene |
| 216387_x_at | — | — |
| 46270_at | UBAP1 | ubiquitin associated protein 1 |
| 221792_s_at | RAB6B | rab6b, member ras oncogene family |
| 201733_at | CLCN3 | chloride channel 3 |
| 211015_s_at | HSPA4 | heat shock 70 kda protein 4 |
| 212902_at | SEC24A | sec24 family, member a (*s. cerevisiae*) |
| 201387_s_at | UCHL1 | ubiquitin carboxyl-terminal esterase 11 (ubiquitin thiolesterase) |
| 220707_s_at | FOXRED2 | fad-dependent oxidoreductase domain containing 2 |
| 218872_at | TESC | Tescalcin |
| 222192_s_at | C2ORF43 | chromosome 2 open reading frame 43 |
| 206776_x_at | ACRV1 | acrosomal vesicle protein 1 |

TABLE E

Increasing Hair Cycle Activation Gene Studies to Generate the Matrix; Down Genes

| 3D2D_down Affy ID | Gene Symbol | Title |
| --- | --- | --- |
| 216109_at | MED13L | mediator complex subunit 13-like |
| 213188_s_at | MINA | myc induced nuclear antigen |
| 204314_s_at | CREB1 | camp responsive element binding protein 1 |
| 218185_s_at | ARMC1 | armadillo repeat containing 1 |
| 204349_at | MED7 | mediator complex subunit 7 |

TABLE E-continued

Increasing Hair Cycle Activation Gene Studies to Generate the Matrix; Down Genes

| 3D2D_down Affy ID | Gene Symbol | Title |
|---|---|---|
| 215067_x_at | PRDX2 | peroxiredoxin 2 |
| 221618_s_at | TAF9B | taf9b rna polymerase ii, tata box binding protein (tbp)-associated factor, 31 kda |
| 212913_at | MSH5 | chromosome 6 open reading frame 26 /// muts homolog 5 (*e. coli*) |
| 210701_at | CFDP1 | craniofacial development protein 1 |
| 212216_at | PREPL | prolyl endopeptidase-like |
| 215252_at | — | |
| 214707_x_at | ALMS1 | alstrom syndrome 1 |
| 203910_at | ARHGAP29 | rho gtpase activating protein 29 |
| 213365_at | ERI2 | eri1 exoribonuclease family member 2 |
| 203105_s_at | DNM1L | dynamin 1-like |
| 215383_x_at | SPG21 | spastic paraplegia 21 (autosomal recessive, mast syndrome) |
| 203987_at | FZD6 | frizzled homolog 6 (*drosophila*) |
| 205893_at | NLGN1 | neuroligin 1 |
| 203553_s_at | MAP4K5 | mitogen-activated protein kinase kinase kinase kinase 5 |
| 221007_s_at | FIP1L1 | fip1 like 1 (*s. cerevisiae*) |
| 213872_at | C6ORF62 | chromosome 6 open reading frame 62 |
| 217208_s_at | DLG1 | discs, large homolog 1 (*drosophila*) |
| 213189_at | MINA | myc induced nuclear antigen |
| 215986_at | — | — |
| 214715_x_at | ZNF160 | zinc finger protein 160 |
| 209738_x_at | PSG6 | pregnancy specific beta-1-glycoprotein 6 |
| 201661_s_at | ACSL3 | acyl-coa synthetase long-chain family member 3 |
| 221046_s_at | GTPBP8 | gtp-binding protein 8 (putative) |
| 201456_s_at | BUB3 | budding uninhibited by benzimidazoles 3 homolog (yeast) |
| 202760_s_at | AKAP2 | a kinase (prka) anchor protein 2 /// palm2-akap2 readthrough |
| 214605_x_at | GPR1 | g protein-coupled receptor 1 |
| 209594_x_at | PSG9 | pregnancy specific beta-1-glycoprotein 9 |
| 209780_at | PHTF2 | putative homeodomain transcription factor 2 |
| 210970_s_at | IBTK | inhibitor of bruton agammaglobulinemia tyrosine kinase |
| 203593_at | CD2AP | cd2-associated protein |
| 202468_s_at | CTNNAL1 | catenin (cadherin-associated protein), alpha-like 1 |
| 204241_at | ACOX3 | acyl-coa oxidase 3, pristanoyl |
| 220352_x_at | FLJ42627 | hypothetical loc645644 |
| 201020_at | YWHAH | tyrosine 3-monooxygenase/tryptophan 5-monooxygenase activation protein, eta polypeptide |
| 201339_s_at | SCP2 | sterol carrier protein 2 |
| 211275_s_at | GYG1 | glycogenin 1 |
| 200729_s_at | ACTR2 | arp2 actin-related protein 2 homolog (yeast) |
| 206144_at | MAGI1 | membrane associated guanylate kinase, ww and pdz domain containing 1 |
| 214594_x_at | ATP8B1 | atpase, aminophospholipid transporter, class i, type 8b, member 1 |
| 222162_s_at | ADAMTS1 | adam metallopeptidase with thrombospondin type 1 motif, 1 |
| 209817_at | PPP3CB | protein phosphatase 3, catalytic subunit, beta isozyme |
| 203253_s_at | PPIP5K2 | diphosphoinositol pentakisphosphate kinase 2 |
| 212530_at | NEK7 | nima (never in mitosis gene a)-related kinase 7 |
| 210195_s_at | PSG1 | pregnancy specific beta-1-glycoprotein 1 |
| 202674_s_at | LMO7 | lim domain 7 |
| 210286_s_at | SLC4A7 | solute carrier family 4, sodium bicarbonate cotransporter, member 7 |
| 213005_s_at | KANK1 | kn motif and ankyrin repeat domains 1 |
| 60794_f_at | ZNF814 | zinc finger protein 814 |
| 204256_at | ELOVL6 | elovl family member 6, elongation of long chain fatty acids (fen1/elo2, sur4/elo3-like, yeast) |
| 204658_at | TRA2A | transformer 2 alpha homolog (*drosophila*) |
| 209849_s_at | RAD51C | rad51 homolog c (*s. cerevisiae*) |
| 203840_at | BLZF1 | basic leucine zipper nuclear factor 1 |
| 208920_at | SRI | sorcin |
| 215694_at | SPATA5L1 | spermatogenesis associated 5-like 1 |
| 219953_s_at | C11ORF17 | chromosome 11 open reading frame 17 |
| 219105_x_at | ORC6 | origin recognition complex, subunit 6 |
| 201308_s_at | 11-SEP | septin 11 |
| 202816_s_at | SS18 | synovial sarcoma translocation, chromosome 18 |
| 202609_at | EPS8 | epidermal growth factor receptor pathway substrate 8 |
| 205194_at | PSPH | phosphoserine phosphatase |
| 213447_at | IPW | imprinted in prader-willi syndrome (non-protein coding) |
| 202720_at | TES | testis derived transcript (3 lim domains) |
| 218365_s_at | DARS2 | aspartyl-trna synthetase 2, mitochondrial |
| 217717_s_at | YWHAB | tyrosine 3-monooxygenase/tryptophan 5-monooxygenase activation protein, beta polypeptide |
| 202169_s_at | AASDHPPT | aminoadipate-semialdehyde dehydrogenase-phosphopantetheinyl transferase |

TABLE E-continued

Increasing Hair Cycle Activation Gene Studies to Generate the Matrix; Down Genes

| 3D2D_down Affy ID | Gene Symbol | Title |
|---|---|---|
| 201487_at | CTSC | cathepsin c |
| 212928_at | TSPYL4 | tspy-like 4 |
| 200728_at | ACTR2 | arp2 actin-related protein 2 homolog (yeast) |
| 218598_at | RINT1 | rad50 interactor 1 |
| 217941_s_at | ERBB2IP | erbb2 interacting protein |
| 217523_at | CD44 | cd44 molecule (indian blood group) |
| 209288_s_at | CDC42EP3 | cdc42 effector protein (rho gtpase binding) 3 |
| 209884_s_at | SLC4A7 | solute carrier family 4, sodium bicarbonate cotransporter, member 7 |
| 206308_at | TRDMT1 | trna aspartic acid methyltransferase 1 |
| 204711_at | KIAA0753 | kiaa0753 |
| 208753_s_at | NAP1L1 | nucleosome assembly protein 1-like 1 |
| 214789_x_at | SRSF8 | serine/arginine-rich splicing factor 8 |
| 213485_s_at | ABCC10 | atp-binding cassette, sub-family c (cftr/mrp), member 10 |
| 203595_s_at | IFIT5 | interferon-induced protein with tetratricopeptide repeats 5 |
| 207489_at | RPS2P45 | ribosomal protein s2 pseudogene 45 |
| 204221_x_at | GLIPR1 | gli pathogenesis-related 1 |
| 55081_at | MICALL1 | mical-like 1 |
| 219949_at | LRRC2 | leucine rich repeat containing 2 |
| 213459_at | RPL37A | ribosomal protein 137a |
| 203078_at | CUL2 | cullin 2 |
| 206108_s_at | SRSF6 | serine/arginine-rich splicing factor 6 |
| 218269_at | DROSHA | drosha, ribonuclease type iii |
| 208137_x_at | ZNF611 | zinc finger protein 611 |
| 57739_at | DND1 | dead end homolog 1 (zebrafish) |
| 203216_s_at | MYO6 | myosin vi |
| 204396_s_at | GRK5 | g protein-coupled receptor kinase 5 |
| 219512_at | DSN1 | dsn1, mind kinetochore complex component, homolog (s. cerevisiae) |
| 203830_at | C17ORF75 | chromosome 17 open reading frame 75 |
| 205126_at | VRK2 | vaccinia related kinase 2 |
| 203820_s_at | IGF2BP3 | insulin-like growth factor 2 mrna binding protein 3 |
| 207098_s_at | MFN1 | mitofusin 1 |
| 215359_x_at | ZNF44 | zinc finger protein 44 |
| 205218_at | POLR3F | polymerase (rna) iii (dna directed) polypeptide f, 39 kda |
| 203607_at | INPP5F | inositol polyphosphate-5-phosphatase f |
| 218470_at | YARS2 | tyrosyl-trna synthetase 2, mitochondrial |
| 208975_s_at | KPNB1 | karyopherin (importin) beta 1 |
| 201671_x_at | USP14 | ubiquitin specific peptidase 14 (trna-guanine transglycosylase) |
| 217946_s_at | SAE1 | sumo1 activating enzyme subunit 1 |
| 215821_x_at | PSG3 | pregnancy specific beta-1-glycoprotein 3 |
| 213959_s_at | RPGRIP1L | rpgrip 1-like |
| 214924_s_at | TRAK1 | trafficking protein, kinesin binding 1 |
| 200842_s_at | EPRS | glutamyl-prolyl-trna synthetase |
| 202491_s_at | IKBKAP | inhibitor of kappa light polypeptide gene enhancer in b-cells, kinase complex-associated protein |
| 202754_at | R3HDM1 | r3h domain containing 1 |
| 218374_s_at | C12ORF4 | chromosome 12 open reading frame 4 |
| 202682_s_at | USP4 | ubiquitin specific peptidase 4 (proto-oncogene) |
| 204853_at | ORC2 | origin recognition complex, subunit 2 |
| 218297_at | FAM188A | family with sequence similarity 188, member a |
| 204313_s_at | CREB1 | camp responsive element binding protein 1 |
| 213878_at | PYROXD1 | pyridine nucleotide-disulphide oxidoreductase domain 1 |
| 215123_at | NPIPL3 | nuclear pore complex interacting protein-like 3 |
| 217679_x_at | — | — |
| 214785_at | VPS13A | vacuolar protein sorting 13 homolog a (s. cerevisiae) |
| 211091_s_at | NF2 | neurofibromin 2 (merlin) |
| 204003_s_at | NUPL2 | nucleoporin like 2 |
| 221509_at | DENR | density-regulated protein |
| 215374_at | PAPOLA | poly(a) polymerase alpha |
| 211379_x_at | B3GALNT1 | beta-1,3-n-acetylgalactosaminyltransferase 1 (globoside blood group) |
| 208134_x_at | PSG2 | pregnancy specific beta-1-glycoprotein 2 |
| 201872_s_at | ABCE1 | atp-binding cassette, sub-family e (oabp), member 1 |
| 203810_at | DNAJB4 | dnaj (hsp40) homolog, subfamily b, member 4 |
| 204235_s_at | GULP1 | gulp, engulfment adaptor ptb domain containing 1 |
| 205339_at | STIL | scl/tal1 interrupting locus |
| 212673_at | METAP1 | methionyl aminopeptidase 1 |
| 200843_s_at | EPRS | glutamyl-prolyl-trna synthetase |
| 213528_at | C1ORF156 | chromosome 1 open reading frame 156 |
| 218252_at | CKAP2 | cytoskeleton associated protein 2 |
| 214473_x_at | PMS2P3 | postmeiotic segregation increased 2 pseudogene 3 |
| 216525_x_at | PMS2P3 | postmeiotic segregation increased 2 pseudogene 3 |
| 218244_at | NOL8 | nucleolar protein 8 |

TABLE E-continued

Increasing Hair Cycle Activation Gene Studies to Generate the Matrix; Down Genes

| 3D2D_down Affy ID | Gene Symbol | Title |
|---|---|---|
| 205401_at | AGPS | alkylglycerone phosphate synthase |
| 202915_s_at | FAM20B | family with sequence similarity 20, member b |
| 201139_at | SSB | sjogren syndrome antigen b (autoantigen la) |
| 221025_x_at | PUS7L | pseudouridylate synthase 7 homolog (*s. cerevisiae*)-like |
| 209286_at | CDC42EP3 | cdc42 effector protein (rho gtpase binding) 3 |
| 201668_x_at | MARCKS | myristoylated alanine-rich protein kinase c substrate |
| 204048_s_at | PHACTR2 | phosphatase and actin regulator 2 |
| 204516_x_at | ATXN7 | ataxin 7 |
| 207733_x_at | PSG9 | pregnancy specific beta-1-glycoprotein 9 |
| 213229_at | DICER1 | dicer 1, ribonuclease type iii |
| 218511_s_at | PNPO | pyridoxamine 5'-phosphate oxidase |
| 212215_at | PREPL | prolyl endopeptidase-like |
| 203486_s_at | ARMC8 | armadillo repeat containing 8 |
| 212756_s_at | UBR2 | ubiquitin protein ligase e3 component n-recognin 2 |
| 221079_s_at | METTL2A | methyltransferase like 2a /// methyltransferase like 2b |
| 213605_s_at | — | — |
| 206169_x_at | ZC3H7B | zinc finger ccch-type containing 7b |
| 219353_at | NHLRC2 | nhl repeat containing 2 |
| 218397_at | FANCL | fanconi anemia, complementation group 1 |
| 204842_x_at | PRKAR2A | protein kinase, camp-dependent, regulatory, type ii, alpha |
| 209421_at | MSH2 | muts homolog 2, colon cancer, nonpolyposis type 1 (*e. coli*) |
| 219981_x_at | ZNF587 | zinc finger protein 587 |
| 213427_at | RPP40 | ribonuclease p/mrp 40 kda subunit |
| 203819_s_at | IGF2BP3 | insulin-like growth factor 2 mrna binding protein 3 |
| 203301_s_at | DMTF1 | cyclin d binding myb-like transcription factor 1 |
| 219279_at | DOCK10 | dedicator of cytokinesis 10 |
| 218003_s_at | FKBP3 | fk506 binding protein 3, 25 kda |
| 219156_at | SYNJ2BP | synaptojanin 2 binding protein |
| 59705_at | SCLY | selenocysteine lyase |
| 203989_x_at | F2R | coagulation factor ii (thrombin) receptor |
| 212956_at | TBC1D9 | tbc1 domain family, member 9 (with gram domain) |
| 209974_s_at | BUB3 | budding uninhibited by benzimidazoles 3 homolog (yeast) |
| 204634_at | NEK4 | nima (never in mitosis gene a)-related kinase 4 |
| 220643_s_at | FAIM | fas apoptotic inhibitory molecule |
| 215190_at | EIF3M | eukaryotic translation initiation factor 3, subunit m |
| 215281_x_at | POGZ | pogo transposable element with znf domain |
| 213289_at | APOOL | apolipoprotein o-like |
| 211800_s_at | USP4 | ubiquitin specific peptidase 4 (proto-oncogene) |
| 46947_at | GNL3L | guanine nucleotide binding protein-like 3 (nucleolar)-like |
| 214544_s_at | SNAP23 | synaptosomal-associated protein, 23 kda |
| 57082_at | LDLRAP1 | low density lipoprotein receptor adaptor protein 1 |
| 222145_at | — | — |
| 219231_at | TGS1 | trimethylguanosine synthase 1 |
| 201823_s_at | RNF14 | ring finger protein 14 |
| 203533_s_at | CUL5 | cullin 5 |
| 213372_at | PAQR3 | progestin and adipoq receptor family member iii |
| 215604_x_at | — | — |
| 212379_at | GART | phosphoribosylglycinamide formyltransferase, phosphoribosylglycinamide synthetase, phosphoribosylaminoimidazole synthetase |
| 215599_at | GUSBP3 | glucuronidase, beta pseudogene 3 |
| 207711_at | C20ORF117 | chromosome 20 open reading frame 117 |
| 215206_at | — | — |
| 215175_at | PCNX | pecanex homolog (*drosophila*) |
| 217482_at | — | — |
| 219130_at | CCDC76 | coiled-coil domain containing 76 |
| 201129_at | SRSF7 | serine/arginine-rich splicing factor 7 |
| 210026_s_at | CARD10 | caspase recruitment domain family, member 10 |
| 215529_x_at | DIP2A | dip2 disco-interacting protein 2 homolog a (*drosophila*) |
| 219843_at | IPP | intracisternal a particle-promoted polypeptide |
| 205584_at | ALG13 | asparagine-linked glycosylation 13 homolog (*s. cerevisiae*) |
| 202091_at | ARL2BP | adp-ribosylation factor-like 2 binding protein |

TABLE F

Increasing Hair Cycle Activation Gene Studies to Generate the Matrix; Up Gene

| 3D2D_up Affy ID | Gene Symbol | Title |
|---|---|---|
| 217388_s_at | KYNU | kynureninase (l-kynurenine hydrolase) |
| 204273_at | EDNRB | endothelin receptor type b |

TABLE F-continued

Increasing Hair Cycle Activation Gene Studies to Generate the Matrix; Up Gene

| 3D2D_up Affy ID | Gene Symbol | Title |
|---|---|---|
| 221541_at | CRISPLD2 | cysteine-rich secretory protein lccl domain containing 2 |
| 210663_s_at | KYNU | kynureninase (l-kynurenine hydrolase) |
| 202388_at | RGS2 | regulator of g-protein signaling 2, 24 kda |
| 204014_at | DUSP4 | dual specificity phosphatase 4 |
| 206025_s_at | TNFAIP6 | tumor necrosis factor, alpha-induced protein 6 |
| 217739_s_at | NAMPT | nicotinamide phosphoribosyltransferase |
| 206026_s_at | TNFAIP6 | tumor necrosis factor, alpha-induced protein 6 |
| 210592_s_at | SAT1 | spermidine/spermine n1-acetyltransferase 1 |
| 201261_x_at | BGN | biglycan |
| 204271_s_at | EDNRB | endothelin receptor type b |
| 203455_s_at | SAT1 | spermidine/spermine n1-acetyltransferase 1 |
| 213905_x_at | BGN | biglycan |
| 203708_at | PDE4B | phosphodiesterase 4b, camp-specific |
| 204464_s_at | EDNRA | endothelin receptor type a |
| 204790_at | SMAD7 | smad family member 7 |
| 212658_at | LHFPL2 | lipoma hmgic fusion partner-like 2 |
| 202123_s_at | ABL1 | c-abl oncogene 1, non-receptor tyrosine kinase |
| 219427_at | FAT4 | fat tumor suppressor homolog 4 (*drosophila*) |
| 202828_s_at | MMP14 | matrix metallopeptidase 14 (membrane-inserted) |
| 203137_at | WTAP | wilms tumor 1 associated protein |
| 203710_at | ITPR1 | inositol 1,4,5-triphosphate receptor, type 1 |
| 201117_s_at | CPE | carboxypeptidase e |
| 202887_s_at | DDIT4 | dna-damage-inducible transcript 4 |
| 202464_s_at | PFKFB3 | 6-phosphofructo-2-kinase/fructose-2,6-biphosphatase 3 |
| 213988_s_at | SAT1 | spermidine/spermine n1-acetyltransferase 1 |
| 201416_at | SOX4 | sry (sex determining region y)-box 4 |
| 210367_s_at | PTGES | prostaglandin e synthase |
| 209732_at | CLEC2B | c-type lectin domain family 2, member b |
| 206796_at | WISP1 | wnt1 inducible signaling pathway protein 1 |
| 201417_at | SOX4 | sry (sex determining region y)-box 4 |
| 213943_at | TWIST1 | twist homolog 1 (*drosophila*) |
| 205289_at | BMP2 | bone morphogenetic protein 2 |
| 202363_at | SPOCK1 | sparc/osteonectin, cwcv and kazal-like domains proteoglycan (testican) 1 |
| 221602_s_at | FAIM3 | fas apoptotic inhibitory molecule 3 |
| 218177_at | CHMP1B | chromatin modifying protein 1b |
| 37005_at | NBL1 | neuroblastoma, suppression of tumorigenicity 1 |
| 201621_at | NBL1 | neuroblastoma, suppression of tumorigenicity 1 |
| 203973_s_at | CEBPD | ccaat/enhancer binding protein (c/ebp), delta |
| 35617_at | MAPK7 | mitogen-activated protein kinase 7 |
| 203835_at | LRRC32 | leucine rich repeat containing 32 |
| 215223_s_at | SOD2 | superoxide dismutase 2, mitochondrial |
| 215506_s_at | DIRAS3 | diras family, gtp-binding ras-like 3 |
| 203045_at | NINJ1 | ninjurin 1 |
| 213113_s_at | SLC43A3 | solute carrier family 43, member 3 |
| 217844_at | CTDSP1 | ctd (carboxy-terminal domain, rna polymerase ii, polypeptide a) small phosphatase 1 |
| 202827_s_at | MMP14 | matrix metallopeptidase 14 (membrane-inserted) |
| 204975_at | EMP2 | epithelial membrane protein 2 |
| 207992_s_at | AMPD3 | adenosine monophosphate deaminase 3 |
| 201035_s_at | HADH | hydroxyacyl-coa dehydrogenase |
| 203085_s_at | TGFB1 | transforming growth factor, beta 1 |
| 203752_s_at | JUND | jun d proto-oncogene |
| 209184_s_at | IRS2 | insulin receptor substrate 2 |
| 212641_at | HIVEP2 | human immunodeficiency virus type i enhancer binding protein 2 |
| 202732_at | PKIG | protein kinase (camp-dependent, catalytic) inhibitor gamma |
| 212642_s_at | HIVEP2 | human immunodeficiency virus type i enhancer binding protein 2 |
| 203417_at | MFAP2 | microfibrillar-associated protein 2 |
| 212803_at | NAB2 | ngfi-a binding protein 2 (egr1 binding protein 2) |
| 213125_at | OLFML2B | olfactomedin-like 2b |
| 36554_at | ASMTL | acetylserotonin o-methyltransferase-like |
| 220757_s_at | UBXN6 | ubx domain protein 6 |
| 211475_s_at | BAG1 | bcl2-associated athanogene |
| 211934_x_at | GANAB | glucosidase, alpha; neutral ab |
| 205548_s_at | BTG3 | btg family, member 3 |
| 204735_at | PDE4A | phosphodiesterase 4a, camp-specific |
| 212091_s_at | COL6A1 | collagen, type vi, alpha 1 |
| 212501_at | CEBPB | ccaat/enhancer binding protein (c/ebp), beta |
| 209017_s_at | LONP1 | lon peptidase 1, mitochondrial |
| 202812_at | GAA | glucosidase, alpha; acid |
| 209356_x_at | EFEMP2 | egf-containing fibulin-like extracellular matrix protein 2 |
| 202734_at | TRIP10 | thyroid hormone receptor interactor 10 |

TABLE F-continued

Increasing Hair Cycle Activation Gene Studies to Generate the Matrix; Up Gene

| 3D2D_up Affy ID | Gene Symbol | Title |
|---|---|---|
| 210788_s_at | DHRS7 | dehydrogenase/reductase (sdr family) member 7 |
| 202185_at | PLOD3 | procollagen-lysine, 2-oxoglutarate 5-dioxygenase 3 |
| 201116_s_at | CPE | carboxypeptidase e |
| 212657_s_at | IL1RN | interleukin 1 receptor antagonist |
| 219213_at | JAM2 | junctional adhesion molecule 2 |
| 202219_at | SLC6A8 | solute carrier family 6 (neurotransmitter transporter, creatine), member 8 |
| 204760_s_at | THRA | nuclear receptor subfamily 1, group d, member 1 /// thyroid hormone receptor, alpha (erythroblastic leukemia viral (v-erb-a) oncogene homolog, avian) |
| 217738_at | NAMPT | nicotinamide phosphoribosyltransferase |
| 209960_at | HGF | hepatocyte growth factor (hepapoietin a; scatter factor) |
| 219062_s_at | ZCCHC2 | zinc finger, cchc domain containing 2 |
| 204385_at | KYNU | kynureninase (l-kynurenine hydrolase) |
| 220975_s_at | C1QTNF1 | c1q and tumor necrosis factor related protein 1 |
| 203574_at | NFIL3 | nuclear factor, interleukin 3 regulated |
| 202637_s_at | ICAM1 | intercellular adhesion molecule 1 |
| 210285_x_at | WTAP | wilms tumor 1 associated protein |
| 220076_at | ANKH | ankylosis, progressive homolog (mouse) |
| 201430_s_at | DPYSL3 | dihydropyrimidinase-like 3 |
| 213921_at | SST | somatostatin |
| 218178_s_at | CHMP1B | chromatin modifying protein 1b |
| 221864_at | ORAI3 | orai calcium release-activated calcium modulator 3 |
| 52255_s_at | COL5A3 | collagen, type v, alpha 3 |
| 218031_s_at | FOXN3 | forkhead box n3 |
| 200904_at | HLA-E | major histocompatibility complex, class i, e |
| 200866_s_at | PSAP | prosaposin |
| 208415_x_at | ING1 | inhibitor of growth family, member 1 |
| 218675_at | SLC22A17 | solute carrier family 22, member 17 |
| 216841_s_at | SOD2 | superoxide dismutase 2, mitochondrial |
| 209652_s_at | PGF | placental growth factor |
| 201751_at | JOSD1 | josephin domain containing 1 |
| 209102_s_at | HBP1 | hmg-box transcription factor 1 |
| 208991_at | STAT3 | signal transducer and activator of transcription 3 (acute-phase response factor) |
| 200654_at | P4HB | prolyl 4-hydroxylase, beta polypeptide |
| 210022_at | PCGF1 | polycomb group ring finger 1 |
| 202140_s_at | CLK3 | cdc-like kinase 3 |
| 203239_at | CNOT3 | ccr4-not transcription complex, subunit 3 |
| 210785_s_at | C1ORF38 | chromosome 1 open reading frame 38 |
| 201412_at | LRP10 | low density lipoprotein receptor-related protein 10 |
| 201178_at | FBXO7 | f-box protein 7 |
| 212110_at | SLC39A14 | solute carrier family 39 (zinc transporter), member 14 |
| 218634_at | PHLDA3 | pleckstrin homology-like domain, family a, member 3 |
| 200743_s_at | TPP1 | tripeptidyl peptidase i |
| 200649_at | NUCB1 | nucleobindin 1 |
| 61734_at | RCN3 | reticulocalbin 3, ef-hand calcium binding domain |
| 219020_at | HS1BP3 | hcls1 binding protein 3 |
| 208928_at | POR | p450 (cytochrome) oxidoreductase |
| 203313_s_at | TGIF1 | tgfb-induced factor homeobox 1 |
| 200794_x_at | DAZAP2 | daz associated protein 2 |
| 206569_at | IL24 | interleukin 24 |
| 209959_at | NR4A3 | nuclear receptor subfamily 4, group a, member 3 |
| 206376_at | SLC6A15 | solute carrier family 6 (neutral amino acid transporter), member 15 |
| 218541_s_at | C8ORF4 | chromosome 8 open reading frame 4 |
| 207815_at | PF4V1 | platelet factor 4 variant 1 |
| 204243_at | RLF | rearranged 1-myc fusion |
| 205686_s_at | CD86 | cd86 molecule |
| 204463_s_at | EDNRA | endothelin receptor type a |
| 203853_s_at | GAB2 | grb2-associated binding protein 2 |
| 31637_s_at | THRA | nuclear receptor subfamily 1, group d, member 1 /// thyroid hormone receptor, alpha (erythroblastic leukemia viral (v-erb-a) oncogene homolog, avian) |
| 201926_s_at | CD55 | cd55 molecule, decay accelerating factor for complement (cromer blood group) |
| 213338_at | TMEM158 | transmembrane protein 158 (gene/pseudogene) |
| 206932_at | CH25H | cholesterol 25-hydroxylase |
| 213169_at | SEMA5A | sema domain, seven thrombospondin repeats (type 1 and type 1-like), transmembrane domain (tm) and short cytoplasmic domain, (semaphorin) 5a |
| 200827_at | PLOD1 | procollagen-lysine 1, 2-oxoglutarate 5-dioxygenase 1 |
| 218631_at | AVPI1 | arginine vasopressin-induced 1 |
| 207196_s_at | TNIP1 | tnfaip3 interacting protein 1 |
| 219155_at | PITPNC1 | phosphatidylinositol transfer protein, cytoplasmic 1 |

TABLE F-continued

Increasing Hair Cycle Activation Gene Studies to Generate the Matrix; Up Gene

| 3D2D_up Affy ID | Gene Symbol | Title |
|---|---|---|
| 201431_s_at | DPYSL3 | dihydropyrimidinase-like 3 |
| 213792_s_at | INSR | insulin receptor |
| 214247_s_at | DKK3 | dickkopf homolog 3 (xenopus laevis) |
| 205052_at | AUH | au rna binding protein/enoyl-coa hydratase |
| 215305_at | PDGFRA | platelet-derived growth factor receptor, alpha polypeptide |
| 203434_s_at | MME | membrane metallo-endopeptidase |
| 212360_at | AMPD2 | adenosine monophosphate deaminase 2 |
| 203827_at | WIPI1 | wd repeat domain, phosphoinositide interacting 1 |
| 209394_at | ASMTL | acetylserotonin o-methyltransferase-like |
| 207543_s_at | P4HA1 | prolyl 4-hydroxylase, alpha polypeptide i |
| 213168_at | SP3 | sp3 transcription factor |
| 41047_at | C9ORF16 | chromosome 9 open reading frame 16 |
| 215836_s_at | PCDHGA1 | protocadherin gamma subfamily a, 1 /// protocadherin gamma subfamily a, 10 /// protocadherin gamma subfamily a, 11 /// protocadherin gamma subfamily a, 12 /// protocadherin gamma subfamily a, 2 /// protocadherin gamma subfamily a, 3 /// protocadherin gamma subfamily a, 4 /// protocadherin gamma subfamily a, 5 /// protocadherin gamma subfamily a, 6 /// protocadherin gamma subfamily a, 7 /// protocadherin gamma subfamily a, 8 /// protocadherin gamma subfamily a, 9 /// protocadherin gamma subfamily b, 1 /// protocadherin gamma subfamily b, 2 /// protocadherin gamma subfamily b, 3 /// protocadherin gamma subfamily b, 4 /// protocadherin gamma subfamily b, 5 /// protocadherin gamma subfamily b, 6 /// protocadherin gamma subfamily b, 7 /// protocadherin gamma subfamily c, 3 /// protocadherin gamma subfamily c, 4 /// protocadherin gamma subfamily c, 5 |
| 211799_x_at | HLA-C | major histocompatibility complex, class i, c |
| 205574_x_at | BMP1 | bone morphogenetic protein 1 |
| 212663_at | FKBP15 | fk506 binding protein 15, 133 kda |
| 203000_at | STMN2 | stathmin-like 2 |
| 218810_at | ZC3H12A | zinc finger ccch-type containing 12a |
| 205205_at | RELB | v-rel reticuloendotheliosis viral oncogene homolog b |
| 31837_at | LMF2 | lipase maturation factor 2 |
| 205681_at | BCL2A1 | bcl2-related protein a1 |
| 219622_at | RAB20 | rab20, member ras oncogene family |
| 202947_s_at | GYPC | glycophorin c (gerbich blood group) |
| 205830_at | CLGN | calmegin |
| 218723_s_at | C13ORF15 | chromosome 13 open reading frame 15 |
| 206701_x_at | EDNRB | endothelin receptor type b |
| 202897_at | SIRPA | signal-regulatory protein alpha |
| 202499_s_at | SLC2A3 | solute carrier family 2 (facilitated glucose transporter), member 3 |
| 208523_x_at | HIST1H2BI | histone cluster 1, h2bi |
| 213652_at | PCSK5 | proprotein convertase subtilisin/kexin type 5 |
| 207292_s_at | MAPK7 | mitogen-activated protein kinase 7 |
| 209166_s_at | MAN2B1 | mannosidase, alpha, class 2b, member 1 |
| 212032_s_at | PTOV1 | prostate tumor overexpressed 1 |
| 218037_at | FAM134A | family with sequence similarity 134, member a |
| 211458_s_at | GABARAPL1 | gaba(a) receptor-associated protein like 1 /// gaba(a) receptors associated protein like 3, pseudogene |
| 204621_s_at | NR4A2 | nuclear receptor subfamily 4, group a, member 2 |
| 216032_s_at | ERGIC3 | ergic and golgi 3 |
| 222101_s_at | DCHS1 | dachsous 1 (drosophila) |
| 215116_s_at | DNM1 | dynamin 1 |
| 204780_s_at | FAS | fas (tnf receptor superfamily, member 6) |
| 202729_s_at | LTBP1 | latent transforming growth factor beta binding protein 1 |
| 201919_at | SLC25A36 | solute carrier family 25, member 36 |
| 221036_s_at | APH1B | anterior pharynx defective 1 homolog b (c. elegans) |
| 49077_at | PPME1 | protein phosphatase methylesterase 1 |
| 205476_s_at | CCL20 | chemokine (c-c motif) ligand 20 |
| 201313_at | ENO2 | enolase 2 (gamma, neuronal) |
| 205916_at | S100A7 | s100 calcium binding protein a7 |
| 208308_s_at | GPI | glucose-6-phosphate isomerase |
| 214743_at | CUX1 | cut-like homeobox 1 |
| 220947_s_at | TBC1D10B | tbc1 domain family, member 10b |
| 204781_s_at | FAS | fas (tnf receptor superfamily, member 6) |
| 202221_s_at | EP300 | e1a binding protein p300 |
| 218097_s_at | CUEDC2 | cue domain containing 2 |
| 209878_s_at | RELA | v-rel reticuloendotheliosis viral oncogene homolog a (avian) |
| 201749_at | ECE1 | endothelin converting enzyme 1 |

TABLE F-continued

Increasing Hair Cycle Activation Gene Studies to Generate the Matrix; Up Gene

| 3D2D_up Affy ID | Gene Symbol | Title |
|---|---|---|
| 219693_at | AGPAT4 | 1-acylglycerol-3-phosphate o-acyltransferase 4 (lysophosphatidic acid acyltransferase, delta) |
| 219168_s_at | PRR5 | proline rich 5 (renal) |
| 202364_at | MXI1 | max interactor 1 |
| 221601_s_at | FAIM3 | fas apoptotic inhibitory molecule 3 |
| 203126_at | IMPA2 | inositol(myo)-1(or 4)-monophosphatase 2 |
| 202455_at | HDAC5 | histone deacetylase 5 |
| 219093_at | PID1 | phosphotyrosine interaction domain containing 1 |
| 201925_s_at | CD55 | cd55 molecule, decay accelerating factor for complement (cromer blood group) |

TABLE G

Retinoic Acid Gene Studies to Generate the Matrix; Down Genes

| Retinoic tk down Affy ID | Gene Symbol | Title |
|---|---|---|
| 204455_at | DST | dystonin |
| 219017_at | ETNK1 | ethanolamine kinase 1 |
| 220924_s_at | SLC38A2 | solute carrier family 38, member 2 |
| 214587_at | COL8A1 | collagen, type viii, alpha 1 |
| 202708_s_at | HIST2H2BE | histone cluster 2, h2be |
| 204653_at | TFAP2A | transcription factor ap-2 alpha (activating enhancer binding protein 2 alpha) |
| 206170_at | ADRB2 | adrenergic, beta-2-, receptor, surface |
| 219503_s_at | TMEM40 | transmembrane protein 40 |
| 219522_at | FJX1 | four jointed box 1 (*drosophila*) |
| 218041_x_at | SLC38A2 | solute carrier family 38, member 2 |
| 212774_at | ZNF238 | zinc finger protein 238 |
| 202769_at | CCNG2 | cyclin g2 |
| 201108_s_at | THBS1 | thrombospondin 1 |
| 217579_x_at | — | — |
| 222162_s_at | ADAMTS1 | adam metallopeptidase with thrombospondin type 1 motif, 1 |
| 221676_s_at | CORO1C | coronin, actin binding protein, 1c |
| 1598_g_at | GAS6 | growth arrest-specific 6 |
| 222108_at | AMIGO2 | adhesion molecule with ig-like domain 2 |
| 213506_at | F2RL1 | coagulation factor ii (thrombin) receptor-like 1 |
| 211559_s_at | CCNG2 | cyclin g2 |
| 202619_s_at | PLOD2 | procollagen-lysine, 2-oxoglutarate 5-dioxygenase 2 |
| 212992_at | AHNAK2 | ahnak nucleoprotein 2 |
| 204917_s_at | MLLT3 | myeloid/lymphoid or mixed-lineage leukemia (trithorax homolog, *drosophila*); translocated to, 3 |
| 205239_at | AREG | amphiregulin |
| 218440_at | MCCC1 | methylcrotonoyl-coa carboxylase 1 (alpha) |
| 201368_at | ZFP36L2 | zinc finger protein 36, c3h type-like 2 |
| 219836_at | ZBED2 | zinc finger, bed-type containing 2 |
| 204602_at | DKK1 | dickkopf homolog 1 (*xenopus laevis*) |
| 201739_at | SGK1 | serum/glucocorticoid regulated kinase 1 |
| 217678_at | SLC7A11 | solute carrier family 7, (cationic amino acid transporter, y+ system) member 11 |
| 221563_at | DUSP10 | dual specificity phosphatase 10 |
| 201109_s_at | THBS1 | thrombospondin 1 |
| 218319_at | PELI1 | pellino homolog 1 (*drosophila*) |
| 215813_s_at | PTGS1 | prostaglandin-endoperoxide synthase 1 (prostaglandin g/h synthase and cyclooxygenase) |
| 35666_at | SEMA3F | sema domain, immunoglobulin domain (ig), short basic domain, secreted, (semaphorin) 3f |
| 204359_at | FLRT2 | fibronectin leucine rich transmembrane protein 2 |
| 209815_at | PTCH1 | patched 1 |
| 209921_at | SLC7A11 | solute carrier family 7, (cationic amino acid transporter, y+ system) member 11 |
| 205157_s_at | KRT17 | keratin 17 |
| 203966_s_at | PPM1A | protein phosphatase, mg2+/mn2+ dependent, 1a |
| 215071_s_at | HIST1H2AC | histone cluster 1, h2ac |
| 203640_at | MBNL2 | muscleblind-like 2 (*drosophila*) |
| 202874_s_at | ATP6V1C1 | atpase, h+ transporting, lysosomal 42 kda, v1 subunit c1 |
| 213568_at | OSR2 | odd-skipped related 2 (*drosophila*) |
| 209674_at | CRY1 | cryptochrome 1 (photolyase-like) |
| 203946_s_at | ARG2 | arginase, type ii |

TABLE G-continued

Retinoic Acid Gene Studies to Generate the Matrix; Down Genes

| Retinoic tk down Affy ID | Gene Symbol | Title |
|---|---|---|
| 203476_at | TPBG | trophoblast glycoprotein |
| 201010_s_at | TXNIP | thioredoxin interacting protein |
| 203865_s_at | ADARB1 | adenosine deaminase, rna-specific, b1 |
| 216092_s_at | SLC7A8 | solute carrier family 7 (amino acid transporter, 1-type), member 8 |
| 218093_s_at | ANKRD10 | ankyrin repeat domain 10 |
| 218886_at | PAK1IP1 | pak1 interacting protein 1 |
| 209101_at | CTGF | connective tissue growth factor |
| 218973_at | EFTUD1 | elongation factor tu gtp binding domain containing 1 |
| 219250_s_at | FLRT3 | fibronectin leucine rich transmembrane protein 3 |
| 219284_at | HSPBAP1 | hspb (heat shock 27 kda) associated protein 1 |
| 205128_x_at | PTGS1 | prostaglandin-endoperoxide synthase 1 (prostaglandin g/h synthase and cyclooxygenase) |
| 209758_s_at | MFAP5 | microfibrillar associated protein 5 |
| 212386_at | TCF4 | transcription factor 4 |
| 215501_s_at | DUSP10 | dual specificity phosphatase 10 |
| 202922_at | GCLC | glutamate-cysteine ligase, catalytic subunit |
| 209383_at | DDIT3 | dna-damage-inducible transcript 3 |
| 201341_at | ENC1 | ectodermal-neural cortex 1 (with btb-like domain) |
| 215564_at | AREG | amphiregulin |
| 209180_at | RABGGTB | rab geranylgeranyltransferase, beta subunit |
| 200962_at | RPL31 | ribosomal protein l31 |
| 212640_at | PTPLB | protein tyrosine phosphatase-like (proline instead of catalytic arginine), member b |
| 209946_at | VEGFC | vascular endothelial growth factor c |
| 204930_s_at | BNIP1 | bcl2/adenovirus e1b 19 kda interacting protein 1 |
| 200790_at | ODC1 | ornithine decarboxylase 1 |
| 219383_at | PRR5L | proline rich 5 like |
| 213624_at | SMPDL3A | sphingomyelin phosphodiesterase, acid-like 3a |
| 203521_s_at | ZNF318 | zinc finger protein 318 |
| 210053_at | TAF5 | taf5 rna polymerase ii, tata box binding protein (tbp)-associated factor, 100 kda |
| 213394_at | MAPKBP1 | mitogen-activated protein kinase binding protein 1 |
| 202220_at | KIAA0907 | kiaa0907 |
| 206156_at | GJB5 | gap junction protein, beta 5, 31.1 kda |
| 207574_s_at | GADD45B | growth arrest and dna-damage-inducible, beta |
| 212190_at | SERPINE2 | serpin peptidase inhibitor, clade e (nexin, plasminogen activator inhibitor type 1), member 2 |
| 215177_s_at | ITGA6 | integrin, alpha 6 |
| 212236_x_at | KRT17 | keratin 17 |
| 206343_s_at | NRG1 | neuregulin 1 |
| 214702_at | FN1 | fibronectin 1 |
| 201925_s_at | CD55 | cd55 molecule, decay accelerating factor for complement (cromer blood group) |
| 220147_s_at | FAM60A | family with sequence similarity 60, member a |
| 208782_at | FSTL1 | follistatin-like 1 |
| 220318_at | EPN3 | epsin 3 |
| 216840_s_at | LAMA2 | laminin, alpha 2 |
| 214169_at | — | — |
| 212614_at | ARID5B | at rich interactive domain 5b (mrf1-like) |
| 203332_s_at | INPP5D | inositol polyphosphate-5-phosphatase, 145 kda |
| 205534_at | PCDH7 | protocadherin 7 |
| 209296_at | PPM1B | protein phosphatase, mg2+/mn2+ dependent, 1b |
| 209457_at | DUSP5 | dual specificity phosphatase 5 |
| 202162_s_at | CNOT8 | ccr4-not transcription complex, subunit 8 |
| 210253_at | HTATIP2 | hiv-1 tat interactive protein 2, 30 kda |
| 210495_x_at | FN1 | fibronectin 1 |
| 202971_s_at | DYRK2 | dual-specificity tyrosine-(y)-phosphorylation regulated kinase 2 |
| 203778_at | MANBA | mannosidase, beta a, lysosomal |
| 206332_s_at | IFI16 | interferon, gamma-inducible protein 16 |
| 201926_s_at | CD55 | cd55 molecule, decay accelerating factor for complement (cromer blood group) |
| 217312_s_at | COL7A1 | collagen, type vii, alpha 1 |
| 204204_at | SLC31A2 | solute carrier family 31 (copper transporters), member 2 |
| 219492_at | CHIC2 | cysteine-rich hydrophobic domain 2 |
| 205000_at | DDX3Y | dead (asp-glu-ala-asp) box polypeptide 3, y-linked |
| 216268_s_at | JAG1 | jagged 1 |
| 218681_s_at | SDF2L1 | stromal cell-derived factor 2-like 1 |
| 204686_at | IRS1 | insulin receptor substrate 1 |
| 201266_at | TXNRD1 | thioredoxin reductase 1 |
| 209185_s_at | IRS2 | insulin receptor substrate 2 |
| 212464_s_at | FN1 | fibronectin 1 |

TABLE G-continued

Retinoic Acid Gene Studies to Generate the Matrix; Down Genes

Retinoic tk down

| Affy ID | Gene Symbol | Title |
|---|---|---|
| 207528_s_at | SLC7A11 | solute carrier family 7, (cationic amino acid transporter, y+ system) member 11 |
| 203743_s_at | TDG | thymine-dna glycosylase |
| 202923_at | GCLC | glutamate-cysteine ligase, catalytic subunit |
| 219410_at | TMEM45A | transmembrane protein 45a |
| 219073_s_at | OSBPL10 | oxysterol binding protein-like 10 |
| 200906_s_at | PALLD | palladin, cytoskeletal associated protein |
| 202934_at | HK2 | hexokinase 2 |
| 208527_x_at | HIST1H2BE | histone cluster 1, h2be |
| 207375_s_at | IL15RA | interleukin 15 receptor, alpha |
| 208070_s_at | REV3L | rev3-like, catalytic subunit of dna polymerase zeta (yeast) |
| 217663_at | ZNF234 | zinc finger protein 234 |
| 206295_at | IL18 | interleukin 18 (interferon-gamma-inducing factor) |
| 202770_s_at | CCNG2 | cyclin g2 |
| 219142_at | RASL11B | ras-like, family 11, member b |
| 202766_s_at | FBN1 | fibrillin 1 |
| 221486_at | ENSA | endosulfine alpha |
| 218107_at | WDR26 | wd repeat domain 26 |
| 221596_s_at | C7ORF64 | chromosome 7 open reading frame 64 |
| 202686_s_at | AXL | axl receptor tyrosine kinase |
| 209317_at | POLR1C | polymerase (rna) i polypeptide c, 30 kda |
| 203945_at | ARG2 | arginase, type ii |
| 205014_at | FGFBP1 | fibroblast growth factor binding protein 1 |
| 206237_s_at | NRG1 | neuregulin 1 |
| 205116_at | LAMA2 | laminin, alpha 2 |
| 217125_at | — | — |
| 205097_at | SLC26A2 | solute carrier family 26 (sulfate transporter), member 2 |
| 212765_at | CAMSAP1L1 | calmodulin regulated spectrin-associated protein 1-like 1 |
| 219610_at | RGNEF | 190 kda guanine nucleotide exchange factor |
| 218178_s_at | CHMP1B | chromatin modifying protein 1b |
| 213807_x_at | MET | met proto-oncogene (hepatocyte growth factor receptor) |
| 207876_s_at | FLNC | filamin c, gamma |
| 221276_s_at | SYNC | syncoilin, intermediate filament protein |
| 219710_at | SH3TC2 | sh3 domain and tetratricopeptide repeats 2 |
| 217127_at | CTH | cystathionase (cystathionine gamma-lyase) |
| 202876_at | PBX2 | pre-b-cell leukemia homeobox 2 |
| 220979_s_at | ST6GALNAC5 | st6 (alpha-n-acetyl-neuraminyl-2,3-beta-galactosyl-1,3)-n-acetylgalactosaminide alpha-2,6-sialyltransferase 5 |
| 201906_s_at | CTDSPL | ctd (carboxy-terminal domain, rna polymerase ii, polypeptide a) small phosphatase-like |
| 204068_at | STK3 | serine/threonine kinase 3 |
| 202364_at | MXI1 | max interactor 1 |
| 204584_at | L1CAM | l1 cell adhesion molecule |
| 222262_s_at | ETNK1 | ethanolamine kinase 1 |
| 209099_x_at | JAG1 | jagged 1 |
| 202342_s_at | TRIM2 | tripartite motif-containing 2 |
| 212660_at | PHF15 | phd finger protein 15 |
| 221249_s_at | FAM117A | family with sequence similarity 117, member a |
| 206032_at | DSC3 | desmocollin 3 |
| 204532_x_at | UGT1A1 | udp glucuronosyltransferase 1 family, polypeptide a1 /// udp glucuronosyltransferase 1 family, polypeptide a10 /// udp glucuronosyltransferase 1 family, polypeptide a4 /// udp glucuronosyltransferase 1 family, polypeptide a6 /// udp glucuronosyltransferase 1 family, polypeptide a8 /// udp glucuronosyltransferase 1 family, polypeptide a9 |
| 220262_s_at | DLK2 | delta-like 2 homolog (*drosophila*) |
| 217599_s_at | MDFIC | myod family inhibitor domain containing |
| 219885_at | SLFN12 | schlafen family member 12 |
| 216309_x_at | JRK | jerky homolog (mouse) |
| 218358_at | CRELD2 | cysteine-rich with egf-like domains 2 |
| 210765_at | CSE1L | cse1 chromosome segregation 1-like (yeast) |
| 202730_s_at | PDCD4 | programmed cell death 4 (neoplastic transformation inhibitor) |
| 214909_s_at | DDAH2 | dimethylarginine dimethylaminohydrolase 2 |
| 202973_x_at | FAM13A | family with sequence similarity 13, member a |
| 211986_at | AHNAK | ahnak nucleoprotein |
| 203612_at | BYSL | bystin-like |
| 216918_s_at | DST | dystonin |
| 219390_at | FKBP14 | fk506 binding protein 14, 22 kda |
| 220240_s_at | TMCO3 | transmembrane and coiled-coil domains 3 |
| 205662_at | B9D1 | b9 protein domain 1 |
| 209633_at | PPP2R3A | protein phosphatase 2, regulatory subunit b'', alpha |
| 203889_at | SCG5 | secretogranin v (7b2 protein) |
| 205535_s_at | PCDH7 | protocadherin 7 |

TABLE G-continued

Retinoic Acid Gene Studies to Generate the Matrix; Down Genes

| Retinoic tk down Affy ID | Gene Symbol | Title |
|---|---|---|
| 219026_s_at | RASAL2 | ras protein activator like 2 |
| 205018_s_at | MBNL2 | muscleblind-like 2 (*drosophila*) |
| 201426_s_at | VIM | vimentin |
| 214093_s_at | FUBP1 | far upstream element (fuse) binding protein 1 |
| 203637_s_at | MID1 | midline 1 (opitz/bbb syndrome) |
| 212667_at | SPARC | secreted protein, acidic, cysteine-rich (osteonectin) |
| 207347_at | ERCC6 | excision repair cross-complementing rodent repair deficiency, complementation group 6 /// piggybac transposable element derived 3 |
| 205415_s_at | ATXN3 | ataxin 3 |
| 215767_at | ZNF804A | zinc finger protein 804a |
| 219529_at | CLIC3 | chloride intracellular channel 3 |
| 211974_x_at | RBPJ | recombination signal binding protein for immunoglobulin kappa j region |
| 209900_s_at | SLC16A1 | solute carrier family 16, member 1 (monocarboxylic acid transporter 1) |
| 209160_at | AKR1C3 | aldo-keto reductase family 1, member c3 (3-alpha hydroxysteroid dehydrogenase, type ii) |
| 204014_at | DUSP4 | dual specificity phosphatase 4 |
| 212124_at | ZMIZ1 | zinc finger, miz-type containing 1 |
| 210220_at | FZD2 | frizzled homolog 2 (*drosophila*) |
| 203096_s_at | RAPGEF2 | rap guanine nucleotide exchange factor (gef) 2 |
| 210105_s_at | FYN | fyn oncogene related to src, fgr, yes |
| 202551_s_at | CRIM1 | cysteine rich transmembrane bmp regulator 1 (chordin-like) |
| 205264_at | CD3EAP | cd3e molecule, epsilon associated protein |
| 202267_at | LAMC2 | laminin, gamma 2 |
| 204136_at | COL7A1 | collagen, type vii, alpha 1 |
| 207147_at | DLX2 | distal-less homeobox 2 |
| 209699_x_at | AKR1C2 | aldo-keto reductase family 1, member c2 (dihydrodiol dehydrogenase 2; bile acid binding protein; 3-alpha hydroxysteroid dehydrogenase, type iii) |

TABLE H

Retinoic Acid Gene Studies to Generate the Matrix; Up Genes

| Retinoic tk UP Affy ID | Gene Symbol | Title |
|---|---|---|
| 201661_s_at | ACSL3 | acyl-coa synthetase long-chain family member 3 |
| 203504_s_at | ABCA1 | atp-binding cassette, sub-family a (abc1), member 1 |
| 221009_s_at | ANGPTL4 | angiopoietin-like 4 |
| 38037_at | HBEGF | heparin-binding egf-like growth factor |
| 205067_at | IL1B | interleukin 1, beta |
| 202481_at | DHRS3 | dehydrogenase/reductase (sdr family) member 3 |
| 200666_s_at | DNAJB1 | dnaj (hsp40) homolog, subfamily b, member 1 |
| 219634_at | CHST11 | carbohydrate (chondroitin 4) sulfotransferase 11 |
| 205220_at | GPR109B | g protein-coupled receptor 109b |
| 203234_at | UPP1 | uridine phosphorylase 1 |
| 39402_at | IL1B | interleukin 1, beta |
| 202936_s_at | SOX9 | sry (sex determining region y)-box 9 |
| 201417_at | SOX4 | sry (sex determining region y)-box 4 |
| 209278_s_at | TFPI2 | tissue factor pathway inhibitor 2 |
| 210001_s_at | SOCS1 | suppressor of cytokine signaling 1 |
| 201609_x_at | ICMT | isoprenylcysteine carboxyl methyltransferase |
| 206074_s_at | HMGA1 | high mobility group at-hook 1 |
| 202998_s_at | LOXL2 | lysyl oxidase-like 2 |
| 202795_x_at | TRIOBP | trio and f-actin binding protein |
| 202393_s_at | KLF10 | kruppel-like factor 10 |
| 204908_s_at | BCL3 | b-cell cll/lymphoma 3 |
| 39248_at | AQP3 | aquaporin 3 (gill blood group) |
| 203373_at | SOCS2 | suppressor of cytokine signaling 2 |
| 201660_at | ACSL3 | acyl-coa synthetase long-chain family member 3 |
| 210762_s_at | DLC1 | deleted in liver cancer 1 |
| 200664_s_at | DNAJB1 | dnaj (hsp40) homolog, subfamily b, member 1 |
| 218627_at | DRAM1 | dna-damage regulated autophagy modulator 1 |
| 209744_x_at | ITCH | itchy e3 ubiquitin protein ligase homolog (mouse) |
| 201242_s_at | ATP1B1 | atpase, na+/k+ transporting, beta 1 polypeptide |
| 202052_s_at | RAI14 | retinoic acid induced 14 |

TABLE H-continued

Retinoic Acid Gene Studies to Generate the Matrix; Up Genes

| Retinoic tk UP Affy ID | Gene Symbol | Title |
|---|---|---|
| 206432_at | HAS2 | hyaluronan synthase 2 |
| 212099_at | RHOB | ras homolog gene family, member b |
| 202207_at | ARL4C | adp-ribosylation factor-like 4c |
| 208394_x_at | ESM1 | endothelial cell-specific molecule 1 |
| 218980_at | FHOD3 | formin homology 2 domain containing 3 |
| 209277_at | TFPI2 | tissue factor pathway inhibitor 2 |
| 208937_s_at | ID1 | inhibitor of dna binding 1, dominant negative helix-loop-helix protein |
| 206632_s_at | APOBEC3B | apolipoprotein b mrna editing enzyme, catalytic polypeptide-like 3b |
| 210095_s_at | IGFBP3 | insulin-like growth factor binding protein 3 |
| 202599_s_at | NRIP1 | nuclear receptor interacting protein 1 |
| 212444_at | — | — |
| 208960_s_at | KLF6 | kruppel-like factor 6 |
| 202638_s_at | ICAM1 | intercellular adhesion molecule 1 |
| 203505_at | ABCA1 | atp-binding cassette, sub-family a (abc1), member 1 |
| 208963_x_at | FADS1 | fatty acid desaturase 1 |
| 212268_at | SERPINB1 | serpin peptidase inhibitor, clade b (ovalbumin), member 1 |
| 204541_at | SEC14L2 | sec14-like 2 (s. cerevisiae) |
| 217739_s_at | NAMPT | nicotinamide phosphoribosyltransferase |
| 218376_s_at | MICAL1 | microtubule associated monoxygenase, calponin and lim domain containing 1 |
| 211668_s_at | PLAU | plasminogen activator, urokinase |
| 217997_at | PHLDA1 | pleckstrin homology-like domain, family a, member 1 |
| 204264_at | CPT2 | carnitine palmitoyltransferase 2 |
| 217992_s_at | EFHD2 | ef-hand domain family, member d2 |
| 218309_at | CAMK2N1 | calcium/calmodulin-dependent protein kinase ii inhibitor 1 |
| 209955_s_at | FAP | fibroblast activation protein, alpha |
| 202384_s_at | TCOF1 | treacher collins-franceschetti syndrome 1 |
| 214783_s_at | ANXA11 | annexin a11 |
| 219239_s_at | ZNF654 | zinc finger protein 654 |
| 211361_s_at | SERPINB13 | serpin peptidase inhibitor, clade b (ovalbumin), member 13 |
| 218181_s_at | MAP4K4 | mitogen-activated protein kinase kinase kinase kinase 4 |
| 203658_at | SLC25A20 | solute carrier family 25 (carnitine/acylcarnitine translocase), member 20 |
| 202637_s_at | ICAM1 | intercellular adhesion molecule 1 |
| 212143_s_at | IGFBP3 | insulin-like growth factor binding protein 3 |
| 211538_s_at | HSPA2 | heat shock 70 kda protein 2 |
| 201889_at | FAM3C | family with sequence similarity 3, member c |
| 205479_s_at | PLAU | plasminogen activator, urokinase |
| 201830_s_at | NET1 | neuroepithelial cell transforming 1 |
| 208961_s_at | KLF6 | kruppel-like factor 6 |
| 201860_s_at | PLAT | plasminogen activator, tissue |
| 207196_s_at | TNIP1 | tnfaip3 interacting protein 1 |
| 200880_at | DNAJA1 | dnaj (hsp40) homolog, subfamily a, member 1 |
| 205780_at | BIK | bcl2-interacting killer (apoptosis-inducing) |
| 203180_at | ALDH1A3 | aldehyde dehydrogenase 1 family, member a3 |
| 202208_s_at | ARL4C | adp-ribosylation factor-like 4c |
| 219257_s_at | SPHK1 | sphingosine kinase 1 |
| 218888_s_at | NETO2 | neuropilin (nrp) and tolloid (tll)-like 2 |
| 218205_s_at | MKNK2 | map kinase interacting serine/threonine kinase 2 |
| 203821_at | HBEGF | heparin-binding egf-like growth factor |
| 216899_s_at | SKAP2 | src kinase associated phosphoprotein 2 |
| 203936_s_at | MMP9 | matrix metallopeptidase 9 (gelatinase b, 92 kda gelatinase, 92 kda type iv collagenase) |
| 215001_s_at | GLUL | glutamate-ammonia ligase |
| 213603_s_at | RAC2 | ras-related c3 botulinum toxin substrate 2 (rho family, small gtp binding protein rac2) |
| 202600_s_at | NRIP1 | nuclear receptor interacting protein 1 |
| 202786_at | STK39 | serine threonine kinase 39 |
| 206200_s_at | ANXA11 | annexin a11 |
| 218284_at | SMAD3 | smad family member 3 |
| 208083_s_at | ITGB6 | integrin, beta 6 |
| 201041_s_at | DUSP1 | dual specificity phosphatase 1 |
| 221884_at | MECOM | mds1 and evi1 complex locus |
| 203372_s_at | SOCS2 | suppressor of cytokine signaling 2 |
| 213288_at | MBOAT2 | membrane bound o-acyltransferase domain containing 2 |
| 201170_s_at | BHLHE40 | basic helix-loop-helix family, member e40 |
| 216945_x_at | PASK | pas domain containing serine/threonine kinase |
| 202037_s_at | SFRP1 | secreted frizzled-related protein 1 |
| 210817_s_at | CALCOCO2 | calcium binding and coiled-coil domain 2 |
| 209108_at | TSPAN6 | tetraspanin 6 |
| 220465_at | LOC80054 | hypothetical loc80054 |
| 208613_s_at | FLNB | filamin b, beta |

TABLE H-continued

Retinoic Acid Gene Studies to Generate the Matrix; Up Genes

| Retinoic tk UP Affy ID | Gene Symbol | Title |
|---|---|---|
| 211113_s_at | ABCG1 | atp-binding cassette, sub-family g (white), member 1 |
| 210786_s_at | FLU | friend leukemia virus integration 1 |
| 204675_at | SRD5A1 | steroid-5-alpha-reductase, alpha polypeptide 1 (3-oxo-5 alpha-steroid delta 4-dehydrogenase alpha 1) |
| 212026_s_at | EXOC7 | exocyst complex component 7 |
| 213017_at | ABHD3 | abhydrolase domain containing 3 |
| 219850_s_at | EHF | ets homologous factor |
| 204105_s_at | NRCAM | neuronal cell adhesion molecule |
| 221832_s_at | LUZP1 | leucine zipper protein 1 |
| 219205_at | SRR | serine racemase |
| 221509_at | DENR | density-regulated protein |
| 203072_at | MYO1E | myosin ie |
| 208084_at | ITGB6 | integrin, beta 6 |
| 200800_s_at | HSPA1A | heat shock 70 kda protein 1a /// heat shock 70 kda protein 1b |
| 217966_s_at | FAM129A | family with sequence similarity 129, member a |
| 203108_at | GPRC5A | g protein-coupled receptor, family c, group 5, member a |
| 37152_at | PPARD | peroxisome proliferator-activated receptor delta |
| 213361_at | TDRD7 | tudor domain containing 7 |
| 202071_at | SDC4 | syndecan 4 |
| 203062_s_at | MDC1 | mediator of dna-damage checkpoint 1 |
| 205122_at | TMEFF1 | transmembrane protein with egf-like and two follistatin-like domains 1 |
| 201669_s_at | MARCKS | myristoylated alanine-rich protein kinase c substrate |
| 217967_s_at | FAM129A | family with sequence similarity 129, member a |
| 218000_s_at | PHLDA1 | pleckstrin homology-like domain, family a, member 1 |
| 201930_at | MCM6 | minichromosome maintenance complex component 6 |
| 201834_at | PRKAB1 | protein kinase, amp-activated, beta 1 non-catalytic subunit |
| 202295_s_at | CTSH | cathepsin h |
| 217996_at | PHLDA1 | pleckstrin homology-like domain, family a, member 1 |
| 204639_at | ADA | adenosine deaminase |
| 210276_s_at | NOL12 | nucleolar protein 12 /// trio and f-actin binding protein |
| 216237_s_at | MCM5 | minichromosome maintenance complex component 5 |
| 201466_s_at | JUN | jun proto-oncogene |
| 218136_s_at | SLC25A37 | solute carrier family 25, member 37 |
| 213680_at | KRT6B | keratin 6b |
| 202949_s_at | FHL2 | four and a half lim domains 2 |
| 209118_s_at | TUBA1A | tubulin, alpha 1a |
| 212186_at | ACACA | acetyl-coa carboxylase alpha |
| 201147_s_at | TIMP3 | timp metallopeptidase inhibitor 3 |
| 204361_s_at | SKAP2 | src kinase associated phosphoprotein 2 |
| 218501_at | ARHGEF3 | rho guanine nucleotide exchange factor (gef) 3 |
| 202859_x_at | IL8 | interleukin 8 |
| 208862_s_at | CTNND1 | catenin (cadherin-associated protein), delta 1 |
| 206971_at | GPR161 | g protein-coupled receptor 161 |
| 211464_x_at | CASP6 | caspase 6, apoptosis-related cysteine peptidase |
| 201662_s_at | ACSL3 | acyl-coa synthetase long-chain family member 3 |
| 202107_s_at | MCM2 | minichromosome maintenance complex component 2 |
| 205032_at | ITGA2 | integrin, alpha 2 (cd49b, alpha 2 subunit of vla-2 receptor) |
| 210229_s_at | CSF2 | colony stimulating factor 2 (granulocyte-macrophage) |
| 218613_at | PSD3 | pleckstrin and sec7 domain containing 3 |
| 201416_at | SOX4 | sry (sex determining region y)-box 4 |
| 217875_s_at | PMEPA1 | prostate transmembrane protein, androgen induced 1 |
| 213916_at | ZNF20 | zinc finger protein 20 /// zinc finger protein 625 |
| 219631_at | LRP12 | low density lipoprotein receptor-related protein 12 |
| 217272_s_at | SERPINB13 | serpin peptidase inhibitor, clade b (ovalbumin), member 13 |
| 204567_s_at | ABCG1 | atp-binding cassette, sub-family g (white), member 1 |
| 218273_s_at | PDP1 | pyruvate dehyrogenase phosphatase catalytic subunit 1 |
| 204420_at | FOSL1 | fos-like antigen 1 |
| 218404_at | SNX10 | sorting nexin 10 |
| 210517_s_at | AKAP12 | a kinase (prka) anchor protein 12 |
| 213372_at | PAQR3 | progestin and adipoq receptor family member iii |
| 204422_s_at | FGF2 | fibroblast growth factor 2 (basic) |
| 207850_at | CXCL3 | chemokine (c-x-c motif) ligand 3 |
| 210792_x_at | SIVA1 | siva1, apoptosis-inducing factor |
| 202581_at | HSPA1A | heat shock 70 kda protein 1a /// heat shock 70 kda protein 1b |
| 212298_at | NRP1 | neuropilin 1 |
| 212276_at | LPIN1 | lipin 1 |
| 207408_at | SLC22A14 | solute carrier family 22, member 14 |
| 202529_at | PRPSAP1 | phosphoribosyl pyrophosphate synthetase-associated protein 1 |
| 206460_at | AJAP1 | adherens junctions associated protein 1 |
| 215017_s_at | FNBP1L | formin binding protein 1-like |
| 219058_x_at | TINAGL1 | tubulointerstitial nephritis antigen-like 1 |
| 202584_at | NFX1 | nuclear transcription factor, x-box binding 1 |

TABLE H-continued

Retinoic Acid Gene Studies to Generate the Matrix; Up Genes

| Retinoic tk UP Affy ID | Gene Symbol | Title |
|---|---|---|
| 217999_s_at | PHLDA1 | pleckstrin homology-like domain, family a, member 1 |
| 202392_s_at | PISD | phosphatidylserine decarboxylase |
| 203991_s_at | KDM6A | lysine (k)-specific demethylase 6a |
| 203837_at | MAP3K5 | mitogen-activated protein kinase kinase kinase 5 |
| 202627_s_at | SERPINE1 | serpin peptidase inhibitor, clade e (nexin, plasminogen activator inhibitor type 1), member 1 |
| 205115_s_at | RBM19 | rna binding motif protein 19 |
| 202206_at | ARL4C | adp-ribosylation factor-like 4c |
| 206972_s_at | GPR161 | g protein-coupled receptor 161 |
| 210118_s_at | IL1A | interleukin 1, alpha |
| 205847_at | PRSS22 | protease, serine, 22 |
| 213392_at | IQCK | iq motif containing k |
| 204200_s_at | PDGFB | platelet-derived growth factor beta polypeptide (simian sarcoma viral (v-sis) oncogene homolog) |
| 212274_at | LPIN1 | lipin 1 |
| 220311_at | N6AMT1 | n-6 adenine-specific dna methyltransferase 1 (putative) |
| 219210_s_at | RAB8B | rab8b, member ras oncogene family |
| 209508_x_at | CFLAR | casp8 and fadd-like apoptosis regulator |
| 213053_at | HAUS5 | haus augmin-like complex, subunit 5 |
| 203855_at | WDR47 | wd repeat domain 47 |
| 203736_s_at | PPFIBP1 | ptprf interacting protein, binding protein 1 (liprin beta 1) |
| 218743_at | CHMP6 | chromatin modifying protein 6 |
| 214119_s_at | FKBP1A | fk506 binding protein 1a, 12 kda |
| 213419_at | APBB2 | amyloid beta (a4) precursor protein-binding, family b, member 2 |
| 209706_at | NKX3-1 | nk3 homeobox 1 |
| 220227_at | CDH4 | cadherin 4, type 1, r-cadherin (retinal) |
| 208705_s_at | EIF5 | eukaryotic translation initiation factor 5 |
| 208779_x_at | DDR1 | discoidin domain receptor tyrosine kinase 1 |
| 213572_s_at | SERPINB1 | serpin peptidase inhibitor, clade b (ovalbumin), member 1 |
| 212729_at | DLG3 | discs, large homolog 3 (*drosophila*) |
| 204475_at | MMP1 | matrix metallopeptidase 1 (interstitial collagenase) |
| 37117_at | ARHGAP8 | rho gtpase activating protein 8 /// prr5-arhgap8 readthrough |
| 217202_s_at | GLUL | glutamate-ammonia ligase |

TABLE I

Hair Count Actives Gene Studies to Generate the Matrix; Down Genes (BJ Table)

| Mx BJ Down Affy ID | Gene Symbol | Title |
|---|---|---|
| 200927_s_at | RAB14 | rab14, member ras oncogene family |
| 201407_s_at | PPP1CB | protein phosphatase 1, catalytic subunit, beta isozyme |
| 201456_s_at | BUB3 | budding uninhibited by benzimidazoles 3 homolog (yeast) |
| 201478_s_at | DKC1 | dyskeratosis congenita 1, dyskerin |
| 202375_at | SEC24D | sec24 family, member d (*s. cerevisiae*) |
| 202416_at | DNAJC7 | dnaj (hsp40) homolog, subfamily c, member 7 |
| 203086_at | KIF2A | kinesin heavy chain member 2a |
| 203091_at | FUBP1 | far upstream element (fuse) binding protein 1 |
| 203298_s_at | JARID2 | jumonji, at rich interactive domain 2 |
| 203418_at | CCNA2 | cyclin a2 |
| 203504_s_at | ABCA1 | atp-binding cassette, sub-family a (abc1), member 1 |
| 203739_at | ZNF217 | zinc finger protein 217 |
| 203908_at | SLC4A4 | solute carrier family 4, sodium bicarbonate cotransporter, member 4 |
| 204088_at | P2RX4 | purinergic receptor p2x, ligand-gated ion channel, 4 |
| 204099_at | SMARCD3 | swi/snf related, matrix associated, actin dependent regulator of chromatin, subfamily d, member 3 |
| 204285_s_at | PMAIP1 | phorbol-12-myristate-13-acetate-induced protein 1 |
| 204348_s_at | AK4 | adenylate kinase 4 |
| 204569_at | ICK | intestinal cell (mak-like) kinase |
| 204809_at | CLPX | clpx caseinolytic peptidase x homolog (*e. coli*) |
| 204887_s_at | PLK4 | polo-like kinase 4 |
| 205173_x_at | CD58 | cd58 molecule |
| 205186_at | DNALI1 | dynein, axonemal, light intermediate chain 1 |
| 205248_at | DOPEY2 | dopey family member 2 |
| 205565_s_at | FXN | frataxin |
| 205757_at | ENTPD5 | ectonucleoside triphosphate diphosphohydrolase 5 |

TABLE I-continued

Hair Count Actives Gene Studies to Generate the Matrix; Down Genes (BJ Table)

| Mx BJ Down Affy ID | Gene Symbol | Title |
|---|---|---|
| 205768_s_at | SLC27A2 | solute carrier family 27 (fatty acid transporter), member 2 |
| 205782_at | FGF7 | fibroblast growth factor 7 |
| 206103_at | RAC3 | ras-related c3 botulinum toxin substrate 3 (rho family, small gtp binding protein rac3) |
| 206302_s_at | NUDT4 | nudix (nucleoside diphosphate linked moiety x)-type motif 4 /// nudix (nucleoside diphosphate linked moiety x)-type motif 4 pseudogene 1 |
| 206412_at | FER | fer (fps/fes related) tyrosine kinase |
| 206624_at | USP9Y | ubiquitin specific peptidase 9, y-linked |
| 206809_s_at | HNRNPA3 | heterogeneous nuclear ribonucleoprotein a3 /// heterogeneous nuclear ribonucleoprotein a3 pseudogene 1 |
| 207264_at | KDELR3 | kdel (lys-asp-glu-leu) endoplasmic reticulum protein retention receptor 3 |
| 207487_at | — | — |
| 207528_s_at | SLC7A11 | solute carrier family 7, (cationic amino acid transporter, y+ system) member 11 |
| 207621_s_at | PEMT | phosphatidylethanolamine n-methyltransferase |
| 208732_at | RAB2A | rab2a, member ras oncogene family |
| 209000_s_at | 8-SEP | septin 8 |
| 209106_at | NCOA1 | nuclear receptor coactivator 1 |
| 209362_at | MED21 | mediator complex subunit 21 |
| 209472_at | CCBL2 | cysteine conjugate-beta lyase 2 |
| 209544_at | RIPK2 | receptor-interacting serine-threonine kinase 2 |
| 209679_s_at | SMAGP | small cell adhesion glycoprotein |
| 209704_at | MTF2 | metal response element binding transcription factor 2 |
| 209713_s_at | SLC35D1 | solute carrier family 35 (udp-glucuronic acid/udp-n-acetylgalactosamine dual transporter), member d1 |
| 209745_at | COQ7 | coenzyme q7 homolog, ubiquinone (yeast) |
| 210044_s_at | LYL1 | lymphoblastic leukemia derived sequence 1 |
| 210058_at | MAPK13 | mitogen-activated protein kinase 13 |
| 210120_s_at | RANBP3 | ran binding protein 3 |
| 210154_at | ME2 | malic enzyme 2, nad(+)-dependent, mitochondrial |
| 210156_s_at | PCMT1 | protein-l-isoaspartate (d-aspartate) o-methyltransferase |
| 210180_s_at | TRA2B | transformer 2 beta homolog (drosophila) |
| 210196_s_at | PSG1 | pregnancy specific beta-1-glycoprotein 1 |
| 210286_s_at | SLC4A7 | solute carrier family 4, sodium bicarbonate cotransporter, member 7 |
| 210317_s_at | YWHAE | tyrosine 3-monooxygenase/tryptophan 5-monooxygenase activation protein, epsilon polypeptide |
| 210420_at | SLC24A1 | solute carrier family 24 (sodium/potassium/calcium exchanger), member 1 |
| 210564_x_at | CFLAR | casp8 and fadd-like apoptosis regulator |
| 210594_x_at | MPZL1 | myelin protein zero-like 1 |
| 210716_s_at | CLIP1 | cap-gly domain containing linker protein 1 |
| 211077_s_at | TLK1 | tousled-like kinase 1 |
| 211090_s_at | PRPF4B | prp4 pre-mrna processing factor 4 homolog b (yeast) |
| 211212_s_at | ORC5 | origin recognition complex, subunit 5 |
| 211368_s_at | CASP1 | caspase 1, apoptosis-related cysteine peptidase (interleukin 1, beta, convertase) |
| 211379_x_at | B3GALNT1 | beta-1,3-n-acetylgalactosaminyltransferase 1 (globoside blood group) |
| 211506_s_at | IL8 | interleukin 8 |
| 211693_at | IGHA1 | immunoglobulin heavy constant alpha 1 |
| 211809_x_at | COL13A1 | collagen, type xiii, alpha 1 |
| 211874_s_at | MYST4 | myst histone acetyltransferase (monocytic leukemia) 4 |
| 211960_s_at | RAB7A | rab7a, member ras oncogene family |
| 212179_at | SFRS18 | splicing factor, arginine/serine-rich 18 |
| 212232_at | FNBP4 | formin binding protein 4 |
| 212331_at | RBL2 | retinoblastoma-like 2 (p130) |
| 212746_s_at | CEP170 | centrosomal protein 170 kda |
| 213149_at | DLAT | dihydrolipoamide s-acetyltransferase |
| 213167_s_at | SLC5A3 | solute carrier family 5 (sodium/myo-inositol cotransporter), member 3 |
| 213321_at | BCKDHB | branched chain keto acid dehydrogenase e1, beta polypeptide |
| 213376_at | ZBTB1 | zinc finger and btb domain containing 1 |
| 213501_at | ACOX1 | acyl-coa oxidase 1, palmitoyl |
| 213926_s_at | AGFG1 | arfgap with fg repeats 1 |
| 214266_s_at | PDLIM7 | pdz and lim domain 7 (enigma) |
| 214507_s_at | EXOSC2 | exosome component 2 |

TABLE I-continued

Hair Count Actives Gene Studies to Generate the Matrix; Down Genes (BJ Table)

| Mx BJ Down Affy ID | Gene Symbol | Title |
|---|---|---|
| 214690_at | TAF1B | tata box binding protein (tbp)-associated factor, rna polymerase i, b, 63 kda |
| 214702_at | FN1 | fibronectin 1 |
| 214843_s_at | USP33 | ubiquitin specific peptidase 33 |
| 214895_s_at | ADAM10 | adam metallopeptidase domain 10 |
| 215084_s_at | LRRC42 | leucine rich repeat containing 42 |
| 215509_s_at | BUB1 | budding uninhibited by benzimidazoles 1 homolog (yeast) |
| 215584_at | HECW1 | hect, c2 and ww domain containing e3 ubiquitin protein ligase 1 |
| 215591_at | SATB2 | satb homeobox 2 |
| 215648_at | — | — |
| 215726_s_at | CYB5A | cytochrome b5 type a (microsomal) |
| 215820_x_at | SNX13 | sorting nexin 13 |
| 216031_x_at | HN1L | hematological and neurological expressed 1-like |
| 216123_x_at | — | — |
| 216125_s_at | RANBP9 | ran binding protein 9 |
| 216316_x_at | GK | glycerol kinase /// glycerol kinase 3 pseudogene |
| 216600_x_at | ALDOB | aldolase b, fructose-bisphosphate |
| 216774_at | — | — |
| 217299_s_at | NBN | nibrin |
| 217540_at | FAM55C | family with sequence similarity 55, member c |
| 217821_s_at | WBP11 | ww domain binding protein 11 |
| 217826_s_at | UBE2J1 | ubiquitin-conjugating enzyme e2, j1 (ubc6 homolog, yeast) |
| 217857_s_at | RBM8A | rna binding motif protein 8a |
| 217999_s_at | PHLDA1 | pleckstrin homology-like domain, family a, member 1 |
| 218036_x_at | NMD3 | nmd3 homolog (s. cerevisiae) |
| 218077_s_at | ZDHHC3 | zinc finger, dhhc-type containing 3 |
| 218111_s_at | CMAS | cytidine monophosphate n-acetylneuraminic acid synthetase |
| 218128_at | NFYB | nuclear transcription factor y, beta |
| 218297_at | FAM188A | family with sequence similarity 188, member a |
| 218386_x_at | USP16 | ubiquitin specific peptidase 16 |
| 218578_at | CDC73 | cell division cycle 73, paf1/rna polymerase ii complex component, homolog (s. cerevisiae) |
| 218653_at | SLC25A15 | solute carrier family 25 (mitochondrial carrier; ornithine transporter) member 15 |
| 218674_at | C5ORF44 | chromosome 5 open reading frame 44 |
| 218716_x_at | MTO1 | mitochondrial translation optimization 1 homolog (s. cerevisiae) |
| 218791_s_at | C15ORF29 | chromosome 15 open reading frame 29 |
| 219248_at | THUMPD2 | thump domain containing 2 |
| 219258_at | TIPIN | timeless interacting protein |
| 219313_at | GRAMD1C | gram domain containing 1c |
| 219523_s_at | ODZ3 | odz, odd oz/ten-m homolog 3 (drosophila) |
| 219617_at | C2ORF34 | chromosome 2 open reading frame 34 |
| 219640_at | CLDN15 | claudin 15 |
| 219648_at | MREG | melanoregulin |
| 219681_s_at | RAB11FIP1 | rab11 family interacting protein 1 (class i) |
| 219793_at | SNX16 | sorting nexin 16 |
| 219875_s_at | PPPDE1 | pppde peptidase domain containing 1 |
| 219885_at | SLFN12 | schlafen family member 12 |
| 220235_s_at | C1ORF103 | chromosome 1 open reading frame 103 |
| 220241_at | TMCO3 | transmembrane and coiled-coil domains 3 |
| 220386_s_at | EML4 | echinoderm microtubule associated protein like 4 |
| 220473_s_at | ZCCHC4 | zinc finger, cchc domain containing 4 |
| 220651_s_at | MCM10 | minichromosome maintenance complex component 10 |
| 220867_s_at | SLC24A2 | solute carrier family 24 (sodium/potassium/calcium exchanger), member 2 |
| 220979_s_at | ST6GALNAC5 | st6 (alpha-n-acetyl-neuraminyl-2,3-beta-galactosyl-1,3)-n-acetylgalactosaminide alpha-2,6-sialyltransferase 5 |
| 221038_at | — | — |
| 221155_x_at | — | — |
| 221204_s_at | CRTAC1 | cartilage acidic protein 1 |
| 221425_s_at | ISCA1 | iron-sulfur cluster assembly 1 homolog (s. cerevisiae) |
| 221770_at | RPE | ribulose-5-phosphate-3-epimerase |
| 37079_at | NUS1P3 | nuclear undecaprenyl pyrophosphate synthase 1 homolog (s. cerevisiae) pseudogene 3 |

TABLE J

Hair Count Actives Gene Studies to Generate the Matrix; Up Genes (BJ Table)

| Mx BJ UP Affy ID | Gene Symbol | Title |
|---|---|---|
| 200035_at | CTDNEP1 | ctd nuclear envelope phosphatase 1 |
| 201350_at | FLOT2 | flotillin 2 |
| 201553_s_at | LAMP1 | lysosomal-associated membrane protein 1 |
| 201671_x_at | USP14 | ubiquitin specific peptidase 14 (trna-guanine transglycosylase) |
| 201674_s_at | AKAP1 | a kinase (prka) anchor protein 1 |
| 201731_s_at | TPR | translocated promoter region (to activated met oncogene) |
| 201882_x_at | B4GALT1 | udp-gal:betaglcnac beta 1,4-galactosyltransferase, polypeptide 1 |
| 201913_s_at | COASY | coa synthase |
| 202102_s_at | BRD4 | bromodomain containing 4 |
| 202685_s_at | AXL | axl receptor tyrosine kinase |
| 202715_at | CAD | carbamoyl-phosphate synthetase 2, aspartate transcarbamylase, and dihydroorotase |
| 202898_at | SDC3 | syndecan 3 |
| 203168_at | ATF6B | activating transcription factor 6 beta |
| 203308_x_at | HPS1 | hermansky-pudlak syndrome 1 |
| 203329_at | PTPRM | protein tyrosine phosphatase, receptor type, m |
| 203419_at | MLL4 | myeloid/lymphoid or mixed-lineage leukemia 4 |
| 203424_s_at | IGFBP5 | insulin-like growth factor binding protein 5 |
| 203444_s_at | MTA2 | metastasis associated 1 family, member 2 |
| 203600_s_at | FAM193A | family with sequence similarity 193, member a |
| 203782_s_at | POLRMT | polymerase (rna) mitochondrial (dna directed) |
| 203793_x_at | PCGF2 | polycomb group ring finger 2 |
| 203797_at | VSNL1 | visinin-like 1 |
| 203808_at | AKT2 | v-akt murine thymoma viral oncogene homolog 2 |
| 203915_at | CXCL9 | chemokine (c—x—c motif) ligand 9 |
| 203917_at | CXADR | coxsackie virus and adenovirus receptor |
| 203952_at | ATF6 | activating transcription factor 6 |
| 203965_at | USP20 | ubiquitin specific peptidase 20 |
| 204144_s_at | PIGQ | phosphatidylinositol glycan anchor biosynthesis, class q |
| 204799_at | ZBED4 | zinc finger, bed-type containing 4 |
| 204907_s_at | BCL3 | b-cell cll/lymphoma 3 |
| 205103_at | C1ORF61 | chromosome 1 open reading frame 61 |
| 205249_at | EGR2 | early growth response 2 |
| 205295_at | CKMT2 | creatine kinase, mitochondrial 2 (sarcomeric) |
| 205322_s_at | MTF1 | metal-regulatory transcription factor 1 |
| 205323_s_at | MTF1 | metal-regulatory transcription factor 1 |
| 205469_s_at | IRF5 | interferon regulatory factor 5 |
| 205524_s_at | HAPLN1 | hyaluronan and proteoglycan link protein 1 |
| 205783_at | KLK13 | kallikrein-related peptidase 13 |
| 206171_at | ADORA3 | adenosine a3 receptor |
| 206187_at | PTGIR | prostaglandin i2 (prostacyclin) receptor (ip) |
| 206264_at | GPLD1 | glycosylphosphatidylinositol specific phospholipase d1 |
| 206789_s_at | POU2F1 | pou class 2 homeobox 1 |
| 206791_s_at | PDE4C | phosphodiesterase 4c, camp-specific |
| 206793_at | PNMT | phenylethanolamine n-methyltransferase |
| 206929_s_at | NFIC | nuclear factor i/c (ccaat-binding transcription factor) |
| 206978_at | CCR2 | chemokine (c-c motif) receptor 2 |
| 206994_at | CST4 | cystatin s |
| 207075_at | NLRP3 | nlr family, pyrin domain containing 3 |
| 207133_x_at | ALPK1 | alpha-kinase 1 |
| 207206_s_at | ALOX12 | arachidonate 12-lipoxygenase |
| 207255_at | LEPR | leptin receptor |
| 207258_at | DSCR4 | down syndrome critical region gene 4 |
| 207343_at | LYZL6 | lysozyme-like 6 |
| 207555_s_at | TBXA2R | thromboxane a2 receptor |
| 207600_at | KCNC3 | potassium voltage-gated channel, shaw-related subfamily, member 3 |
| 207636_at | SERPINI2 | serpin peptidase inhibitor, clade i (pancpin), member 2 |
| 207801_s_at | RNF10 | ring finger protein 10 |
| 207839_s_at | TMEM8B | transmembrane protein 8b |
| 207976_at | KLHL18 | kelch-like 18 (*drosophila*) |
| 207990_x_at | ACRV1 | acrosomal vesicle protein 1 |
| 208161_s_at | ABCC3 | atp-binding cassette, sub-family c (cftr/mrp), member 3 |
| 208205_at | PCDHA9 | protocadherin alpha 9 |
| 208376_at | CCR4 | chemokine (c-c motif) receptor 4 |
| 208390_s_at | GLP1R | glucagon-like peptide 1 receptor |
| 208464_at | GRIA4 | glutamate receptor, ionotrophic, ampa 4 |
| 208466_at | RAB3D | rab3d, member ras oncogene family |
| 208685_x_at | BRD2 | bromodomain containing 2 |
| 208890_s_at | PLXNB2 | plexin b2 |
| 209094_at | DDAH1 | dimethylarginine dimethylaminohydrolase 1 |

TABLE J-continued

Hair Count Actives Gene Studies to Generate the Matrix; Up Genes
(BJ Table)

| Mx BJ UP Affy ID | Gene Symbol | Title |
| --- | --- | --- |
| 209235_at | CLCN7 | chloride channel 7 |
| 209367_at | STXBP2 | syntaxin binding protein 2 |
| 209423_s_at | PHF20 | phd finger protein 20 |
| 209441_at | RHOBTB2 | rho-related btb domain containing 2 |
| 209500_x_at | TNFSF13 | tnfsf12-tnfsf13 readthrough /// tumor necrosis factor (ligand) superfamily, member 13 |
| 209530_at | CACNB3 | calcium channel, voltage-dependent, beta 3 subunit |
| 209637_s_at | RGS12 | regulator of g-protein signaling 12 |
| 209777_s_at | SLC19A1 | solute carrier family 19 (folate transporter), member 1 |
| 210172_at | SF1 | splicing factor 1 |
| 210273_at | PCDH7 | protocadherin 7 |
| 210469_at | DLG5 | discs, large homolog 5 (*drosophila*) |
| 210495_x_at | FN1 | fibronectin 1 |
| 210689_at | CLDN14 | claudin 14 |
| 210750_s_at | DLGAP1 | discs, large (*drosophila*) homolog-associated protein 1 |
| 210872_x_at | GAS7 | growth arrest-specific 7 |
| 211074_at | FOLR1 | folate receptor 1 (adult) |
| 211112_at | SLC12A4 | solute carrier family 12 (potassium/chloride transporters), member 4 |
| 211171_s_at | PDE10A | phosphodiesterase 10a |
| 211280_s_at | NRF1 | nuclear respiratory factor 1 |
| 211295_x_at | CYP2A6 | cytochrome p450, family 2, subfamily a, polypeptide 6 |
| 211301_at | KCND3 | potassium voltage-gated channel, shal-related subfamily, member 3 |
| 211402_x_at | NR6A1 | nuclear receptor subfamily 6, group a, member 1 |
| 211417_x_at | GGT1 | gamma-glutamyltransferase 1 |
| 211484_s_at | DSCAM | down syndrome cell adhesion molecule |
| 212001_at | SUGP2 | surp and g patch domain containing 2 |
| 212103_at | KPNA6 | karyopherin alpha 6 (importin alpha 7) |
| 212351_at | EIF2B5 | eukaryotic translation initiation factor 2b, subunit 5 epsilon, 82 kda |
| 212576_at | MGRN1 | mahogunin, ring finger 1 |
| 212933_x_at | RPL13 | ribosomal protein l13 |
| 213307_at | SHANK2 | sh3 and multiple ankyrin repeat domains 2 |
| 213448_at | — | — |
| 213770_at | KSR1 | kinase suppressor of ras 1 |
| 213811_x_at | TCF3 | transcription factor 3 (e2a immunoglobulin enhancer binding factors e12/e47) |
| 213854_at | SYNGR1 | synaptogyrin 1 |
| 213890_x_at | RPS16 | ribosomal protein s16 |
| 213897_s_at | MRPL23 | mitochondrial ribosomal protein l23 |
| 213948_x_at | CADM3 | cell adhesion molecule 3 |
| 214004_s_at | VGLL4 | vestigial like 4 (*drosophila*) |
| 214014_at | CDC42EP2 | cdc42 effector protein (rho gtpase binding) 2 |
| 214058_at | MYCL1 | v-myc myelocytomatosis viral oncogene homolog 1, lung carcinoma derived (avian) |
| 214069_at | ACSM2A | acyl-coa synthetase medium-chain family member 2a /// acyl-coa synthetase medium-chain family member 2b |
| 214088_s_at | FUT3 | fucosyltransferase 3 (galactoside 3(4)-1-fucosyltransferase, lewis blood group) |
| 214373_at | — | — |
| 214471_x_at | LHB | luteinizing hormone beta polypeptide |
| 214495_at | CACNG2 | calcium channel, voltage-dependent, gamma subunit 2 |
| 214748_at | N4BP2L2 | nedd4 binding protein 2-like 2 |
| 214757_at | PMS2L2 | postmeiotic segregation increased 2-like 2 pseudogene |
| 214953_s_at | APP | amyloid beta (a4) precursor protein |
| 214968_at | DDX51 | dead (asp-glu-ala-asp) box polypeptide 51 |
| 215105_at | CG030 | hypothetical cg030 |
| 215121_x_at | IGLC7 | immunoglobulin lambda constant 7 /// immunoglobulin lambda variable 1-44 /// immunoglobulin lambda light chain-like |
| 215419_at | ZFR2 | zinc finger rna binding protein 2 |
| 215421_at | LOC100131510 | hypothetical loc100131510 |
| 215496_at | SAMD4A | sterile alpha motif domain containing 4a |
| 215860_at | SYT12 | synaptotagmin xii |
| 215864_at | — | — |
| 215927_at | ARFGEF2 | adp-ribosylation factor guanine nucleotide-exchange factor 2 (brefeldin a-inhibited) |
| 215938_s_at | PLA2G6 | phospholipase a2, group vi (cytosolic, calcium-independent) |
| 216034_at | ZNF280A | zinc finger protein 280a |
| 216042_at | TNFRSF25 | tumor necrosis factor receptor superfamily, member 25 |
| 216063_at | HBBP1 | hemoglobin, beta pseudogene 1 |
| 216081_at | LAMA4 | laminin, alpha 4 |

TABLE J-continued

Hair Count Actives Gene Studies to Generate the Matrix; Up Genes
(BJ Table)

| Mx BJ UP Affy ID | Gene Symbol | Title |
|---|---|---|
| 216114_at | NCKIPSD | nck interacting protein with sh3 domain |
| 216354_at | — | — |
| 216372_at | — | — |
| 216658_at | — | — |
| 216738_at | — | — |
| 216811_at | — | — |
| 217003_s_at | ADAM5P | adam metallopeptidase domain 5, pseudogene |
| 217153_at | ARHGAP1 | rho gtpase activating protein 1 |
| 218072_at | COMMD9 | comm domain containing 9 |
| 218275_at | SLC25A10 | solute carrier family 25 (mitochondrial carrier; dicarboxylate transporter), member 10 |
| 218441_s_at | RPAP1 | rna polymerase ii associated protein 1 |
| 218554_s_at | ASH1L | ash1 (absent, small, or homeotic)-like (*drosophila*) |
| 218665_at | FZD4 | frizzled homolog 4 (*drosophila*) |
| 218727_at | SLC38A7 | solute carrier family 38, member 7 |
| 218741_at | CENPM | centromere protein m |
| 218742_at | NARFL | nuclear prelamin a recognition factor-like |
| 218873_at | GON4L | gon-4-like (*c. elegans*) |
| 218920_at | FAM193B | family with sequence similarity 193, member b |
| 218944_at | PYCRL | pyrroline-5-carboxylate reductase-like |
| 219280_at | BRWD1 | bromodomain and wd repeat domain containing 1 |
| 219323_s_at | IL18BP | interleukin 18 binding protein |
| 219434_at | TREM1 | triggering receptor expressed on myeloid cells 1 |
| 219508_at | GCNT3 | glucosaminyl (n-acetyl) transferase 3, mucin type |
| 219745_at | TMEM180 | transmembrane protein 180 |
| 219754_at | RBM41 | rna binding motif protein 41 |
| 219755_at | CBX8 | chromobox homolog 8 |
| 219838_at | TTC23 | tetratricopeptide repeat domain 23 |
| 219866_at | CLIC5 | chloride intracellular channel 5 |
| 219963_at | DUSP13 | dual specificity phosphatase 13 |
| 219999_at | MAN2A2 | mannosidase, alpha, class 2a, member 2 |
| 220131_at | FXYD7 | fxyd domain containing ion transport regulator 7 |
| 220208_at | ADAMTS13 | adam metallopeptidase with thrombospondin type 1 motif, 13 |
| 220463_at | TRPM3 | transient receptor potential cation channel, subfamily m, member 3 |
| 220470_at | BET1L | blocked early in transport 1 homolog (*s. cerevisiae*)-like |
| 220541_at | MMP26 | matrix metallopeptidase 26 |
| 220689_at | — | — |
| 220727_at | KCNK10 | potassium channel, subfamily k, member 10 |
| 220788_s_at | RNF31 | ring finger protein 31 |
| 220820_at | — | — |
| 220853_at | GTDC1 | glycosyltransferase-like domain containing 1 |
| 220923_s_at | PNMA3 | paraneoplastic antigen ma3 |
| 221300_at | C15ORF2 | chromosome 15 open reading frame 2 |
| 221324_at | TAS2R1 | taste receptor, type 2, member 1 |
| 221344_at | OR12D2 | olfactory receptor, family 12, subfamily d, member 2 |
| 221655_x_at | EPS8L1 | eps8-like 1 |
| 221683_s_at | CEP290 | centrosomal protein 290 kda |
| 221745_at | DCAF7 | ddb1 and cul4 associated factor 7 |
| 221820_s_at | MYST1 | myst histone acetyltransferase 1 |
| 221857_s_at | TJAP1 | tight junction associated protein 1 (peripheral) |
| 221867_at | N4BP1 | nedd4 binding protein 1 |
| 32029_at | PDPK1 | 3-phosphoinositide dependent protein kinase-1 |
| 34260_at | TELO2 | tel2, telomere maintenance 2, homolog (*s. cerevisiae*) |
| 35671_at | GTF3C1 | general transcription factor iiic, polypeptide 1, alpha 220 kda |
| 46947_at | GNL3L | guanine nucleotide binding protein-like 3 (nucleolar)-like |

TABLE K

Hair Count Actives Gene Studies to Generate the Matrix; Down Genes
(Keratinocyte Table)

| Mx tKC Down Affy ID | Gene Symbol | Title |
|---|---|---|
| 200927_s_at | RAB14 | rab14, member ras oncogene family |
| 201196_s_at | AMD1 | adenosylmethionine decarboxylase 1 |
| 201292_at | TOP2A | topoisomerase (dna) ii alpha 170 kda |

TABLE K-continued

Hair Count Actives Gene Studies to Generate the Matrix; Down Genes
(Keratinocyte Table)

| Mx tKC Down Affy ID | Gene Symbol | Title |
|---|---|---|
| 201370_s_at | CUL3 | cullin 3 |
| 201436_at | EIF4E | eukaryotic translation initiation factor 4e |
| 202126_at | PRPF4B | prp4 pre-mrna processing factor 4 homolog b (yeast) |
| 202162_s_at | CNOT8 | ccr4-not transcription complex, subunit 8 |
| 202240_at | PLK1 | polo-like kinase 1 |
| 202254_at | SIPA1L1 | signal-induced proliferation-associated 1 like 1 |
| 202392_s_at | PISD | phosphatidylserine decarboxylase |
| 202417_at | KEAP1 | kelch-like ech-associated protein 1 |
| 202463_s_at | MBD3 | methyl-cpg binding domain protein 3 |
| 202506_at | SSFA2 | sperm specific antigen 2 |
| 202547_s_at | ARHGEF7 | rho guanine nucleotide exchange factor (gef) 7 |
| 202571_s_at | DLGAP4 | discs, large (*drosophila*) homolog-associated protein 4 |
| 202849_x_at | GRK6 | g protein-coupled receptor kinase 6 |
| 202970_at | DYRK2 | dual-specificity tyrosine-(y)-phosphorylation regulated kinase 2 |
| 203089_s_at | HTRA2 | htra serine peptidase 2 |
| 203244_at | PEX5 | peroxisomal biogenesis factor 5 |
| 203394_s_at | HES1 | hairy and enhancer of split 1, (*drosophila*) |
| 203504_s_at | ABCA1 | atp-binding cassette, sub-family a (abc1), member 1 |
| 203505_at | ABCA1 | atp-binding cassette, sub-family a (abc1), member 1 |
| 203652_at | MAP3K11 | mitogen-activated protein kinase kinase kinase 11 |
| 203705_s_at | FZD7 | frizzled homolog 7 (*drosophila*) |
| 203837_at | MAP3K5 | mitogen-activated protein kinase kinase 5 |
| 203901_at | TAB1 | tgf-beta activated kinase 1/map3k7 binding protein 1 |
| 203906_at | IQSEC1 | iq motif and sec7 domain 1 |
| 203976_s_at | CHAF1A | chromatin assembly factor 1, subunit a (p150) |
| 204088_at | P2RX4 | purinergic receptor p2x, ligand-gated ion channel, 4 |
| 204096_s_at | ELL | elongation factor rna polymerase ii |
| 204109_s_at | NFYA | nuclear transcription factor y, alpha |
| 204178_s_at | RBM14 | rna binding motif protein 14 |
| 204241_at | ACOX3 | acyl-coa oxidase 3, pristanoyl |
| 204244_s_at | DBF4 | dbf4 homolog (*s. cerevisiae*) |
| 204367_at | SP2 | sp2 transcription factor |
| 204370_at | CLP1 | clp1, cleavage and polyadenylation factor i subunit, homolog (*s. cerevisiae*) |
| 204407_at | TTF2 | transcription termination factor, rna polymerase ii |
| 204434_at | SPATA2 | spermatogenesis associated 2 |
| 204477_at | RABIF | rab interacting factor |
| 204529_s_at | TOX | thymocyte selection-associated high mobility group box |
| 204827_s_at | CCNF | cyclin f |
| 204859_s_at | APAF1 | apoptotic peptidase activating factor 1 |
| 204884_s_at | HUS1 | hus1 checkpoint homolog (*s. pombe*) |
| 204886_at | PLK4 | polo-like kinase 4 |
| 205018_s_at | MBNL2 | muscleblind-like 2 (*drosophila*) |
| 205250_s_at | CEP290 | centrosomal protein 290 kda |
| 205279_s_at | GLRB | glycine receptor, beta |
| 205284_at | URB2 | urb2 ribosome biogenesis 2 homolog (*s. cerevisiae*) |
| 205339_at | STIL | scl/tal1 interrupting locus |
| 205379_at | CBR3 | carbonyl reductase 3 |
| 205646_s_at | PAX6 | paired box 6 |
| 205659_at | HDAC9 | histone deacetylase 9 |
| 205705_at | ANKRD26 | ankyrin repeat domain 26 |
| 206240_s_at | ZNF136 | zinc finger protein 136 |
| 206314_at | ZNF167 | zinc finger protein 167 |
| 206332_s_at | IFI16 | interferon, gamma-inducible protein 16 |
| 206382_s_at | BDNF | brain-derived neurotrophic factor |
| 206907_at | TNFSF9 | tumor necrosis factor (ligand) superfamily, member 9 |
| 207181_s_at | CASP7 | caspase 7, apoptosis-related cysteine peptidase |
| 207219_at | ZNF643 | zinc finger protein 643 |
| 207247_s_at | ZFX | zinc finger protein, x-linked /// zinc finger protein, y-linked |
| 207558_s_at | PITX2 | paired-like homeodomain 2 |
| 207624_s_at | RPGR | retinitis pigmentosa gtpase regulator |
| 207845_s_at | ANAPC10 | anaphase promoting complex subunit 10 |
| 207980_s_at | CITED2 | cbp/p300-interacting transactivator, with glu/asp-rich carboxy-terminal domain, 2 |
| 208995_s_at | PPIG | peptidylprolyl isomerase g (cyclophilin g) |
| 209112_at | CDKN1B | cyclin-dependent kinase inhibitor 1b (p27, kip1) |
| 209172_at | CENPF | centromere protein f, 350/400 kda (mitosin) |
| 209288_s_at | CDC42EP3 | cdc42 effector protein (rho gtpase binding) 3 |
| 209378_s_at | FAM190B | family with sequence similarity 190, member b |
| 209390_at | TSC1 | tuberous sclerosis 1 |
| 209475_at | USP15 | ubiquitin specific peptidase 15 |
| 209535_s_at | — | — |

TABLE K-continued

Hair Count Actives Gene Studies to Generate the Matrix; Down Genes (Keratinocyte Table)

| Mx tKC Down Affy ID | Gene Symbol | Title |
|---|---|---|
| 209602_s_at | GATA3 | gata binding protein 3 |
| 209891_at | SPC25 | spc25, ndc80 kinetochore complex component, homolog (*s. cerevisiae*) |
| 210023_s_at | PCGF1 | polycomb group ring finger 1 |
| 210160_at | PAFAH1B2 | platelet-activating factor acetylhydrolase 1b, catalytic subunit 2 (30 kda) |
| 210826_x_at | RAD17 | rad17 homolog (*s. pombe*) |
| 211373_s_at | PSEN2 | presenilin 2 (alzheimer disease 4) |
| 212289_at | ANKRD12 | ankyrin repeat domain 12 |
| 212355_at | KHNYN | kh and nyn domain containing |
| 212407_at | METTL13 | methyltransferase like 13 |
| 212603_at | MRPS31 | mitochondrial ribosomal protein s31 |
| 212711_at | CAMSAP1 | calmodulin regulated spectrin-associated protein 1 |
| 212970_at | APBB2 | amyloid beta (a4) precursor protein-binding, family b, member 2 |
| 212985_at | APBB2 | amyloid beta (a4) precursor protein-binding, family b, member 2 |
| 213118_at | UHRF1BP1L | uhrf1 binding protein 1-like |
| 213206_s_at | GOSR2 | golgi snap receptor complex member 2 |
| 213324_at | SRC | v-src sarcoma (schmidt-ruppin a-2) viral oncogene homolog (avian) |
| 213455_at | FAM114A1 | family with sequence similarity 114, member a1 |
| 213526_s_at | LIN37 | lin-37 homolog (*c. elegans*) |
| 213656_s_at | KLC1 | kinesin light chain 1 |
| 213677_s_at | PMS1 | pms1 postmeiotic segregation increased 1 (*s. cerevisiae*) |
| 213861_s_at | FAM119B | family with sequence similarity 119, member b |
| 213929_at | EXPH5 | exophilin 5 |
| 214130_s_at | PDE4DIP | phosphodiesterase 4d interacting protein |
| 214144_at | POLR2D | polymerase (rna) ii (dna directed) polypeptide d |
| 214237_x_at | PAWR | prkc, apoptosis, wt1, regulator |
| 214252_s_at | CLN5 | ceroid-lipofuscinosis, neuronal 5 |
| 214525_x_at | MLH3 | mutl homolog 3 (*e. coli*) |
| 214604_at | HOXD11 | homeobox d11 |
| 214666_x_at | IREB2 | iron-responsive element binding protein 2 |
| 214684_at | MEF2A | myocyte enhancer factor 2a |
| 214710_s_at | CCNB1 | cyclin b1 |
| 214867_at | — | — |
| 214943_s_at | RBM34 | at rich interactive domain 4b (rbp1-like) /// rna binding motif protein 34 |
| 215073_s_at | NR2F2 | nuclear receptor subfamily 2, group f, member 2 |
| 215926_x_at | SNAPC4 | small nuclear rna activating complex, polypeptide 4, 190 kda |
| 216060_s_at | DAAM1 | dishevelled associated activator of morphogenesis 1 |
| 216713_at | KRIT1 | krit1, ankyrin repeat containing |
| 216913_s_at | RRP12 | ribosomal rna processing 12 homolog (*s. cerevisiae*) |
| 217125_at | — | — |
| 217144_at | UBB | ubiquitin b |
| 217579_x_at | — | — |
| 217864_s_at | PIAS1 | protein inhibitor of activated stat, 1 |
| 217888_s_at | ARFGAP1 | adp-ribosylation factor gtpase activating protein 1 |
| 217955_at | BCL2L13 | bcl2-like 13 (apoptosis facilitator) |
| 218043_s_at | AZI2 | 5-azacytidine induced 2 |
| 218199_s_at | NOL6 | nucleolar protein family 6 (rna-associated) |
| 218308_at | TACC3 | transforming, acidic coiled-coil containing protein 3 |
| 218319_at | PELI1 | pellino homolog 1 (*drosophila*) |
| 218402_s_at | HPS4 | hermansky-pudlak syndrome 4 |
| 218419_s_at | TMUB2 | transmembrane and ubiquitin-like domain containing 2 |
| 218528_s_at | RNF38 | ring finger protein 38 |
| 218631_at | AVPI1 | arginine vasopressin-induced 1 |
| 218712_at | C1ORF109 | chromosome 1 open reading frame 109 |
| 218846_at | MED23 | mediator complex subunit 23 |
| 218862_at | ASB13 | ankyrin repeat and socs box-containing 13 |
| 218875_s_at | FBXO5 | f-box protein 5 |
| 218895_at | GPATCH3 | g patch domain containing 3 |
| 218913_s_at | GMIP | gem interacting protein |
| 218937_at | ZNF434 | zinc finger protein 434 |
| 219031_s_at | NIP7 | nuclear import 7 homolog (*s. cerevisiae*) |
| 219086_at | ZNF839 | zinc finger protein 839 |
| 219242_at | CEP63 | centrosomal protein 63 kda |
| 219286_s_at | RBM15 | rna binding motif protein 15 |
| 219299_at | TRMT12 | trna methyltransferase 12 homolog (*s. cerevisiae*) |
| 219315_s_at | TMEM204 | transmembrane protein 204 |
| 219340_s_at | CLN8 | ceroid-lipofuscinosis, neuronal 8 (epilepsy, progressive with mental retardation) |

TABLE K-continued

Hair Count Actives Gene Studies to Generate the Matrix; Down Genes
(Keratinocyte Table)

| Mx tKC Down Affy ID | Gene Symbol | Title |
|---|---|---|
| 219388_at | GRHL2 | grainyhead-like 2 (*drosophila*) |
| 219673_at | MCM9 | minichromosome maintenance complex component 9 |
| 219787_s_at | ECT2 | epithelial cell transforming sequence 2 oncogene |
| 219817_at | C12ORF47 | chromosome 12 open reading frame 47 |
| 220102_at | FOXL2 | forkhead box l2 |
| 220153_at | ENTPD7 | ectonucleoside triphosphate diphosphohydrolase 7 |
| 220729_at | — | — |
| 220853_at | GTDC1 | glycosyltransferase-like domain containing 1 |
| 221012_s_at | TRIM8 | tripartite motif-containing 8 |
| 221016_s_at | TCF7L1 | transcription factor 7-like 1 (t-cell specific, hmg-box) |
| 221044_s_at | TRIM34 | tripartite motif-containing 34 /// trim6-trim34 readthrough |
| 221258_s_at | KIF18A | kinesin family member 18a |
| 221520_s_at | CDCA8 | cell division cycle associated 8 |
| 221528_s_at | ELMO2 | engulfment and cell motility 2 |
| 221571_at | TRAF3 | tnf receptor-associated factor 3 |
| 221621_at | C17ORF86 | chromosome 17 open reading frame 86 |
| 221818_at | INTS5 | integrator complex subunit 5 |
| 221848_at | ZGPAT | zinc finger, ccch-type with g patch domain |
| 221864_at | ORAI3 | orai calcium release-activated calcium modulator 3 |
| 222136_x_at | ZNF43 | zinc finger protein 43 |
| 31826_at | FKBP15 | fk506 binding protein 15, 133 kda |
| 37793_r_at | RAD51L3 | rad51-like 3 (*s. cerevisiae*) |
| 40255_at | DDX28 | dead (asp-glu-ala-asp) box polypeptide 28 |
| 41037_at | TEAD4 | tea domain family member 4 |
| 45633_at | GINS3 | gins complex subunit 3 (psf3 homolog) |
| 46323_at | CANT1 | calcium activated nucleotidase 1 |
| 48825_at | ING4 | inhibitor of growth family, member 4 |
| 50400_at | PAOX | polyamine oxidase (exo-n4-amino) |

TABLE L

Hair Count Actives Gene Studies to Generate the Matrix; Up Genes
(Keratinocyte Table)

| Mx tKC UP Affy ID | Gene Symbol | Title |
|---|---|---|
| 200012_x_at | RPL21 | ribosomal protein l21 |
| 200022_at | RPL18 | ribosomal protein l18 |
| 200024_at | RPS5 | ribosomal protein s5 |
| 200026_at | RPL34 | ribosomal protein l34 |
| 200081_s_at | RPS6 | ribosomal protein s6 |
| 200088_x_at | RPL12 | ribosomal protein l12 |
| 200674_s_at | RPL32 | ribosomal protein l32 |
| 200735_x_at | NACA | nascent polypeptide-associated complex alpha subunit |
| 200763_s_at | RPLP1 | ribosomal protein, large, p1 |
| 200781_s_at | RPS15A | ribosomal protein s15a |
| 200801_x_at | ACTB | actin, beta |
| 200933_x_at | RPS4X | ribosomal protein s4, x-linked |
| 200949_x_at | RPS20 | ribosomal protein s20 |
| 201039_s_at | RAD23A | rad23 homolog a (*s. cerevisiae*) |
| 201049_s_at | RPS18 | ribosomal protein s18 |
| 201134_x_at | COX7C | cytochrome c oxidase subunit viic |
| 201171_at | ATP6V0E1 | atpase, h+ transporting, lysosomal 9 kda, v0 subunit e1 |
| 201289_at | CYR61 | cysteine-rich, angiogenic inducer, 61 |
| 201530_x_at | EIF4A1 | eukaryotic translation initiation factor 4a1 |
| 201621_at | NBL1 | neuroblastoma, suppression of tumorigenicity 1 |
| 201665_x_at | RPS17 | ribosomal protein s17 |
| 201728_s_at | KIAA0100 | kiaa0100 |
| 201793_x_at | SMG7 | smg-7 homolog, nonsense mediated mrna decay factor (*c. elegans*) |
| 201891_s_at | B2M | beta-2-microglobulin |
| 202067_s_at | LDLR | low density lipoprotein receptor |
| 202102_s_at | BRD4 | bromodomain containing 4 |
| 202192_s_at | GAS7 | growth arrest-specific 7 |
| 202210_x_at | GSK3A | glycogen synthase kinase 3 alpha |
| 202482_x_at | RANBP1 | ran binding protein 1 |
| 202590_s_at | PDK2 | pyruvate dehydrogenase kinase, isozyme 2 |
| 202648_at | — | — |
| 202729_s_at | LTBP1 | latent transforming growth factor beta binding protein 1 |

TABLE L-continued

Hair Count Actives Gene Studies to Generate the Matrix; Up Genes
(Keratinocyte Table)

| Mx tKC UP Affy ID | Gene Symbol | Title |
|---|---|---|
| 203130_s_at | KIF5C | kinesin family member 5c |
| 203168_at | ATF6B | activating transcription factor 6 beta |
| 203657_s_at | CTSF | cathepsin f |
| 203666_at | CXCL12 | chemokine (c—x—c motif) ligand 12 |
| 203878_s_at | MMP11 | matrix metallopeptidase 11 (stromelysin 3) |
| 204431_at | TLE2 | transducin-like enhancer of split 2 (e(sp1) homolog, drosophila) |
| 204556_s_at | DZIP1 | daz interacting protein 1 |
| 204833_at | ATG12 | atg12 autophagy related 12 homolog (s. cerevisiae) |
| 204843_s_at | PRKAR2A | protein kinase, camp-dependent, regulatory, type ii, alpha |
| 204863_s_at | IL6ST | interleukin 6 signal transducer (gp130, oncostatin m receptor) |
| 204981_at | SLC22A18 | solute carrier family 22, member 18 |
| 205158_at | RNASE4 | ribonuclease, rnase a family, 4 |
| 205500_at | C5 | complement component 5 |
| 205614_x_at | MST1 | macrophage stimulating 1 (hepatocyte growth factor-like) |
| 206216_at | SRPK3 | srsf protein kinase 3 |
| 206455_s_at | RHO | rhodopsin |
| 206635_at | CHRNB2 | cholinergic receptor, nicotinic, beta 2 (neuronal) |
| 206686_at | PDK1 | pyruvate dehydrogenase kinase, isozyme 1 |
| 206832_s_at | SEMA3F | sema domain, immunoglobulin domain (ig), short basic domain, secreted, (semaphorin) 3f |
| 206850_at | RASL10A | ras-like, family 10, member a |
| 207041_at | MASP2 | mannan-binding lectin serine peptidase 2 |
| 207078_at | MED6 | mediator complex subunit 6 |
| 207100_s_at | VAMP1 | vesicle-associated membrane protein 1 (synaptobrevin 1) |
| 207227_x_at | RFPL2 | ret finger protein-like 2 |
| 207287_at | FLJ14107 | hypothetical loc80094 |
| 207357_s_at | GALNT10 | udp-n-acetyl-alpha-d-galactosamine:polypeptide n-acetylgalactosaminyltransferase 10 (galnac-t10) |
| 207657_x_at | TNPO1 | transportin 1 |
| 207801_s_at | RNF10 | ring finger protein 10 |
| 208138_at | GAST | gastrin |
| 208187_s_at | — | — |
| 208540_x_at | S100A11 | s100 calcium binding protein a11 |
| 208624_s_at | EIF4G1 | eukaryotic translation initiation factor 4 gamma, 1 |
| 208629_s_at | HADHA | hydroxyacyl-coa dehydrogenase/3-ketoacyl-coa thiolase/enoyl-coa hydratase (trifunctional protein), alpha subunit |
| 208645_s_at | RPS14 | ribosomal protein s14 |
| 208661_s_at | TTC3 | tetratricopeptide repeat domain 3 |
| 208668_x_at | HMGN2 | high-mobility group nucleosomal binding domain 2 |
| 208704_x_at | APLP2 | amyloid beta (a4) precursor-like protein 2 |
| 208790_s_at | PTRF | polymerase i and transcript release factor |
| 208906_at | BSCL2 | berardinelli-seip congenital lipodystrophy 2 (seipin) |
| 208929_x_at | RPL13 | ribosomal protein l13 |
| 209226_s_at | TNPO1 | transportin 1 |
| 209251_x_at | TUBA1C | tubulin, alpha 1c |
| 209539_at | ARHGEF6 | rac/cdc42 guanine nucleotide exchange factor (gef) 6 |
| 210226_at | NR4A1 | nuclear receptor subfamily 4, group a, member 1 |
| 210513_s_at | VEGFA | vascular endothelial growth factor a |
| 210704_at | FEZ2 | fasciculation and elongation protein zeta 2 (zygin ii) |
| 210764_s_at | CYR61 | cysteine-rich, angiogenic inducer, 61 |
| 210867_at | CNOT4 | ccr4-not transcription complex, subunit 4 |
| 211398_at | FGFR2 | fibroblast growth factor receptor 2 |
| 211454_x_at | FKSG49 | fksg49 |
| 211487_x_at | RPS17 | 40s ribosomal protein s17-like /// ribosomal protein s17 |
| 211809_x_at | COL13A1 | collagen, type xiii, alpha 1 |
| 211972_x_at | RPLPO | ribosomal protein, large, p0 |
| 212082_s_at | MYL6 | myosin, light chain 6, alkali, smooth muscle and non-muscle |
| 212089_at | LMNA | lamin a/c |
| 212236_x_at | KRT17 | keratin 17 |
| 212270_x_at | RPL17 | ribosomal protein l17 |
| 212433_x_at | RPS2 | ribosomal protein s2 |
| 212451_at | SECISBP2L | secis binding protein 2-like |
| 212537_x_at | RPL17 | ribosomal protein l17 |
| 212578_x_at | RPS17 | 40s ribosomal protein s17-like /// ribosomal protein s17 |

TABLE L-continued

Hair Count Actives Gene Studies to Generate the Matrix; Up Genes
(Keratinocyte Table)

| Mx tKC UP Affy ID | Gene Symbol | Title |
| --- | --- | --- |
| 212808_at | NFATC2IP | nuclear factor of activated t-cells, cytoplasmic, calcineurin-dependent 2 interacting protein |
| 212933_x_at | RPL13 | ribosomal protein l13 |
| 213015_at | BBX | bobby sox homolog (*drosophila*) |
| 213084_x_at | RPL23A | ribosomal protein l23a |
| 213296_at | RER1 | rer1 retention in endoplasmic reticulum 1 homolog (*s. cerevisiae*) |
| 213356_x_at | HNRNPA1 | heterogeneous nuclear ribonucleoprotein a1 /// heterogeneous nuclear ribonucleoprotein a1-like 2 /// heterogeneous nuclear ribonucleoprotein a1 pseudogene 10 |
| 213414_s_at | RPS19 | ribosomal protein s19 |
| 213564_x_at | LDHB | lactate dehydrogenase b |
| 213791_at | PENK | proenkephalin |
| 213801_x_at | RPSA | ribosomal protein sa |
| 213816_s_at | MET | met proto-oncogene (hepatocyte growth factor receptor) |
| 213827_at | ARHGAP33 | rho gtpase activating protein 33 |
| 213969_x_at | RPL29 | ribosomal protein l29 |
| 213981_at | COMT | catechol-o-methyltransferase |
| 214093_s_at | FUBP1 | far upstream element (fuse) binding protein 1 |
| 214339_s_at | MAP4K1 | mitogen-activated protein kinase kinase kinase kinase 1 |
| 214365_at | TPM3 | tropomyosin 3 |
| 214564_s_at | PCDHGC3 | protocadherin gamma subfamily c, 3 |
| 214635_at | CLDN9 | claudin 9 |
| 214730_s_at | GLG1 | golgi glycoprotein 1 |
| 214953_s_at | APP | amyloid beta (a4) precursor protein |
| 215157_x_at | PABPC1 | poly(a) binding protein, cytoplasmic 1 |
| 215270_at | LFNG | lfng o-fucosylpeptide 3-beta-n-acetylglucosaminyltransferase |
| 215275_at | TRAF3IP3 | traf3 interacting protein 3 |
| 215668_s_at | PLXNB1 | plexin b1 |
| 215683_at | C18ORF22 | chromosome 18 open reading frame 22 |
| 215705_at | PPP5C | protein phosphatase 5, catalytic subunit |
| 215756_at | LOC730227 | hypothetical loc730227 |
| 215866_at | — | — |
| 215893_x_at | — | — |
| 216110_x_at | — | — |
| 216476_at | OR7E87P | similar to seven transmembrane helix receptor /// seven transmembrane helix receptor /// olfactory receptor, family 7, subfamily e, member 87 pseudogene |
| 216621_at | — | — |
| 216882_s_at | NEBL | nebulette |
| 217227_x_at | IGLV1-40 | immunoglobulin lambda variable 1-40 /// immunoglobulin lambda variable 1-44 |
| 217269_s_at | TMPRSS15 | transmembrane protease, serine 15 |
| 217543_s_at | MBTPS1 | membrane-bound transcription factor peptidase, site 1 |
| 217696_at | FUT7 | fucosyltransferase 7 (alpha (1,3) fucosyltransferase) |
| 217802_s_at | NUCKS1 | nuclear casein kinase and cyclin-dependent kinase substrate 1 |
| 217817_at | ARPC4 | actin related protein 2/3 complex, subunit 4, 20 kda |
| 218272_at | TTC38 | tetratricopeptide repeat domain 38 |
| 218427_at | SDCCAG3 | serologically defined colon cancer antigen 3 |
| 218760_at | COQ6 | coenzyme q6 homolog, monooxygenase (*s. cerevisiae*) |
| 218765_at | SIDT2 | sid1 transmembrane family, member 2 |
| 219236_at | PAQR6 | progestin and adipoq receptor family member vi |
| 219268_at | ETNK2 | ethanolamine kinase 2 |
| 219707_at | CPNE7 | copine vii |
| 219784_at | LOC100288525 | hypothetical protein loc100288525 |
| 219825_at | CYP26B1 | cytochrome p450, family 26, subfamily b, polypeptide 1 |
| 219831_at | CDKL3 | cyclin-dependent kinase-like 3 |
| 220010_at | KCNE1L | kcne1-like |
| 220151_at | C19ORF73 | chromosome 19 open reading frame 73 |
| 220182_at | SLC25A23 | solute carrier family 25 (mitochondrial carrier; phosphate carrier), member 23 |
| 220558_x_at | TSPAN32 | tetraspanin 32 |
| 220684_at | TBX21 | t-box 21 |
| 221036_s_at | APH1B | anterior pharynx defective 1 homolog b (*c. elegans*) |
| 221053_s_at | TDRKH | tudor and kh domain containing |
| 221123_x_at | ZNF395 | zinc finger protein 395 |
| 221466_at | P2RY4 | pyrimidinergic receptor p2y, g-protein coupled, 4 |
| 221707_s_at | VPS53 | vacuolar protein sorting 53 homolog (*s. cerevisiae*) |
| 221775_x_at | RPL22 | ribosomal protein l22 |
| 221811_at | PGAP3 | post-gpi attachment to proteins 3 |

TABLE L-continued

Hair Count Actives Gene Studies to Generate the Matrix; Up Genes (Keratinocyte Table)

| Mx tKC UP Affy ID | Gene Symbol | Title |
|---|---|---|
| 221829_s_at | TNPO1 | transportin 1 |
| 222152_at | PDCD6 | programmed cell death 6 |
| 222160_at | AKAP8L | a kinase (prka) anchor protein 8-like |
| 222380_s_at | PDCD6 | programmed cell death 6 |
| 81811_at | — | — |

TABLE M

Monoamine Oxidase B Inhibitor-Related Genes; Down Genes (BJ Table)

| Affy ID | Gene Symbol | Title |
|---|---|---|
| 222359_x_at | KDSR | 3-ketodihydrosphingosine reductase |
| 206201_s_at | MEOX2 | mesenchyme homeobox 2 |
| 217005_at | — | — |
| 217229_at | ASB4 | ankyrin repeat and socs box-containing 4 |
| 220546_at | MLL | myeloid/lymphoid or mixed-lineage leukemia (trithorax homolog, *drosophila*) |
| 211506_s_at | IL8 | interleukin 8 |
| 220793_at | SAGE1 | sarcoma antigen 1 |
| 204712_at | WIF1 | wnt inhibitory factor 1 |
| 210327_s_at | AGXT | alanine-glyoxylate aminotransferase |
| 211900_x_at | CD6 | cd6 molecule |
| 210355_at | PTHLH | parathyroid hormone-like hormone |
| 202833_s_at | SERPINA1 | serpin peptidase inhibitor, clade a (alpha-1 antiproteinase, antitrypsin), member 1 |
| 207850_at | CXCL3 | chemokine (c—x—c motif) ligand 3 |
| 216725_at | DCLK2 | doublecortin-like kinase 2 |
| 211598_x_at | VIPR2 | vasoactive intestinal peptide receptor 2 |
| 211646_at | IGH@ | immunoglobulin heavy locus /// immunoglobulin heavy constant alpha 1 |
| 207195_at | CNTN6 | contactin 6 |
| 210572_at | PCDHA2 | protocadherin alpha 2 |
| 217281_x_at | IGH@ | immunoglobulin heavy locus /// immunoglobulin heavy constant alpha 1 |
| 216030_s_at | SEMG2 | semenogelin ii |
| 206761_at | CD96 | cd96 molecule |
| 203844_at | VHL | von hippel-lindau tumor suppressor |
| 209977_at | PLG | plasminogen |
| 210464_at | C8ORF71 | chromosome 8 open reading frame 71 |
| 208181_at | HIST1H4H | histone cluster 1, h4h |
| 211545_at | GHRHR | growth hormone releasing hormone receptor |
| 208196_x_at | NFATC1 | nuclear factor of activated t-cells, cytoplasmic, calcineurin-dependent 1 |
| 211030_s_at | SLC6A6 | solute carrier family 6 (neurotransmitter transporter, taurine), member 6 |
| 208576_s_at | HIST1H3B | histone cluster 1, h3b |
| 204953_at | SNAP91 | synaptosomal-associated protein, 91 kda homolog (mouse) |
| 217351_at | — | — |
| 208584_at | SNCG | synuclein, gamma (breast cancer-specific protein 1) |
| 208487_at | LMX1B | lim homeobox transcription factor 1, beta |
| 204753_s_at | HLF | hepatic leukemia factor |
| 206070_s_at | EPHA3 | eph receptor a3 |
| 221149_at | GPR77 | g protein-coupled receptor 77 |
| 205332_at | RCE1 | rce1 homolog, prenyl protein peptidase (*s. cerevisiae*) |
| 204006_s_at | FCGR3A | fc fragment of igg, low affinity iiia, receptor (cd16a) /// fc fragment of igg |
| 214999_s_at | RAB11FIP3 | rab11 family interacting protein 3 (class ii) |
| 211740_at | ICA1 | islet cell autoantigen 1, 69 kda |
| 211468_s_at | RECQL5 | recq protein-like 5 |
| 220539_at | C10ORF92 | chromosome 10 open reading frame 92 |
| 210808_s_at | NOX1 | nadph oxidase 1 |
| 217143_s_at | TRA@ | t cell receptor alpha locus /// t cell receptor delta locus |
| 213674_x_at | IGHD | immunoglobulin heavy constant delta |
| 211412_at | PADI4 | peptidyl arginine deiminase, type iv |
| 213660_s_at | TOP3B | topoisomerase (dna) iii beta |
| 220476_s_at | C1ORF183 | chromosome 1 open reading frame 183 |
| 219059_s_at | LYVE1 | lymphatic vessel endothelial hyaluronan receptor 1 |
| 206658_at | UPK3B | uroplakin 3b |
| 205478_at | PPP1R1A | protein phosphatase 1, regulatory (inhibitor) subunit 1a |

TABLE M-continued

Monoamine Oxidase B Inhibitor-Related Genes; Down Genes (BJ Table)

| Affy ID | Gene Symbol | Title |
| --- | --- | --- |
| 215532_x_at | ZNF492 | zinc finger protein 492 |
| 215506_s_at | DIRAS3 | diras family, gtp-binding ras-like 3 |
| 215934_at | — | — |
| 209764_at | MGAT3 | mannosyl (beta-1,4-)-glycoprotein beta-1,4-n-acetylglucosaminyltransferase |
| 216490_x_at | — | — |
| 203601_s_at | ZBTB17 | zinc finger and btb domain containing 17 |
| 220035_at | NUP210 | nucleoporin 210 kda |
| 207673_at | NPHS1 | nephrosis 1, congenital, finnish type (nephrin) |
| 208526_at | OR2F1 | olfactory receptor, family 2, subfamily f, member 1 |
| 210550_s_at | RASGRF1 | ras protein-specific guanine nucleotide-releasing factor 1 |
| 205569_at | LAMP3 | lysosomal-associated membrane protein 3 |
| 217121_at | TNKS | tankyrase, trf1-interacting ankyrin-related adp-ribose polymerase |
| 220747_at | HSPC072 | hypothetical loc29075 |
| 213781_at | LRRC68 | leucine rich repeat containing 68 |
| 211419_s_at | CHN2 | chimerin (chimaerin) 2 |
| 91826_at | EPS8L1 | eps8-like 1 |
| 205906_at | FOXJ1 | forkhead box j1 |
| 210632_s_at | SGCA | sarcoglycan, alpha (50 kda dystrophin-associated glycoprotein) |
| 205242_at | CXCL13 | chemokine (c—x—c motif) ligand 13 |
| 220679_s_at | CDH7 | cadherin 7, type 2 |
| 207230_at | CDON | cdon homolog (mouse) |
| 207963_at | C6ORF54 | chromosome 6 open reading frame 54 |
| 206517_at | CDH16 | cadherin 16, ksp-cadherin |
| 215964_at | — | — |
| 216650_at | — | — |
| 215410_at | PMS2L1 | pms2 postmeiotic segregation increased 2 (*s. cerevisiae*)-like /// |
| 217497_at | TYMP | thymidine phosphorylase |
| 206286_s_at | TDGF1 | teratocarcinoma-derived growth factor 1 /// teratocarcinoma-derived growth factor 3 |
| 208592_s_at | CD1E | cd1e molecule |
| 214388_at | — | — |
| 217662_x_at | — | — |
| 209269_s_at | SYK | spleen tyrosine kinase |
| 215389_s_at | TNNT2 | troponin t type 2 (cardiac) |
| 217288_at | — | — |
| 209924_at | CCL18 | chemokine (c-c motif) ligand 18 (pulmonary and activation-regulated) |
| 211839_s_at | CSF1 | colony stimulating factor 1 (macrophage) |
| 219502_at | NEIL3 | nei endonuclease viii-like 3 (*e. coli*) |
| 213979_s_at | — | — |
| 217067_s_at | DMP1 | dentin matrix acidic phosphoprotein 1 |
| 211865_s_at | FZR1 | fizzy/cell division cycle 20 related 1 (*drosophila*) |
| 210437_at | MAGEA9 | melanoma antigen family a, 9 /// melanoma antigen family a, 9b |
| 206812_at | ADRB3 | adrenergic, beta-3-, receptor |
| 204073_s_at | C11ORF9 | chromosome 11 open reading frame 9 |
| 206981_at | SCN4A | sodium channel, voltage-gated, type iv, alpha subunit |
| 209516_at | SMYD5 | smyd family member 5 |
| 217016_x_at | TMEM212 | transmembrane protein 212 |
| 214316_x_at | — | — |
| 207766_at | CDKL1 | cyclin-dependent kinase-like 1 (cdc2-related kinase) |
| 210270_at | RGS6 | regulator of g-protein signaling 6 |
| 214546_s_at | P2RY11 | purinergic receptor p2y, g-protein coupled, 11 |
| 221228_s_at | — | — |
| 221879_at | CALML4 | calmodulin-like 4 |
| 205177_at | TNNI1 | troponin i type 1 (skeletal, slow) |
| 222363_at | — | — |
| 221724_s_at | CLEC4A | c-type lectin domain family 4, member a |
| 220505_at | C9ORF53 | chromosome 9 open reading frame 53 |
| 214037_s_at | CCDC22 | coiled-coil domain containing 22 |
| 212064_x_at | MAZ | myc-associated zinc finger protein (purine-binding transcription factor) |
| 210196_s_at | PSG1 | pregnancy specific beta-1-glycoprotein 1 |
| 204142_at | ENOSF1 | enolase superfamily member 1 |
| 216345_at | KIAA0913 | kiaa0913 |
| 208211_s_at | ALK | anaplastic lymphoma receptor tyrosine kinase |
| 210388_at | PLCB2 | phospholipase c, beta 2 |
| 219119_at | NAA38 | n(alpha)-acetyltransferase 38, natc auxiliary subunit |
| 207853_s_at | SNCB | synuclein, beta |
| 219648_at | MREG | melanoregulin |
| 216799_at | — | — |
| 200914_x_at | KTN1 | kinectin 1 (kinesin receptor) |

TABLE M-continued

Monoamine Oxidase B Inhibitor-Related Genes; Down Genes (BJ Table)

| Affy ID | Gene Symbol | Title |
| --- | --- | --- |
| 204171_at | RPS6KB1 | ribosomal protein s6 kinase, 70 kda, polypeptide 1 |
| 215371_at | MED27 | mediator complex subunit 27 |
| 211698_at | EID1 | ep300 interacting inhibitor of differentiation 1 |
| 215406_at | — | — |
| 205801_s_at | RASGRP3 | ras guanyl releasing protein 3 (calcium and dag-regulated) |
| 207520_at | TROVE2 | trove domain family, member 2 |
| 222351_at | PPP2R1B | protein phosphatase 2, regulatory subunit a, beta |
| 204740_at | CNKSR1 | connector enhancer of kinase suppressor of ras 1 |
| 204285_s_at | PMAIP1 | phorbol-12-myristate-13-acetate-induced protein 1 |
| 210202_s_at | BIN1 | bridging integrator 1 |
| 219819_s_at | MRPS28 | mitochondrial ribosomal protein s28 |
| 32062_at | LRRC14 | leucine rich repeat containing 14 |
| 204409_s_at | EIF1AY | eukaryotic translation initiation factor 1a, y-linked |
| 219566_at | PLEKHF1 | pleckstrin homology domain containing, family f (with fyve domain) member 1 |
| 204694_at | AFP | alpha-fetoprotein |
| 212866_at | R3HCC1 | r3h domain and coiled-coil containing 1 |
| 205420_at | PEX7 | peroxisomal biogenesis factor 7 |
| 201926_s_at | CD55 | cd55 molecule, decay accelerating factor for complement (cromer blood group) |
| 209067_s_at | HNRPDL | heterogeneous nuclear ribonucleoprotein d-like |
| 214385_s_at | MUC5AC | similar to mucin /// mucin 5ac, oligomeric mucus/gel-forming |
| 203971_at | SLC31A1 | solute carrier family 31 (copper transporters), member 1 |
| 212292_at | SLC7A1 | solute carrier family 7 (cationic amino acid transporter, y+ system), member 1 |
| 204871_at | MTERF | mitochondrial transcription termination factor |
| 210493_s_at | MFAP3L | microfibrillar-associated protein 3-like |
| 206038_s_at | NR2C2 | nuclear receptor subfamily 2, group c, member 2 |
| 216243_s_at | IL1RN | interleukin 1 receptor antagonist |
| 204569_at | ICK | intestinal cell (mak-like) kinase |
| 219793_at | SNX16 | sorting nexin 16 |
| 207748_at | — | — |
| 220159_at | ABCA11P | atp-binding cassette, sub-family a (abc1), member 11 (pseudogene) |
| 205181_at | ZNF193 | zinc finger protein 193 |
| 205087_at | RWDD3 | rwd domain containing 3 |
| 215426_at | ZCCHC14 | zinc finger, cchc domain containing 14 |
| 215109_at | LOC100288007 | hypothetical protein loc100288007 |
| 218339_at | MRPL22 | mitochondrial ribosomal protein l22 |
| 205126_at | VRK2 | vaccinia related kinase 2 |
| 214337_at | COPA | coatomer protein complex, subunit alpha |
| 208072_s_at | DGKD | diacylglycerol kinase, delta 130 kda |
| 204991_s_at | NF2 | neurofibromin 2 (merlin) |
| 204385_at | KYNU | kynureninase (1-kynurenine hydrolase) |
| 203791_at | DMXL1 | dmx-like 1 |
| 205995_x_at | IQCB1 | iq motif containing b1 |
| 203228_at | PAFAH1B3 | platelet-activating factor acetylhydrolase 1b, catalytic subunit 3 (29 kda) |
| 221456_at | TAS2R3 | taste receptor, type 2, member 3 |
| 215694_at | SPATA5L1 | spermatogenesis associated 5-like 1 |
| 207335_x_at | ATP5I | atp synthase, h+ transporting, mitochondrial f0 complex, subunit e |
| 218239_s_at | GTPBP4 | gtp binding protein 4 |
| 218470_at | YARS2 | tyrosyl-trna synthetase 2, mitochondrial |
| 214214_s_at | C1QBP | complement component 1, q subcomponent binding protein |
| 218407_x_at | NENF | neuron derived neurotrophic factor |
| 201699_at | PSMC6 | proteasome (prosome, macropain) 26s subunit, atpase, 6 |
| 209803_s_at | PHLDA2 | pleckstrin homology-like domain, family a, member 2 |
| 206448_at | ZNF365 | zinc finger protein 365 |
| 203317_at | PSD4 | pleckstrin and sec7 domain containing 4 |
| 206199_at | CEACAM7 | carcinoembryonic antigen-related cell adhesion molecule 7 |
| 204491_at | PDE4D | phosphodiesterase 4d, camp-specific |
| 221613_s_at | ZFAND6 | zinc finger, and-type domain 6 |
| 209106_at | NCOA1 | nuclear receptor coactivator 1 |
| 212432_at | GRPEL1 | grpe-like 1, mitochondrial (e. coli) |
| 216194_s_at | TBCB | tubulin folding cofactor b |
| 214356_s_at | KIAA0368 | kiaa0368 |
| 204552_at | INPP4A | inositol polyphosphate-4-phosphatase, type i, 107 kda |
| 203832_at | SNRPF | small nuclear ribonucleoprotein polypeptide f |
| 203360_s_at | MYCBP | c-myc binding protein |
| 219862_s_at | NARF | nuclear prelamin a recognition factor |
| 201975_at | CLIP1 | cap-gly domain containing linker protein 1 |

TABLE M-continued

Monoamine Oxidase B Inhibitor-Related Genes; Down Genes (BJ Table)

| Affy ID | Gene Symbol | Title |
|---|---|---|
| 206792_x_at | PDE4C | phosphodiesterase 4c, camp-specific |
| 202653_s_at | 7-MAR | membrane-associated ring finger (c3hc4) 7 |
| 203336_s_at | ITGB1BP1 | integrin beta 1 binding protein 1 |
| 201136_at | PLP2 | proteolipid protein 2 (colonic epithelium-enriched) |
| 203008_x_at | TXNDC9 | thioredoxin domain containing 9 |
| 201923_at | PRDX4 | peroxiredoxin 4 |
| 211763_s_at | UBE2B | ubiquitin-conjugating enzyme e2b (rad6 homolog) |
| 203359_s_at | MYCBP | c-myc binding protein |
| 218485_s_at | SLC35C1 | solute carrier family 35, member c1 |
| 201327_s_at | CCT6A | chaperonin containing tcp1, subunit 6a (zeta 1) |
| 208905_at | CYCS | cytochrome c, somatic |
| 221844_x_at | SPCS3 | signal peptidase complex subunit 3 homolog (*s. cerevisiae*) |
| 201323_at | EBNA1BP2 | ebna1 binding protein 2 |
| 216988_s_at | PTP4A2 | protein tyrosine phosphatase type iva, member 2 |

TABLE N

Monoamine Oxidase B Inhibitor-Related Genes; Up Genes (BJ Table)

| Affy ID | Gene Symbol | Title |
|---|---|---|
| 202190_at | CSTF1 | cleavage stimulation factor, 3' pre-rna, subunit 1, 50 kda |
| 200667_at | UBE2D3 | ubiquitin-conjugating enzyme e2d 3 (ubc4/5 homolog, yeast) |
| 203450_at | CBY1 | chibby homolog 1 (*drosophila*) |
| 209658_at | CDC16 | cell division cycle 16 homolog (*s. cerevisiae*) |
| 200603_at | PRKAR1A | protein kinase, camp-dependent, regulatory, type i, alpha (tissue specific extinguisher 1) |
| 203353_s_at | MBD1 | methyl-cpg binding domain protein 1 |
| 218682_s_at | SLC4A1AP | solute carrier family 4 (anion exchanger), member 1, adaptor protein |
| 212345_s_at | CREB3L2 | camp responsive element binding protein 3-like 2 |
| 215128_at | — | — |
| 218803_at | CHFR | checkpoint with forkhead and ring finger domains |
| 219547_at | COX15 | cox15 homolog, cytochrome c oxidase assembly protein (yeast) |
| 202530_at | MAPK14 | mitogen-activated protein kinase 14 |
| 210993_s_at | SMAD1 | smad family member 1 |
| 213607_x_at | NADK | nad kinase |
| 202974_at | MPP1 | membrane protein, palmitoylated 1, 55 kda |
| 212351_at | EIF2B5 | eukaryotic translation initiation factor 2b, subunit 5 epsilon, 82 kda |
| 214784_x_at | XPO6 | exportin 6 |
| 213702_x_at | ASAH1 | n-acylsphingosine amidohydrolase (acid ceramidase) 1 |
| 202512_s_at | ATG5 | atg5 autophagy related 5 homolog (*s. cerevisiae*) |
| 212946_at | KIAA0564 | kiaa0564 |
| 204313_s_at | CREB1 | camp responsive element binding protein 1 |
| 212813_at | JAM3 | junctional adhesion molecule 3 |
| 209002_s_at | CALCOCO1 | calcium binding and coiled-coil domain 1 |
| 213626_at | CBR4 | carbonyl reductase 4 |
| 213261_at | TRANK1 | tetratricopeptide repeat and ankyrin repeat containing 1 |
| 219334_s_at | OBFC2A | oligonucleotide/oligosaccharide-binding fold containing 2a |
| 219135_s_at | LMF1 | lipase maturation factor 1 |
| 209530_at | CACNB3 | calcium channel, voltage-dependent, beta 3 subunit |
| 217786_at | PRMT5 | protein arginine methyltransferase 5 |
| 206308_at | TRDMT1 | trna aspartic acid methyltransferase 1 |
| 203706_s_at | FZD7 | frizzled homolog 7 (*drosophila*) |
| 209778_at | TRIP11 | thyroid hormone receptor interactor 11 |
| 209522_s_at | CRAT | carnitine o-acetyltransferase |
| 219069_at | ANKRD49 | ankyrin repeat domain 49 |
| 203168_at | ATF6B | activating transcription factor 6 beta |
| 212128_s_at | DAG1 | dystroglycan 1 (dystrophin-associated glycoprotein 1) |
| 221864_at | ORAI3 | orai calcium release-activated calcium modulator 3 |
| 217904_s_at | BACE1 | beta-site app-cleaving enzyme 1 |
| 213060_s_at | CHI3L2 | chitinase 3-like 2 |
| 214373_at | — | — |
| 204020_at | PURA | purine-rich element binding protein a |
| 217736_s_at | EIF2AK1 | eukaryotic translation initiation factor 2-alpha kinase 1 |
| 201888_s_at | IL13RA1 | interleukin 13 receptor, alpha 1 |
| 205824_at | HSPB2 | heat shock 27 kda protein 2 |
| 213388_at | PDE4DIP | phosphodiesterase 4d interacting protein |

TABLE N-continued

Monoamine Oxidase B Inhibitor-Related Genes; Up Genes (BJ Table)

| Affy ID | Gene Symbol | Title |
|---|---|---|
| 221616_s_at | TAF9B | taf9b rna polymerase ii, tata box binding protein (tbp)-associated factor, 31 kda |
| 202223_at | STT3A | stt3, subunit of the oligosaccharyltransferase complex, homolog a (s. cerevisiae) |
| 203605_at | SRP54 | signal recognition particle 54 kda |
| 218550_s_at | LRRC20 | leucine rich repeat containing 20 |
| 218243_at | RUFY1 | run and fyve domain containing 1 |
| 203464_s_at | EPN2 | epsin 2 |
| 204547_at | RAB40B | rab40b, member ras oncogene family |
| 207976_at | KLHL18 | kelch-like 18 (drosophila) |
| 217302_at | OR2F2 | olfactory receptor, family 2, subfamily f, member 2 |
| 202696_at | OXSR1 | oxidative-stress responsive 1 |
| 219801_at | ZNF34 | zinc finger protein 34 |
| 218974_at | SOBP | sine oculis binding protein homolog (drosophila) |
| 211067_s_at | GAS7 | growth arrest-specific 7 |
| 219280_at | BRWD1 | bromodomain and wd repeat domain containing 1 |
| 218047_at | OSBPL9 | oxysterol binding protein-like 9 |
| 216250_s_at | LPXN | leupaxin |
| 212862_at | CDS2 | cdp-diacylglycerol synthase (phosphatidate cytidylyltransferase) 2 |
| 206129_s_at | ARSB | arylsulfatase b |
| 218055_s_at | WDR41 | wd repeat domain 41 |
| 209007_s_at | C1ORF63 | chromosome 1 open reading frame 63 |
| 206404_at | FGF9 | fibroblast growth factor 9 (glia-activating factor) |
| 209475_at | USP15 | ubiquitin specific peptidase 15 |
| 205013_s_at | CYTSA | adenosine a2a receptor /// cytospin a |
| 212062_at | ATP9A | atpase, class ii, type 9a |
| 203383_s_at | GOLGA1 | golgin a1 |
| 210844_x_at | CTNNA1 | catenin (cadherin-associated protein), alpha 1, 102 kda |
| 204880_at | MGMT | o-6-methylguanine-dna methyltransferase |
| 212380_at | FTSJD2 | ftsj methyltransferase domain containing 2 |
| 37549_g_at | BBS9 | bardet-biedl syndrome 9 |
| 212608_s_at | — | — |
| 201954_at | ARPC1B | actin related protein 2/3 complex, subunit 1b, 41 kda |
| 221814_at | GPR124 | g protein-coupled receptor 124 |
| 206625_at | PRPH2 | peripherin 2 (retinal degeneration, slow) |
| 219310_at | TMEM90B | transmembrane protein 90b |
| 214506_at | GPR182 | g protein-coupled receptor 182 |
| 214357_at | C1ORF105 | chromosome 1 open reading frame 105 |
| 206187_at | PTGIR | prostaglandin i2 (prostacyclin) receptor (ip) |
| 207919_at | ART1 | adp-ribosyltransferase 1 |
| 217605_at | USP27X | ubiquitin specific peptidase 27, x-linked |
| 220974_x_at | SFXN3 | sideroflexin 3 |
| 209954_x_at | SS18 | synovial sarcoma translocation, chromosome 18 |
| 202156_s_at | CELF2 | cugbp, elav-like family member 2 |
| 208270_s_at | RNPEP | arginyl aminopeptidase (aminopeptidase b) |
| 209940_at | PARP3 | poly (adp-ribose) polymerase family, member 3 |
| 212703_at | TLN2 | talin 2 |
| 220032_at | C7ORF58 | chromosome 7 open reading frame 58 |
| 220862_s_at | USP22 | ubiquitin specific peptidase 22 |
| 202082_s_at | SEC14L1 | sec14-like 1 (s. cerevisiae) |
| 213103_at | STARD13 | star-related lipid transfer (start) domain containing 13 |
| 207169_x_at | DDR1 | discoidin domain receptor tyrosine kinase 1 |
| 201706_s_at | PEX19 | peroxisomal biogenesis factor 19 |
| 213823_at | HOXA11 | homeobox a11 |
| 212409_s_at | TOR1AIP1 | torsin a interacting protein 1 |
| 220439_at | RIN3 | ras and rab interactor 3 |
| 210407_at | PPM1A | protein phosphatase, mg2+/mn2+ dependent, 1a |
| 201838_s_at | SUPT7L | suppressor of ty 7 (s. cerevisiae)-like |
| 215070_x_at | RABGAP1 | rab gtpase activating protein 1 |
| 215927_at | ARFGEF2 | adp-ribosylation factor guanine nucleotide-exchange factor 2 (brefeldin a-inhibited) |
| 217287_s_at | TRPC6 | transient receptor potential cation channel, subfamily c, member 6 |
| 206793_at | PNMT | phenylethanolamine n-methyltransferase |
| 214616_at | HIST1H3E | histone cluster 1, h3e |
| 202379_s_at | NKTR | natural killer-tumor recognition sequence |
| 215895_x_at | PLIN2 | perilipin 2 |
| 206204_at | GRB14 | growth factor receptor-bound protein 14 |
| 213345_at | NFATC4 | nuclear factor of activated t-cells, cytoplasmic, calcineurin-dependent 4 |
| 215695_s_at | GYG2 | glycogenin 2 |
| 205514_at | ZNF415 | zinc finger protein 415 |
| 203141_s_at | AP3B1 | adaptor-related protein complex 3, beta 1 subunit |
| 208464_at | GRIA4 | glutamate receptor, ionotropic, ampa 4 |

TABLE N-continued

Monoamine Oxidase B Inhibitor-Related Genes; Up Genes (BJ Table)

| Affy ID | Gene Symbol | Title |
|---|---|---|
| 205455_at | MST1R | macrophage stimulating 1 receptor (c-met-related tyrosine kinase) |
| 205786_s_at | ITGAM | integrin, alpha m (complement component 3 receptor 3 subunit) |
| 201060_x_at | STOM | stomatin |
| 37201_at | ITIH4 | inter-alpha (globulin) inhibitor h4 (plasma kallikrein-sensitive glycoprotein) |
| 211424_x_at | METTL7A | methyltransferase like 7a |
| 216847_at | — | — |
| 209286_at | CDC42EP3 | cdc42 effector protein (rho gtpase binding) 3 |
| 208161_s_at | ABCC3 | atp-binding cassette, sub-family c (cftr/mrp), member 3 |
| 209726_at | CA11 | carbonic anhydrase xi |
| 213779_at | EMID1 | emi domain containing 1 |
| 201224_s_at | SRRM1 | serine/arginine repetitive matrix 1 |
| 214464_at | CDC42BPA | cdc42 binding protein kinase alpha (dmpk-like) |
| 210756_s_at | NOTCH2 | notch homolog 2 (*drosophila*) |
| 211584_s_at | NPAT | nuclear protein, ataxia-telangiectasia locus |
| 219749_at | SH2D4A | sh2 domain containing 4a |
| 217525_at | OLFML1 | olfactomedin-like 1 |
| 215554_at | GPLD1 | glycosylphosphatidylinositol specific phospholipase d1 |
| 221412_at | VN1R1 | vomeronasal 1 receptor 1 |
| 217153_at | ARHGAP1 | rho gtpase activating protein 1 |
| 215150_at | YOD1 | yod1 otu deubiquinating enzyme 1 homolog (*s. cerevisiae*) |
| 220749_at | C10ORF68 | chromosome 10 open reading frame 68 |
| 208467_at | KLF12 | kruppel-like factor 12 |
| 221413_at | KCNAB3 | potassium voltage-gated channel, shaker-related subfamily, beta member 3 |
| 205646_s_at | PAX6 | paired box 6 |
| 200930_s_at | VCL | vinculin |
| 207797_s_at | LRP2BP | lrp2 binding protein |
| 218480_at | AGBL5 | atp/gtp binding protein-like 5 |
| 213385_at | CHN2 | chimerin (chimaerin) 2 |
| 204749_at | NAP1L3 | nucleosome assembly protein 1-like 3 |
| 212763_at | CAMSAP1L1 | calmodulin regulated spectrin-associated protein 1-like 1 |
| 211435_at | — | — |
| 212073_at | CSNK2A1 | casein kinase 2, alpha 1 polypeptide /// casein kinase 2, alpha 1 polypeptide pseudogene |
| 207527_at | KCNJ9 | potassium inwardly-rectifying channel, subfamily j, member 9 |
| 215901_at | ZNF81 | zinc finger protein 81 |
| 205400_at | WAS | wiskott-aldrich syndrome (eczema-thrombocytopenia) |
| 216082_at | NEU3 | sialidase 3 (membrane sialidase) |
| 207764_s_at | HIPK3 | homeodomain interacting protein kinase 3 |
| 215115_x_at | NTRK3 | neurotrophic tyrosine kinase, receptor, type 3 |
| 202046_s_at | GRLF1 | glucocorticoid receptor dna binding factor 1 |
| 206149_at | CHP2 | calcineurin b homologous protein 2 |
| 216098_s_at | HTR7 | 5-hydroxytryptamine (serotonin) receptor 7 (adenylate cyclase-coupled) |
| 213706_at | GPD1 | glycerol-3-phosphate dehydrogenase 1 (soluble) |
| 222368_at | — | — |
| 211610_at | KLF6 | kruppel-like factor 6 |
| 221142_s_at | PECR | peroxisomal trans-2-enoyl-coa reductase |
| 206318_at | SPINLW1 | serine peptidase inhibitor-like, with kunitz and wap domains 1 (eppin) |
| 41397_at | ZNF821 | zinc finger protein 821 |
| 208465_at | GRM2 | glutamate receptor, metabotropic 2 |
| 205625_s_at | CALB1 | calbindin 1, 28 kda |
| 205946_at | VIPR2 | vasoactive intestinal peptide receptor 2 |
| 208034_s_at | PROZ | protein z, vitamin k-dependent plasma glycoprotein |
| 219658_at | PTCD2 | pentatricopeptide repeat domain 2 |
| 215817_at | SERPINB13 | serpin peptidase inhibitor, clade b (ovalbumin), member 13 |
| 219263_at | RNF128 | ring finger protein 128 |
| 220849_at | LOC79999 | hypothetical loc79999 |
| 209843_s_at | SOX10 | sry (sex determining region y)-box 10 |
| 218627_at | DRAM1 | dna-damage regulated autophagy modulator 1 |
| 202150_s_at | NEDD9 | neural precursor cell expressed, developmentally down-regulated 9 |
| 205673_s_at | ASB9 | ankyrin repeat and socs box-containing 9 |
| 211554_s_at | APAF1 | apoptotic peptidase activating factor 1 |
| 211751_at | PDE4DIP | phosphodiesterase 4d interacting protein |
| 212095_s_at | MTUS1 | microtubule associated tumor suppressor 1 |
| 206832_s_at | SEMA3F | sema domain, immunoglobulin domain (ig), short basic domain, secreted, (semaphorin) 3f |
| 221352_at | — | — |
| 211448_s_at | RGS6 | regulator of g-protein signaling 6 |

TABLE N-continued

Monoamine Oxidase B Inhibitor-Related Genes; Up Genes (BJ Table)

| Affy ID | Gene Symbol | Title |
|---|---|---|
| 220830_at | IMPG2 | interphotoreceptor matrix proteoglycan 2 |
| 204754_at | HLF | hepatic leukemia factor |
| 208176_at | DUX1 | double homeobox, 1 |
| 218346_s_at | SESN1 | sestrin 1 |
| 210850_s_at | ELK1 | elk1, member of ets oncogene family |
| 202269_x_at | GBP1 | guanylate binding protein 1, interferon-inducible, 67 kda |
| 217641_at | GPR135 | g protein-coupled receptor 135 |
| 221980_at | EMILIN2 | elastin microfibril interfacer 2 |
| 207600_at | KCNC3 | potassium voltage-gated channel, shaw-related subfamily, member 3 |
| 209138_x_at | IGL@ | immunoglobulin lambda locus |
| 217565_at | GRIA3 | glutamate receptor, ionotrophic, ampa 3 |
| 216402_at | SEC14L4 | sec14-like 4 (*s. cerevisiae*) |
| 210762_s_at | DLC1 | deleted in liver cancer 1 |
| 214319_at | FRY | furry homolog (*drosophila*) |
| 208022_s_at | CDC14B | cdc14 cell division cycle 14 homolog b (*s. cerevisiae*) |
| 205163_at | MYLPF | myosin light chain, phosphorylatable, fast skeletal muscle |
| 203628_at | IGF1R | insulin-like growth factor 1 receptor |
| 216886_at | CHRNA4 | cholinergic receptor, nicotinic, alpha 4 |
| 208455_at | PVRL1 | poliovirus receptor-related 1 (herpesvirus entry mediator c) |
| 205576_at | SERPIND1 | serpin peptidase inhibitor, clade d (heparin cofactor), member 1 |
| 206929_s_at | NFIC | nuclear factor i/c (ccaat-binding transcription factor) |
| 217034_at | — | — |
| 210079_x_at | KCNAB1 | potassium voltage-gated channel, shaker-related subfamily, beta member 1 |
| 221161_at | ASCL3 | achaete-scute complex homolog 3 (*drosophila*) |
| 204555_s_at | PPP1R3D | protein phosphatase 1, regulatory (inhibitor) subunit 3d |
| 221150_at | MEPE | matrix extracellular phosphoglycoprotein |
| 210356_x_at | MS4A1 | membrane-spanning 4-domains, subfamily a, member 1 |
| 215168_at | TIMM17A | translocase of inner mitochondrial membrane 17 homolog a (yeast) |
| 216465_at | — | — |
| 206775_at | CUBN | cubilin (intrinsic factor-cobalamin receptor) |
| 221441_at | GSC2 | goosecoid homeobox 2 |
| 213947_s_at | NUP210 | nucleoporin 210 kda |
| 205751_at | SH3GL2 | sh3-domain grb2-like 2 |
| 221431_s_at | OR12D3 | olfactory receptor, family 12, subfamily d, member 3 |
| 212079_s_at | MLL | myeloid/lymphoid or mixed-lineage leukemia (trithorax homolog, *drosophila*) |
| 205524_s_at | HAPLN1 | hyaluronan and proteoglycan link protein 1 |
| 220154_at | DST | dystonin |
| 210881_s_at | IGF2 | insulin-like growth factor 2 (somatomedin a) /// ins-igf2 readthrough transcript |
| 216839_at | LAMA2 | laminin, alpha 2 |
| 220203_at | BMP8A | bone morphogenetic protein 8a |
| 207686_s_at | CASP8 | caspase 8, apoptosis-related cysteine peptidase |
| 219804_at | SYNPO2L | synaptopodin 2-like |
| 208475_at | FRMD4A | ferm domain containing 4a |
| 209999_x_at | SOCS1 | suppressor of cytokine signaling 1 |
| 214309_s_at | — | — |
| 206243_at | TIMP4 | timp metallopeptidase inhibitor 4 |
| 211824_x_at | NLRP1 | nlr family, pyrin domain containing 1 |
| 215085_x_at | DLEC1 | deleted in lung and esophageal cancer 1 |

TABLE O

Monoamine Oxidase B Inhibitor-Related Genes; Down Genes (Keratinocyte Table)

| Affy ID | Gene Symbol | Title |
|---|---|---|
| 207750_at | — | — |
| 218730_s_at | OGN | osteoglycin |
| 204933_s_at | TNFRSF11B | tumor necrosis factor receptor superfamily, member 11b |
| 217513_at | C17ORF60 | chromosome 17 open reading frame 60 |
| 215904_at | MLLT4 | myeloid/lymphoid or mixed-lineage leukemia (trithorax homolog, *drosophila*); translocated to, 4 |
| 216758_at | — | — |
| 221583_s_at | KCNMA1 | potassium large conductance calcium-activated channel, subfamily m, alpha member 1 |

TABLE O-continued

Monoamine Oxidase B Inhibitor-Related Genes; Down Genes
(Keratinocyte Table)

| Affy ID | Gene Symbol | Title |
|---|---|---|
| 204471_at | GAP43 | growth associated protein 43 |
| 206512_at | ZRSR1 | zinc finger (ccch type), rna-binding motif and serine/arginine rich 1 |
| 217005_at | — | — |
| 214774_x_at | TOX3 | tox high mobility group box family member 3 |
| 220125_at | DNAI1 | dynein, axonemal, intermediate chain 1 |
| 216604_s_at | SLC7A8 | solute carrier family 7 (amino acid transporter, 1-type), member 8 |
| 207722_s_at | BTBD2 | btb (poz) domain containing 2 |
| 220037_s_at | LYVE1 | lymphatic vessel endothelial hyaluronan receptor 1 |
| 211617_at | ALDOAP2 | aldolase a, fructose-bisphosphate pseudogene 2 |
| 213993_at | SPON1 | spondin 1, extracellular matrix protein |
| 214811_at | RIMBP2 | rims binding protein 2 |
| 213158_at | — | — |
| 215447_at | — | — |
| 220646_s_at | KLRF1 | killer cell lectin-like receptor subfamily f, member 1 |
| 214745_at | PLCH1 | phospholipase c, eta 1 |
| 220184_at | NANOG | nanog homeobox |
| 204041_at | MAOB | monoamine oxidase b |
| 207523_at | C6ORF10 | chromosome 6 open reading frame 10 |
| 205168_at | DDR2 | discoidin domain receptor tyrosine kinase 2 |
| 215147_at | — | — |
| 211556_at | MAPRE2 | microtubule-associated protein, rp/eb family, member 2 |
| 205051_s_at | KIT | v-kit hardy-zuckerman 4 feline sarcoma viral oncogene homolog |
| 207869_s_at | CACNA1G | calcium channel, voltage-dependent, t type, alpha 1g subunit |
| 210738_s_at | SLC4A4 | solute carrier family 4, sodium bicarbonate cotransporter, member 4 |
| 220373_at | DCHS2 | dachsous 2 (*drosophila*) |
| 203751_x_at | JUND | jun d proto-oncogene |
| 222240_s_at | ISYNA1 | inositol-3-phosphate synthase 1 |
| 207119_at | PRKG1 | protein kinase, cgmp-dependent, type i |
| 207666_x_at | SSX3 | synovial sarcoma, x breakpoint 3 |
| 210576_at | CYP4F8 | cytochrome p450, family 4, subfamily f, polypeptide 8 |
| 207314_x_at | KIR3DL1 | killer cell immunoglobulin-like receptor, three domains, long cytoplasmic tail, 1 |
| 216872_at | HR44 | hr44 antigen |
| 207496_at | MS4A2 | membrane-spanning 4-domains, subfamily a, member 2 |
| 206743_s_at | ASGR1 | asialoglycoprotein receptor 1 |
| 220821_at | GALR1 | galanin receptor 1 |
| 208321_s_at | CABP1 | calcium binding protein 1 |
| 213413_at | STON1 | stonin 1 |
| 216720_at | CYP2U1 | cytochrome p450, family 2, subfamily u, polypeptide 1 |
| 215524_x_at | TRA@ | t cell receptor alpha locus |
| 207226_at | HIST1H2BN | histone cluster 1, h2bn |
| 204941_s_at | ALDH3B2 | aldehyde dehydrogenase 3 family, member b2 |
| 206069_s_at | ACADL | acyl-coa dehydrogenase, long chain |
| 219708_at | NT5M | 5',3'-nucleotidase, mitochondrial |
| 222194_at | FAM66D | family with sequence similarity 66, member d |
| 208605_s_at | NTRK1 | neurotrophic tyrosine kinase, receptor, type 1 |
| 213375_s_at | N4BP2L1 | nedd4 binding protein 2-like 1 |
| 210914_at | — | — |
| 216078_at | — | — |
| 217287_s_at | TRPC6 | transient receptor potential cation channel, subfamily c, member 6 |
| 207321_s_at | ABCB9 | atp-binding cassette, sub-family b (mdr/tap), member 9 |
| 210262_at | CRISP2 | cysteine-rich secretory protein 2 |
| 207317_s_at | CASQ2 | calsequestrin 2 (cardiac muscle) |
| 221149_at | GPR77 | g protein-coupled receptor 77 |
| 204850_s_at | DCX | doublecortin |
| 209367_at | STXBP2 | syntaxin binding protein 2 |
| 222013_x_at | FAM86A | family with sequence similarity 86, member a |
| 216921_s_at | KRT35 | keratin 35 |
| 219145_at | LPHN1 | latrophilin 1 |
| 216813_at | — | — |
| 206107_at | RGS11 | regulator of g-protein signaling 11 |
| 216427_at | — | — |
| 203908_at | SLC4A4 | solute carrier family 4, sodium bicarbonate cotransporter, member 4 |
| 203673_at | TG | thyroglobulin |
| 220108_at | GNA14 | guanine nucleotide binding protein (g protein), alpha 14 |
| 217434_at | MC2R | melanocortin 2 receptor (adrenocorticotropic hormone) |
| 206598_at | INS | insulin |

TABLE O-continued

Monoamine Oxidase B Inhibitor-Related Genes; Down Genes
(Keratinocyte Table)

| Affy ID | Gene Symbol | Title |
|---|---|---|
| 208134_x_at | PSG2 | pregnancy specific beta-1-glycoprotein 2 |
| 208295_x_at | CSHL1 | chorionic somatomammotropin hormone-like 1 |
| 208601_s_at | TUBB1 | tubulin, beta 1 |
| 210472_at | MT1G | metallothionein 1g |
| 213825_at | OLIG2 | oligodendrocyte lineage transcription factor 2 |
| 213539_at | CD3D | cd3d molecule, delta (cd3-tcr complex) |
| 61874_at | C9ORF7 | chromosome 9 open reading frame 7 |
| 211525_s_at | GP5 | glycoprotein v (platelet) |
| 220384_at | TXNDC3 | thioredoxin domain containing 3 (spermatozoa) |
| 205041_s_at | ORM1 | orosomucoid 1 /// orosomucoid 2 |
| 214065_s_at | CIB2 | calcium and integrin binding family member 2 |
| 202747_s_at | ITM2A | integral membrane protein 2a |
| 215350_at | SYNE1 | spectrin repeat containing, nuclear envelope 1 |
| 210521_s_at | FETUB | fetuin b |
| 221130_s_at | — | — |
| 208465_at | GRM2 | glutamate receptor, metabotropic 2 |
| 214208_at | KLHL35 | kelch-like 35 (*drosophila*) |
| 218045_x_at | PTMS | parathymosin |
| 204874_x_at | BAIAP3 | bai1-associated protein 3 |
| 216639_at | SRPX2 | sushi-repeat-containing protein, x-linked 2 |
| 216925_s_at | TAL1 | t-cell acute lymphocytic leukemia 1 |
| 209699_x_at | AKR1C2 | aldo-keto reductase family 1, member c2 |
| 209879_at | SELPLG | selectin p ligand |
| 217793_at | RAB11B | rab11b, member ras oncogene family |
| 216568_x_at | — | — |
| 217353_at | HNRNPA1 | heterogeneous nuclear ribonucleoprotein a1 |
| 214746_s_at | ZNF467 | zinc finger protein 467 |
| 206439_at | EPYC | epiphycan |
| 215053_at | SRCAP | snf2-related crebbp activator protein |
| 216657_at | ATXN3 | ataxin 3 |
| 220771_at | LOC51152 | melanoma antigen |
| 213913_s_at | TBC1D30 | tbc1 domain family, member 30 |
| 216706_x_at | IGHG1 | immunoglobulin heavy constant gamma 1 (g1m marker) |
| 205319_at | PSCA | prostate stem cell antigen |
| 220912_at | — | — |
| 206067_s_at | WT1 | wilms tumor 1 |
| 216425_at | — | — |
| 207569_at | ROS1 | c-ros oncogene 1, receptor tyrosine kinase |
| 213171_s_at | MMP24 | matrix metallopeptidase 24 (membrane-inserted) |
| 206453_s_at | NDRG2 | ndrg family member 2 |
| 209160_at | AKR1C3 | aldo-keto reductase family 1, member c3 (3-alpha hydroxysteroid dehydrogenase, type ii) |
| 215865_at | SYT12 | synaptotagmin xii |
| 206982_at | CRYBA1 | crystallin, beta a1 |
| 206389_s_at | PDE3A | phosphodiesterase 3a, cgmp-inhibited |
| 205654_at | C4BPA | complement component 4 binding protein, alpha |
| 207053_at | SLC8A1 | solute carrier family 8 (sodium/calcium exchanger), member 1 |
| 209975_at | CYP2E1 | cytochrome p450, family 2, subfamily e, polypeptide 1 |
| 221944_at | FLJ42627 | hypothetical loc645644 |
| 203240_at | FCGBP | fc fragment of igg binding protein |
| 209409_at | GRB10 | growth factor receptor-bound protein 10 |
| 207459_x_at | GYPB | glycophorin b (mns blood group) |
| 208558_at | OR10H1 | olfactory receptor, family 10, subfamily h, member 1 |
| 202410_x_at | IGF2 | insulin-like growth factor 2 (somatomedin a) /// ins-igf2 readthrough transcript |
| 220425_x_at | ROPN1B | ropporin, rhophilin associated protein 1b |
| 210753_s_at | EPHB1 | eph receptor b1 |
| 207154_at | DIO3 | deiodinase, iodothyronine, type iii |
| 211153_s_at | TNFSF11 | tumor necrosis factor (ligand) superfamily, member 11 |
| 213003_s_at | CEBPD | ccaat/enhancer binding protein (c/ebp), delta |
| 213443_at | TRADD | tnfrsf1a-associated via death domain |
| 215420_at | IHH | indian hedgehog homolog (*drosophila*) |
| 210746_s_at | EPB42 | erythrocyte membrane protein band 4.2 |
| 208547_at | HIST1H2BB | histone cluster 1, h2bb |
| 43934_at | GPR137 | g protein-coupled receptor 137 |
| 219888_at | SPAG4 | sperm associated antigen 4 |
| 204040_at | RNF144A | ring finger protein 144a |
| 201313_at | ENO2 | enolase 2 (gamma, neuronal) |
| 218876_at | TPPP3 | tubulin polymerization-promoting protein family member 3 |
| 220249_at | HYAL4 | hyaluronoglucosaminidase 4 |
| 52837_at | KIAA1644 | kiaa1644 |
| 208267_at | TRPV5 | transient receptor potential cation channel, subfamily v, member 5 |

TABLE O-continued

Monoamine Oxidase B Inhibitor-Related Genes; Down Genes
(Keratinocyte Table)

| Affy ID | Gene Symbol | Title |
|---|---|---|
| 222347_at | LOC644450 | hypothetical protein loc644450 |
| 206380_s_at | CFP | complement factor properdin |
| 207197_at | ZIC3 | zic family member 3 (odd-paired homolog, *drosophila*) |
| 219684_at | RTP4 | receptor (chemosensory) transporter protein 4 |
| 208018_s_at | HCK | hemopoietic cell kinase |
| 207925_at | CST5 | cystatin d |
| 207980_s_at | CITED2 | cbp/p300-interacting transactivator, with glu/asp-rich carboxy-terminal domain, 2 |
| 215473_at | — | — |
| 209952_s_at | MAP2K7 | mitogen-activated protein kinase kinase 7 |
| 207193_at | AGRP | agouti related protein homolog (mouse) |
| 205456_at | CD3E | cd3e molecule, epsilon (cd3-tcr complex) |
| 214574_x_at | LST1 | leukocyte specific transcript 1 |
| 214354_x_at | SFTPB | surfactant protein b |
| 210023_s_at | PCGF1 | polycomb group ring finger 1 |
| 221332_at | BMP15 | bone morphogenetic protein 15 |
| 205804_s_at | TRAF3IP3 | traf3 interacting protein 3 |
| 207933_at | ZP2 | zona pellucida glycoprotein 2 (sperm receptor) |
| 222290_at | OR2A5 | olfactory receptor, family 2, subfamily a, member 20 pseudogene |
| 217424_at | — | — |
| 218523_at | LHPP | phospholysine phosphohistidine inorganic pyrophosphate phosphatase |
| 217246_s_at | DIAPH2 | diaphanous homolog 2 (*drosophila*) |
| 219090_at | SLC24A3 | solute carrier family 24 (sodium/potassium/calcium exchanger), member 3 |
| 206644_at | NR0B1 | nuclear receptor subfamily 0, group b, member 1 |
| 210357_s_at | SMOX | spermine oxidase |
| 211633_x_at | — | — |
| 219666_at | MS4A6A | membrane-spanning 4-domains, subfamily a, member 6a |
| 220534_at | TRIM48 | tripartite motif-containing 48 |
| 219309_at | C22ORF46 | chromosome 22 open reading frame 46 |
| 205043_at | CFTR | cystic fibrosis transmembrane conductance regulator (atp-binding cassette sub-family c, member 7) |
| 211641_x_at | IGH@ | immunoglobulin heavy locus /// immunoglobulin heavy constant alpha 1 |
| 216229_x_at | HCG2P7 | hla complex group 2 pseudogene 7 |
| 221019_s_at | COLEC12 | collectin sub-family member 12 |
| 219670_at | BEND5 | ben domain containing 5 |
| 206286_s_at | TDGF1 | teratocarcinoma-derived growth factor 1 /// teratocarcinoma-derived growth factor 3, pseudogene |
| 221424_s_at | OR51E2 | olfactory receptor, family 51, subfamily e, member 2 |
| 207794_at | CCR2 | chemokine (c-c motif) receptor 2 |
| 208408_at | PTN | pleiotrophin |
| 217302_at | OR2F2 | olfactory receptor, family 2, subfamily f, member 2 |
| 215468_at | LOC647070 | hypothetical loc647070 |
| 220332_at | CLDN16 | claudin 16 |
| 219963_at | DUSP13 | dual specificity phosphatase 13 |
| 214865_at | DOT1L | dot1-like, histone h3 methyltransferase (*s. cerevisiae*) |
| 204746_s_at | PICK1 | protein interacting with prkca 1 |
| 204381_at | LRP3 | low density lipoprotein receptor-related protein 3 |
| 221339_at | OR10C1 | olfactory receptor, family 10, subfamily c, member 1 |
| 207263_x_at | VEZT | vezatin, adherens junctions transmembrane protein |
| 206048_at | OVOL2 | ovo-like 2 (*drosophila*) |
| 209850_s_at | CDC42EP2 | cdc42 effector protein (rho gtpase binding) 2 |
| 207793_s_at | EPB41 | erythrocyte membrane protein band 4.1 (elliptocytosis 1, rh-linked) |
| 202340_x_at | NR4A1 | nuclear receptor subfamily 4, group a, member 1 |
| 207315_at | CD226 | cd226 molecule |
| 216346_at | SEC14L3 | sec14-like 3 (*s. cerevisiae*) |
| 207937_x_at | FGFR1 | fibroblast growth factor receptor 1 |
| 37028_at | PPP1R15A | protein phosphatase 1, regulatory (inhibitor) subunit 15a |
| 208312_s_at | PRAMEF1 | prame family member 1 /// prame family member 2 |
| 220860_at | PURG | purine-rich element binding protein g |
| 216045_at | CCDC144A | coiled-coil domain containing 144a |
| 215521_at | PHC3 | polyhomeotic homolog 3 (*drosophila*) |
| 215163_at | — | — |
| 207239_s_at | CDK16 | cyclin-dependent kinase 16 |
| 210245_at | ABCC8 | atp-binding cassette, sub-family c (cftr/mrp), member 8 |
| 201310_s_at | C5ORF13 | chromosome 5 open reading frame 13 |
| 205468_s_at | IRF5 | interferon regulatory factor 5 |
| 205592_at | SLC4A1 | solute carrier family 4, anion exchanger, member 1 |
| 221163_s_at | MLXIPL | mlx interacting protein-like |
| 212937_s_at | COL6A1 | collagen, type vi, alpha 1 |

TABLE O-continued

Monoamine Oxidase B Inhibitor-Related Genes; Down Genes
(Keratinocyte Table)

| Affy ID | Gene Symbol | Title |
|---|---|---|
| 204848_x_at | HBG1 | hemoglobin, gamma a /// hemoglobin, gamma g |
| 211046_at | KCNH6 | potassium voltage-gated channel, subfamily h (eag-related), member 6 |
| 210556_at | NFATC3 | nuclear factor of activated t-cells, cytoplasmic, calcineurin-dependent 3 |
| 216130_at | — | — |
| 213658_at | — | — |
| 206191_at | ENTPD3 | ectonucleoside triphosphate diphosphohydrolase 3 |
| 60084_at | CYLD | cylindromatosis (turban tumor syndrome) |
| 205127_at | PTGS1 | prostaglandin-endoperoxide synthase 1 (prostaglandin g/h synthase and cyclooxygenase) |
| 209230_s_at | NUPR1 | nuclear protein, transcriptional regulator, 1 |
| 209206_at | SEC22B | sec22 vesicle trafficking protein homolog b (*s. cerevisiae*) (gene/pseudogene) |
| 202768_at | FOSB | fbj murine osteosarcoma viral oncogene homolog b |
| 214939_x_at | MLLT4 | myeloid/lymphoid or mixed-lineage leukemia (trithorax homolog, *drosophila*); translocated to, 4 |
| 207597_at | ADAM18 | adam metallopeptidase domain 18 |
| 203937_s_at | TAF1C | tata box binding protein (tbp)-associated factor, ma polymerase i, c, 110 kda |
| 214705_at | INADL | inad-like (*drosophila*) |
| 222282_at | — | — |
| 201069_at | MMP2 | matrix metallopeptidase 2 (gelatinase a, 72 kda gelatinase, 72 kda type iv collagenase) |
| 207528_s_at | SLC7A11 | solute carrier family 7, (cationic amino acid transporter, y+ system) member 11 |
| 206436_at | MPPED1 | metallophosphoesterase domain containing 1 |
| 214715_x_at | ZNF160 | zinc finger protein 160 |
| 208512_s_at | MLLT4 | myeloid/lymphoid or mixed-lineage leukemia (trithorax homolog, *drosophila*); translocated to, 4 |
| 218586_at | C20ORF20 | chromosome 20 open reading frame 20 |
| 222207_x_at | — | — |
| 205291_at | IL2RB | interleukin 2 receptor, beta |
| 205769_at | SLC27A2 | solute carrier family 27 (fatty acid transporter), member 2 |
| 208227_x_at | ADAM22 | adam metallopeptidase domain 22 |
| 221165_s_at | IL22 | interleukin 22 |
| 38521_at | CD22 | cd22 molecule |
| 39318_at | TCL1A | t-cell leukemia/lymphoma 1a |
| 222311_s_at | SFRS15 | splicing factor, arginine/serine-rich 15 |
| 214688_at | TLE4 | transducin-like enhancer of split 4 (e(sp1) homolog, *drosophila*) |
| 217347_at | — | — |
| 216248_s_at | NR4A2 | nuclear receptor subfamily 4, group a, member 2 |
| 210210_at | MPZL1 | myelin protein zero-like 1 |
| 215898_at | TTLL5 | tubulin tyrosine ligase-like family, member 5 |
| 221128_at | ADAM19 | adam metallopeptidase domain 19 (meltrin beta) |
| 215529_x_at | DIP2A | dip2 disco-interacting protein 2 homolog a (*drosophila*) |
| 218060_s_at | C16ORF57 | chromosome 16 open reading frame 57 |
| 206632_s_at | APOBEC3B | apolipoprotein b mrna editing enzyme, catalytic polypeptide-like 3b |
| 212156_at | VPS39 | vacuolar protein sorting 39 homolog (*s. cerevisiae*) |
| 214171_s_at | U2AF2 | u2 small nuclear rna auxiliary factor 2 |
| 210263_at | KCNF1 | potassium voltage-gated channel, subfamily f, member 1 |
| 210326_at | AGXT | alanine-glyoxylate aminotransferase |
| 217482_at | — | — |
| 215064_at | SC5DL | sterol-c5-desaturase (erg3 delta-5-desaturase homolog, *s. cerevisiae*)-like |
| 209518_at | SMARCD1 | swi/snf related, matrix associated, actin dependent regulator of chromatin, subfamily d, member 1 |
| 215587_x_at | — | — |
| 216303_s_at | MTMR1 | myotubularin related protein 1 |
| 204684_at | NPTX1 | neuronal pentraxin i |
| 209200_at | MEF2C | myocyte enhancer factor 2c |
| 220592_at | CCDC40 | coiled-coil domain containing 40 |
| 206869_at | CHAD | chondroadherin |
| 205923_at | RELN | reelin |
| 208452_x_at | MYO9B | myosin ixb |
| 1294_at | UBA7 | ubiquitin-like modifier activating enzyme 7 |
| 217679_x_at | — | — |
| 46323_at | CANT1 | calcium activated nucleotidase 1 |
| 213601_at | SLIT1 | slit homolog 1 (*drosophila*) |
| 210358_x_at | GATA2 | gata binding protein 2 |
| 203297_s_at | JARID2 | jumonji, at rich interactive domain 2 |

TABLE O-continued

Monoamine Oxidase B Inhibitor-Related Genes; Down Genes
(Keratinocyte Table)

| Affy ID | Gene Symbol | Title |
|---|---|---|
| 219997_s_at | COPS7B | cop9 constitutive photomorphogenic homolog subunit 7b (arabidopsis) |
| 207683_at | FOXN1 | forkhead box n1 |
| 206313_at | HLA-DOA | major histocompatibility complex, class ii, do alpha |
| 220071_x_at | HAUS2 | haus augmin-like complex, subunit 2 |
| 61732_r_at | IFT74 | intraflagellar transport 74 homolog (chlamydomonas) |
| 217048_at | — | — |
| 202392_s_at | PISD | phosphatidylserine decarboxylase |
| 203308_x_at | HPS1 | hermansky-pudlak syndrome 1 |
| 218419_s_at | TMUB2 | transmembrane and ubiquitin-like domain containing 2 |
| 215302_at | LOC257152 | hypothetical protein loc257152 |
| 206005_s_at | KIAA1009 | kiaa1009 |
| 222219_s_at | TLE6 | transducin-like enhancer of split 6 (e(sp1) homolog, *drosophila*) |
| 218367_x_at | USP21 | ubiquitin specific peptidase 21 |
| 220720_x_at | FAM128B | family with sequence similarity 128, member b |
| 201357_s_at | SF3A1 | splicing factor 3a, subunit 1, 120 kda |
| 214561_at | LILRP2 | leukocyte immunoglobulin-like receptor pseudogene 2 |
| 203722_at | ALDH4A1 | aldehyde dehydrogenase 4 family, member a1 |
| 219632_s_at | TRPV1 | transient receptor potential cation channel, subfamily v, member 1 |
| 206684_s_at | ATF7 | activating transcription factor 7 |
| 202801_at | PRKACA | protein kinase, camp-dependent, catalytic, alpha |
| 207506_at | GLRX3 | glutaredoxin 3 |
| 215737_x_at | USF2 | upstream transcription factor 2, c-fos interacting |
| 216176_at | HCRP1 | hepatocellular carcinoma-related hcrp1 |
| 207954_at | GATA2 | gata binding protein 2 |
| 201851_at | SH3GL1 | sh3-domain grb2-like 1 |
| 221907_at | TRMT61A | trna methyltransferase 61 homolog a (*s. cerevisiae*) |
| 205781_at | C16ORF7 | chromosome 16 open reading frame 7 |
| 202479_s_at | TRIB2 | tribbles homolog 2 (*drosophila*) |
| 216993_s_at | COL11A2 | collagen, type xi, alpha 2 |
| 215067_x_at | PRDX2 | peroxiredoxin 2 |
| 216735_x_at | — | — |
| 218218_at | APPL2 | adaptor protein, phosphotyrosine interaction, ph domain and leucine zipper containing 2 |
| 209695_at | PTP4A3 | protein tyrosine phosphatase type iva, member 3 |
| 213437_at | RUFY3 | run and fyve domain containing 3 |
| 218480_at | AGBL5 | atp/gtp binding protein-like 5 |
| 216684_s_at | SS18 | synovial sarcoma translocation, chromosome 18 |
| 221604_s_at | PEX16 | peroxisomal biogenesis factor 16 |
| 215563_s_at | MST1P9 | macrophage stimulating 1 (hepatocyte growth factor-like) pseudogene 9 |
| 207514_s_at | GNAT1 | guanine nucleotide binding protein (g protein), alpha transducing activity polypeptide 1 |
| 204987_at | ITIH2 | inter-alpha (globulin) inhibitor h2 |
| 208246_x_at | — | — |
| 205011_at | VWA5A | von willebrand factor a domain containing 5a |
| 208876_s_at | PAK2 | p21 protein (cdc42/rac)-activated kinase 2 |
| 215622_x_at | PHF7 | phd finger protein 7 |
| 205749_at | CYP1A1 | cytochrome p450, family 1, subfamily a, polypeptide 1 |
| 208082_x_at | — | — |
| 205372_at | PLAG1 | pleiomorphic adenoma gene 1 |
| 212026_s_at | EXOC7 | exocyst complex component 7 |
| 215604_x_at | — | — |
| 215538_at | LARGE | like-glycosyltransferase |
| 208996_s_at | POLR2C | polymerase (rna) ii (dna directed) polypeptide c, 33 kda |
| 216913_s_at | RRP12 | ribosomal rna processing 12 homolog (*s. cerevisiae*) |
| 218749_s_at | SLC24A6 | solute carrier family 24 (sodium/potassium/calcium exchanger), member 6 |
| 211054_at | INVS | inversin |
| 211960_s_at | RAB7A | rab7a, member ras oncogene family |
| 208715_at | TMCO1 | transmembrane and coiled-coil domains 1 |
| 202437_s_at | CYP1B1 | cytochrome p450, family 1, subfamily b, polypeptide 1 |
| 205057_s_at | IDUA | iduronidase, alpha-1- |
| 214902_x_at | — | — |
| 211802_x_at | CACNA1G | calcium channel, voltage-dependent, t type, alpha 1g subunit |
| 204387_x_at | MRP63 | mitochondrial ribosomal protein 63 |
| 217713_x_at | — | — |
| 205745_x_at | ADAM17 | adam metallopeptidase domain 17 |
| 215769_at | TRD@ | t cell receptor delta locus |
| 213497_at | ABTB2 | ankyrin repeat and btb (poz) domain containing 2 |
| 211373_s_at | PSEN2 | presenilin 2 (alzheimer disease 4) |

TABLE O-continued

Monoamine Oxidase B Inhibitor-Related Genes; Down Genes
(Keratinocyte Table)

| Affy ID | Gene Symbol | Title |
|---|---|---|
| 211810_s_at | GALC | galactosylceramidase |
| 218581_at | ABHD4 | abhydrolase domain containing 4 |
| 218363_at | EXD2 | exonuclease 3'-5' domain containing 2 |
| 217741_s_at | ZFAND5 | zinc finger, and-type domain 5 |
| 55705_at | C19ORF22 | chromosome 19 open reading frame 22 |
| 203241_at | UVRAG | uv radiation resistance associated gene |
| 214144_at | POLR2D | polymerase (rna) ii (dna directed) polypeptide d |
| 202980_s_at | SIAH1 | seven in absentia homolog 1 (drosophila) |
| 47560_at | LPHN1 | latrophilin 1 |
| 204458_at | PLA2G15 | phospholipase a2, group xv |
| 202416_at | DNAJC7 | dnaj (hsp40) homolog, subfamily c, member 7 |
| 213254_at | TNRC6B | trinucleotide repeat containing 6b |
| 214109_at | LRBA | lps-responsive vesicle trafficking, beach and anchor containing |
| 78495_at | ZNF783 | zinc finger family member 783 |
| 209288_s_at | CDC42EP3 | cdc42 effector protein (rho gtpase binding) 3 |
| 218072_at | COMMD9 | comm domain containing 9 |
| 202531_at | IRF1 | interferon regulatory factor 1 |
| 215933_s_at | HHEX | hematopoietically expressed homeobox |
| 218449_at | UFSP2 | ufm1-specific peptidase 2 |
| 212855_at | DCUN1D4 | dcn1, defective in cullin neddylation 1, domain containing 4 (s. cerevisiae) |
| 218885_s_at | GALNT12 | udp-n-acetyl-alpha-d-galactosamine:polypeptide n-acetylgalactosaminyltransferase 12 (galnac-t12) |
| 202053_s_at | ALDH3A2 | aldehyde dehydrogenase 3 family, member a2 |
| 211852_s_at | ATRN | Attractin |
| 204738_s_at | KRIT1 | krit1, ankyrin repeat containing |
| 202561_at | TNKS | tankyrase, trf1-interacting ankyrin-related adp-ribose polymerase |
| 219759_at | ERAP2 | endoplasmic reticulum aminopeptidase 2 |
| 204477_at | RABIF | rab interacting factor |
| 219587_at | TTC12 | tetratricopeptide repeat domain 12 |
| 219431_at | ARHGAP10 | rho gtpase activating protein 10 |
| 219336_s_at | ASCC1 | activating signal cointegrator 1 complex subunit 1 |
| 218617_at | TRIT1 | trna isopentenyltransferase 1 |

TABLE P

Monoamine Oxidase B Inhibitor-Related Genes; Up Genes
(Keratinocyte Table)

| Affy ID | Gene Symbol | Title |
|---|---|---|
| 208659_at | CLIC1 | chloride intracellular channel 1 |
| 218398_at | MRPS30 | mitochondrial ribosomal protein s30 |
| 202589_at | TYMS | thymidylate synthetase |
| 203577_at | GTF2H4 | general transcription factor iih, polypeptide 4, 52 kda |
| 200783_s_at | STMN1 | stathmin 1 |
| 200599_s_at | HSP90B1 | heat shock protein 90 kda beta (grp94), member 1 |
| 219288_at | C3ORF14 | chromosome 3 open reading frame 14 |
| 202297_s_at | RER1 | rer1 retention in endoplasmic reticulum 1 homolog (s. cerevisiae) |
| 201934_at | WDR82 | wd repeat domain 82 |
| 203415_at | PDCD6 | programmed cell death 6 |
| 208617_s_at | PTP4A2 | protein tyrosine phosphatase type iva, member 2 |
| 218040_at | PRPF38B | prp38 pre-mrna processing factor 38 (yeast) domain containing b |
| 222108_at | AMIGO2 | adhesion molecule with ig-like domain 2 |
| 205024_s_at | RAD51 | rad51 homolog (reca homolog, e. coli) (s. cerevisiae) |
| 205300_s_at | SNRNP35 | small nuclear ribonucleoprotein 35 kda (u11/u12) |
| 210554_s_at | CTBP2 | c-terminal binding protein 2 |
| 221506_s_at | TNPO2 | transportin 2 |
| 202031_s_at | WIPI2 | wd repeat domain, phosphoinositide interacting 2 |
| 221819_at | RAB35 | rab35, member ras oncogene family |
| 212786_at | CLEC16A | c-type lectin domain family 16, member a |
| 201305_x_at | ANP32B | acidic (leucine-rich) nuclear phosphoprotein 32 family, member b |
| 221859_at | SYT13 | synaptotagmin xiii |
| 218783_at | INTS7 | integrator complex subunit 7 |
| 208639_x_at | PDIA6 | protein disulfide isomerase family a, member 6 |
| 205000_at | DDX3Y | dead (asp-glu-ala-asp) box polypeptide 3, y-linked |

TABLE P-continued

Monoamine Oxidase B Inhibitor-Related Genes; Up Genes
(Keratinocyte Table)

| Affy ID | Gene Symbol | Title |
|---|---|---|
| 213136_at | PTPN2 | protein tyrosine phosphatase, non-receptor type 2 |
| 213803_at | KPNB1 | karyopherin (importin) beta 1 |
| 209773_s_at | RRM2 | ribonucleotide reductase m2 |
| 202211_at | ARFGAP3 | adp-ribosylation factor gtpase activating protein 3 |
| 209191_at | TUBB6 | tubulin, beta 6 |
| 211936_at | HSPA5 | heat shock 70 kda protein 5 (glucose-regulated protein, 78 kda) |
| 201890_at | RRM2 | ribonucleotide reductase m2 |
| 205227_at | IL1RAP | interleukin 1 receptor accessory protein |
| 204123_at | LIG3 | ligase iii, dna, atp-dependent |
| 204026_s_at | ZWINT | zw10 interactor |
| 208880_s_at | PRPF6 | prp6 pre-mrna processing factor 6 homolog (*s. cerevisiae*) |
| 201956_s_at | GNPAT | glyceronephosphate o-acyltransferase |
| 218520_at | TBK1 | tank-binding kinase 1 |
| 204497_at | ADCY9 | adenylate cyclase 9 |
| 218149_s_at | ZNF395 | zinc finger protein 395 |
| 202788_at | MAPKAPK3 | mitogen-activated protein kinase-activated protein kinase 3 |
| 202052_s_at | RAI14 | retinoic acid induced 14 |
| 218796_at | FERMT1 | fermitin family homolog 1 (*drosophila*) |
| 201795_at | LBR | lamin b receptor |
| 204391_x_at | TRIM24 | tripartite motif-containing 24 |
| 204159_at | CDKN2C | cyclin-dependent kinase inhibitor 2c (p18, inhibits cdk4) |
| 202397_at | NUTF2 | nuclear transport factor 2 |
| 210053_at | TAF5 | taf5 rna polymerase ii, tata box binding protein (tbp)-associated factor, 100 kda |
| 209441_at | RHOBTB2 | rho-related btb domain containing 2 |
| 220831_at | GCNT4 | glucosaminyl (n-acetyl) transferase 4, core 2 |
| 205442_at | MFAP3L | microfibrillar-associated protein 3-like |
| 205733_at | BLM | bloom syndrome, recq helicase-like |
| 208353_x_at | ANK1 | ankyrin 1, erythrocytic |
| 214186_s_at | HCG26 | hla complex group 26 (non-protein coding) |
| 207566_at | MR1 | major histocompatibility complex, class i-related |
| 210094_s_at | PARD3 | par-3 partitioning defective 3 homolog (*c. elegans*) |
| 206462_s_at | NTRK3 | neurotrophic tyrosine kinase, receptor, type 3 |
| 212750_at | PPP1R16B | protein phosphatase 1, regulatory (inhibitor) subunit 16b |
| 216701_at | C1ORF68 | chromosome 1 open reading frame 68 |
| 211109_at | JAK3 | janus kinase 3 |
| 215202_at | LOC91316 | glucuronidase, beta/immunoglobulin lambda-like polypeptide 1 pseudogene |
| 216939_s_at | HTR4 | 5-hydroxytryptamine (serotonin) receptor 4 |
| 216167_at | LRRN2 | leucine rich repeat neuronal 2 |
| 222101_s_at | DCHS1 | dachsous 1 (*drosophila*) |
| 208450_at | LGALS2 | lectin, galactoside-binding, soluble, 2 |

TABLE Q

Theme Approach: Highly Variable Expressed Genes in Balding;
Down Genes

| Affy ID | Gene Symbol | Title |
|---|---|---|
| 215001_s_at | GLUL | glutamate-ammonia ligase (glutamine synthetase) |
| 221561_at | SOAT1 | sterol o-acyltransferase (acyl-coenzyme a: cholesterol acyltransferase) 1 |
| 210397_at | DEFB1 | defensin, beta 1 |
| 201242_s_at | ATP1B1 | atpase, na+/k+ transporting, beta 1 polypeptide |
| 202668_at | EFNB2 | ephrin-b2 |
| 208804_s_at | SFRS6 | splicing factor, arginine/serine-rich 6 |
| 200759_x_at | NFE2L1 | nuclear factor (erythroid-derived 2)-like 1 |
| 37005_at | NBL1 | neuroblastoma, suppression of tumorigenicity 1 |
| 204121_at | GADD45G | growth arrest and dna-damage-inducible, gamma |
| 215269_at | TMEM1 | transmembrane protein 1 |
| 211069_s_at | SUMO1 | smt3 suppressor of mif two 3 homolog 1 (*s. cerevisiae*) |
| 202727_s_at | IFNGR1 | interferon gamma receptor 1 |
| 221675_s_at | CHPT1 | choline phosphotransferase 1 |
| 217751_at | GSTK1 | glutathione s-transferase kappa 1 |
| 209329_x_at | HIGD2A | hig1 domain family, member 2a |
| 209250_at | DEGS1 | degenerative spermatocyte homolog 1, lipid desaturase (*drosophila*) |
| 32069_at | N4BP1 | nedd4 binding protein 1 |

TABLE Q-continued

Theme Approach: Highly Variable Expressed Genes in Balding; Down Genes

| Affy ID | Gene Symbol | Title |
|---|---|---|
| 203221_at | TLE1 | transducin-like enhancer of split 1 (e(sp1) homolog, *drosophila*) |
| 207668_x_at | PDIA6 | protein disulfide isomerase family a, member 6 |
| 201243_s_at | ATP1B1 | atpase, na+/k+ transporting, beta 1 polypeptide |
| 206542_s_at | SMARCA2 | swi/snf related, matrix associated, actin dependent regulator of chromatin, subfamily a, member 2 |
| 208701_at | APLP2 | amyloid beta (a4) precursor-like protein 2 |
| 221423_s_at | YIPF5 | yip1 domain family, member 5 |
| 202064_s_at | SEL1L | sel-1 suppressor of lin-12-like (*c. elegans*) |
| 201732_s_at | CLCN3 | chloride channel 3 |
| 214428_x_at | C4A /// C4B | complement component 4a (rodgers blood group) /// complement component 4b (childo blood group) |
| 201587_s_at | IRAK1 | interleukin-1 receptor-associated kinase 1 |
| 213868_s_at | DHRS7 | dehydrogenase/reductase (sdr family) member 7 |
| 206861_s_at | CGGBP1 | cgg triplet repeat binding protein 1 |
| 213480_at | VAMP4 | vesicle-associated membrane protein 4 |
| 209522_s_at | CRAT | carnitine acetyltransferase |
| 202036_s_at | SFRP1 | secreted frizzled-related protein 1 |
| 212912_at | RPS6KA2 | ribosomal protein s6 kinase, 90 kda, polypeptide 2 |
| 209694_at | PTS | 6-pyruvoyltetrahydropterin synthase |
| 208634_s_at | MACF1 | microtubule-actin crosslinking factor 1 |
| 212274_at | LPIN1 | lipin 1 |
| 212239_at | PIK3R1 | phosphoinositide-3-kinase, regulatory subunit 1 (p85 alpha) |
| 217959_s_at | TRAPPC4 | trafficking protein particle complex 4 |
| 201011_at | RPN1 | ribophorin i |
| 204017_at | KDELR3 | kdel (lys-asp-glu-leu) endoplasmic reticulum protein retention receptor 3 |
| 200701_at | NPC2 | niemann-pick disease, type c2 |
| 213843_x_at | SLC6A8 | solute carrier family 6 (neurotransmitter transporter, creatine), member 8 |
| 201506_at | TGFBI | transforming growth factor, beta-induced, 68 kda |
| 201147_s_at | TIMP3 | timp metallopeptidase inhibitor 3 (sorsby fundus dystrophy, pseudoinflammatory) |
| 217728_at | S100A6 | s100 calcium binding protein a6 |
| 210612_s_at | SYNJ2 | synaptojanin 2 |
| 208767_s_at | LAPTM4B | lysosomal associated protein transmembrane 4 beta |
| 207431_s_at | DEGS1 | degenerative spermatocyte homolog 1, lipid desaturase (*drosophila*) |
| 212074_at | UNC84A | unc-84 homolog a (*c. elegans*) |
| 212195_at | IL6ST | interleukin 6 signal transducer (gp130, oncostatin m receptor) |
| 202037_s_at | SFRP1 | secreted frizzled-related protein 1 |
| 217707_x_at | SMARCA2 | swi/snf related, matrix associated, actin dependent regulator of chromatin, subfamily a, member 2 |
| 202250_s_at | WDR42A | wd repeat domain 42a |
| 201362_at | IVNS1ABP | influenza virus ns1a binding protein |
| 202748_at | GBP2 | guanylate binding protein 2, interferon-inducible |
| 215076_s_at | COL3A1 | collagen, type iii, alpha 1 (ehlers-danlos syndrome type iv, autosomal dominant) |
| 202489_s_at | FXYD3 | fxyd domain containing ion transport regulator 3 |
| 212144_at | UNC84B | unc-84 homolog b (*c. elegans*) |
| 214733_s_at | YIPF1 | yip1 domain family, member 1 |
| 204772_s_at | TTF1 | transcription termination factor, rna polymerase i |
| 211813_x_at | DCN | decorin |
| 1598_g_at | GAS6 | growth arrest-specific 6 |
| 218026_at | CCDC56 | coiled-coil domain containing 56 |
| 200844_s_at | PRDX6 | peroxiredoxin 6 |
| 204062_s_at | ULK2 | unc-51-like kinase 2 (*c. elegans*) |
| 212312_at | BCL2L1 | bcl2-like 1 |
| 221962_s_at | UBE2H | ubiquitin-conjugating enzyme e2h (ubc8 homolog, yeast) |
| 208704_x_at | APLP2 | amyloid beta (a4) precursor-like protein 2 |
| 216231_s_at | B2M | beta-2-microglobulin |
| 213011_s_at | TPI1 | triosephosphate isomerase 1 |
| 201348_at | GPX3 | glutathione peroxidase 3 (plasma) |
| 202769_at | CCNG2 | cyclin g2 |
| 208734_x_at | RAB2A | rab2a, member ras oncogene family |
| 221934_s_at | DALRD3 | dalr anticodon binding domain containing 3 |
| 200822_x_at | TPI1 | triosephosphate isomerase 1 |
| 201852_x_at | COL3A1 | collagen, type iii, alpha 1 (ehlers-danlos syndrome type iv, autosomal dominant) |
| 200737_at | PGK1 | phosphoglycerate kinase 1 |
| 215184_at | DAPK2 | death-associated protein kinase 2 |
| 208837_at | TMED3 | transmembrane emp24 protein transport domain containing 3 |
| 210968_s_at | RTN4 | reticulon 4 |
| 208248_x_at | APLP2 | amyloid beta (a4) precursor-like protein 2 |
| 211896_s_at | DCN | decorin |

TABLE Q-continued

Theme Approach: Highly Variable Expressed Genes in Balding; Down Genes

| Affy ID | Gene Symbol | Title |
|---|---|---|
| 206170_at | ADRB2 | adrenergic, beta-2-, receptor, surface |
| 207474_at | SNRK | snf related kinase |
| 209412_at | TMEM1 | transmembrane protein 1 |
| 213795_s_at | PTPRA | protein tyrosine phosphatase, receptor type, a |
| 204834_at | FGL2 | fibrinogen-like 2 |
| 211760_s_at | VAMP4 | vesicle-associated membrane protein 4 |
| 201901_s_at | YY1 | yy1 transcription factor |
| 204255_s_at | VDR | vitamin d (1,25-dihydroxyvitamin d3) receptor |
| 201893_x_at | DCN | decorin |
| 207808_s_at | PROS1 | protein s (alpha) |
| 205251_at | PER2 | period homolog 2 (*drosophila*) |
| 202597_at | IRF6 | interferon regulatory factor 6 |
| 204400_at | EFS | embryonal fyn-associated substrate |
| 200947_s_at | GLUD1 | glutamate dehydrogenase 1 |
| 201150_s_at | TIMP3 | timp metallopeptidase inhibitor 3 (sorsby fundus dystrophy, pseudoinflammatory) |
| 217917_s_at | DYNLRB1 | dynein, light chain, roadblock-type 1 |
| 200748_s_at | FTH1 | ferritin, heavy polypeptide 1 |
| 202147_s_at | IFRD1 | interferon-related developmental regulator 1 |
| 211769_x_at | SERINC3 | serine incorporator 3 |
| 202137_s_at | ZMYND11 | zinc finger, mynd domain containing 11 |
| 209163_at | CYB561 | cytochrome b-561 |
| 205225_at | ESR1 | estrogen receptor 1 |
| 219970_at | GIPC2 | gipc pdz domain containing family, member 2 |
| 205383_s_at | ZBTB20 | zinc finger and btb domain containing 20 |
| 208656_s_at | CCNI | cyclin i |
| 217993_s_at | MAT2B | methionine adenosyltransferase ii, beta |
| 207643_s_at | TNFRSF1A | tumor necrosis factor receptor superfamily, member 1a |
| 208761_s_at | SUMO1 | smt3 suppressor of mif two 3 homolog 1 (*s. cerevisiae*) |
| 202825_at | SLC25A4 | solute carrier family 25 (mitochondrial carrier; adenine nucleotide translocator), member 4 |
| 202598_at | S100A13 | s100 calcium binding protein a13 |
| 205480_s_at | UGP2 | udp-glucose pyrophosphorylase 2 |
| 217776_at | RDH11 | retinol dehydrogenase 11 (all-trans/9-cis/11-cis) |
| 210790_s_at | SAR1A | sar1 gene homolog a (*s. cerevisiae*) |
| 210788_s_at | DHRS7 | dehydrogenase/reductase (sdr family) member 7 |
| 214923_at | ATP6V1D | atpase, h+ transporting, lysosomal 34 kda, v1 subunit d |
| 212249_at | PIK3R1 | phosphoinositide-3-kinase, regulatory subunit 1 (p85 alpha) |
| 215168_at | TIMM17A | translocase of inner mitochondrial membrane 17 homolog a (yeast) |
| 218856_at | TNFRSF21 | tumor necrosis factor receptor superfamily, member 21 |
| 217913_at | VPS4A | vacuolar protein sorting 4 homolog a (*s. cerevisiae*) |
| 205684_s_at | DENND4C | denn/madd domain containing 4c |
| 212489_at | COL5A1 | collagen, type v, alpha 1 |
| 204862_s_at | NME3 | non-metastatic cells 3, protein expressed in |
| 218078_s_at | ZDHHC3 | zinc finger, dhhc-type containing 3 |
| 208916_at | SLC1A5 | solute carrier family 1 (neutral amino acid transporter), member 5 |
| 207700_s_at | NCOA3 | nuclear receptor coactivator 3 |
| 201599_at | OAT | ornithine aminotransferase (gyrate atrophy) |

TABLE R

Theme Approach: Highly Variable Expressed Genes in Balding; Up Genes

| Affy ID | Gene Symbol | Title |
|---|---|---|
| 202917_s_at | S100A8 | s100 calcium binding protein a8 |
| 214370_at | S100A8 | s100 calcium binding protein a8 |
| 206662_at | GLRX | glutaredoxin (thioltransferase) |
| 203128_at | SPTLC2 | serine palmitoyltransferase, long chain base subunit 2 |
| 220620_at | CRCT1 | cysteine-rich c-terminal 1 |
| 220800_s_at | TMOD3 | tropomodulin 3 (ubiquitous) |
| 201061_s_at | STOM | stomatin |
| 203821_at | HBEGF | heparin-binding egf-like growth factor |
| 200762_at | DPYSL2 | dihydropyrimidinase-like 2 |
| 201060_x_at | STOM | stomatin |
| 213273_at | ODZ4 | odz, odd oz/ten-m homolog 4 (*drosophila*) |
| 203700_s_at | DIO2 | deiodinase, iodothyronine, type ii |
| 205206_at | KAL1 | kallmann syndrome 1 sequence |
| 201767_s_at | ELAC2 | elac homolog 2 (*e. coli*) |
| 201549_x_at | JARID1B | jumonji, at rich interactive domain 1b |

TABLE R-continued

Theme Approach: Highly Variable Expressed Genes in Balding; Up Genes

| Affy ID | Gene Symbol | Title |
|---|---|---|
| 215377_at | CTBP2 | c-terminal binding protein 2 |
| 215704_at | FLG | filaggrin |
| 206306_at | RYR3 | ryanodine receptor 3 |
| 201614_s_at | RUVBL1 | ruvb-like 1 (e. coli) |
| 213852_at | RBM8A | rna binding motif protein 8a |
| 213479_at | NPTX2 | neuronal pentraxin ii |
| 209647_s_at | SOCS5 | suppressor of cytokine signaling 5 |
| 212865_s_at | COL14A1 | collagen, type xiv, alpha 1 (undulin) |
| 203166_at | CFDP1 | craniofacial development protein 1 |
| 201449_at | TIA1 | tial cytotoxic granule-associated rna binding protein |
| 221958_s_at | GPR177 | g protein-coupled receptor 177 |
| 201489_at | PPIF | peptidylprolyl isomerase f (cyclophilin f) |
| 214157_at | GNAS | gnas complex locus |
| 216921_s_at | KRT35 | keratin 35 |
| 201448_at | TIA1 | tial cytotoxic granule-associated rna binding protein |
| 216733_s_at | GATM | glycine amidinotransferase (1-arginine:glycine amidinotransferase) |
| 216092_s_at | SLC7A8 | solute carrier family 7 (cationic amino acid transporter, y+ system), member 8 |
| 202393_s_at | KLF10 | kruppel-like factor 10 |
| 203517_at | MTX2 | metaxin 2 |
| 204527_at | MYO5A | myosin va (heavy chain 12, myoxin) |
| 208676_s_at | PA2G4 | proliferation-associated 2g4, 38 kda |
| 214727_at | BRCA2 | breast cancer 2, early onset |
| 212321_at | SGPL1 | sphingosine-1-phosphate lyase 1 |
| 213621_s_at | GUK1 | guanylate kinase 1 |
| 214043_at | PTPRD | protein tyrosine phosphatase, receptor type, d |
| 203379_at | RPS6KA1 | ribosomal protein s6 kinase, 90 kda, polypeptide 1 |
| 203476_at | TPBG | trophoblast glycoprotein |
| 202084_s_at | SEC14L1 | sec14-like 1 (s. cerevisiae) |
| 208393_s_at | RAD50 | rad50 homolog (s. cerevisiae) |
| 217856_at | RBM8A | rna binding motif protein 8a |
| 217750_s_at | UBE2Z | ubiquitin-conjugating enzyme e2z (putative) |
| 213063_at | ZC3H14 | zinc finger ccch-type containing 14 |
| 209090_s_at | SH3GLB1 | sh3-domain grb2-like endophilin b1 |
| 203696_s_at | RFC2 | replication factor c (activator 1) 2, 40 kda |
| 221773_s_at | ELK3 | elk3, ets-domain protein (srf accessory protein 2) |
| 218014_at | NUP85 | nucleoporin 85 kda |
| 201417_at | SOX4 | sry (sex determining region y)-box 4 |
| 205463_s_at | PDGFA | platelet-derived growth factor alpha polypeptide |
| 211980_at | COL4A1 | collagen, type iv, alpha 1 |
| 210809_s_at | POSTN | periostin, osteoblast specific factor |
| 214247_s_at | DKK3 | dickkopf homolog 3 (xenopus laevis) |
| 205110_s_at | FGF13 | fibroblast growth factor 13 |
| 204050_s_at | CLTA | clathrin, light chain (lca) |
| 201220_x_at | CTBP2 | c-terminal binding protein 2 |
| 202007_at | NID1 | nidogen 1 |
| 204727_at | WDHD1 | wd repeat and hmg-box dna binding protein 1 |
| 206400_at | LGALS7 | lectin, galactoside-binding, soluble, 7 (galectin 7) |
| 212810_s_at | SLC1A4 | solute carrier family 1 (glutamate/neutral amino acid transporter), member 4 |
| 203625_x_at | MCAM | melanoma cell adhesion molecule |
| 212527_at | D15WSU75E | dna segment, chr 15, wayne state university 75, expressed |
| 212211_at | ANKRD17 | ankyrin repeat domain 17 |
| 202196_s_at | DKK3 | dickkopf homolog 3 (xenopus laevis) |
| 209885_at | RHOD | ras homolog gene family, member d |
| 209567_at | RRS1 | rrs1 ribosome biogenesis regulator homolog (s. cerevisiae) |
| 201006_at | PRDX2 | peroxiredoxin 2 |
| 209852_x_at | PSME3 | proteasome (prosome, macropain) activator subunit 3 (pa28 gamma; ki) |
| 212010_s_at | CDV3 | cdv3 homolog (mouse) |
| 202483_s_at | RANBP1 | ran binding protein 1 |
| 201976_s_at | MYO10 | myosin x |
| 221489_s_at | SPRY4 | sprouty homolog 4 (drosophila) |
| 200999_s_at | CKAP4 | cytoskeleton-associated protein 4 |
| 218683_at | PTBP2 | polypyrimidine tract binding protein 2 |
| 201939_at | PLK2 | polo-like kinase 2 (drosophila) |
| 211379_x_at | B3GALNT1 | beta-1,3-n-acetylgalactosaminyltransferase 1 (globoside blood group) |
| 207069_s_at | SMAD6 | smad family member 6 |
| 216604_s_at | SLC7A8 | solute carrier family 7 (cationic amino acid transporter, y+ system), member 8 |
| 212464_s_at | FN1 | fibronectin 1 |
| 217718_s_at | YWHAB | tyrosine 3-monooxygenase/tryptophan 5-monooxygenase activation protein, beta polypeptide |

TABLE R-continued

Theme Approach: Highly Variable Expressed Genes in Balding; Up Genes

| Affy ID | Gene Symbol | Title |
|---|---|---|
| 203427_at | ASF1A | asf1 anti-silencing function 1 homolog a (*s. cerevisiae*) |
| 212364_at | MYO1B | myosin ib |
| 211042_x_at | MCAM | melanoma cell adhesion molecule |
| 213923_at | RAP2B | rap2b, member of ras oncogene family |
| 209659_s_at | CDC16 | cell division cycle 16 homolog (*s. cerevisiae*) |
| 205763_s_at | DDX18 | dead (asp-glu-ala-asp) box polypeptide 18 |
| 212980_at | USP34 | ubiquitin specific peptidase 34 |
| 201105_at | LGALS1 | lectin, galactoside-binding, soluble, 1 (galectin 1) |
| 208658_at | PDIA4 | protein disulfide isomerase family a, member 4 |
| 220983_s_at | SPRY4 | sprouty homolog 4 (*drosophila*) |
| 207540_s_at | SYK | spleen tyrosine kinase |
| 219186_at | ZBTB7A | zinc finger and btb domain containing 7a |
| 209815_at | PTCH1 | patched homolog 1 (*drosophila*) |
| 208015_at | SMAD1 | smad family member 1 |
| 209360_s_at | RUNX1 | runt-related transcription factor 1 (acute myeloid leukemia 1; aml1 oncogene) |
| 213344_s_at | H2AFX | h2a histone family, member x |
| 217673_x_at | GNAS | gnas complex locus |
| 220239_at | KLHL7 | kelch-like 7 (*drosophila*) |
| 209816_at | PTCH1 | patched homolog 1 (*drosophila*) |
| 222328_x_at | MEG3 | maternally expressed 3 |
| 203818_s_at | SF3A3 | splicing factor 3a, subunit 3, 60 kda |
| 209032_s_at | CADM1 | cell adhesion molecule 1 |
| 210093_s_at | MAGOH | mago-nashi homolog, proliferation-associated (*drosophila*) |
| 218847_at | IGF2BP2 | insulin-like growth factor 2 mrna binding protein 2 |
| 214548_x_at | GNAS | gnas complex locus |
| 201234_at | ILK | integrin-linked kinase |
| 201136_at | PLP2 | proteolipid protein 2 (colonic epithelium-enriched) |
| 208670_s_at | EID1 | ep300 interacting inhibitor of differentiation 1 |
| 208896_at | DDX18 | dead (asp-glu-ala-asp) box polypeptide 18 |
| 214782_at | CTTN | cortactin |
| 38290_at | RGS14 | regulator of g-protein signalling 14 |
| 201548_s_at | JARID1B | jumonji, at rich interactive domain 1b |
| 218271_s_at | PARL | presenilin associated, rhomboid-like |
| 210477_x_at | MAPK8 | mitogen-activated protein kinase 8 |
| 201787_at | FBLN1 | fibulin 1 |
| 215389_s_at | TNNT2 | troponin t type 2 (cardiac) |
| 207266_x_at | RBMS1 | rna binding motif, single stranded interacting protein 1 |
| 210582_s_at | LIMK2 | lim domain kinase 2 |
| 210701_at | CFDP1 | craniofacial development protein 1 |
| 201663_s_at | SMC4 | structural maintenance of chromosomes 4 |
| 217028_at | CXCR4 | chemokine (c-x-c motif) receptor 4 |
| 218093_s_at | ANKRD10 | ankyrin repeat domain 10 |
| 218009_s_at | PRC1 | protein regulator of cytokinesis 1 |
| 211058_x_at | TUBA1B | tubulin, alpha 1b |
| 211072_x_at | TUBA1B | tubulin, alpha 1b |
| 213622_at | COL9A2 | collagen, type ix, alpha 2 |

TABLE S

Cosmetic Actionable Materials Tested in the DP survival assay from the C-map library

| CONCENTRATION | Chemical |
|---|---|
| 0.02 mM | 1,2-Hexanediol |
| 0.02 mM | 2-Methoxycinnamic acid |
| 0.02 mM | 3-Aminopyridine |
| 0.02 mM | 3-Indoleacetic acid |
| 0.02 mM | 3-O-Methyl-D-glucopyranose |
| 0.02 mM | 4-Aminobenzoic acid |
| 0.02 mM | 4-Methoxybenzoic acid |
| 0.02 mM | 6-Benzylaminopurine |
| 0.02 mM | Acetyl tributyl citrate |
| 0.02 mM | Acetyl-DL-carnitine hydrochloride |
| 0.02 mM | Allantoin |
| 0.02 mM | Aminophyllin Hydrate |
| 0.02 mM | 3-Pyridinecarboxylic acid, benzyl ester |
| 0.02 mM | beta-carotene |
| 0.02 mM | 2,6-Di-tert-butyl-4-methylphenol |
| 0.02 mM | Biotin |

TABLE S-continued

Cosmetic Actionable Materials Tested in the DP survival assay from the C-map library

| CONCENTRATION | Chemical |
|---|---|
| 0.02 mM | Bisabolol |
| 0.02 mM | Citric acid |
| 0.02 mM | PESTANAL |
| 0.02 mM | Coenzyme Q10 |
| 0.02 mM | Copper(II) D-gluconate |
| 0.02 mM | Creatine, anhydrous |
| 0.02 mM | Curcumin from Curcuma longa (Tumeric) |
| 0.002 mM | (−)-Epigallocatechin gallate |
| 0.02 mM | Daidzein |
| 0.02 mM | trans-Dehydroandrosterone |
| 0.02 mM | Dibutyl phthalate |
| 0.02 mM | Polydimethylsiloxane, trimethylsiloxy terminated, mw 237 |
| 0.02 mM | Polydimethylsiloxane, trimethylsiloxy terminated, mw 410 |
| 0.02 mM | N,N-Dimethylethanolamine |
| 0.02 mM | Ethylenediaminetetraacetic acid |
| 0.02 mM | Ethyl 4-hydroxybenzoate |
| 0.02 mM | Eugenol |
| 0.02 mM | Ferulic acid |
| 0.02 mM | Folic acid |
| 0.02 mM | Gallic acid |
| 0.02 mM | 4'',5,7-Trihydroxyisoflavone |
| 0.02 mM | D-(+)-Gluconic acid ?-lactone |
| 0.02 mM | L-Glutathione, Reduced |
| 0.02 mM | Glycolic acid |
| 0.02 mM | 6-Furfurylaminopurine |
| 0.02 mM | Kojic acid |
| 0.02 mM | Lactic acid |
| 0.02 mM | Lactobionic acid |
| 0.02 mM | L-Carnitine inner salt |
| 0.02 mM | L-(−)-Fucose |
| 0.02 mM | (R)-(+)-1,2-Dithiolane-3-pentanoic acid |
| 0.02 mM | D-Mannitol |
| 0.02 mM | Menthol |
| 0.02 mM | Methyl sulfone |
| 0.02 mM | N-methyl-L-serine |
| 0.02 mM | 2-Ethylhexyl 2-cyano-3,3-diphenylacrylate |
| 0.02 mM | Oleuropein |
| 0.02 mM | 2-Hydroxy-4-methoxy-benzophenone |
| 0.02 mM | D-Panthenol |
| 0.02 mM | Poly(ethylene glycol) average Mn 380-420 |
| 0.02 mM | Potassium D-gluconate |
| 0.02 mM | Pyruvic acid |
| 0.02 mM | Raspberry ketone |
| 0.02 mM | Resveratrol |
| 0.02 mM | Salicylic acid |
| 0.02 mM | Sorbic acid |
| 0.02 mM | Taurine |
| 0.02 mM | Tetrahexadecyl ascorbate |
| 0.02 mM | Thymol |
| 0.02 mM | Tributyl citrate |
| 0.02 mM | Urea |
| 0.02 mM | L-Ascorbic Acid |
| 0.02 mM | Vitamin E (alpha-tocopherol) |
| 0.02 mM | Xylitol |
| 0.02% | Boswellin CG |
| 0.002% | Boswellin CG |
| 0.002 mM | Ellagic acid |
| 0.002 mM | ?-Thujaplicin |
| 0.002 mM | Menthyl anthranilate |
| 0.002 mM | Oleanolic acid |
| 0.002% | Emblica A |
| 0.0002% | Emblica A |
| 0.02% | Jojoba oil from Simmondsia chinensis |
| 0.002% | Jojoba oil from Simmondsia chinensis |
| 0.02% | Sodium PEG-7 olive oil carboxylate |
| 0.002% | Sodium PEG-7 olive oil carboxylate |
| 0.02 mM | Flavone |
| 0.005% | Lanol |
| 0.02% | Symcalmin |
| 0.02% | Panax ginseng extract |
| 0.002% | Panax ginseng extract |
| 0.02 mM | Poly-L-lysine hydrobromide average MW 500-2000 |
| 0.02 mM | Tween 80 |
| 0.02 mM | Zinc gluconate trihydrate |
| 0.02 mM | Zincidone |

TABLE S-continued

Cosmetic Actionable Materials Tested in the DP survival assay from the C-map library

| CONCENTRATION | Chemical |
|---|---|
| 0.02 mM | 1,3-Dihydroxyacetone dimer |
| 0.02 mM | 1-Naphthol |
| 0.02 mM | 5-Amino-o-cresol |
| 0.02 mM | 4-Amino-3-Nitrophenol |
| 0.02 mM | alpha-iso-Methylionone |
| 0.02 mM | Asiaticoside |
| 0.02 mM | AZULENE |
| 0.02 mM | 2-Hydroxy-4-methoxybenzophenone |
| 0.02 mM | BENZYL ALCOHOL |
| 0.02 mM | Berberine Chloride |
| 0.02 mM | Betaine anhydrous |
| 0.02 mM | caffeic acid |
| 0.02 mM | (+−)-Camphor |
| 0.02 mM | 1-Hexadecanol |
| 0.02 mM | Chlorogenic acid |
| 0.02 mM | CINNAMYL ALCOHOL |
| 0.02 mM | COUMARIN |
| 0.02 mM | CREATININE, Anhydrous |
| 0.02 mM | DECAMETHYLCYCLOPENTASILOXANE |
| 0.02 mM | D-carvone |
| 0.02 mM | 4-Hydroxy-4-methyl-2-pentanone |
| 0.02 mM | DIAZOLIDINYL UREA |
| 0.02 mM | Diethanolamine |
| 0.02 mM | Isosorbid-dimethyl ether |
| 0.02 mM | D-Isoascorbic acid |
| 0.02 mM | meso-Erythritol |
| 0.02 mM | Diethylene glycolmonoethyl ether |
| 0.02 mM | trans, trans-Farnesol |
| 0.02 mM | GERANIOL |
| 0.02 mM | D-Gluconic acid, Sodium salt |
| 0.02 mM | rac-1-Lauroglycerol |
| 0.02 mM | Hesperidin |
| 0.02 mM | HYDROQUINONE |
| 0.02 mM | Imidazolidinyl Urea |
| 0.02 mM | myo-inositol |
| 0.02 mM | N-(2-Hydroxyethyl)lactamide |
| 0.02 mM | N,N-diethanollauramide |
| 0.02 mM | Dodecanoic Acid |
| 0.02 mM | Levulinic Acid |
| 0.02 mM | LINALOOL |
| 0.02 mM | DL-Malic acid |
| 0.02 mM | Maltitol |
| 0.02% | MALTODEXTRIN |
| 0.002% | MALTODEXTRIN |
| 0.02 mM | L-menthyl-Lactate |
| 0.02 mM | METHYL SALICYLATE |
| 0.02 mM | Tergitol NP 10 |
| 0.02 mM | Oleic Acid |
| 0.02 mM | D-(−) Pantolactone |
| 0.02 mM | PHENETHYL ALCOHOL |
| 0.02 mM | 2-Phenoxyethanol |
| 0.02 mM | 2-Phenyl-5-benzimidazole-sulfonic acid |
| 0.02 mM | PHYLLOQUINONE |
| 0.02 mM | Pluronic L101 |
| 0.02 mM | Propyl Gallate |
| 0.02 mM | PYRIDOXINE HCL |
| 0.02 mM | Resorcinol |
| 0.02 mM | (−)-Riboflavin |
| 0.02 mM | SARCOSINE |
| 0.02 mM | Dehydroacetic Acid Sodium salt |
| 0.02 mM | SODIUM SACCHARIN salt hydrate |
| 0.02 mM | D-SORBITOL |
| 0.02 mM | DL-Tartaric Acid anhyrdrous |
| 0.02 mM | tert-BUTYL HYDROQUINONE |
| 0.02 mM | Thiamine Hydrochloride |
| 0.002 mM | Ursolic acid |
| 0.0002% | Coleus Extract |
| 0.0002% | Neem oil Limonoids |
| 0.000624% | Retinol 15 D |
| 0.1 mM | Thymol |
| 0.4 mM | Chelidonic Acid |
| 0.4 mM | 5-Hydroxyisophthalic acid |
| 0.4 mM | DL-Tropic Acid |
| 0.02 mM | beta-cyclodextrin |
| 0.02 mM | Nicotinic Acid n-Hexyl Ester |

TABLE S-continued

Cosmetic Actionable Materials Tested in the DP survival assay from the C-map library

| CONCENTRATION | Chemical |
|---|---|
| 0.02 mM | Polyethylene (20) Sorbitan Monoisostearare |
| 0.02 mM | Glycerol Monoisosterare |
| 0.02 mM | PADIMATE O |
| 0.02 mM | 3-Methyl-1-phenyl-2-pyrazoline-5-one |
| 0.02 mM | Retinol |
| 0.02 mM | Sodium Dodecylbenzenesulfonate |
| 0.02 mM | 6-Hydroxy-1,3-benzoxathio1-2-one |
| 0.02 mM | Triacetin |
| 0.02 mM | OCTAMETHYLTRISILOXANE |
| 0.02 mM | Undecylenic Acid |
| 0.02 mM | Uric acid |
| 0.02 mM | VANILLIN |
| 0.02 mM | xymenynic acid |
| 0.02 mM | 1,4-Phenylenediamine |
| 0.02 mM | DL-Mandelic Acid |
| 0.02 mM | DL-Batyl Alcohol |
| 0.002 mM | Ergocalciferol |
| 0.02 mM | gamma-Nonalactone |
| 0.02 mM | omega-pentadecalactone |
| 0.02 mM | Tannic acid |
| 0.02 mM | Irgasan |
| 0.02 mM | Adipic Acid Diisopropyl Ether |
| 0.02 mM | 2-(2-Hydroxy-5-methyl-phenyl)benzotriazole |
| 0.02 mM | 2-Methyl Resorcinol |
| 0.02 mM | Pyrogallol |
| 0.02 mM | Ricinoleic acid |
| 0.02 mM | N-Acetylethanolamine |
| 0.02 mM | Abietic acid, 75% |
| 0.02 mM | delta-Nonalactone |
| 0.02 mM | 5-Benzoyl-4-hydroxy-2-methoxybenzenesulfonic acid |
| 0.02 mM | Avobenzone |
| 0.02 mM | Carmine Red |
| 0.02 mM | D+/− Trehalose Dihydrate |
| 0.02% | Rosemary oil |
| 0.002% | Rosemary oil |
| 0.02 mM | Guanine |
| 0.02 mM | 1-Dodecyl-2-pyrrolidone |
| 0.02 mM | Cyanocobalamin |
| 0.02 mM | Methyl dihydrojasmonate |
| 0.02 mM | 2-tert-Butyl-6-(5-chloro-2H-benzotriazol-2-yl)-4-methylphenol |
| 0.02 mM | Pramoxine hydrochloride |
| 0.02 mM | 3,4,4?-Trichlorocarbanilide |
| 0.02 mM | Rutin Hydrate |
| 0.02 mM | erythro-Aleuritic acid |
| 0.02 mM | Asiatic acid |
| 0.02 mM | 4-Methoxyphenol |
| 0.002% | Centellin ® CG |
| 0.002 mM | Piroctone olamine |
| 0.02% | Aesculus Hippocastanum |
| 0.002% | Aesculus Hippocastanum |
| 0.02% | Saponin |
| 0.002% | Saponin |
| 0.02 mM | Glycyrrhizic acid, ammonium salt |
| 0.02 mM | 3,3-diindolylmethane |
| 0.02 mM | L-Carcinine |
| 0.02% | Carrot seed oil |
| 0.002% | Carrot seed oil |
| 0.02% | Laminarghane |
| 0.02 mM | gamma-Linolenic acid |
| 0.0002% | Arjun |
| 0.002 mM | 6-HYDROXYINDOLE |
| 0.000624% | Retinol 15 D |
| 0.02 mM | Guanosine |
| 0.02 mM | 3,4-Dihydroxyphenyl Ethanol |
| 0.02 mM | Oleyl alchol |
| 0.02 mM | 4-Methoxycinnamic Acid 2-Ethyl Hexyl Ether |
| 0.02 mM | 2-Aminoethanethiosulfonic S-Acid |
| 0.02 mM | Tyramine |
| 0.02 mM | Anethole |
| 0.02 mM | cis-Jasmone |
| 0.02 mM | 5-Dodecanolide |
| 0.02 mM | (3aR)-(+)-Sclareolide |
| 0.02 mM | Chrysin |
| 0.02 mM | 3-butylidenephthalide |
| 0.02 mM | Ethyl pyruvate |

TABLE S-continued

Cosmetic Actionable Materials Tested in the DP survival assay from the C-map library

| CONCENTRATION | Chemical |
|---|---|
| 0.02 mM | L-Carvone |
| 0.02 mM | Acid Yellow 23 |
| 0.02 mM | D-(+)-Xylose |
| 0.02 mM | Maltol |
| 0.02 mM | Cholic acid |
| 0.02% | Castor oil |
| 0.002% | Castor oil |
| 0.02 mM | Azofuchsin |
| 0.02 mM | Cosmpoerine |
| 0.02 mM | Monoolein |
| 0.02 mM | AMMONIUM GLYCOLATE 80% |
| 0.02 mM | Laurydone |
| 0.02% | TEGO-BETAIN CK |
| 0.002% | TEGO-BETAIN CK |
| 0.02% | Oryza Sativa (Rice) Bran Oil |
| 0.002% | Oryza Sativa (Rice) Bran Oil |
| 0.02% | Refined Rice Bran Oil |
| 0.002% | Refined Rice Bran Oil |
| 0.02% | Arginine/Lysine polypeptide(Amadorine) |
| 0.002% | Arginine/Lysine polypeptide(Amadorine) |
| 0.02 mM | cis-4-Hydroxydodec-6-enoic acid lactone |
| 0.002 mM | HP-101 |
| 0.0002 mM | HP-101 |
| 0.002 mM | Octopirox |
| 0.0002 mM | Octopirox |
| 0.02 mM | Ginsenoside Rb1 |
| 0.02 mM | 2-Propylpentanoic acid sodium |
| 0.02 mM | N-Stearoyl-Phytosphingosine |
| 0.02 mM | D-Glucoheptono-1,4-lactone |
| 0.02 mM | Hydantoin |
| 0.02 mM | Astaxanthin |
| 0.02 mM | Azelaic Acid |
| 0.02 mM | Etidronic Acid Monohydrate |
| 0.002 mM | n-Dodecyl ?-D-glucopyranoside |
| 0.0002% | Polyphenon 60 |
| 0.00002% | Polyphenon 60 |
| 0.02 mM | 2-Methyl-4-isothiazolin-3-one |
| 0.02% | Methyl-4,6-O-benzylidene-alpha-D-glucopyranoside |
| 0.02% | Dimethylcaffeic acid |
| 0.02% | Norcamphor |
| 0.02% | 2,3-Dimethoxybenzoic acid |
| 0.02% | 4-Methoxycinnamic acid |
| 0.02% | 2-Methoxycinnamic acid |
| 0.02 mM | Ascorbic acid 6-palmitate |
| 0.02 mM | Esculin hydrate |
| 0.02 mM | 4-isopropyl-3-methylphenol |
| 0.02 mM | r-(+)-limonene |
| 0.02 mM | 3,3,5-Trimethylcyclohexyl Salicylate |
| 0.02 mM | D-(+)-chiro-Inositol 95% |
| 0.02 mM | 5-Aminoimidazole-4-carboxamide 1-?-D-ribofuranoside Acadesine |
| 0.02 mM | Polyvinylpyrrolidinone(PVP) |
| 0.02 mM | Silymarin |
| 0.02% | Cocamidopropyl Betaine |
| 0.002% | Cocamidopropyl Betaine |
| 0.02% | 4-Phenylmorpholine |
| 0.02% | 1,3,5-Benzenetriol, dihydrate |
| 0.02% | (+−)-Dihydro-3-amino-2(3H)-thiophenone hydrochloride |
| 0.02% | Pinoxide |
| 0.02% | NET-Tocotrienols |
| 0.02% | mucic acid powder (from apples) |
| 0.02 mM | D-Pantothenic acid hemicalcium salt |
| 0.02 mM | 1-Phenoxy-2-propanol 93% |
| 0.02 mM | Beta-Citronellol |
| 0.02 mM | Rosmarinic acid |
| 0.02 mM | Triethanolamine |
| 0.02 mM | Tolnaftate |
| 0.02 mM | (R)-(−)-alpha-Acetylmendelic acid |
| 0.02 mM | 4-Methoxybenzyl alcohol |
| 0.002 mM | Methyl 2-octynoate |
| 0.02% | Peppermint oil |
| 0.002% | Peppermint oil |
| 0.02 mM | N-Phenyl-1,4-phenylenediamine |
| 0.02 mM | N-Ethyl-p-toluene sulfonamide |
| 0.04 mM | Nonivamide; 8-Nordihydrocapsaicin |
| 0.04 mM | Carbazole |

TABLE S-continued

Cosmetic Actionable Materials Tested in the DP survival assay from the C-map library

| CONCENTRATION | Chemical |
|---|---|
| 0.04 mM | [2,2?]-Furildioxime monohydrate |
| 0.04 mM | 2-Benzimidazolamine |
| 0.04 mM | 4-Aminopiazthiole |
| 0.02 mM | (−)-Borneol; aka: (1S,2R,4S)-1,7,7-trimethylbicyclo[2.2.1]heptan-2-ol |
| 0.02 mM | (+)-Borneol; aka: (1R,2S,4R)-1,7,7-trimethylbicyclo[2.2.1]heptan-2-ol |
| 0.02 mM | (−)-Camphor: aka: (1S,4S)-1,7,7-trimethylbicyclo[2.2.1]heptan-2-one |
| 0.02 mM | D-Camphor: aka: (1R,4R)-1,7,7-trimethylbicyclo[2.2.1]heptan-2-one |
| 0.002 mM | Phytantriol |
| 0.002 mM | PHYTOSPHINGOSINE-HCl |
| 0.002 mM | Tannic acid |
| 0.002 mM | Escin |
| 0.002 mM | Linolenic acid |
| 0.002 mM | Carnosic acid |
| 0.002 mM | Brij 98 |
| 0.002 mM | Chlorhexidine dihydrochloride |
| 0.4 mM | Pyruvic Acid, Sodium salt |
| 0.02 mM | L-Arginine |
| 0.02 mM | (S)-6-Methoxy-alpha-methyl-2-naphthaleneacetic acid sodium |
| 0.02 mM | (1-Hydroxy-3-(methylpentylamino)propylidene)bisphosphonic acid sodium |
| 0.02 mM | cAMP; 3',5'-Cyclic AMP |
| 0.02 mM | L-Buthionine-sulfoxime |
| 0.002% | Hyaluronic acid sodium salt from rooster comb |
| 0.02 mM | L-GLUTAMIC ACID |
| 0.02 mM | Polyethylene Glycol 20,000 Flake |
| 0.02 mM | L-Phenylalanine |
| 0.02 mM | Sodium Benzoate |
| 0.02 mM | L-Carnosine |
| 0.02 mM | 6-Aminocaproic acid |
| 0.002% | Xanthan gum |
| 0.02 mM | trans-4-Hydroxy-L-proline |
| 0.02 mM | Manganese gluconate |
| 0.02 mM | Magnesium gluconate |
| 0.02 mM | Calcium gluconate |
| 0.002% | Laminarghane |
| 0.02 mM | Aginine/Lysine dipeptide (Amadorine) |
| 0.02 mM | Calcium PCA |
| 0.02% | Laminarghane |
| 0.02 mM | 1-citrulline |
| 0.02 mM | d-(+)-glucosamine hydrochloride |
| 0.02 mM | L-2-aminoadipic acid |
| 0.02 mM | p-CPA |
| 0.02 mM | Usnic Acid |
| 0.002 mM | (S)-alpha-Methyltyrosine |
| 0.02 mM | Theobromine |
| 0.002% | Alginic acid from brown algae |
| 0.002% | Chitosan, Low Molecular Weight |
| 0.02% | Glutamylamidoethyl Indole |
| 0.04 mM | Ethanedial dihydrate |
| 0.02% | DL-erythro-Aleuritic acid |
| 0.02 mM | Beta-Sitosterol |
| 0.02 mM | Cholesterol |
| 0.02 mM | Lanosterol |
| 0.002 mM | Diosgenin |
| 0.02 mM | 1-Eicosanol |
| 0.002% | Cocamide MEA |
| 0.02% | Pyridoxine Triisopalmitate |
| 0.04 mM | 4,4?-Dimethyl-2,2?-bipyridine |
| 0.005% | Carapa guianensis Oil |
| 0.001% | Phytosterols |
| 0.006% | Triacetyl sphinganine |
| 0.006% | N-Hexanoyl sphinganine |
| 0.02% | Camphor white oil |
| 0.002% | Camphor white oil |
| 0.002 mM | Diosgenin |
| 0.0002% | Cocamide MEA |

TABLE T

DP Survival Assay; Down Genes

| Affy ID | Title | Gene Symbol |
|---|---|---|
| 1598_g_at | growth arrest-specific 6 | GAS6 |
| 200686_s_at | serine/arginine-rich splicing factor 11 | SRSF11 |
| 200721_s_at | arp1 actin-related protein 1 homolog a, centractin alpha (yeast) | ACTR1A |
| 200726_at | protein phosphatase 1, catalytic subunit, gamma isozyme | PPP1CC |
| 200919_at | polyhomeotic homolog 2 (*drosophila*) | PHC2 |
| 200940_s_at | arginine-glutamic acid dipeptide (re) repeats | RERE |
| 201074_at | swi/snf related, matrix associated, actin dependent regulator of chromatin, subfamily c, member 1 | SMARCC1 |
| 201165_s_at | pumilio homolog 1 (*drosophila*) | PUM1 |
| 201178_at | f-box protein 7 | FBXO7 |
| 201210_at | dead (asp-glu-ala-asp) box polypeptide 3, x-linked | DDX3X |
| 201423_s_at | cullin 4a | CUL4A |
| 201545_s_at | poly(a) binding protein, nuclear 1 | PABPN1 |
| 201564_s_at | fascin homolog 1, actin-bundling protein (*strongylocentrotus purpuratus*) | FSCN1 |
| 201678_s_at | chromosome 3 open reading frame 37 | C3ORF37 |
| 201817_at | ubiquitin protein ligase e3c | UBE3C |
| 201853_s_at | cell division cycle 25 homolog b (*s. pombe*) | CDC25B |
| 201908_at | dishevelled, dsh homolog 3 (*drosophila*) | DVL3 |
| 201945_at | furin (paired basic amino acid cleaving enzyme) | FURIN |
| 202406_s_at | tial cytotoxic granule-associated rna binding protein-like 1 | TIAL1 |
| 202421_at | immunoglobulin superfamily, member 3 | IGSF3 |
| 202449_s_at | retinoid x receptor, alpha | RXRA |
| 202466_at | pap associated domain containing 7 | PAPD7 |
| 202484_s_at | methyl-cpg binding domain protein 2 | MBD2 |
| 202519_at | mlx interacting protein | MLXIP |
| 202670_at | mitogen-activated protein kinase kinase 1 | MAP2K1 |
| 202805_s_at | atp-binding cassette, sub-family c (cftr/mrp), member 1 | ABCC1 |
| 202894_at | eph receptor b4 | EPHB4 |
| 202932_at | v-yes-1 yamaguchi sarcoma viral oncogene homolog 1 | YES1 |
| 203221_at | transducin-like enhancer of split 1 (e(sp1) homolog, *drosophila*) | TLE1 |
| 203233_at | interleukin 4 receptor | IL4R |
| 203275_at | interferon regulatory factor 2 | IRF2 |
| 203392_s_at | c-terminal binding protein 1 | CTBP1 |
| 203464_s_at | epsin 2 | EPN2 |
| 203600_s_at | family with sequence similarity 193, member a | FAM193A |
| 203693_s_at | e2f transcription factor 3 | E2F3 |
| 203875_at | swi/snf related, matrix associated, actin dependent regulator of chromatin, subfamily a, member 1 | SMARCA1 |
| 203933_at | rab11 family interacting protein 3 (class ii) | RAB11FIP3 |
| 203966_s_at | protein phosphatase, mg2+/mn2+ dependent, 1a | PPM1A |
| 204009_s_at | v-ki-ras2 kirsten rat sarcoma viral oncogene homolog | KRAS |
| 204321_at | neogenin 1 | NEO1 |
| 204497_at | adenylate cyclase 9 | ADCY9 |
| 204866_at | phd finger protein 16 | PHF16 |
| 205105_at | mannosidase, alpha, class 2a, member 1 | MAN2A1 |
| 205292_s_at | heterogeneous nuclear ribonucleoprotein a2/b1 | HNRNPA2B1 |
| 205372_at | pleiomorphic adenoma gene 1 | PLAG1 |
| 206174_s_at | protein phosphatase 6, catalytic subunit | PPP6C |
| 206335_at | galactosamine (n-acetyl)-6-sulfate sulfatase | GALNS |
| 208351_s_at | mitogen-activated protein kinase 1 | MAPK1 |
| 208718_at | dead (asp-glu-ala-asp) box polyoeptide 17 | DDX17 |
| 208766_s_at | heterogeneous nuclear ribonucleoprotein r | HNRNPR |
| 208821_at | small nuclear ribonucleoprotein polypeptides b and b1 | SNRPB |
| 208948_s_at | staufen, rna binding protein, homolog 1 (*drosophila*) | STAU1 |
| 208979_at | nuclear receptor coactivator 6 | NCOA6 |
| 208989_s_at | lysine (k)-specific demethylase 2a | KDM2A |
| 209053_s_at | wolf-hirschhorn syndrome candidate 1 | WHSC1 |
| 209152_s_at | transcription factor 3 (e2a immunoglobulin enhancer binding factors e12/e47) | TCF3 |
| 209272_at | ngfi-a binding protein 1 (egr1 binding protein 1) | NAB1 |
| 209497_s_at | rna binding motif protein 4b | RBM4B |
| 209502_s_at | bai1-associated protein 2 | BAIAP2 |
| 209593_s_at | torsin family 1, member b (torsin b) | TOR1B |
| 210740_s_at | inositol 1,3,4-triphosphate 5/6 kinase | ITPK1 |
| 211946_s_at | hla-b associated transcript 2-like 2 | BAT2L2 |
| 212017_at | family with sequence similarity 168, member b | FAM168B |
| 212064_x_at | myc-associated zinc finger protein (purine-binding transcription factor) | MAZ |
| 212129_at | non imprinted in prader-willi/angelman syndrome 2 | NIPA2 |
| 212137_at | la ribonucleoprotein domain family, member 1 | LARP1 |
| 212138_at | pds5, regulator of cohesion maintenance, homolog a (*s. cerevisiae*) | PDS5A |
| 212219_at | proteasome (prosome, macropain) activator subunit 4 | PSME4 |

TABLE T-continued

DP Survival Assay; Down Genes

| Affy ID | Title | Gene Symbol |
|---|---|---|
| 212248_at | metadherin | MTDH |
| 212306_at | cytoplasmic linker associated protein 2 | CLASP2 |
| 212377_s_at | notch 2 | NOTCH2 |
| 212436_at | tripartite motif-containing 33 | TRIM33 |
| 212517_at | attractin | ATRN |
| 212621_at | transmembrane protein 194a | TMEM194A |
| 212625_at | syntaxin 10 | STX10 |
| 212655_at | zinc finger, cchc domain containing 14 | ZCCHC14 |
| 212747_at | ankyrin repeat and sterile alpha motif domain containing 1a | ANKS1A |
| 212863_x_at | c-terminal binding protein 1 | CTBP1 |
| 213037_x_at | staufen, rna binding protein, homolog 1 (drosophila) | STAU1 |
| 213073_at | zinc finger, fyve domain containing 26 | ZFYVE26 |
| 213123_at | microfibrillar-associated protein 3 | MFAP3 |
| 213151_s_at | septin 7 | 7-SEP |
| 213435_at | satb homeobox 2 | SATB2 |
| 213567_at | karyopherin alpha 4 (importin alpha 3) | KPNA4 |
| 213573_at | — | — |
| 213618_at | arfgap with rhogap domain, ankyrin repeat and ph domain 2 | ARAP2 |
| 213848_at | dual specificity phosphatase 7 | DUSP7 |
| 214313_s_at | eukaryotic translation initiation factor 5b | EIF5B |
| 214743_at | cut-like homeobox 1 | CUX1 |
| 214869_x_at | gtpase activating protein and vps9 domains 1 | GAPVD1 |
| 215903_s_at | microtubule associated serine/threonine kinase 2 | MAST2 |
| 216153_x_at | reversion-inducing-cysteine-rich protein with kazal motifs | RECK |
| 216652_s_at | down-regulator of transcription 1, tbp-binding (negative cofactor 2) | DR1 |
| 217612_at | translocase of inner mitochondrial membrane 50 homolog (s. cerevisiae) | TIMM50 |
| 217746_s_at | programmed cell death 6 interacting protein | PDCD6IP |
| 217844_at | ctd (carboxy-terminal domain, rna polymerase ii, polypeptide a) small phosphatase 1 | CTDSP1 |
| 217910_x_at | max-like protein x | MLX |
| 218019_s_at | pyridoxal (pyridoxine, vitamin b6) kinase | PDXK |
| 218062_x_at | cdc42 effector protein (rho gtpase binding) 4 | CDC42EP4 |
| 218173_s_at | wolf-hirschhorn syndrome candidate 1-like 1 | WHSC1L1 |
| 218295_s_at | nucleoporin 50 kda | NUP50 |
| 218324_s_at | spermatogenesis associated, serine-rich 2 | SPATS2 |
| 218366_x_at | methyltransferase 11 domain containing 1 | METT11D1 |
| 218670_at | pseudouridylate synthase 1 | PUS1 |
| 219129_s_at | sap30-like | SAP30L |
| 219307_at | prenyl (decaprenyl) diphosphate synthase, subunit 2 | PDSS2 |
| 219620_x_at | chromosome 9 open reading frame 167 | C9ORF167 |
| 219631_at | low density lipoprotein receptor-related protein 12 | LRP12 |
| 219821_s_at | glucose-fructose oxidoreductase domain containing 1 | GFOD1 |
| 220974_x_at | sideroflexin 3 | SFXN3 |
| 221481_x_at | heterogeneous nuclear ribonucleoprotein d (au-rich element rna binding protein 1, 37 kda) | HNRNPD |
| 221743_at | cugbp, elav-like family member 1 | CELF1 |
| 45572_s_at | golgi-associated, gamma adaptin ear containing, arf binding protein 1 | GGA1 |
| 47571_at | zinc finger protein 236 | ZNF236 |
| 50277_at | golgi-associated, gamma adaptin ear containing, arf binding protein 1 | GGA1 |
| 55065_at | map/microtubule affinity-regulating kinase 4 | MARK4 |

TABLE U

DP Survival Assay; Up Genes

| Affy ID | Title | Gene Symbol |
|---|---|---|
| 200612_s_at | adaptor-related protein complex 2, beta 1 subunit | AP2B1 |
| 200622_x_at | calmodulin 3 (phosphorylase kinase, delta) | CALM3 |
| 200707_at | protein kinase c substrate 80k-h | PRKCSH |
| 200755_s_at | Calumenin | CALU |
| 200810_s_at | cold inducible rna binding protein | CIRBP |
| 200811_at | cold inducible rna binding protein | CIRBP |
| 200848_at | adenosylhomocysteinase-like 1 | AHCYL1 |
| 200868_s_at | ring finger protein 114 | RNF114 |
| 200902_at | 15 kda selenoprotein | 15-SEP |

TABLE U-continued

DP Survival Assay; Up Genes

| Affy ID | Title | Gene Symbol |
|---|---|---|
| 200904_at | major histocompatibility complex, class i, e | HLA-E |
| 200935_at | calreticulin | CALR |
| 200961_at | selenophosphate synthetase 2 | SEPHS2 |
| 201001_s_at | tmem189-ube2v1 readthrough /// ubiquitin-conjugating enzyme e2 variant 1 | UBE2V1 |
| 201010_s_at | thioredoxin interacting protein | TXNIP |
| 201063_at | reticulocalbin 1, ef-hand calcium binding domain | RCN1 |
| 201079_at | synaptogyrin 2 | SYNGR2 |
| 201194_at | selenoprotein w, 1 | SEPW1 |
| 201295_s_at | wd repeat and socs box-containing 1 | WSB1 |
| 201301_s_at | annexin a4 | ANXA4 |
| 201302_at | annexin a4 | ANXA4 |
| 201351_s_at | yme1-like 1 (*s. cerevisiae*) | YME1L1 |
| 201352_at | yme1-like 1 (*s. cerevisiae*) | YME1L1 |
| 201407_s_at | protein phosphatase 1, catalytic subunit, beta isozyme | PPP1CB |
| 201413_at | hydroxysteroid (17-beta) dehydrogenase 4 | HSD17B4 |
| 201538_s_at | dual specificity phosphatase 3 | DUSP3 |
| 201551_s_at | lysosomal-associated membrane protein 1 | LAMP1 |
| 201582_at | sec23 homolog b (*s. cerevisiae*) | SEC23B |
| 201583_s_at | sec23 homolog b (*s. cerevisiae*) | SEC23B |
| 201617_x_at | caldesmon 1 | CALD1 |
| 201647_s_at | scavenger receptor class b, member 2 | SCARB2 |
| 201648_at | janus kinase 1 | JAK1 |
| 201653_at | cornichon homolog (*drosophila*) | CNIH |
| 201658_at | adp-ribosylation factor-like 1 | ARL1 |
| 201659_s_at | adp-ribosylation factor-like 1 | ARL1 |
| 201683_x_at | tox high mobility group box family member 4 | TOX4 |
| 201685_s_at | tox high mobility group box family member 4 | TOX4 |
| 201689_s_at | tumor protein d52 | TPD52 |
| 201705_at | proteasome (prosome, macropain) 26s subunit, non-atpase, 7 | PSMD7 |
| 201765_s_at | hexosaminidase a (alpha polypeptide) | HEXA |
| 201880_at | ariadne homolog, ubiquitin-conjugating enzyme e2 binding protein, 1 (*drosophila*) | ARIH1 |
| 201900_s_at | aldo-keto reductase family 1, member a1 (aldehyde reductase) | AKR1A1 |
| 201953_at | calcium and integrin binding 1 (calmyrin) | CIB1 |
| 201954_at | actin related protein 2/3 complex, subunit 1b, 41 kda | ARPC1B |
| 201980_s_at | ras suppressor protein 1 | RSU1 |
| 202025_x_at | acetyl-coa acyltransferase 1 | ACAA1 |
| 202121_s_at | chromatin modifying protein 2a | CHMP2A |
| 202140_s_at | cdc-like kinase 3 | CLK3 |
| 202148_s_at | pyrroline-5-carboxylate reductase 1 | PYCR1 |
| 202166_s_at | protein phosphatase 1, regulatory (inhibitor) subunit 2 | PPP1R2 |
| 202203_s_at | autocrine motility factor receptor | AMFR |
| 202243_s_at | proteasome (prosome, macropain) subunit, beta type, 4 | PSMB4 |
| 202257_s_at | cd2 (cytoplasmic tail) binding protein 2 | CD2BP2 |
| 202295_s_at | cathepsin h | CTSH |
| 202296_s_at | rer1 retention in endoplasmic reticulum 1 homolog (*s. cerevisiae*) | RER1 |
| 202381_at | adam metallopeptidase domain 9 | ADAM9 |
| 202393_s_at | kruppel-like factor 10 | KLF10 |
| 202424_at | mitogen-activated protein kinase kinase 2 | MAP2K2 |
| 202433_at | solute carrier family 35, member b1 | SLC35B1 |
| 202494_at | peptidylprolyl isomerase e (cyclophilin e) | PPIE |
| 202528_at | udp-galactose-4-epimerase | GALE |
| 202552_s_at | cysteine rich transmembrane bmp regulator 1 (chordin-like) | CRIM1 |
| 202584_at | nuclear transcription factor, x-box binding 1 | NFX1 |
| 202623_at | e2f-associated phosphoprotein | EAPP |
| 202671_s_at | pyridoxal (pyridoxine, vitamin b6) kinase | PDXK |
| 202682_s_at | ubiquitin specific peptidase 4 (proto-oncogene) | USP4 |
| 202736_s_at | lsm4 homolog, u6 small nuclear rna associated (*s. cerevisiae*) | LSM4 |
| 202767_at | acid phosphatase 2, lysosomal | ACP2 |
| 202811_at | stam binding protein | STAMBP |
| 202908_at | wolfram syndrome 1 (wolframin) | WFS1 |
| 203041_s_at | lysosomal-associated membrane protein 2 | LAMP2 |
| 203042_at | lysosomal-associated membrane protein 2 | LAMP2 |
| 203054_s_at | t-cell leukemia translocation altered gene | TCTA |
| 203102_s_at | mannosyl (alpha-1,6-)-glycoprotein beta-1,2-n-acetylglucosaminyltransferase | MGAT2 |
| 203116_s_at | ferrochelatase | FECH |
| 203197_s_at | chromosome 1 open reading frame 123 | C1ORF123 |
| 203198_at | cyclin-dependent kinase 9 | CDK9 |
| 203216_s_at | myosin vi | MYO6 |

TABLE U-continued

DP Survival Assay; Up Genes

| Affy ID | Title | Gene Symbol |
|---|---|---|
| 203226_s_at | tetraspanin 31 | TSPAN31 |
| 203227_s_at | tetraspanin 31 | TSPAN31 |
| 203247_s_at | zinc finger protein 24 | ZNF24 |
| 203335_at | phytanoyl-coa 2-hydroxylase | PHYH |
| 203384_s_at | golgin a1 | GOLGA1 |
| 203429_s_at | chromosome 1 open reading frame 9 | C1ORF9 |
| 203430_at | heme binding protein 2 | HEBP2 |
| 203450_at | chibby homolog 1 (drosophila) | CBY1 |
| 203614_at | utp14, u3 small nucleolar ribonucleoprotein, homolog c (yeast) | UTP14C |
| 203669_s_at | diacylglycerol o-acyltransferase 1 | DGAT1 |
| 203735_x_at | ptprf interacting protein, binding protein 1 (liprin beta 1) | PPFIBP1 |
| 203758_at | cathepsin o | CTSO |
| 203763_at | dynein, cytoplasmic 2, light intermediate chain 1 | DYNC2LI1 |
| 203801_at | mitochondrial ribosomal protein s14 | MRPS14 |
| 203900_at | kiaa0467 | KIAA0467 |
| 203981_s_at | atp-binding cassette, sub-family d (ald), member 4 | ABCD4 |
| 204017_at | kdel (lys-asp-glu-leu) endoplasmic reticulum protein retention receptor 3 | KDELR3 |
| 204024_at | oxidative stress induced growth inhibitor family member 2 | OSGIN2 |
| 204091_at | phosphodiesterase 6d, cgmp-specific, rod, delta | PDE6D |
| 204148_s_at | pom121 and zp3 fusion /// zona pellucida glycoprotein 3 (sperm receptor) | ZP3 |
| 204180_s_at | zinc finger and btb domain containing 43 | ZBTB43 |
| 204209_at | phosphate cytidylyltransferase 1, choline, alpha | PCYT1A |
| 204234_s_at | zinc finger protein 195 | ZNF195 |
| 204294_at | aminomethyltransferase | AMT |
| 204314_s_at | camp responsive element binding protein 1 | CREB1 |
| 204333_s_at | aspartylglucosaminidase | AGA |
| 204420_at | fos-like antigen 1 | FOSL1 |
| 204453_at | zinc finger protein 84 | ZNF84 |
| 204576_s_at | clusterin associated protein 1 | CLUAP1 |
| 204642_at | sphingosine-1-phosphate receptor 1 | S1PR1 |
| 204726_at | cadherin 13, h-cadherin (heart) | CDH13 |
| 205089_at | zinc finger protein 7 | ZNF7 |
| 205162_at | excision repair cross-complementing rodent repair deficiency, complementation group 8 | ERCC8 |
| 205170_at | signal transducer and activator of transcription 2, 113 kda | STAT2 |
| 205398_s_at | smad family member 3 | SMAD3 |
| 205416_s_at | ataxin 3 | ATXN3 |
| 205427_at | zinc finger protein 354a | ZNF354A |
| 205746_s_at | adam metallopeptidase domain 17 | ADAM17 |
| 205762_s_at | dihydrouridine synthase 4-like (s. cerevisiae) | DUS4L |
| 205796_at | t-complex 11 (mouse)-like 1 | TCP11L1 |
| 205964_at | zinc finger protein 426 | ZNF426 |
| 206059_at | zinc finger protein 91 | ZNF91 |
| 206188_at | zinc finger protein 623 | ZNF623 |
| 206332_s_at | interferon, gamma-inducible protein 16 | IFI16 |
| 206492_at | fragile histidine triad gene | FHIT |
| 206652_at | zinc finger, mym-type 5 | ZMYM5 |
| 206833_s_at | acylphosphatase 2, muscle type | ACYP2 |
| 207128_s_at | zinc finger protein 223 | ZNF223 |
| 207156_at | histone cluster 1, h2ag | HIST1H2AG |
| 207233_s_at | microphthalmia-associated transcription factor | MITF |
| 207263_x_at | vezatin, adherens junctions transmembrane protein | VEZT |
| 207265_s_at | kdel (lys-asp-glu-leu) endoplasmic reticulum protein retention receptor 3 | KDELR3 |
| 207405_s_at | rad17 homolog (s. pombe) | RAD17 |
| 207439_s_at | solute carrier family 35 (udp-galactose transporter), member a2 | SLC35A2 |
| 207876_s_at | filamin c, gamma | FLNC |
| 207974_s_at | s-phase kinase-associated protein 1 | SKP1 |
| 208174_x_at | zinc finger (ccch type), rna-binding motif and serine/arginine rich 2 | ZRSR2 |
| 208249_s_at | tdp-glucose 4,6-dehydratase | TGDS |
| 208478_s_at | bcl2-associated x protein | BAX |
| 208490_x_at | histone cluster 1, h2bf | HIST1H2BF |
| 208527_x_at | histone cluster 1, h2be | HIST1H2BE |
| 208546_x_at | histone cluster 1, h2bh | HIST1H2BH |
| 208579_x_at | h2b histone family, member s | H2BFS |
| 208631_s_at | hydroxyacyl-coa dehydrogenase/3-ketoacyl-coa thiolase/enoyl-coa hydratase (trifunctional protein), alpha subunit | HADHA |
| 208705_s_at | eukaryotic translation initiation factor 5 | EIF5 |

TABLE U-continued

DP Survival Assay; Up Genes

| Affy ID | Title | Gene Symbol |
|---|---|---|
| 208803_s_at | signal recognition particle 72 kda | SRP72 |
| 208822_s_at | death associated protein 3 | DAP3 |
| 208934_s_at | lectin, galactoside-binding, soluble, 8 | LGALS8 |
| 208945_s_at | beclin 1, autophagy related | BECN1 |
| 209036_s_at | malate dehydrogenase 2, nad (mitochondrial) | MDH2 |
| 209111_at | ring finger protein 5 | RNF5 |
| 209122_at | perilipin 2 | PLIN2 |
| 209130_at | synaptosomal-associated protein, 23 kda | SNAP23 |
| 209288_s_at | cdc42 effector protein (rho gtpase binding) 3 | CDC42EP3 |
| 209326_at | solute carrier family 35 (udp-galactose transporter), member a2 | SLC35A2 |
| 209357_at | cbp/p300-interacting transactivator, with glu/asp-rich carboxy-terminal domain, 2 | CITED2 |
| 209382_at | polymerase (rna) iii (dna directed) polypeptide c (62 kd) | POLR3C |
| 209398_at | histone cluster 1, h1c | HIST1H1C |
| 209422_at | phd finger protein 20 | PHF20 |
| 209424_s_at | alpha-methylacyl-coa racemase /// c1q and tumor necrosis factor related protein 3 | AMACR |
| 209428_s_at | zinc finger protein-like 1 | ZFPL1 |
| 209432_s_at | camp responsive element binding protein 3 | CREB3 |
| 209459_s_at | 4-aminobutyrate aminotransferase | ABAT |
| 209475_at | ubiquitin specific peptidase 15 | USP15 |
| 209517_s_at | ash2 (absent, small, or homeotic)-like (*drosophila*) | ASH2L |
| 209531_at | glutathione transferase zeta 1 | GSTZ1 |
| 209544_at | receptor-interacting serine-threonine kinase 2 | RIPK2 |
| 209565_at | ring finger protein 113a | RNF113A |
| 209622_at | serine/threonine kinase 16 | STK16 |
| 209649_at | signal transducing adaptor molecule (sh3 domain and itam motif) 2 | STAM2 |
| 209668_x_at | carboxylesterase 2 | CES2 |
| 209715_at | chromobox homolog 5 | CBX5 |
| 209746_s_at | coenzyme q7 homolog, ubiquinone (yeast) | COQ7 |
| 209759_s_at | dodecenoyl-coa isomerase | DCI |
| 209911_x_at | histone cluster 1, h2bd | HIST1H2BD |
| 209922_at | brca1 associated protein | BRAP |
| 209935_at | atpase, ca++ transporting, type 2c, member 1 | ATP2C1 |
| 209947_at | ubiquitin associated protein 2-like | UBAP2L |
| 210004_at | oxidized low density lipoprotein (lectin-like) receptor 1 | OLR1 |
| 210009_s_at | golgi snap receptor complex member 2 | GOSR2 |
| 210088_x_at | myosin, light chain 4, alkali; atrial, embryonic | MYL4 |
| 210138_at | regulator of g-protein signaling 20 | RGS20 |
| 210224_at | major histocompatibility complex, class i-related | MR1 |
| 210293_s_at | sec23 homolog b (*s. cerevisiae*) | SEC23B |
| 210385_s_at | endoplasmic reticulum aminopeptidase 1 | ERAP1 |
| 210502_s_at | peptidylprolyl isomerase e (cyclophilin e) | PPIE |
| 210517_s_at | a kinase (prka) anchor protein 12 | AKAP12 |
| 210534_s_at | b9 protein domain 1 | B9D1 |
| 210707_x_at | postmeiotic segregation increased 2 pseudogene 11 | PMS2P11 |
| 210762_s_at | deleted in liver cancer 1 | DLC1 |
| 210820_x_at | coenzyme q7 homolog, ubiquinone (yeast) | COQ7 |
| 210876_at | annexin a2 pseudogene 1 | ANXA2P1 |
| 210935_s_at | wd repeat domain 1 | WDR1 |
| 210970_s_at | inhibitor of bruton agammaglobulinemia tyrosine kinase | IBTK |
| 211061_s_at | mannosyl (alpha-1,6-)-glycoprotein beta-1,2-n-acetylglucosaminyltransferase | MGAT2 |
| 211064_at | zinc finger protein 493 | ZNF493 |
| 211126_s_at | cysteine and glycine-rich protein 2 | CSRP2 |
| 211681_s_at | pdz and lim domain 5 | PDLIM5 |
| 211799_x_at | major histocompatibility complex, class i, c | HLA-C |
| 211800_s_at | ubiquitin specific peptidase 4 (proto-oncogene) | USP4 |
| 212014_x_at | cd44 molecule (indian blood group) | CD44 |
| 212057_at | kiaa0182 | KIAA0182 |
| 212084_at | testis expressed 261 | TEX261 |
| 212111_at | syntaxin 12 | STX12 |
| 212175_s_at | adenylate kinase 2 | AK2 |
| 212189_s_at | component of oligomeric golgi complex 4 | COG4 |
| 212216_at | prolyl endopeptidase-like | PREPL |
| 212246_at | multiple coagulation factor deficiency 2 | MCFD2 |
| 212263_at | quaking homolog, kh domain rna binding (mouse) | QKI |
| 212334_at | glucosamine (n-acetyl)-6-sulfatase | GNS |
| 212340_at | yip1 domain family, member 6 | YIPF6 |
| 212355_at | kh and nyn domain containing | KHNYN |
| 212406_s_at | protein-l-isoaspartate (d-aspartate) o-methyltransferase domain containing 2 | PCMTD2 |
| 212481_s_at | tropomyosin 4 | TPM4 |
| 212506_at | phosphatidylinositol binding clathrin assembly protein | PICALM |

TABLE U-continued

DP Survival Assay; Up Genes

| Affy ID | Title | Gene Symbol |
|---|---|---|
| 212508_at | modulator of apoptosis 1 | MOAP1 |
| 212511_at | phosphatidylinositol binding clathrin assembly protein | PICALM |
| 212527_at | pppde peptidase domain containing 2 | PPPDE2 |
| 212557_at | zinc finger protein 451 | ZNF451 |
| 212632_at | syntaxin 7 | STX7 |
| 212662_at | poliovirus receptor | PVR |
| 212675_s_at | centrosomal protein 68 kda | CEP68 |
| 212731_at | ankyrin repeat domain 46 | ANKRD46 |
| 212763_at | calmodulin regulated spectrin-associated protein 1-like 1 | CAMSAP1L1 |
| 212773_s_at | translocase of outer mitochondrial membrane 20 homolog (yeast) | TOMM20 |
| 212818_s_at | ankyrin repeat and socs box-containing 1 | ASB1 |
| 212819_at | ankyrin repeat and socs box-containing 1 | ASB1 |
| 212887_at | sec23 homolog a (*s. cerevisiae*) | SEC23A |
| 212948_at | calmodulin binding transcription activator 2 | CAMTA2 |
| 212954_at | dual-specificity tyrosine-(y)-phosphorylation regulated kinase 4 | DYRK4 |
| 213017_at | abhydrolase domain containing 3 | ABHD3 |
| 213203_at | small nuclear rna activating complex, polypeptide 5, 19 kda | SNAPC5 |
| 213220_at | non-protein coding rna 81 | NCRNA00081 |
| 213225_at | protein phosphatase, mg2+/mn2+ dependent, 1b | PPM1B |
| 213311_s_at | transcription factor 25 (basic helix-loop-helix) | TCF25 |
| 213315_x_at | chromosome x open reading frame 40a | CXORF40A |
| 213326_at | vesicle-associated membrane protein 1 (synaptobrevin 1) | VAMP1 |
| 213388_at | phosphodiesterase 4d interacting protein | PDE4DIP |
| 213405_at | rab22a, member ras oncogene family | RAB22A |
| 213440_at | rab1a, member ras oncogene family | RAB1A |
| 213480_at | vesicle-associated membrane protein 4 | VAMP4 |
| 213508_at | chromosome 14 open reading frame 147 | C14ORF147 |
| 213593_s_at | transformer 2 alpha homolog (*drosophila*) | TRA2A |
| 213624_at | sphingomyelin phosphodiesterase, acid-like 3a | SMPDL3A |
| 213627_at | melanoma antigen family d, 2 | MAGED2 |
| 213684_s_at | pdz and lim domain 5 | PDLIM5 |
| 213698_at | hypothetical protein loc100130633 /// zinc finger, mym-type 6 | ZMYM6 |
| 213737_x_at | golgin a8 family, member h | GOLGA8H |
| 213878_at | pyridine nucleotide-disulphide oxidoreductase domain 1 | PYROXD1 |
| 213893_x_at | postmeiotic segregation increased 2 pseudogene 5 | PMS2P5 |
| 213896_x_at | family with sequence similarity 149, member b1 | FAM149B1 |
| 213984_at | pds5, regulator of cohesion maintenance, homolog a (*s. cerevisiae*) | PDS5A |
| 214274_s_at | acetyl-coa acyltransferase 1 | ACAA1 |
| 214310_s_at | zinc finger protein-like 1 | ZFPL1 |
| 214336_s_at | coatomer protein complex, subunit alpha | COPA |
| 214455_at | histone cluster 1, h2bc | HIST1H2BC |
| 214473_x_at | postmeiotic segregation increased 2 pseudogene 3 | PMS2P3 |
| 214526_x_at | postmeiotic segregation increased 2 pseudogene 1 | PMS2P1 |
| 214553_s_at | camp-regulated phosphoprotein, 19 kda | ARPP19 |
| 214590_s_at | ubiquitin-conjugating enzyme e2d 1 (ubc4/5 homolog, yeast) | UBE2D1 |
| 214657_s_at | nuclear paraspeckle assembly transcript 1 (non-protein coding) | NEAT1 |
| 214670_at | zinc finger with krab and scan domains 1 | ZKSCAN1 |
| 214756_x_at | postmeiotic segregation increased 2 pseudogene 1 | PMS2P1 |
| 215029_at | — | — |
| 215082_at | elovl family member 5, elongation of long chain fatty acids (fen1/elo2, sur4/elo3-like, yeast) | ELOVL5 |
| 215182_x_at | — | — |
| 215203_at | golgin a4 | GOLGA4 |
| 215252_at | — | — |
| 215359_x_at | zinc finger protein 44 | ZNF44 |
| 215411_s_at | traf3 interacting protein 2 | TRAF3IP2 |
| 215412_x_at | postmeiotic segregation increased 2-like 2 pseudogene | PMS2L2 |
| 215667_x_at | pms2 postmeiotic segregation increased 2 (*s. cerevisiae*)-like /// postmeiotic segregation increased 2-like 2 pseudogene /// postmeiotic segregation increased 2 pseudogene 1 /// postmeiotic segregation increased 2 pseudogene 6 | PMS2L2 |
| 215743_at | n-myristoyltransferase 2 | NMT2 |
| 215936_s_at | kiaa1033 | KIAA1033 |
| 215984_s_at | adp-ribosylation factor related protein 1 | ARFRP1 |
| 215985_at | non-protein coding rna 171 | NCRNA00171 |
| 216006_at | — | — |
| 216111_x_at | postmeiotic segregation increased 2 pseudogene 3 | PMS2P3 |
| 216304_x_at | ymel-like 1 (*s. cerevisiae*) | YME1L1 |

TABLE U-continued

DP Survival Assay; Up Genes

| Affy ID | Title | Gene Symbol |
|---|---|---|
| 216525_x_at | postmeiotic segregation increased 2 pseudogene 3 | PMS2P3 |
| 216682_s_at | family with sequence similarity 48, member a | FAM48A |
| 216698_x_at | olfactory receptor, family 7, subfamily e, member 35 pseudogene /// olfactory receptor, family 7, subfamily e, member 37 pseudogene | OR7E35P |
| 216806_at | — | — |
| 216841_s_at | superoxide dismutase 2, mitochondrial | SOD2 |
| 216843_x_at | postmeiotic segregation increased 2 pseudogene 1 | PMS2P1 |
| 216933_x_at | adenomatous polyposis coli | APC |
| 216960_s_at | zinc finger protein 133 | ZNF133 |
| 217346_at | peptidyl-prolyl cis-trans isomerase a-like /// peptidylprolyl isomerase a (cyclophilin a) | PPIA |
| 217370_x_at | fused in sarcoma | FUS |
| 217436_x_at | major histocompatibility complex, class i, a /// major histocompatibility complex, class i, f /// major histocompatibility complex, class i, j (pseudogene) | HLA-A |
| 217485_x_at | postmeiotic segregation increased 2 pseudogene 1 | PMS2P1 |
| 217503_at | serine/threonine kinase 17b | STK17B |
| 217653_x_at | — | |
| 217682_at | — | |
| 217722_s_at | neugrin, neurite outgrowth associated | NGRN |
| 217731_s_at | integral membrane protein 2b | ITM2B |
| 217738_at | nicotinamide phosphoribosyltransferase | NAMPT |
| 217748_at | adiponectin receptor 1 | ADIPOR1 |
| 217763_s_at | rab31, member ras oncogene family | RAB31 |
| 217785_s_at | ykt6 v-snare homolog (s. cerevisiae) | YKT6 |
| 217790_s_at | signal sequence receptor, gamma (translocon-associated protein gamma) | SSR3 |
| 217930_s_at | toll interacting protein | TOLLIP |
| 217973_at | dicarbonyl/l-xylulose reductase | DCXR |
| 217988_at | cyclin b1 interacting protein 1 | CCNB1IP1 |
| 218021_at | dehydrogenase/reductase (sdr family) member 4 /// dehydrogenase/reductase (sdr family) member 4 like 2 | DHRS4 |
| 218024_at | brain protein 44-like | BRP44L |
| 218032_at | stannin | SNN |
| 218046_s_at | mitochondrial ribosomal protein s16 | MRPS16 |
| 218047_at | oxysterol binding protein-like 9 | OSBPL9 |
| 218124_at | retinol saturase (all-trans-retinol 13,14-reductase) | RETSAT |
| 218125_s_at | coiled-coil domain containing 25 | CCDC25 |
| 218143_s_at | secretory carrier membrane protein 2 | SCAMP2 |
| 218217_at | serine carboxypeptidase 1 | SCPEP1 |
| 218241_at | golgin a5 | GOLGA5 |
| 218262_at | required for meiotic nuclear division 5 homolog b (s. cerevisiae) | RMND5B |
| 218264_at | brca2 and cdkn1a interacting protein | BCCIP |
| 218288_s_at | coiled-coil domain containing 90b | CCDC90B |
| 218296_x_at | misato homolog 1 (drosophila) /// misato homolog 2 pseudogene | MSTO1 |
| 218297_at | family with sequence similarity 188, member a | FAM188A |
| 218377_s_at | rwd domain containing 2b | RWDD2B |
| 218391_at | snf8, escrt-ii complex subunit, homolog (s. cerevisiae) | SNF8 |
| 218496_at | ribonuclease h1 | RNASEH1 |
| 218497_s_at | ribonuclease h1 | RNASEH1 |
| 218498_s_at | ero1-like (s. cerevisiae) | ERO1L |
| 218572_at | chromatin modifying protein 4a | CHMP4A |
| 218582_at | membrane-associated ring finger (c3hc4) 5 | 5-MAR |
| 218584_at | tectonic family member 1 | TCTN1 |
| 218640_s_at | pleckstrin homology domain containing, family f (with fyve domain) member 2 | PLEKHF2 |
| 218760_at | coenzyme q6 homolog, monooxygenase (s. cerevisiae) | COQ6 |
| 218769_s_at | ankyrin repeat, family a (rfxank-like), 2 | ANKRA2 |
| 218773_s_at | methionine sulfoxide reductase b2 | MSRB2 |
| 218789_s_at | chromosome 11 open reading frame 71 | C11ORF71 |
| 218817_at | signal peptidase complex subunit 3 homolog (s. cerevisiae) | SPCS3 |
| 218861_at | ring finger protein 25 | RNF25 |
| 218936_s_at | coiled-coil domain containing 59 | CCDC59 |
| 218992_at | chromosome 9 open reading frame 46 | C9ORF46 |
| 219125_s_at | recombination activating gene 1 activating protein 1 | RAG1AP1 |
| 219237_s_at | dnaj (hsp40) homolog, subfamily b, member 14 | DNAJB14 |
| 219239_s_at | zinc finger protein 654 | ZNF654 |
| 219329_s_at | chromosome 2 open reading frame 28 | C2ORF28 |
| 219362_at | n(alpha)-acetyltransferase 35, natc auxiliary subunit | NAA35 |
| 219406_at | chromosome 1 open reading frame 50 | C1ORF50 |
| 219538_at | wd repeat domain 5b | WDR5B |
| 219543_at | phenazine biosynthesis-like protein domain containing | PBLD |

TABLE U-continued

DP Survival Assay; Up Genes

| Affy ID | Title | Gene Symbol |
|---|---|---|
| 219546_at | bmp2 inducible kinase | BMP2K |
| 219571_s_at | zinc finger protein 12 | ZNF12 |
| 219603_s_at | zinc finger protein 226 | ZNF226 |
| 219629_at | family with sequence similarity 118, member a | FAM118A |
| 219662_at | chromosome 2 open reading frame 49 | C2ORF49 |
| 219763_at | denn/madd domain containing 1a | DENND1A |
| 219854_at | zinc finger protein 14 | ZNF14 |
| 219901_at | fyve, rhogef and ph domain containing 6 | FGD6 |
| 219920_s_at | gdp-mannose pyrophosphorylase b | GMPPB |
| 219924_s_at | zinc finger, mym-type 6 | ZMYM6 |
| 219956_at | udp-n-acetyl-alpha-d-galactosamine: polypeptide n-acetylgalactosaminyltransferase 6 (galnac-t6) | GALNT6 |
| 220052_s_at | terf1 (trf1)-interacting nuclear factor 2 | TINF2 |
| 220127_s_at | f-box and leucine-rich repeat protein 12 | FBXL12 |
| 220159_at | atp-binding cassette, sub-family a (abc1), member 11 (pseudogene) | ABCA11P |
| 220171_x_at | kiaa1704 | KIAA1704 |
| 220588_at | breast carcinoma amplified sequence 4 | BCAS4 |
| 220610_s_at | leucine rich repeat (in flii) interacting protein 2 | LRRFIP2 |
| 220690_s_at | dehydrogenase/reductase (sdr family) member 7b | DHRS7B |
| 220760_x_at | zinc finger protein 665 | ZNF665 |
| 220925_at | n(alpha)-acetyltransferase 35, natc auxiliary subunit | NAA35 |
| 220990_s_at | microrna 21 /// transmembrane protein 49 | MIR21 |
| 221036_s_at | anterior pharynx defective 1 homolog b (c. elegans) | APH1B |
| 221104_s_at | nipsnap homolog 3b (c. elegans) | NIPSNAP3B |
| 221499_s_at | syntaxin 16 | STX16 |
| 221500_s_at | syntaxin 16 | STX16 |
| 221515_s_at | leucine carboxyl methyltransferase 1 | LCMT1 |
| 221534_at | chromosome 11 open reading frame 68 | C11ORF68 |
| 221553_at | magnesium transporter 1 | MAGT1 |
| 221588_x_at | aldehyde dehydrogenase 6 family, member a1 | ALDH6A1 |
| 221589_s_at | hypothetical loc100506517 | LOC100506517 |
| 221590_s_at | aldehyde dehydrogenase 6 family, member a1 | ALDH6A1 |
| 221597_s_at | transmembrane protein 208 | TMEM208 |
| 221645_s_at | zinc finger protein 83 | ZNF83 |
| 221689_s_at | phosphatidylinositol glycan anchor biosynthesis, class p | PIGP |
| 221782_at | dnaj (hsp40) homolog, subfamily c, member 10 | DNAJC10 |
| 221797_at | chromosome 17 open reading frame 90 | C17ORF90 |
| 221803_s_at | nuclear receptor binding factor 2 | NRBF2 |
| 221881_s_at | chloride intracellular channel | CLIC4 |
| 221994_at | pdz and lim domain 5 | PDLIM5 |
| 222104_x_at | general transcription factor iih, polypeptide 3, 34 kda | GTF2H3 |
| 222133_s_at | phd finger protein 20-like 1 | PHF20L1 |
| 222158_s_at | pppde peptidase domain containing 1 | PPPDE1 |
| 222282_at | — | — |
| 222286_at | small nuclear rna activating complex, polypeptide 3, 50 kda | SNAPC3 |
| 266_s_at | cd24 molecule | CD24 |
| 32088_at | basic leucine zipper nuclear factor 1 | BLZF1 |
| 36553_at | acetylserotonin o-methyltransferase-like | ASMTL |
| 37254_at | zinc finger protein 133 | ZNF133 |
| 43544_at | mediator complex subunit 16 | MED16 |
| 49878_at | peroxisomal biogenesis factor 16 | PEX16 |
| 50374_at | chromosome 17 open reading frame 90 | C17ORF90 |
| 51774_s_at | ubiquitin-conjugating enzyme e2d 4 (putative) | UBE2D4 |
| 59644_at | bmp2 inducible kinase | BMP2K |
| 62212_at | chromosome 1 open reading frame 50 | C1ORF50 |
| 65086_at | yip1 domain family, member 2 | YIPF2 |
| 78047_s_at | — | — |
| 78383_at | hypothetical loc100129250 | LOC100129250 |

I. Systems and Devices

Figure 2:
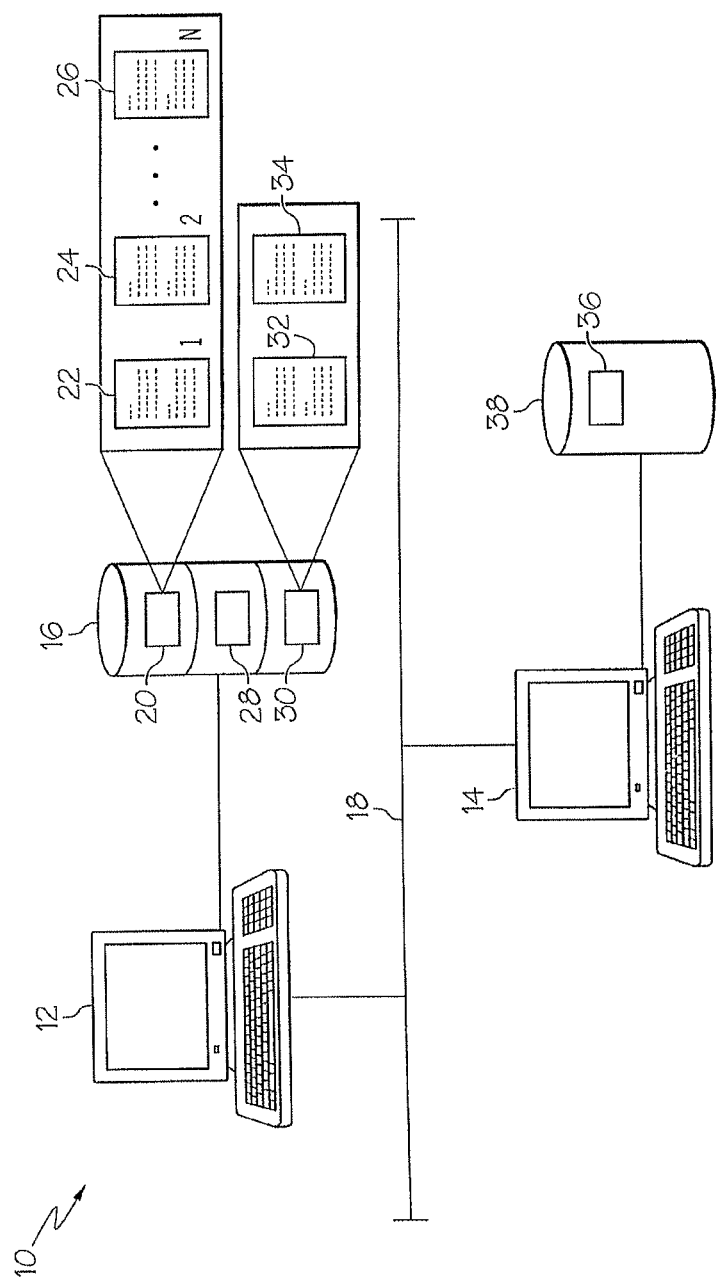
FIG. 2 is a schematic illustration of a computer system suitable for use with the present invention.
Figure 4:
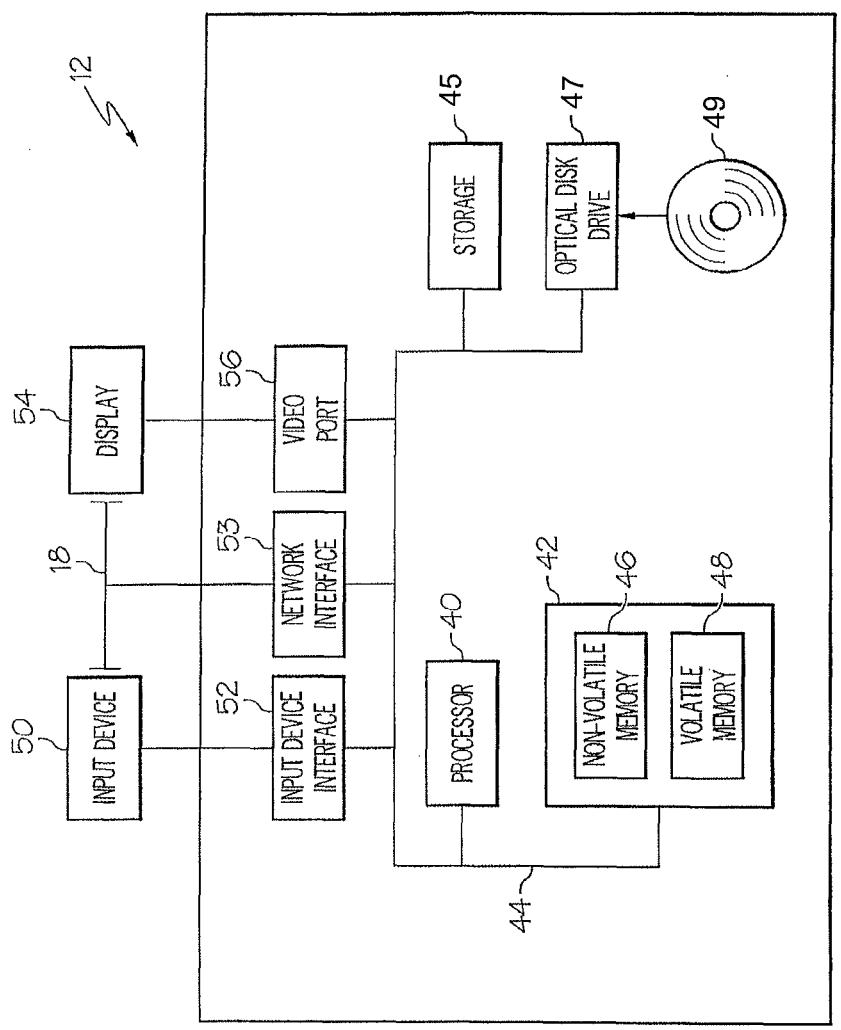
FIG. 4 is a schematic illustration of a programmable computer suitable for use with the present invention.
Figure 5:
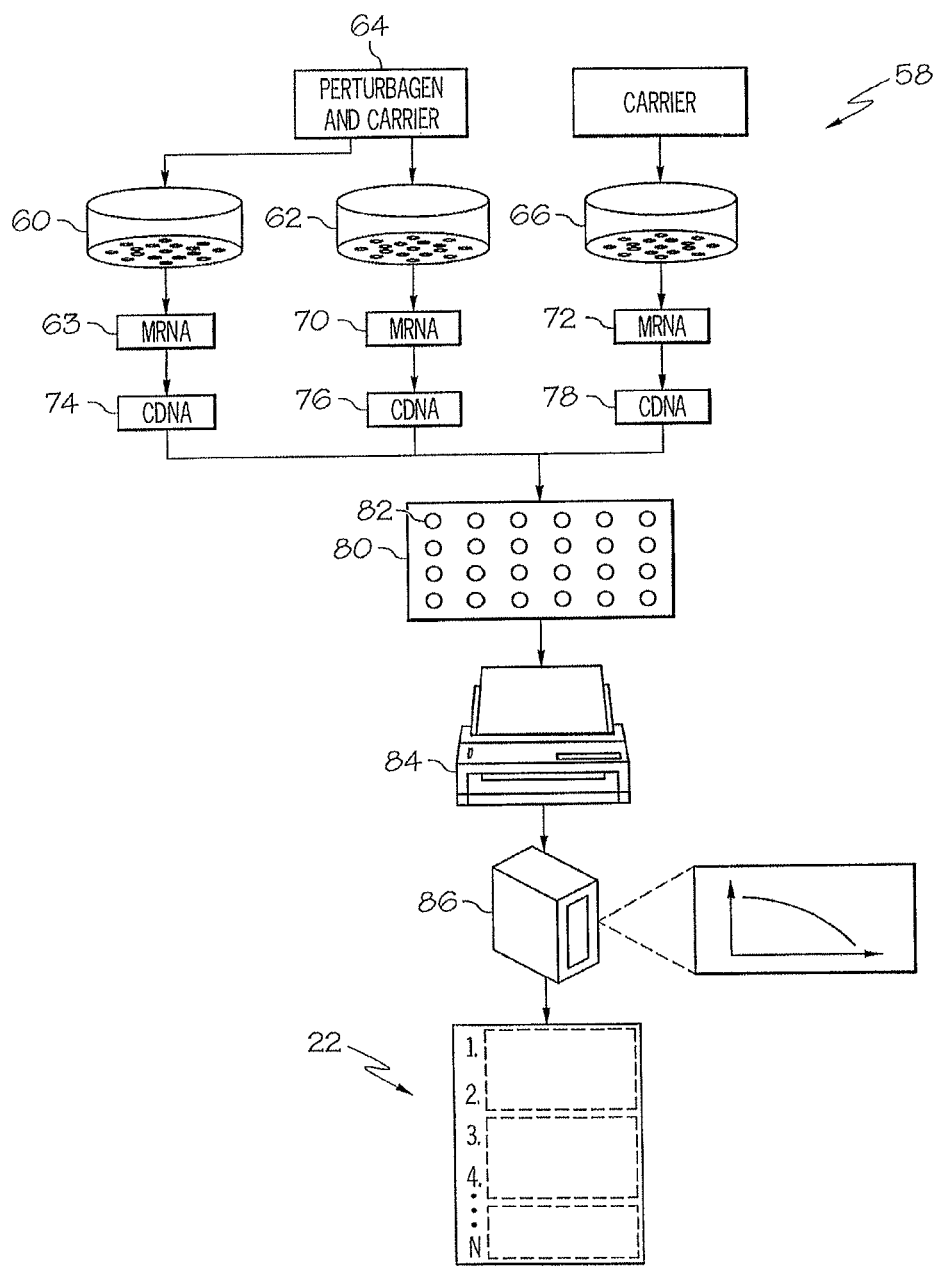
FIG. 5 is a schematic illustration of an exemplary system for generating an instance.

Referring to FIGS. 2, 4 and 5, some examples of systems and devices in accordance with embodiments of the present invention for use in identifying relationships between perturbagens, hair biology conditions, and genes associated with the hair biology condition will now be described. System 10 comprises one or more of computing devices 12, 14, a computer readable medium 16 associated with the computing device 12, and communication network 18.

The computer readable medium 16, which may be provided as a hard disk drive, comprises a digital file 20, such as a database file, comprising a plurality of instances 22, 24, and 26 stored in a data structure associated with the digital file 20. The plurality of instances may be stored in relational tables and indexes or in other types of computer readable media. The instances 22, 24, and 26 may also be distributed across a plurality of digital files, a single digital file 20 being described herein however for simplicity.

The digital file 20 can be provided in wide variety of formats, including but not limited to a word processing file format (e.g., Microsoft Word), a spreadsheet file format (e.g., Microsoft Excel), and a database file format. Some common examples of suitable file formats include, but are not limited to, those associated with file extensions such as

*.xls, *.xld, *.xlk, *.xll, *.xlt, *.xlxs, *.dif, *.db, *.dbf, *.accdb, *.mdb, *.mdf, *.cdb, *.fdb, *.csv, *.sql, *.xml, *.doc, *.txt, *.rtf, *.log, *.docx, *.ans, *.pages, *.wps, etc.

Figure 3:
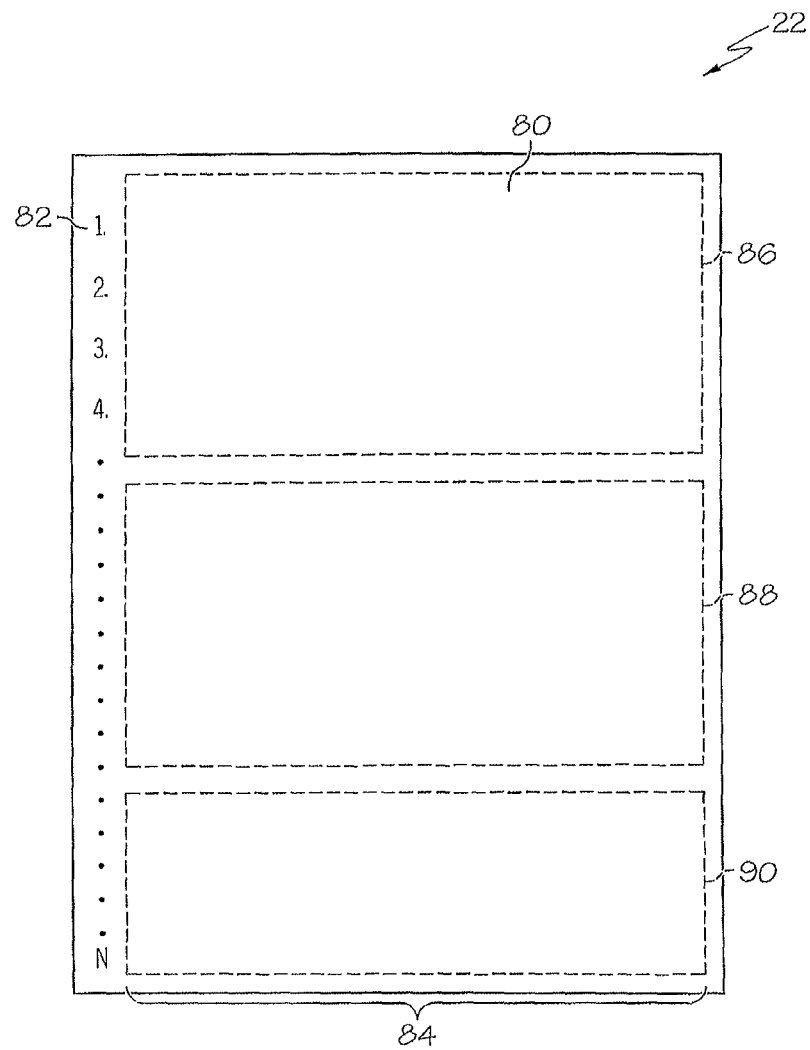
FIG. 3 is a schematic illustration of an instance associated with a computer readable medium of the computer system of FIG. 2.

Referring to FIG. 3, in some embodiments the instance 22 may comprise an ordered listing of microarray probe set IDs, wherein the value of N is equal to the total number of probes on the microarray used in analysis. Common microarrays include Affymetrix GeneChips and Illumina BeadChips, both of which comprise probe sets and custom probe sets. To generate the reference gene profiles according to the invention, preferred chips are those designed for profiling the human genome. Examples of Affymetrix chips with utility in the instant invention include model Human Genome (HG)-U133 Plus 2.0. A specific Affymetrix chip employed by the instant investigators is HG-U133A2.0, however it will be understood by a person or ordinary skill in the art that any chip or microarray, regardless of proprietary origin, is suitable so long as the probe sets of the chips used to construct a data architecture according to the invention are substantially similar.

Instances derived from microarray analyses utilizing Affymetrix GeneChips may comprise an ordered listing of gene probe set IDs where the list comprises, for example, 22,000 or more IDs. The ordered listing may be stored in a data structure of the digital file 20 and the data arranged so that, when the digital file is read by the software application 28, a plurality of character strings are reproduced representing the ordered listing of probe set IDs. While it is preferred that each instance comprise a full list of the probe set IDs, it is contemplated that one or more of the instances may comprise less than all of the probe set IDs of a microarray. It is also contemplated that the instances may include other data in addition to or in place of the ordered listing of probe set IDs. For example, an ordered listing of equivalent gene names and/or gene symbols may be substituted for the ordered listing of probe set IDs. Additional data may be stored with an instance and/or the digital file 20. In some embodiments, the additional data is referred to as metadata and can include one or more of cell line identification, batch number, exposure duration, and other empirical data, as well as any other descriptive material associated with an instance ID. The ordered list may also comprise a numeric value associated with each identifier that represents the ranked position of that identifier in the ordered list.

Referring again to FIGS. 2, 3 and 4, the computer readable medium 16 may also have a second digital file 30 stored thereon. The second digital file 30 comprises one or more lists 32 of microarray probe set IDs associated with one or more hair biology-related gene expression signatures. The listing 32 of microarray probe set IDs typically comprises a much smaller list of probe set IDs than the instances of the first digital file 20. In some embodiments, the list comprises between 2 and 1000 probe set IDs. In other embodiments the list comprises greater than 10, 50, 100, 200, or 300 and/or less than about 800, 600, or about 400 probe set IDs. The listing 32 of probe set IDs of the second digital file 30 comprises a list of probe set IDs representing up, and/or down-regulated genes selected to represent a hair biology condition of interest. In some embodiments, a first list may represent the up-regulated genes and a second list may represent the down-regulated genes of the gene expression signature. The listing(s) may be stored in a data structure of the digital file 30 and the data arranged so that, when the digital file is read by the software application 28, a plurality of character strings are reproduced representing the list of probe set IDs. Instead of probe set IDs, equivalent gene names and/or gene symbols (or another nomenclature) may be substituted for a list of probe set IDs. Additional data may be stored with the gene expression signature and/or the digital file 30 and this is commonly referred to as metadata, which may include any associated information, for example, cell line or sample source, and microarray identification. Examples of listings of probe set IDs for hair biology signatures are set forth in Tables A (down-regulated) and B (up-regulated). In some embodiments, one or more hair biology gene expression signatures may be stored in a plurality of digital files and/or stored on a plurality of computer readable media. In other embodiments, a plurality of gene expression signatures (e.g., 32, 34) may be stored in the same digital file (e.g., 30) or stored in the same digital file or database that comprises the instances 22, 24, and 26.

As previously described, the data stored in the first and second digital files may be stored in a wide variety of data structures and/or formats. In some embodiments, the data is stored in one or more searchable databases, such as free databases, commercial databases, or a company's internal proprietary database. The database may be provided or structured according to any model known in the art, such as for example and without limitation, a flat model, a hierarchical model, a network model, a relational model, a dimensional model, or an object-oriented model. In some embodiments, at least one searchable database is a company's internal proprietary database. A user of the system 10 may use a graphical user interface associated with a database management system to access and retrieve data from the one or more databases or other data sources to which the system is operably connected. In some embodiments, the first digital file 20 is provided in the form of a first database and the second digital file 30 is provided in the form of a second database. In other embodiments, the first and second digital files may be combined and provided in the form of a single file.

In some embodiments, the first digital file 20 may include data that is transmitted across the communication network 18 from a digital file 36 stored on the computer readable medium 38. In one embodiment, the first digital file 20 may comprise gene expression data obtained from a cell line (e.g., a fibroblast cell line and/or a keratinocyte cell line) as well as data from the digital file 36, such as gene expression data from other cell lines or cell types, gene expression signatures, perturbagen information, clinical trial data, scientific literature, chemical databases, pharmaceutical databases, and other such data and metadata. The digital file 36 may be provided in the form of a database, including but not limited to Sigma-Aldrich LOPAC collection, Broad Institute C-map collection, GEO collection, and Chemical Abstracts Service (CAS) databases.

The computer readable medium 16 (or another computer readable media, such as 16) may also have stored thereon one or more digital files 28 comprising computer readable instructions or software for reading, writing to, or otherwise managing and/or accessing the digital files 20, 30. The computer readable medium 16 may also comprise software or computer readable and/or executable instructions that cause the computing device 12 to perform one or more steps of the methods of embodiments of the present invention, including for example and without limitation, the step(s) associated with comparing a gene expression signature stored in digital file 30 to instances 22, 24, and 26 stored in digital file 20. In specific embodiments, the one or more digital files 28 may form part of a database management system for managing the digital files 20, 28. Non-limiting examples of database management systems are described in U.S. Pat. Nos. 4,967,341 and 5,297,279. One or more, or part of, methods described herein can be performed/run on one or more computers or computing devices 12 using computer software.

The computer readable medium 16 may form part of or otherwise be connected to the computing device 12. The computing device 12 can be provided in a wide variety of forms, including but not limited to any general or special purpose computer such as a server, a desktop computer, a laptop computer, a tower computer, a microcomputer, a mini computer, and a mainframe computer. While various computing devices may be suitable for use with the present invention, a generic computing device 12 is illustrated in FIG. 4. The computing device 12 may comprise one or more components selected from a processor 40, system memory 42, and a system bus 44. The system bus 44 provides an interface for system components including but not limited to the system memory 42 and processor 40. The system bus 36 can be any of several types of bus structures that may further interconnect to a memory bus (with or without a memory controller), a peripheral bus, and a local bus using any of a variety of commercially available bus architectures. Examples of a local bus include an industrial standard architecture (USA) bus, a microchannel architecture (MSA) bus, an extended ISA (EISA) bus, a peripheral component interconnect (PCI) bus, a universal serial (USB) bus, and a small computer systems interface (SCSI) bus. The processor 40 may be selected from any suitable processor, including but not limited to, dual microprocessor and other multi-processor architectures. The processor executes a set of stored instructions associated with one or more program applications or software.

The system memory 42 can include non-volatile memory 46 (e.g., read only memory (ROM), erasable programmable read only memory (EPROM), electrically erasable programmable read only memory (EEPROM), etc.) and/or volatile memory 48 (e.g., random access memory (RAM)). A basic input/output system (BIOS) can be stored in the non-volatile memory 38, and can include the basic routines that help to transfer information between elements within the computing device 12. The volatile memory 48 can also include a high-speed RAM such as static RAM for caching data.

The computing device 12 may further include a storage 45, which may comprise, for example, an internal hard disk drive [HDD, e.g., enhanced integrated drive electronics (EIDE) or serial advanced technology attachment (SATA)] for storage. The computing device 12 may further include an optical disk drive 47 (e.g., for reading a CD-ROM or DVD-ROM 49). The drives and associated computer-readable media provide non-volatile storage of data, data structures and the data architecture of the present invention, computer-executable instructions, and so forth. For the computing device 12, the drives and media accommodate the storage of any data in a suitable digital format. Although the description of computer-readable media above refers to an HDD and optical media such as a CD-ROM or DVD-ROM, it should be appreciated by those skilled in the art that other types of media which are readable by a computer, such as Zip disks, magnetic cassettes, flash memory cards, cartridges, and the like may also be used, and further, that any such media may contain computer-executable instructions for performing the methods of the present invention.

A number of software applications can be stored on the drives 44 and volatile memory 48, including an operating system and one or more software applications, which implement, in whole or part, the functionality and/or methods described herein. It is to be appreciated that the embodiments can be implemented with various commercially available operating systems or combinations of operating systems. The central processing unit 40, in conjunction with the software applications in the volatile memory 48, may serve as a control system for the computing device 12 that is configured to, or adapted to, implement the functionality described herein.

A user may be able to enter commands and information into the computing device 12 through one or more wired or wireless input devices 50, for example, a keyboard, a pointing device, such as a mouse (not illustrated), or a touch screen. These and other input devices are often connected to the central processing unit 40 through an input device interface 52 that is coupled to the system bus 44 but can be connected by other interfaces, such as a parallel port, an IEEE 1394 serial port, a game port, a universal serial bus (USB) port, an IR interface, etc. The computing device 12 may drive a separate or integral display device 54, which may also be connected to the system bus 44 via an interface, such as a video port 56.

The computing devices 12, 14 may operate in a networked environment across network 18 using a wired and/or wireless network communications interface 58. The network interface port 58 can facilitate wired and/or wireless communications. The network interface port can be part of a network interface card, network interface controller (NIC), network adapter, or LAN adapter. The communication network 18 can be a wide area network (WAN) such as the Internet, or a local area network (LAN). The communication network 18 can comprise a fiber optic network, a twisted-pair network, a T1/E1 line-based network or other links of the T-carrier/E carrier protocol, or a wireless local area or wide area network (operating through multiple protocols such as ultra-mobile band (UMB), long term evolution (LTE), etc.). Additionally, communication network 18 can comprise base stations for wireless communications, which include transceivers, associated electronic devices for modulation/demodulation, and switches and ports to connect to a backbone network for backhaul communication such as in the case of packet-switched communications.

II. Methods for Creating a Plurality of Instances

In some embodiments, the methods of the present invention may comprise populating at least the first digital file 20 with a plurality of instances (e.g., 22, 24, 26) comprising data derived from a plurality of gene expression profiling experiments, wherein one or more of the experiments comprise exposing dermal fibroblast cells and/or keratinocyte cells (or other hair-related cell types) to at least one perturbagen. For simplicity of discussion, the gene expression profiling discussed hereafter will be in the context of a microarray experiment.

Referring to FIG. 5, one embodiment of a method of the present invention is illustrated. The method 58 comprises exposing a fibroblast cells 60 and/or keratinocyte cells 62 to a perturbagen 64. The perturbagen may be dissolved in a carrier, such as dimethyl sulfoxide (DMSO). After exposure, mRNA is extracted from the cells exposed to the perturbagen and reference cells 66 (e.g., fibroblast or keratinocyte cells) which are exposed to only the carrier. The mRNA 63, 70, 72 may be reverse transcribed to cDNA 74, 76, 78 and marked with different fluorescent dyes (e.g., red and green) if a two color microarray analysis is to be performed. Alternatively, the samples may be prepped for a one color microarray analysis as described in Example 1, and further a plurality of replicates may be processed if desired. The cDNA samples may be co-hybridized to the microarray 80 comprising a plurality of probes 82. The microarray may comprise thousands of probes 82. In some embodiments, there are between 10,000 and 50,000 gene probes 82 present on the microarray 80. The microarray is scanned by a scanner 84, which excites the dyes and measures the amount of fluorescence. A computing device 86 may be used to analyze the raw images to determine the expression levels of a gene in the cells 60, 62 relative to the reference cells 66. The scanner 84 may incorporate the functionality of the computing device 86. The expression levels include: i) up-regulation [e.g., greater binding of the test material (e.g., cDNA 74, 76) to the probe than the reference material (e.g., cDNA 78)], or ii) down-regulation [e.g., greater binding of the reference material (e.g., cDNA 78) to the probe than the test material (e.g., cDNA 74, 76)], iii) expressed but not differentially [e.g., similar binding of the reference material (e.g., cDNA 78) to the probe than the test material (e.g., cDNA 74. 76)], and iv) no detectable signal or noise. The up- and down-regulated genes are referred to as differentially expressed. Microarrays and microarray analysis techniques are well known in the art, and it is contemplated that other microarray techniques may be used with the methods, devices and systems of the present invention. For example, any suitable commercial or non-commercial microarray technology and associated techniques may used. Good results have been obtained with Affymetrix GeneChip® technology and Illumina BeadChip™ technology. One illustrative technique is described in Example 1. However, one of skill in the art will appreciate that the present invention is not limited to the methodology of the example and that other methods and techniques are also contemplated to be within its scope.

In a very specific embodiment, an instance consists of the rank ordered data for all of the probe sets on the Affymetrix HG-U133A2.0 GeneChip wherein each probe on the chip has a unique probe set IDentifier. The probe sets are rank ordered by the fold change relative to the controls in the same C-map batch (single instance/average of controls). The probe set IDentifiers are rank-ordered to reflect the most up-regulated to the most down-regulated.

Notably, even for the non-differentially regulated genes the signal values for a particular probe set are unlikely to be identical for the instance and control so a fold change different from 1 will be calculated that can be used for comprehensive rank ordering. In accordance with methods disclosed by Lamb et al. (2006), data are adjusted using 2 thresholds to minimize the effects of genes that may have very low noisy signal values, which can lead to spurious large fold changes. The thresholding is preferably done before the rank ordering. An example for illustrative purposes includes a process wherein a first threshold is set at 20. If the signal for a probe set is below 20, it is adjusted to 20. Ties for ranking are broken with a second threshold wherein the fold changes are recalculated and any values less than 2 are set to 2. For any remaining ties the order depends on the specific sorting algorithm used but is essentially random. The probe sets in the middle of the list do not meaningfully contribute to an actual connectivity score.

The rank ordered data are stored as an instance. The probes may be sorted into a list according to the level of gene expression regulation detected, wherein the list progresses from up-regulated to marginal or no regulation to down-regulated, and this rank ordered listing of probe IDs is stored as an instance (e.g., 22) in the first digital file 20. Referring to FIG. 3, the data associated with an instance comprises the probe ID 80 and a value 82 representing its ranking in the list (e.g., 1, 2, 3, 4 . . . N, where N represents the total number of probes on the microarray). The ordered list 84 may generally comprise approximately three groupings of probe IDs: a first grouping 86 of probe IDs associated with up-regulated genes, a second group 88 of probe IDs associated with genes with marginal regulation or no detectable signal or noise, and a third group 90 of probe IDs associated with down-regulated genes. The most up regulated genes are at or near the top of the list 84 and the most down-regulated genes are at or near the bottom of the list 84. The groupings are shown for illustration, but the lists for each instance may be continuous and the number of regulated genes will depend on the strength of the effect of the perturbagen associated with the instance. Other arrangements within the list 84 may be provided. For example, the probe IDs associated with the down-regulated genes may be arranged at the top of the list 84. This instance data may also further comprise metadata such as perturbagen identification, perturbagen concentration, cell line or sample source, and microarray identification.

In some embodiments, one or more instances comprise at least about 1,000, 2,500, 5,000, 10,000, or 20,000 identifiers and/or less than about 30,000, 25,000, or 20,000 identifiers. In some embodiments, the database comprises at least about 50, 100, 250, 500, or 1,000 instances and/or less than about 50,000, 20,000, 15,000, 10,000, 7,500, 5,000, or 2,500 instances. Replicates of an instance may create, and the same perturbagen may be used to derive a first instance from fibroblast cells and a second instance from keratinocyte cells and a third instance from another hair-related cell type.

III. Methods for Deriving Hair Biology-Related Gene Expression Signatures

Some methods of the present invention comprise identifying a gene expression signature that represents the up-regulated and down-regulated genes associated with a hair biology condition of interest. A hair biology condition typically involves complex processes involving numerous known and unknown extrinsic and intrinsic factors, as well as responses to such factors that are subtle over a relatively short period of time but non-subtle over a longer period of time. This is in contrast to what is typically observed in drug screening methods, wherein a specific target, gene, or mechanism of action is of interest. Due to the unique screening challenges associated with a hair biology condition, the quality of the gene expression signature representing the condition of interest can be important for distinguishing between the gene expression data actually associated with a response to a perturbagen from the background expression data. One challenge in developing hair biology-related gene expression signatures is that the number of genes selected needs to be adequate to reflect the dominant and key biology but not so large as to include many genes that have achieved a level of statistical significance by random chance and are non-informative. Thus, query signatures should be carefully derived since the predictive value may be dependent upon the quality of the gene expression signature.

One factor that can impact the quality of the query signature is the number of genes included in the signature. The present inventors have found that, with respect to a cosmetic data architecture and connectivity map, too few genes can result in a signature that is unstable with regard to the highest scoring instances. In other words, small changes to the gene expression signature can result significant differences in the highest scoring instance. Conversely, too many genes may tend to partially mask the dominant biological responses and will include a higher fraction of genes meeting statistical cutoffs by random chance—thereby adding undesirable noise to the signature. The inventors have found that the number of genes desirable in a gene expression signature is also a function of the strength of the biological response associated with the condition and the number of genes needed to meet minimal values (e.g., a p-value less than about 0.05) for statistical significance. When the biology is weaker, such as is the case typically with cosmetic condition phenotypes, fewer genes than those which may meet the statistical requisite for inclusion in the prior art, may be used to avoid adding noisy genes.

While a gene expression signature may represent all significantly regulated genes associated with hair biology condition of interest; typically it represents a subset of such genes. The present inventors have discovered that hair biology gene expression signatures comprising between about 50-200 of approximately equal numbers of up-regulated and/or down-regulated genes are stable, reliable, and can provide predictive results (though from 1-800 are conceived of herein, and suitable gene expression signature may have from about 1-250 genes, 250-300 genes, 300-350 genes, 350-400 genes, 400-450 genes, 450-500 genes, 500-550 genes, 550-600 genes, 600-650 genes, 650-700 genes, 700-750 genes, and 750-800 genes). However, one of skill in the art will appreciate that gene expression signatures comprising fewer or more genes are also within the scope of the various embodiments of the invention. For purposes of depicting a gene expression signature, the probe set IDs associated with the genes are preferably separated into a first list comprising the most up-regulated genes and a second list comprising the most down-regulated.

Figure 6:
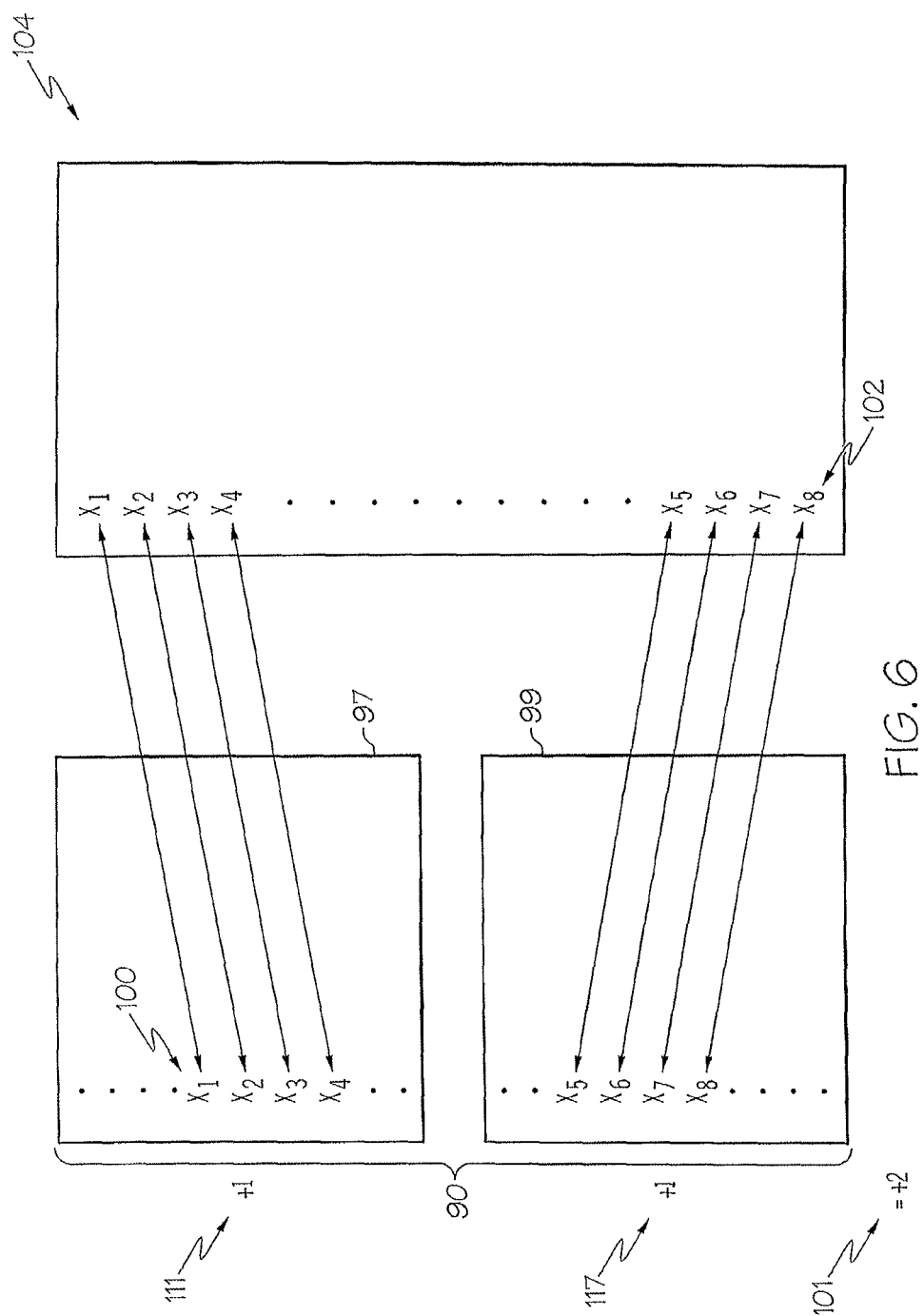
FIG. 6 is a schematic illustration of a comparison between a gene expression signature and an instance, wherein there is a positive correlation between the lists.
Figure 7:
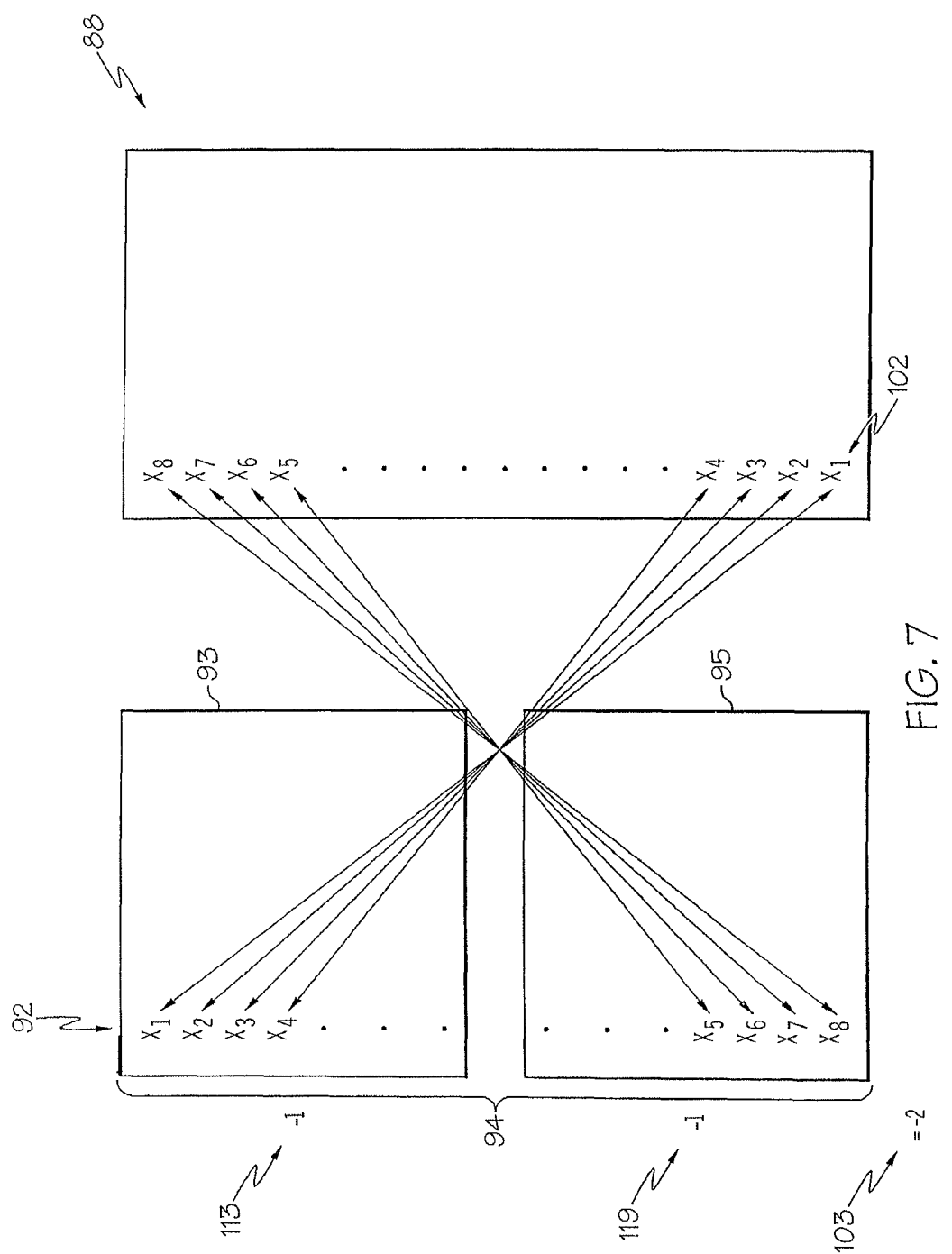
FIG. 7 is a schematic illustration of a comparison between a gene expression signature and an instance, wherein there is a negative correlation between the lists.
Figure 8:
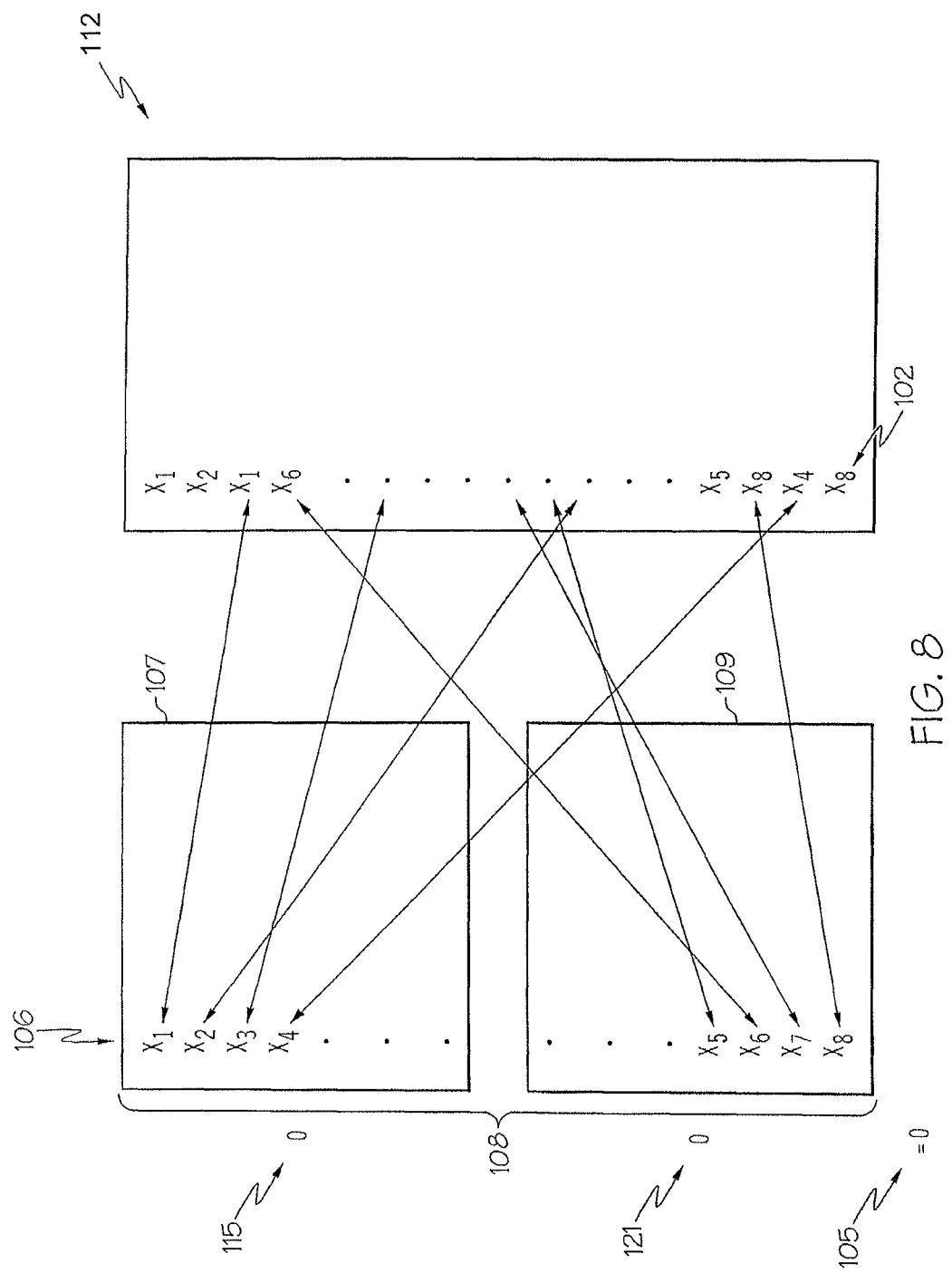
FIG. 8 is a schematic illustration of a comparison between a gene expression signature and an instance, wherein there is a neutral correlation between the lists.

IV. Methods for Comparing a Plurality of Instances to One or Hair Biology-Related Gene Expression Signatures Referring to FIG. 6 and FIG. 7, a method for querying a plurality of instances with one or more hair biology-related gene signatures will now be described. Broadly, the method comprises querying a plurality of instances with one or more hair biology-related gene signatures and applying a statistical method to determine how strongly the signature genes match the regulated genes in an instance. Positive connectivity occurs when the genes in the up-regulated signature list are enriched among the up-regulated genes in an instance and the genes in the down-regulated signature list are enriched among the down-regulated genes in an instance. On the other hand, if the up-regulated genes of the signature are predominantly found among the down-regulated genes of the instance, and vice versa, this is scored as negative connectivity. FIG. 6 schematically illustrates an extreme example of a positive connectivity between signature 90 and the instance 104 comprising the probe IDs 102, wherein the probe IDs of the instance are ordered from most up-regulated to most down-regulated. In this example, the probe IDs 100 (e.g. $X_1$, $X_2$, $X_3$, $X_4$, $X_5$, $X_6$, $X_7$, $X_8$) of the gene signature 90, comprising an up list 97 and a down list 99, have a one to one positive correspondence with the most up-regulated and down-regulated probe IDs 102 of the instance 104, respectively. Similarly, FIG. 7 schematically illustrates an extreme example of a negative connectivity between signature 94 and the instance 88 comprising the probe IDs 92, wherein the probe IDs of the instance are ordered from most up-regulated to most down-regulated. In this example, the probe IDs of the up list 93 (e.g., $X_1$, $X_2$ $X_3$, $X_4$) correspond exactly with the most down-regulated genes of the instance 88, and the probe IDs of the down list 95 (e.g., $X_5$, $X_6$, $X_7$, $X_8$) correspond exactly to the most up-regulated probe IDs of the instance 88. FIG. 8 schematically illustrates an extreme example of neutral connectivity, wherein there is no consistent enrichment of the up- and down-regulated genes of the signature among the up- and down-regulated genes of the instance, either positive or negative. Hence the probe IDs 106 (e.g., $X_1$, $X_2$ $X_3$, $X_4$, $X_5$, $X_6$, $X_7$, $X_8$) of a gene signature 108 (comprising an up list 107 and a down list 109) are scattered with respect to rank with the probe IDs 102 of the instance 112, wherein the probe IDs of the instance are ordered from most up-regulated to most down-regulated. While the above embodiments illustrate process where the gene signature comprises a both an up list and a down list representative of the most significantly up- and down-regulated genes of a hair biology condition, it is contemplated that the gene signature may comprise only an up list or a down list when the dominant biology associated with a condition of interest shows gene regulation in predominantly one direction.

In some embodiments, the connectivity score can be a combination of an up-score and a down score, wherein the up-score represents the correlation between the up-regulated genes of a gene signature and an instance and the down-score represents the correlation between the down-regulated genes of a gene signature and an instance. The up score and down score may have values between +1 and −1. For an up score (and down score) a high positive value indicates that the corresponding perturbagen of an instance induced the expression of the microarray probes of the up-regulated (or down-regulated) genes of the gene signature, and a high negative value indicates that the corresponding perturbagen associated with the instance repressed the expression of the microarray probes of the up-regulated (or down-regulated) genes of the gene signature. The up-score can be calculated by comparing each identifier of an up list of a gene signature comprising the up-regulated genes to an ordered instance list while the down-score can be calculated by comparing each identifier of a down list of a gene signature comprising the down-regulated genes to an ordered instance list. In these embodiments, the gene signature comprises the combination of the up list and the down list.

In some embodiments, the connectivity score value may range from +2 (greatest positive connectivity) to −2 (greatest negative connectivity), wherein the connectivity score (e.g., 101, 103, and 105) is the combination of the up score (e.g., 111, 113, 115) and the down score (e.g., 117, 119, 121) derived by comparing each identifier of a gene signature to the identifiers of an ordered instance list. In other embodiments the connectivity range may be between +1 and −1. Examples of the scores are illustrated in FIGS. 6, 7 and 8 as reference numerals 101, 103, 105, 111, 113, 115, 117, 119, and 121.

The strength of matching between a signature and an instance represented by the up scores and down scores and/or the connectivity score may be derived by one or more approaches known in the art and include, but are not limited to, parametric and non-parametric approaches. Examples of parametric approaches include Pearson correlation (or Pearson r) and cosine correlation. Examples of non-parametric approaches include Spearman's Rank (or rank-order) correlation, Kendall's Tau correlation, and the Gamma statistic. Generally, in order to eliminate a requirement that all profiles be generated on the same microarray platform, a non-parametric, rank-based pattern matching strategy based on the Kolmogorov-Smirnov statistic (see M. Hollander et al. *"Nonparametric Statistical Methods"*; Wiley, New York, ed. 2, 1999) (see, e.g., pp. 178-185). It is noted, however, that where all expression profiles are derived from a single technology platform, similar results may be obtained using conventional measures of correlation, for example, the Pearson correlation coefficient.

In specific embodiments, the methods and systems of the present invention employ the nonparametric, rank-based pattern-matching strategy based on the Kolmogorov-Smirnov statistic, which has been refined for gene profiling data by Lamb's group, commonly known in the art as Gene Set Enrichment Analysis (GSEA) (see, e.g., Lamb et al. 2006 and Subramanian, A. et al. (2005) *Proc. Natl. Acad Sci U.S.A*, 102, 15545-15550). For each instance, a down score is calculated to reflect the match between the down-regulated genes of the query and the instance, and an up score is calculated to reflect the correlation between the up-regulated genes of the query and the instance. In certain embodiments the down score and up score each may range between −1 and +1. The combination represents the strength of the overall match between the query signature and the instance.

The combination of the up score and down score is used to calculate an overall connectivity score for each instance, and in embodiments where up and down score ranges are set between −1 and +1, the connectivity score ranges from −2 to +2, and represents the strength of match between a query signature and the instance. The sign of the overall score is determined by whether the instance links positivity or negatively to the signature. Positive connectivity occurs when the perturbagen associated with an instance tends to up-regulate the genes in the up list of the signature and down-regulate the genes in the down list. Conversely, negative connectivity occurs when the perturbagen tends to reverse the up and down signature gene expression changes, The magnitude of the connectivity score is the sum of the absolute values of the up and down scores when the up and down scores have different signs. A high positive connectivity score predicts that the perturbagen will tend to induce the condition that was used to generate the query signature, and a high negative connectivity score predicts that the perturbagen will tend to reverse the condition associated with the query signature. A zero score is assigned where the up and down scores have the same sign, indicating that a perturbagen did not have a consistent impact the condition signature (e.g., up-regulating both the up and down lists).

According to Lamb et al. (2006), there is no standard for estimating statistical significance of connections observed. Lamb teaches that the power to detect connections may be greater for compounds with many replicates. Replicating in this context means that the same perturbagen is profiled multiple times. Where batch to batch variation must be avoided, a perturbagen should be profiled multiple times in each batch. However, since microarray experiments tend to have strong batch effects it is desirable to replicate instances in different batches (i.e., experiments) to have the highest confidence that connectivity scores are meaningful and reproducible.

Each instance may be rank ordered according to its connectivity score to the query signature and the resulting rank ordered list displayed to a user using any suitable software and computer hardware allowing for visualization of data.

In some embodiments, the methods of the present invention may further comprise testing the selected candidate cosmetic agent, using in vitro assays and/or in vivo testing, to validate the activity of the agent and usefulness as a cosmetic agent. Any suitable in vitro test method can be used, including those known in the art, and most preferably in vitro models having an established nexus to the desired in vivo result.

V. Cosmetic Compositions and Personal Care Products for Hair/Scalp Care Compositions Cosmetic agents identified by the methods, devices, and systems of the present invention may be incorporated in a wide variety of cosmetic compositions for topical application to hair and its surrounding skin. The cosmetic compositions may be provided in a wide variety of forms, including but not limited to shampoo, conditioner, gels, serum, mask, creams, tonic, sprays, jelly, solution, oil, intensive treatments, fluid, supplement, mousse, lotions, emulsions, colloids, solutions, suspensions, ointments, milks, sprays, capsules, tablets, liquids, sticks, solids, powders, compacts, pencils, spray-on formulations, brush-on formulations, cloths, and wipes. Non-limiting examples of topical compositions and products may include shampoos, conditioners, leave-on products, sprays, styling gels, serums, tonics, creams, hair dyes, mousses, moisturizers, soaps, exfoliants, astringents, depilatories, shaving, pre-shaving and after shaving products, moisturizers, cleansers, and rinses. It is contemplated that the cosmetic compositions and personal care products may treat or improve the appearance of unhealthy hair conditions, including: (i) improving vitality of hair follicles (ii) improving hair count, i.e, boosting hair growth and regrowth; (iii) improving hair fiber quality, such as increase hair diameter, boost hair lustrous, revert the thinning, fragile hair into thick, strong, healthy and beautiful; (iv) delay the graying process associate with aging and stress; and (v) improve scalp condition to reduce itching, sensitivity and oily buildup.

The cosmetic agents may be combined with a dermatologically acceptable carrier, as known in the art. The phrase "dermatologically acceptable carrier", as used herein, means that the carrier is suitable for topical application to hair and skin tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. Non-limiting examples include simple solutions (e.g., aqueous, organic solvent, or oil based), emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

The aqueous phase typically comprises water. However, in other embodiments, the aqueous phase may comprise components other than water, including but not limited to water-soluble moisturizing agents, conditioning agents, antimicrobials, humectants and/or other water-soluble hair/scalp care actives. In one embodiment, the non-water component of the composition comprises a humectant such as glycerin and/or other polyols. However, it should be recognized that the composition may be substantially (i.e., less than 1% water) or fully anhydrous.

A suitable carrier is selected to yield a desired product form. In one embodiment, an oil-in-water or water-in-oil emulsion is preferred. Emulsions may further comprise an emulsifier. The composition may comprise any suitable percentage of emulsifier to sufficiently emulsify the carrier. Suitable weight ranges include from about 0.1% to about 10% or about 0.2% to about 5% of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and *McCutcheon's Detergents and Emulsifiers*, North American Edition, pages 317-324 (1986). Suitable emulsions may have a wide range of viscosities, depending on the desired product form. The carrier may further comprise a thickening agent as are well known in the art to provide compositions having a suitable viscosity and rheological character.

The hair/scalp care compositions of the present invention may include optional components such as anti-acne actives, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, and other useful hair/scalp care actives, which are described in further detail in U.S. application publication No. US2006/0275237A1 and US2004/0175347A1. Examples of other optional ingredients include: abrasives, absorbents, aesthetic components such as fragrances, pigments, colorings/colorants, essential oils, anti-caking agents, antifoaming agents, antimicrobials, binders, biological additives, buffering agents, bulking agents, chelating agents, chemical additives, colorants, cosmetic astringents, cosmetic biocides, denaturants, drug astringents, emollients, external analgesics, film formers or materials, opacifying agents, pH adjusters, preservatives, propellants, reducing agents, sequestrants, hair/scalp cooling agents, hair/scalp protectants, thickeners viscosity modifiers, vitamins, and combinations thereof.

The hair/scalp care compositions of the present invention are generally prepared by conventional methods such as are known in the art of making topical compositions. Such methods typically involve mixing of the ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared such as to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

Various methods of treatment, application, regulation, or improvement may utilize the aforementioned hair/scalp care compositions. The composition may be applied to base of the hair fibers or scalp surface. The composition may be applied to hair or scalp surface to treat one or more signs of hair loss, loss of hair pigmentation and hair damage.

VI. Methods for Formulating a Hair Care Composition by Identifying Connections Between and Genes Associated with One or More Hair Biology Conditions With a background as to cosmetic compositions and personal care products herein provided, details of specific embodiments are herein discussed below. Specific embodiments describe a method for formulating a hair care composition by identifying connections between perturbagens and genes associated with one or more hair biology conditions, comprising: (a) accessing a plurality of instances stored on at least one computer readable medium, wherein each instance is associated with a perturbagen and a hair-related cell type and wherein each instance comprises an ordered list comprising a plurality of identifiers representing a plurality of up-regulated and a plurality of down regulated genes; (b) accessing at least one hair biology-related gene expression signature stored on the at least one computer readable medium, wherein the at least one hair biology-related gene expression signature comprises one or more lists comprising a plurality of identifiers representing a plurality of up-regulated genes and a plurality of down-regulated genes associated with a hair biology-related condition; c) comparing the at least one hair biology-related gene expression signature to the plurality of the instances, wherein the comparison comprises comparing each identifier in the one or more gene expression signature lists with the position of the same identifier in the ordered lists for each of the plurality of instances; (d) assigning a connectivity score to each of the plurality of instances; and (e) formulating a hair care composition comprising a dermatologically acceptable carrier and at least one perturbagen, wherein the connectivity score of the instance associated with the at least one perturbagen has a negative correlation.

Specific embodiment include a method further comprising applying the hair care composition to a plurality of human subjects having the hair biology condition. Yet more specific embodiments include a method wherein the hair care composition improves the appearance of facial fine lines or wrinkles of one or more of the plurality of human subjects. Specific embodiments may include a method wherein the identifiers are selected from the group consisting of gene names, gene symbols, and microarray probe set ID values.

More specific embodiments include methods wherein: each instance comprises between about 50 and about 400 identifiers; the plurality of instances comprises between about 50 and about 50,000 instances; the plurality of instances comprises between about 1000 and about 20,000 instances; at least one perturbagen is a cosmetic agent; at least one perturbagen is a botanical; a botanical is derived from one or more of a root, stem, bark, leaf, seed, or fruit of a plant; and wherein steps described are performed by a programmable computer.

Yet more specific embodiments herein describe a method wherein the at least one hair biology-relevant gene expression signature comprises a plurality of hair biology-relevant gene expression signatures and each of the plurality of instances has a connectivity score assigned thereto for each of the plurality of hair biology-relevant gene expression signatures. Specific embodiments include methods wherein: the connectivity score for each of the plurality of instances is a combination of the connectivity scores assigned to each instance for each of the plurality of hair biology-relevant gene expression signatures; the plurality of hair biology-relevant gene expression signatures comprises a plurality of hair biology-relevant gene expression signatures; as well as wherein the plurality of hair biology-relevant gene expression signatures represents genes differentially expressed in association with at least one condition selected from the group consisting of follicular miniaturization, dermal papilla activation, hair density disorders, hair diameter disorders; and combinations thereof.

Specific embodiments describe a method wherein a plurality of hair biology-relevant gene expression signatures comprises a plurality of follicular miniaturization gene expression signatures. More specific embodiments describe a method wherein each of the plurality of the hair biology-relevant gene expression signatures comprises one or more gene expression signature lists comprising a plurality of identifiers representing a plurality of up-regulated genes and a plurality of down-regulated genes, wherein an identifier for between about 80% and about 100% of the up-regulated genes are set forth in Table A and wherein an identifier for between about 80% and about 100% of the down-regulated genes are set forth in Table B.

Specific embodiments describe wherein: each connectivity score assigned to the instance associated with the at least one perturbagen of the hair care composition has a negative correlation; the plurality of instances are stored in a database on the at least one computer readable medium; the plurality of instances comprises a plurality of instances associated with a first hair-related cell type and a plurality of instances associated with a second hair-related cell type; as well as embodiments wherein the first hair-related cell type is a human dermal fibroblast and the second hair-related cell type is a human keratinocyte; each of the plurality of instances further comprises metadata associated with the hair-related cell type and the perturbagen associated therewith.

Yet more specific embodiments describe a method wherein the metadata comprises a name for the hair-related cell type and a name for the perturbagen, or wherein the plurality of instances are stored in a first digital file and the at least one hair biology-relevant gene expression signature is stored in a second digital file, or describe a hair care formulation.

VII. Methods for Constructing a Data Architecture for Use in Identifying Connections Between Perturbens and Genes Associated with One or More Hair Biology Conditions Specific embodiments herein described include a method for constructing a data architecture for use in identifying connections between perturbagens and genes associated with one or more hair biology conditions, comprising: (a) providing a gene expression profile for a control human fibroblast cell; (b) generating a gene expression profile for a human fibroblast cell exposed to at least one perturbagen; (c) identifying genes differentially expressed in response to the at least one perturbagen by comparing the gene expression profiles of (a) and (b); (d) creating an ordered list comprising identifiers representing the differentially expressed genes, wherein the identifiers are ordered according to the differential expression of the genes; (e) storing the ordered list as a fibroblast instance on at least one computer readable medium; and (f) constructing a data architecture of stored fibroblast instances by repeating (a) through (e), wherein the at least one perturbagen of step (a) is different for each fibroblast instance.

More specific embodiments describe a method comprising using a programmable computer to perform one or more of the steps described herein. Even more specific embodiments include: wherein an ordered list comprises the ordered list of identifiers in association with a numerical ranking for the identifier corresponding to its rank in the ordered list; the step of generating is performed by extracting a biological sample from the treated cell and subjecting the biological sample to microarray analysis; the biological sample comprises mRNA; as well as wherein the microarray is a global microarray or a specific microarray, wherein the specific microarray comprises oligonucleotides which hybridize to genes corresponding to a gene expression signature for a cellular phenotype.

Yet more specific embodiments include wherein the step of constructing the data architecture of stored instances comprises repeating steps herein described (such as steps (a) through (e) herein described above) for between about 50 and about 50,000 instances. Other specific embodiments include a method wherein: the step of constructing a gene expression data bases of stored instances comprises repeating steps (a) through (e) for between about 1000 and about 20,000 instances; at least one perturbagen is a cosmetic agent; as well as wherein each of the different perturbagens is a cosmetic agent; the identifiers are selected from the group consisting of gene names, gene symbols, microarray probe set ID values, and combinations thereof.

Even more specific embodiments include wherein the ordered list is arranged so that an identifier associated with a most up-regulated gene is positioned at the top of the ordered list and an identifier associated with a most down-regulated gene is positioned at the bottom of the ordered list; the ordered list of each instance is arranged so that an identifier associated with each gene that is not differentially expressed is positioned between the identifier associated with the most up-regulated gene and the identifier associated with the most down-regulated gene; each instance comprises between about 1,000 and about 50,000 identifiers, as well as wherein each instance comprises metadata for the at least one perturbagen associated with the instance.

Specific embodiments include a method according to claim 1, further comprising; (g) providing a gene expression profile for a control human keratinocyte cell; (h) generating a gene expression profile for a human keratinocyte cell exposed to at least one perturbagen; (i) identifying genes differentially expressed in response to the at least one perturbagen by comparing the gene expression profiles of (g) and (h); (j) creating an ordered list comprising identifiers representing the differentially expressed genes, wherein the identifiers are ordered according to the differential expression of the genes identified in (i); (k) storing the ordered list created in step (j) as a keratinocyte instance on the at least one computer readable medium; and (l) constructing a data base of stored keratinocyte instances by repeating (g) through (k), wherein the at least one perturbagen of step (h) is different for each keratinocyte instance. Other embodiments include a method wherein: at least one perturbagen of step (a) is the same as the at least one perturbagen of step (g); at least one perturbagen is a botanical; the botanical is derived from one or more of a root, stem, bark, leaf, seed, or fruit of a plant; the at least one perturbagen is selected from the group consisting of a vitamin compound, a sugar amine, a phytosterol, hexamidine, a hydroxy acid, a ceramide, an amino acid, and a polyol; the vitamin compound is selected from the group consisting of a vitamin B3 compound, a vitamin B5 compound, a vitamin B6 compound, a vitamin B9 compound, a vitamin A compound, a vitamin C compound, a vitamin E compound, and derivatives and combinations thereof; as well as wherein the vitamin compound is selected from the group consisting of retinol, retinyl esters, niacinamide, folic acid, panthenol, ascorbic acid, tocopherol, and tocopherol acetate.

Even more specific embodiments describe a method for implementing the data architecture to generate connections useful for identifying cosmetic agents effective for treating hair, the method comprising querying the data architecture with at least hair biology-relevant gene expression signature, wherein querying comprises comparing the at least one hair biology-relevant gene expression signature to each stored fibroblast instance, wherein the hair biology-relevant gene expression signature represents genes differentially expressed in association with at least one hair biology condition. Specific embodiments describe a method wherein: the comparison of the at least one hair biology-relevant gene expression signature to each stored fibroblast instance is performed by a programmable computer; at least one hair biology condition is selected from the group consisting of follicular miniaturization, dermal papilla activation, hair density disorders, hair diameter disorders; and combinations thereof.

Specific embodiments describe a method wherein the at least one hair biology-relevant gene expression signature is constructed by a method comprising (i) identifying genes having up-regulated expression in the at least one hair biology condition when compared to a control; (ii) identifying genes having down-regulated expression in the at least one hair biology condition when compared to a control; (iii) creating one or more gene expression signature lists associated with the at least one hair biology-relevant gene expression signature comprising identifiers corresponding to a plurality of the genes identified in (i) and (ii); and storing the one or more gene expression signature lists on the at least one computer readable medium. Specific embodiments also described herein include a method wherein: the number of genes having up-regulated expression in the at least one hair biology condition is between about 10 and about 400, and the number of genes down-regulated in the at least one hair biology condition is between about 10 and about 400; the identifiers for from between about 80% and about 100% of the up-regulated genes are set forth as in Table B and wherein identifiers for from between about 80% and about 100% of the down-regulated genes are set forth in Table A; and wherein the identifiers representing the genes identified in (i) and (ii) are selected from the group consisting of gene names, gene symbols, and microarray probe set ID values.

Specific embodiments include a method wherein the one or more gene expression signature lists comprises a first list representing a plurality of the up-regulated genes identified in (i) and a second list representing a plurality of down-regulated genes identified in (ii). Specific embodiments include a method wherein: at least hair sample is taken from a human subject exhibiting the at least one hair biology condition, a biological sample is extracted from the hair sample, and a gene expression profile of the at least one hair sample is generated prior to at least one of the steps (i) and (ii); at least one human subject is between the ages of about 18 and about 80; the hair sample comprises cells from a vertex of a head of the human subject; the comparison further comprises assigning a connectivity score to each of plurality of instances; a plurality of connectivity scores represents a positive correlation and a plurality of the connectivity scores represents a negative correlation; as well as wherein the connectivity score has a value between +2 and −2.

Yet more specific embodiments describe a method for constructing a data architecture for use in identifying connections between perturbens and genes associated with improving hair biology, comprising: (a) providing a gene expression profile for a control human cell, wherein the control cell is from a human cell line selected from the group consisting of fibroblast, keratinocyte, and dermal papilla cell lines; (b) generating a gene expression profile for a human cell exposed to at least one perturbagen, wherein the cell is selected from the same cell line as the control cell; (c) identifying genes differentially expressed in response to at least one perturbagen by comparing the gene expression profiles of (a) and (b); (d) creating an ordered list comprising identifiers representing the differentially expressed genes, wherein the identifiers are ordered according to the differential expression of the genes; (e) storing the ordered list as an instance on at least one computer readable medium, wherein the instance is a fibroblast, keratinocyte, or dermal papilla instance according to the selection in (a); and (f) constructing a data architecture of stored instances by repeating (a) through (e), wherein the at least one perturben of step (a) through (e), wherein the at least one perturben of step (a) is different qualitatively or quantitatively for each instance. Other embodiments include a method for implementing the data architecture to identify at least one putative agent having potential efficacy in treating a hair biology condition, the method comprising querying the data architecture with a hair biology-relevant gene expression signature, wherein querying comprises comparing the hair biology-relevant gene expression signature to each stored cell instance, wherein the hair biology-relevant expression signature represents genes differentially expressed in a human tissue affected with a hair biology condition or genes differentially expressed in cells treated with at least one benchmark agent having known efficacy in treating a hair condition, further wherein cell instances are derived from a fibroblast, keratinocyte, or a human dermal papilla cell line and the hair biology-relevant gene expression signature is derived from either a corresponding cell line or a cell derived from a human tissue affected with a hair biology condition.

Specific embodiments include a method comprising using a programmable computer to perform one or more steps herein described. Other embodiments include a method wherein: the ordered list comprises the ordered list of identifiers in association with a numerical ranking for the identifier corresponding to its rank in the ordered list; the biological sample comprises mRNA; the microarray is a global microarray or a specific microarray, wherein the specific microarray comprises oligonucleotides which hybridize to genes according to a gene expression signature for a cellular phenotype; the step of constructing the data architecture of stored instances by repeating steps (a) through (e) comprises repeating steps (a) through (e) for between about 50 and about 50,000 instances or between about 1000 and 20,000 instances; wherein the at least one perturben comprises an agent modifying hair follicle cycling; as well as wherein modifying hair follicle cycling comprises transitioning dermal papilla cells from a resting telogen stage to a growing anagen stage.

VIII. Methods for Generating a Gene Expression Signature for Use in Identifying Connections Between Perturbens and Genes Associated with One or More Hair Biology Conditions Specific embodiments outlined herein describe a method for generating a gene expression signature for use in identifying connections between perturbagens and genes associated with one or more hair biology conditions, comprising: (a) providing a gene expression profile for a reference sample of human hair-related cells; (b) generating a gene expression profile for at least one sample of human hair-related cells from a subject exhibiting at least one hair biology condition, (c) comparing the expression profiles of (a) and (b) to determine a gene expression signature comprising a set of genes differentially expressed in (a) and (b); (d) assigning an identifier to each gene constituting the gene expression signature and ordering the identifiers according to the direction of differential expression to create one or more gene expression signature lists; (e) storing the one or more gene expression signature lists on at least one computer readable medium.

Non-limiting specific embodiments are herein described. Specific embodiments include embodiments where a human subject is between the age of about 18 to about 80 years. In specific embodiments a gene expression signature is determined and has from about 50 to about 400 genes differentially up-regulated in at least one hair biology condition and about 50 to about 400 differentially down-regulated in at least one hair biology condition. In yet more specific embodiments identifiers are selected from the group consisting of gene names, gene symbols, and microarray probe set IDs. In yet more specific embodiments at least one sample of human hair-related cells comprises a plurality of samples and wherein one of the plurality of hair-related samples is taken from sites that are losing hair such as the vertex and sites that are less prone to hair loss such as the occipital region. Other specific embodiments include a method wherein the sample taken is a hair pluck or FUE or dissected hair follicle or LCM isolated cell sample.

In specific embodiments a sample of human hair-related cells from a subject is from a vertex of a head of the human subject; in others the sample is from non-vertex areas; in specific embodiments of males or females, the sample is taken/removed/and/or sampled from the scalp; in specific embodiments the sample is removed from the frontal scalp area.

IX. A System for Identifying Connections Between Perturbens and Genes Associated with One or More Hair Biology Conditions Specific embodiments herein described detail a system for identifying connections between perturbagens and genes associated with one or more hair biology conditions, comprising: at least one computer readable medium having stored thereon a plurality of instances, and at least one hair biology-relevant gene expression signature, wherein the instances and the gene expression signature are derived from a human dermal fibroblast cell, wherein each instance comprises an instance list of rank-ordered identifiers of differentially expressed genes, and wherein the at least one hair biology-relevant gene expression signature comprises one or more gene expression signature lists of identifiers representing differentially expressed genes associated with a hair biology condition; (b) a programmable computer comprising computer-readable instructions that cause the programmable computer to execute one or more of the following: (i) accessing the plurality of instances and the at least one hair biology-relevant gene expression signature stored on the computer readable medium; (ii) comparing the at least one hair biology-relevant gene expression signature to the plurality of the instances, wherein the comparison comprises comparing each identifier in the gene expression signature list with the position of the same identifier in the instance list for each of the plurality of instances; and (iii) assigning a connectivity score to each of the plurality of instances. The specific embodiments herein described detail a system according to claim comprising a plurality of instances and at least one gene expression signature derived from a human keratinocyte cell. More specific embodiments detail a system comprising: a microarray scanner for receiving a sample comprising human dermal fibroblast cells and/or human keratinocyte cells; and a second programmable computer for transmitting gene expression data from the scanner to the first programmable computer. Even more specific embodiments include a system comprising an array of perturbagens for application to the dermal fibroblast cells and the keratinocyte cells. Specific embodiments may include a plurality of instances comprising between about 50 and about 50,000 instances, or alternatively, between about 1,000 and about 20,000 instances.

Embodiments herein described include a computer readable medium, comprising: a data architecture comprising a digital file stored in a spreadsheet file format, a word processing file format, or a database file format suitable to be read by a respective spreadsheet, word processing, or database computer program, the first digital file comprising data arranged to provide one or more gene expression signature lists comprising a plurality of identifiers when read by the respective spreadsheet, word processing, or database computer program; and wherein each identifier is selected from the group consisting of a microarray probe set ID, a human gene name, a human gene symbol, and combinations thereof representing a gene set forth in any of Tables A-R and T-U wherein each of the one or more gene expression signature lists comprises between about 50 and about 600 identifiers. In specific embodiments a computer readable medium can comprise computer readable instructions for reading a digital file.

X. Selected Gene Expression Signatures

In specific embodiments herein described, genes are selected from gene expression signatures from tables herein included. For example, specific embodiments include a gene expression signature consisting of genes selected from the genes set forth in Tables C and D.

Specific embodiments include an immobilized array of oligonucleotides which hybridize to the genes selected for the gene expression signature. The gene expression signature may be stored on a memory device accessible by a programmable computer. The gene expression signature can comprise from 50-100 genes identified to be up-regulated in Table D. The gene expression signature can comprise from 50-100 genes identified to be down-regulated in Table C. The gene expression signature can comprise a set of genes identified to be up-regulated and a set of genes identified to be down-regulated.

Specific embodiments include a gene expression signature consisting of genes selected from the genes set forth in Tables E and F. Specific embodiments include an immobilized array of oligonucleotides which hybridize to the genes selected for the gene expression signature. The gene expression signature may be stored on a memory device accessible by a programmable computer. The gene expression signature can comprise from 50-100 genes identified to be up-regulated in Table F. The gene expression signature can comprise from 50-100 genes identified to be down-regulated in Table E. The gene expression signature can comprise a set of genes identified to be up-regulated and a set of genes identified to be down-regulated.

EXAMPLES

The present invention will be better understood by reference to the following examples which are offered by way of illustration not limitation.

Example 1

Generating Instances

Individual experiments (referred to as batches) generally comprise 30 to 96 samples analyzed using Affymetrix GeneChip® technology platforms, containing 6 replicates of the vehicle control (e.g., DSMO), 2 replicate samples of a positive control that gives a strong reproducible effect in the cell type used (e.g., all trans-retinoic acid for fibroblast cells), and samples of the test material/perturbagen. Replication of the test material is done in separate batches due to batch effects. In vitro testing was performed in 6-well plates to provide sufficient RNA for GeneChip® analysis (2-4 μg total RNA yield/well).

Human telomerized keratinocytes (tKC) were obtained from the University of Texas, Southwestern Medical Center, Dallas, Tex. tKC cells were grown in EpiLife® media with 1× Human Keratinocyte Growth Supplement (Invitrogen, Carlsbad, Calif.) on collagen I coated cell culture flasks and plates (Becton Dickinson, Franklin Lakes, N.J.). Keratinocytes were seeded into 6-well plates at 20,000 cells/cm$^2$ 24 hours before chemical exposure. Human skin fibroblasts (BJ cell line from ATCC, Manassas, Va.) were grown in Eagle's Minimal Essential Medium (ATCC) supplemented with 10% fetal bovine serum (HyClone, Logan, Utah) in normal cell culture flasks and plates (Corning, Lowell, Mass.). BJ fibroblasts were seeded into 6-well plates at 12,000 cells/cm$^2$ 24 hours before chemical exposure.

All cells were incubated at 37° C. in a humidified incubator with 5% $CO_2$. At t=−24 hours cells were trypsinized from T-75 flasks and plated into 6-well plates in basal growth medium. At t=0 media was removed and replaced with the appropriate dosing solution as per the experimental design. Dosing solutions were prepared the previous day in sterile 4 ml Falcon snap cap tubes. Pure test materials may be prepared at a concentration of 1-200 μM, and botanical extracts may be prepared at a concentration of 0.001 to 1% by weight of the dosing solution. After 6 to 24 hours of chemical exposure, cells were viewed and imaged. The wells were examined with a microscope before cell lysis and RNA isolation to evaluate for morphologic evidence of toxicity. If morphological changes were sufficient to suggest cytotoxicity, a lower concentration of the perturbagen was tested. Cells were then lysed with 350 ul/well of RLT buffer containing β-mercaptoethanol (Qiagen, Valencia, Calif.), transferred to a 96-well plate, and stored at −20° C.

RNA from cell culture batches was isolated from the RLT buffer using Agencourt® RNAdvance Tissue-Bind magnetic beads (Beckman Coulter) according to manufacturer's instructions. 1 μg of total RNA per sample was labeled using Ambion Message Amp™ II Biotin Enhanced kit (Applied Biosystems Incorporated) according to manufacturer's instructions. The resultant biotin labeled and fragmented cRNA was hybridized to an Affymetrix HG-U133A 2.0 GeneChip®, which was then washed, stained and scanned using the protocol provided by Affymetrix.

Example 2

General Development of Expression Gene Signatures from Clinical Samples

A clinical survey study to obtain biopsy specimens for use in the investigation of gene expression patterns associated with hair biology was performed. Samples of hair or skin surrounding the hair has been taken. Samples can be taken by plucking, cutting, punch biopsies, other biopsies, FUE (follicular unit extraction) or laser capture microdissection (LCM), among other methods. The following procedure describes generation of a C-map signature associated with Androgenetic Alopecia (male pattern baldness).

15 Balding and 15 non-balding male patients were recruited for a two (consecutive) day study. Scalp punch biopsies (4 mm) were taken from both the vertex and occipital regions of each patient. The punch biopsies were collected in a manner that followed the hair shaft resulting in obtaining full-length hair follicles. The punch from the occipital region represents an area of actively growing hair from both the balding and non-balding patients. The vertex site represents actively growing hair in the non-balding patients however in the balding patients this sample will represent hair follicles as they are transitioning into the balding phenotype. Vertex punch biopsies from the balding patients will be collected from the edge, or transitional area, between the balding and non-balding zones). The occipital site representing actively growing hair from each patient will serve as an internal control for each patient when attempting to make correlations with the genomic data.

The punches were bisected and then embedded in Optimal Cutting Temperature (OCT) medium and snap frozen on dry ice with a metal heat sink chilled in liquid nitrogen. The frozen blocks containing the biopsy tissue were cut into 20 μm sections in a cryostat. The sections were placed onto glass PEN membrane slides, individual hair follicles were obtained using laser capture microdissection (LCM) and served as the source of RNA samples for genomic analysis.

RNA samples of 20 ng each were amplified and biotin labeled using the Ovation™ RNA Amplification and Labeling System (NuGEN Technologies, Inc.) according to the manufacturer's instructions. The resultant amplified and biotinylated cDNA targets were hybridized overnight to a single lot of Human Genome U133 Plus 2.0 Arrays (Affymetrix, Inc.) according to the specifications of the labeling kit (NuGEN Technologies, Inc.). The U133 GeneChips® were processed and scanned according to Affymetrix standard procedures. All sample handing steps, including labeling and chip processing, were executed in an order designed to minimize systematic processing errors.

Following the statistic analysis, two set of t-test results: (1) Nonbald vertex vs. Bald Vertex and (2) Bald occipital vs. Bald Vertex were used to generate a signature to capture the biological differences between growing hair and terminal hair.

a. Filtering based on U133A Chip Design.

The samples were analyzed on the Affymetrix HG-U133 Plus 2.0 GeneChips, which contain 54,613 probe sets complementary to the transcripts of more than 20,000 genes. However, instances in the provided database used were derived from gene expression profiling experiments using Affymetrix HG-U133A 2.0 GeneChips, containing 22,214 probe sets, which are a subset of those present on the Plus 2.0 GeneChip. Therefore, in developing gene expression signatures from the clinical data, the probe sets were filtered for those included in the HG-U133A 2.0 gene chips.

b. Filtering Based on Absent/Margin/Present Calls.

This filter creates a list of potential genes for inclusion in the gene expression signature. For example, in the Bold/Non Bald study, at least one sample was required to have a Present call for each probe set. Meanwhile, for the C-map database, at least one sample in all the chemical treatments was required to have a Present call for each probe set. Also at least one sample in all the chemical treatments must have a signal value more than 200. Present calls are derived from processing the raw GeneChip data and provide evidence that the gene transcript complementary to a probe set that is actually expressed in the biological sample. The probes that are absent from all samples are likely to be just noisy measurements. In the U133 Affymetrix chip, a signal value less than 200 is most likely generated from noise. This step is important to filter out probe sets that do not contribute meaningful data to the signature.

c. Filtering According to a Statistical Measure.

For example, a suitable statistical measure may be p-values from a t-test, ANOVA, correlation coefficient, or other model-based analysis. As one example, p-values may be chosen as the statistical measure and a cutoff value of p=0.05 may be chosen. Limiting the signature list to genes that meet some reasonable cutoff for statistical significance compared to an appropriate control is important to allow selection of genes that are characteristic of the biological state of interest. This is preferable to using a fold change value, which does not take into account the noise around the measurements. The t-statistic was used to select the probe sets in the signatures because it provides an indication of the directionality of the gene expression changes (i.e. up- or down-regulated) as well as statistical significance. If more than one comparison indicated the same type of biological changes, further filtering is performed on the data while requiring in all these comparisons that the probes were changed in the same direction to minimize noises. In this specific example, a requirement was set for the probes to be either up-regulated in the above two conditions, or down-regulated in the above two conditions. In case of Bald/NonBald study, a requirement was made that in both t-test result of the two comparisons, the gene changed into same direction with a p value less or equal than 0.1.

d. Sorting the Probe Sets.

All the probe sets are sorted into sets of up-regulated and down-regulated sets using the statistical measure. For example, if a t-test was used to compute p-values, the values (positive and negative) of the t-statistic are used to sort the list since p-values are always positive. The sorted t-statistics will place the sets with the most significant p-values at the top and bottom of the list with the non-significant ones near the middle.

e. Creation of the Gene Expression Signature.

Using the filtered and sorted list created, a suitable number of probe sets from the top and bottom are selected to create a gene expression signature that preferably has approximately the same number of sets chosen from the top as chosen from the bottom. For example, the gene expression signature created may have at least about 10, 50, 100, 200, or 300 and/or less than about 800, 600, or about 400 genes corresponding to a probe set on the chip. The number of probe sets approximately corresponds to the number of genes, but a single gene may be represented by more than one probe set. It is understood that the phrase "number of genes" as used herein, corresponds generally with the phrase "number of probe sets." The number of genes included in the signature was based upon the observations in preliminary studies that indicated signatures with from 50 to 300, or 200 to 800 probe sets equally divided between up- and down-regulated genes provide stable results with regard to the top scoring chemical instances when using the signature to query the provided database. In the Bald/Non Bald study, we selected the top 200 and bottom 200 probes from the filtered list as signature for Follicular Miniaturization.

Example 3

Specific Signatures for Use Singly and in Combination

Figure 9:
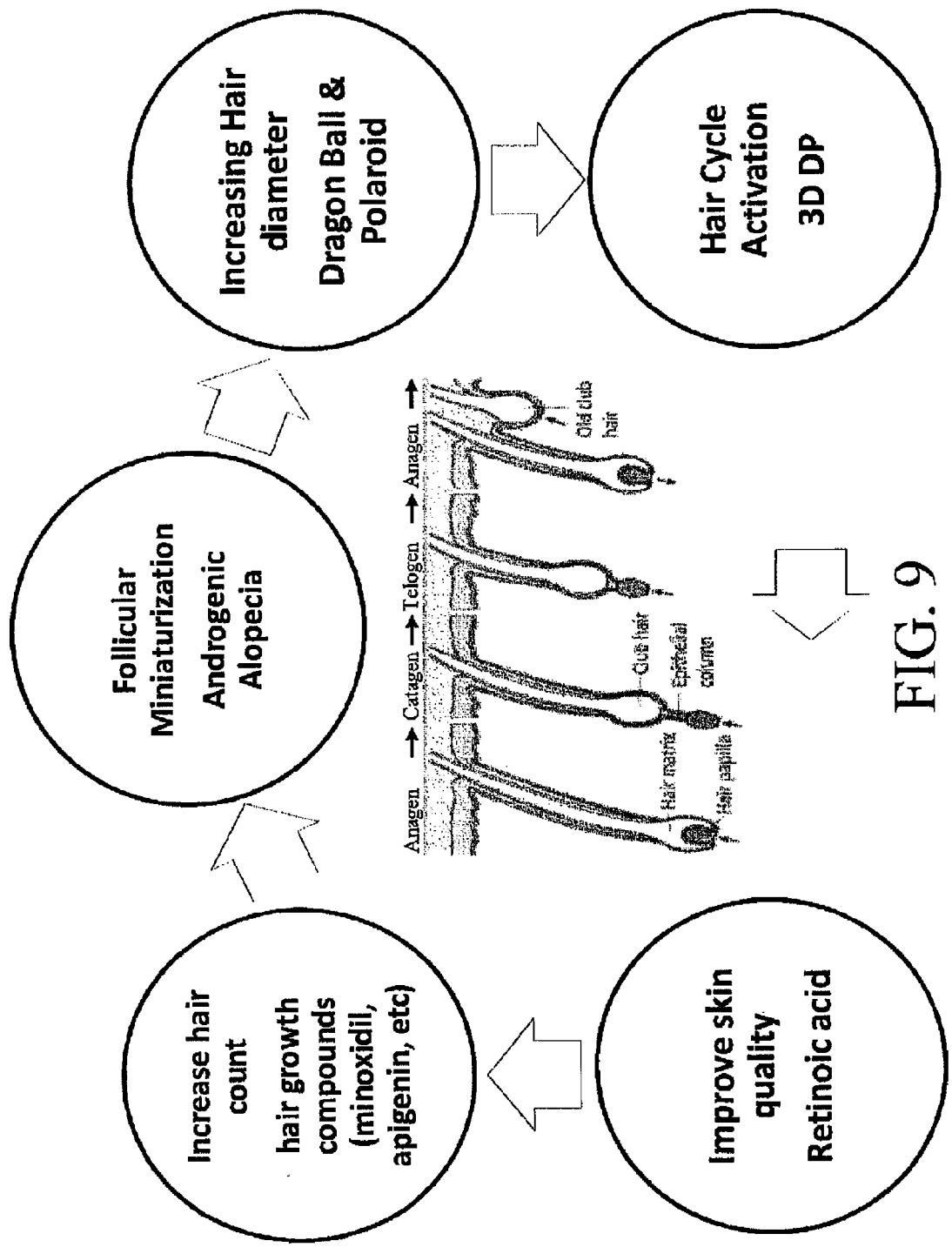
FIG. 9 provides a visual depiction of hair biology complexity and the value of using several hair biology-relevant gene expression signatures together.

Hair biology is complicated involving many different biological processes and cell types. This Example illustrates several hair biology-relevant gene expression signatures generated according to the invention and how they can be combined together with signatures generated from clinical studies to capture different aspect of hair biology (see FIG. 9 for a visual depiction of this). C-map signatures were developed to compare the effects of clinical candidate materials from the in vitro assays with gene expression patterns beneficial to hair biology.

The signatures conceivably can be used independently or in combination; the combination of activity in the in vitro assays and correlation with beneficial gene expression patterns in cells provides advantages in specific circumstances so as to increase the likelihood of success in the clinic. One example combination method involved the following: for each of the 5 signatures, the average score is calculated for each candidate chemical tested at same concentration on same cell line. The top 10% of these average scores are marked as green (2 points), the top 25% will are marked as yellow (1 point) and the others are marked as gray (0 point). The total points are recorded for all 5 signatures to afford an overall assessment of the effect of each candidate chemical on hair biology.

A. Follicular Miniaturization.

This signature (described in the example 2 in detail) was developed from a clinical study on Androgenetic Alopecia which used laser capture microdissection (LCM) to compare terminal anagen hairs from the vertex of balding men to those on non-balding regions of balding men (occipital) and the vertex of non-balding men. By comparing terminal hairs, this signature captures the gene changes present in a terminal hair before it miniaturizes. The illustrative signatures are set forth in Tables A, B respectively.

B. Increasing Hair Diameter.

This signature was developed from data from two clinical studies, Dragonball and Polaroid, using topical Caffeine (0.75%), Niacinamide (2.5%) and Panthenol (0.15%) treatment. Subjects were treated once/day. Hair pluck samples were collected from 20 responders and 20 non-responders for genomic analysis at 3 timepoints: baseline, 4 weeks and 12 weeks. Anova tests for Responder vs. Non-Responder at 12 weeks were used from both Dragonball and Polaroid study. Consistently changed genes in both comparisons were further filtered using the methods described in example 2. Top 200 up-regulated probes with $p<=0.1$ and bottom 200 down-regulated genes with $p<=0.14$ were selected as signature. The consistent biological difference between these groups demonstrates the improved biology in the Responders relative to the Nonresponders. Because all of the subjects were treated with product, this signature will capture the gene changes involved with increasing hair diameter. The illustrative signatures are set forth in Tables C, D respectively.

C. Hair Cycle Activation.

The dermal papilla (DP) of the follicle is important for the regulation of follicle cycling and a critical step as the hair follicle transitions from the resting telogen stage to the growing anagen stage is the enlargement of the DP. An in vitro assay has been developed that mimics this transition and responds to known hair growth activators. A unique process was developed in P&G which creates a 3D equivalent of the dermal papilla, a cycle control center of the human hair follicle. This process is most robust using hTERT-DP cell lines. The ability of dermal papilla cells to form condensates is a key identified feature for maintaining hair inductive signaling potential in long term culture (see references). The similarities to the human dermal papilla, its potential advantages for hair end-point measures compared with 2D culture of dermal papilla cells, and its utility in generating more complex 3D equivalents of human hair were evaluated in a genomic study. The signature were generated using the consistently changed gene from the following 4 comparisons: (1) 3D_vs_2D_(DP cell line A) (2) 3D_vs_2D_(DP_cell_line B) (3) 3D_vs_Intermediate Stage (DP cell_line_A) (4) 3D_vs_Intermediate Stage (DP cell_line B). The top 300 gene for up-regulation (with $p<=0.05$) and the bottom 300 gene for down-regulation (with $p<=0.1$) were selected as the signature. This signature will capture biology critical for this step of the reactivation of the hair follicle cycle. The illustrative signatures are set forth in Tables E, F respectively.

D. Retinoic Acid Signature.

Retinoic acid is a material that can provide improvements in skin condition and can reduce wrinkles; it can also be beneficial for increasing hair diameter. Via in vitro assays for hair biology, a Retinoic Acid signature was developed. A retinoic acid C-map signature has been developed to increase hair diameter and improve scalp health, and the illustrative signatures are set forth Tables G, H respectively.

E. Hair Count Actives.

In clinical studies, Minoxidil has always provided a significant increase in hair count. Apigenin also provided a significant hair count benefit. A C-map signature has been developed from these materials, concentrating on the biology leading to increased hair counts (and deemphasize other biology the materials might have, for example Minoxidil's blood pressure lowering activity). Two signatures were developed based on the effect of Minoxidil and Apigenin on keratinocytes and on fibroblasts to capture the hair biology effects of these two compounds. The illustrative signatures are set forth in Tables I, J respectively (For BJ cells), and Tables K, L respectively (for Keratinocytes).

F. Monoamine Oxidase B Inhibitor Signature.

MAOB inhibitors have been demonstrated to improve the activation of hair biology. MAOB was identified as a gene of interest through a set of cross study comparisons of hair biology gene expression studies. A series of inhibitors of the enzyme were demonstrated (for example Selegiline) to activate hair growth alone as well as to increase the hair growth activity of Minoxidil. The C-map material dataset was capitalized on to generate signatures from the hair biology active MAOB inhibitors in the dataset and to identify materials with similar gene expression activity.

Separate signature work was done for tert-keratinocytes and for BJ Fibroblasts. The MAOB inhibitors that produced hair growth were used as the positives. Non-MAOB inhibitor instances were used as the negatives. Also, certain materials with high replication in the C-map database (e.g. Triac and retinoic acid) and Minoxidil were removed.

C-Map Signature Criteria t-test <0.1 in all 3 comparisons
1) The t-test of the Signal change for the comparison of the positives to all DMSO controls.
2) The t-test of the Signal change for the comparison of the positives to the same batch DMSO control.
3) The t-test of both the Signal and True-fold change be <0.1 for the comparison of the positives to Non-MAOB inhibitor instances.

Direction had to be consistent in all 3 comparisons
4) Signal for the positives to all DMSO controls.
5) Signal for the positives to the same batch DMSO control.
6) Signal for the positives to Non-MAOB instances.

MAOB Inhibitor Work and FaceMap Criteria:

FaceMap uses the algorithm used in facial recognition software to utilize over 3000 genes to identify materials with similar biological effects without using conventional C-map signatures. The similarity of two materials is defined by the distance in multidimensional space that is calculated between them using the facial recognition software.

For this ranking, each of 23 C-map MAOB inhibitor instances were used to rank materials by the similarity distance. The two criteria for selection were that the material had to be in the top 10% of instances and the distance from the instance to the known MAOB inhibitor had to be less than 0.5. If these criteria were met, the instance got a score of 1.

This was repeated across all of the MAOB inhibitor instances for each cell type and the scores of all of the instances of a given material at the same concentration were averaged to give a final score.

In Vitro Results on Materials Identified Using Signatures Created from Affy Data.

Affy signatures yielded 60 materials that were plated and provided for evaluation in a MAOB enzyme inhibition assay and 46 pure material were tested in a MAOB reporter assay. Active materials were defined as demonstrating 1) >=40% inhibition in the enzyme assay, 2) >=60% inhibition in the reporter assay and 3) showing a dose response with the higher doses having more activity than the lower doses.

The results are presented in Table V, below, and show that there are very relatively few hits from the list of C-map identified candidates, 3 out of 46 for the enzyme assay and 4 of 46 for the reporter assay. One material was a common active for both assays, quinacrine, a known monoamine oxide inhibitor.

TABLE V

| Cell Type | C-map Score | FaceMap Score | # Chemicals Selected | Enzyme Active >=40% | Reporter Active >=60% | Same Hit in both Assays |
|---|---|---|---|---|---|---|
| tert KC | >=0.14 | >=10.25 | 10 | 0 | 0 | 0 |
| tert KC | >=0.14 | <10.25 | 8 | 0 | 0 | 0 |
| tert KC | <0.14 | >=10.25 | 12 | 0 | 0 | 0 |
| BJ FB | >=0.16 | >=7.2 | 3 | 0 | 0 | 0 |
| BJ FB | >=0.16 | <7.2 | 8 | 2 | 1 | 0 |
| BJ FB | <0.16 | >=7.2 | 5 | 1 | 3 | 1 |

Cell Type Effect.

However, analysis of the Affy selected materials by cell type shows an interesting trend. The MAOB inhibitors identified from the BJ fibroblast cells were much more effective than those identified from the tert-keratinocytes. There were 16 materials selected from the BJ Fibroblasts with 3 hits in the enzyme assay (19%) and 4 hits in the reporter assay (25%). There was only one BJ fibroblast-identified material that was a hit in both assays, quinacrine, for a 6% hit rate. For tert-keratinocytes, there were 30 materials selected with no hits in either the enzyme assay or the reporter assay. Lowering the "active material" criteria to 20% inhibition identified more materials but showed the same trend with BJ Fibroblasts producing more materials.

MAOB Expression in BJ Fibroblasts and Tert-Keratinocytes.

One conclusion from this work is that BJ fibroblasts are the better cell line for identifying MAOB inhibitors. However, it is surprising that the BJ cells are better for identifying MAOB inhibitors since the enzyme is expressed at a lower level than the tert-KCs. Below are data from the best expressed Affy probe set.

Another difference between the cell lines is that MAOA is expressed at a much lower level in BJ cells, almost not expressed at all. It may be the ratio of the MAOB to MAOA that results in BJ fibroblasts being the more predictive cell line for identifying MAOB inhibitors.

FIGS. 22 and 23 includes Table M and N showing Monoamine Oxidase B Inhibitor-Related Genes; Down and Up Genes respectively for BJ cells (Table O and Table P show the same for keratinocyte cells)

Example 4

Theme-Based Approach

Analysis of genes in a theme-based approach offer potential advantages in identifying and understanding genes and processes related to improvements for hair biology. An example is described herein below. One example theme involves highly variable genes from hair growth studies. Gene expression variability patterns provide the potential of being indicators of disease or aging status. High variable genes have traditionally been ignored by typical gene expression analysis. Here we explored the group of genes de-regulated in balding vertex (with higher expression variance in balding vertex vs. in normal vertex.). Those genes with function (mapped by gene ontology) in adenylate cyclase activity, mitochondrial iron transport, immune response, endopeptidase inhibitor, epithelial cell differentiation and Wnt receptor signaling were used as signature to pull out hair growth chemicals from a C-map database. It is interesting that some of these genes are regulated in different directions by different hair growth chemicals, such as Triac and minoxidil. The current analysis suggests that the highly variable genes can provide new insight about the biological changes associated with disease and chemical treatment.

(I) Background

Gene expression variability patterns have been suggested to be an indicator of disease or aging status (Pritchard et al 2001; Bahar et al 2006; Cheung et al 2003). Scientists have noticed that genes associated with immune-modulation, stress and hormonal regulation often exhibit high variability of expression. Individual gene expression variability has also been observed in cardiomyocytes in old mice compare with young mice, and in human lymphoblastoid cells. Such elevated expression variability has been attributed to dysregulation of gene expression during cell death, disease or DNA damage accumulated through aging (Pritchard et al 2001; Bahar et al 2006; Cheung et al 2003).

Typical microarray analysis focuses on the differentially expressed genes with low variance, ignoring all of the genes with highly variable expression. In order to find out what new information could be obtained from those highly variable genes, highly variable genes were identified and the biological functions of these genes were noted, and a determination was made as to whether the genes could be used as a signature to identify possible hair growth chemicals.

(II) Methods and Results:

An F-test was performed to compare the known standard deviations of two independent samples: gene expression in bald vertex and non-balding vertex. High variance genes were looked at in the Human Balding Study and focus was placed on those genes with significantly higher variance in the balding vertex samples compared to the non-balding vertex sample.

The top biological themes based upon gene ontology mapping for these high variance genes were:

1. G protein signaling, regulation of adenylate cyclase activity
2. mitochondrial iron ion transport
3. dendrite development
4. monocyte differentiation & other immune response
5. developmental process
6. endopeptidase inhibitor activity
7. integrin binding
8. hemidesmosome
9. epithelial cell differentiation
10. fat cell differentiation
11. wnt receptor signaling The following table, Table W, shows the KEGG pathways with more than 5 high variable genes, the three highlighted pathways are only significant in high variance genes in bald vertex, not significant in high variance genes in bald occipital or high variances genes in nonbalding vertex or occipital.

TABLE W

| High variance gene number in KEGG pathways (bold means bald vertex specific) | High variance in bald vertex | Total Probe | % |
| --- | --- | --- | --- |
| Ubiquitin mediated proteolysis | 17 | 39 | 43.59% |
| Alkaloid biosynthesis II | 8 | 21 | 38.10% |
| Pyrimidine metabolism | 6 | 23 | 26.09% |
| GnRH signaling pathway | 11 | 74 | 14.86% |
| Hedgehog signaling pathway | 5 | 35 | 14.29% |
| Folate biosynthesis | 7 | 53 | 13.21% |
| All Cell Communication | 18 | 137 | 13.14% |
| Tight junction | 11 | 85 | 12.94% |
| Glycan structures - degradation | 6 | 48 | 12.50% |
| Natural killer cell mediated cytotoxicity | 9 | 73 | 12.33% |
| Glycan structures - biosynthesis 1 | 11 | 97 | 11.34% |
| Leukocyte transendothelial migration | 15 | 135 | 11.11% |
| Calcium signaling pathway | 20 | 183 | 10.93% |
| ABC transporters | 5 | 49 | 10.20% |
| Neuroactive ligand-receptor interaction | 10 | 101 | 9.90% |
| Oxidative phosphorylation | 10 | 102 | 9.80% |
| Regulation of actin cytoskeleton | 5 | 56 | 8.93% |
| Insulin signaling pathway | 7 | 79 | 8.86% |
| Methionine metabolism | 58 | 670 | 8.66% |
| Purine metabolism | 165 | 2040 | 8.09% |
| Axon guidance | 7 | 93 | 7.53% |
| Cell adhesion molecules (CAMs) | 9 | 124 | 7.26% |
| Aminoacyl-tRNA biosynthesis | 7 | 104 | 6.73% |
| Ribosome | 7 | 196 | 3.57% |

A focus was placed on 2861 genes that are deregulated in Balding vertex (T-test p<0.05 and present >1 in vertex). Only 1157 of these genes were present at least once in the reference C-map database used. The list was further restricted by requiring at least one probe in a study of natural mouse hair cycle to show significant changes comparing telogen vs. anagen (day 1 vs. day 23, p-value is less than or equal to 0.05). This left 203 genes up-regulated and 202 genes down-regulated. After removing overlapping genes, there was a signature of 128 down-regulated genes and 129 up-regulated genes (See Tables Q and R including down genes and up genes respectively for a Theme Approach: Highly Variable Expressed Genes). When the signature was run against a C-map database, it returned the following linkages for chemicals appearing at least twice in the top and bottom 200 instances from a total of 2266 instances, as shown in Tables X and Y, below, respectively:

TABLE Y

Bottom 200:

2 1-Hydroxypyridine-2-thione Zinc Salt
2 2-Phenyl-5-benzimidazole-sulfonic acic
2 Amiloride hydrochloride
2 Cetirizin dihydrochloride
2 Climbazole
2 Diethanolamine
2 DL-alpha-Difluoromethylornithine hydrochloride hydrate (Vaniqa)
2 D-Panthenol
2 HG 423
2 IL1b
2 IL20
2 IL26d
2 KGF
2 Minoxidil
2 Retinol 15 D

TABLE Y-continued

Bottom 200:

2 Rosemary oil
2 tamoxifen
2 Taurine
3 SeS
4 cyclosporin
4 estradiol
4 Nicotinamide
4 triac

TABLE X

Top 200:

2 18-beta-Glycirrhetinic acid
2 Adenosine
2 Arlatone Dioic DCA
2 (+/−)-Brompheniramine maleate
2 Climbazole
2 Dithranol
2 Fluoxetine hydrochloride
2 GBR-12909 dihydrochloride
2 Irgasan
2 Ketoconazole
2 LI-229
2 Raloxifene hydrochloride
2 SB 202190
2 Sunitinub Maleate
2 tert-BUTYL HYDROQUINONE
2 Tetrahydrocurcumin CG
2 ZPT
3 Clobetasol Propionate
3 geldanamycin
3 MG132
3 Sepiwhite MSH
4 NEOSH101

(III) Summary

The highly variably expressed genes are a group of genes that have been dysregulated by disease or treatment. Here highly variable genes were identified associated with the balding vertex and used to identify possible hair growth materials.

Example 5

Use of C-Map in Combination with Survival Assays

In certain cases it is important to know if application of a specific treatment will be beneficial to cells related to hair growth or not. Therefore C-map has been used to predict the response of relevant cells, such as dermal papilla cells, to the application of chemicals. A survival assay has been used.

The following cells were cultured as described: Dermal papilla cells (Cell Applications) were grown on collagen I T75 flasks in Amniomax Complete media or DMEM (No Glucose)+10% FCS (Invitrogen), plated in 96 well plates (2,500 cells/well) and treated for 48 hours at 37° C./5% CO2 (DMEM+BSA+/−glucose). Cells were harvested using Cell Titer Glo reagent (Promega) and the level of ATP remaining in each well quantitated by luminescence. The effect of each treatment was compared to a DMSO control (0.1% or 0.5%) and reported as % control. Adenosine (Sigma, 20 mM stock; 100, 20, 2, 0.2 µM final) on each plate was used as a positive control. Compounds that measured >50% increase in survival and >20% increase in proliferation were considered "hits".

A total of 381 cosmetic actionable materials were tested (See Table S) in the DP survival assay from the C-map library. The DP survival data was mapped to C-map gene expression profiles to identify the chemicals which can prolong the life of the dermal papilla cells under the starved condition. Of the chemicals tested, 362 had a counterpart tested in the C-map study. After excluding chemicals with a sugar component which gives false positives and chemicals that acted differently in the DP survival assay at different concentration (for example, higher concentration as toxic and lower concentration as activator), there were 50 active and 286 non-active chemicals mapping to 646 gene expression profiles. Thus, the hit rate defined from screening the C-map Cosmetically Actionable collection was 14.8%. These 646 profiles were used as the training data to build the DP survival assay models to predict a chemical's activity.

The first modeling approach used was based on the expression of individual genes. The overall comparison being made is that the average of the signal value (and the fold change against DMSO) is significantly different between the active and the non-active chemicals (Student t test $p<=0.05$). Also removed were genes with low expression as determined by less than 90% detection in all the actives or all the non-actives or all the DMSO controls.

The gene list was used as follows: the genes that were up-regulated and down-regulated in the actives were used to create a C-map signature to identify possible active chemicals (See Tables T and U for down and up-regulated genes of the DP Survival Assay). Four TREENET® models were also built (using the Salford Data Miner System) based on either the signal, the fold change value or the p-value of the significantly changed biological theme to predict the DP survival activity (active vs. non-active) or the DP survival scores (ranging from 0-3000, $>=150$ as active). The TREENET® algorithm generates a series of small decision trees based on the expression of individual genes that sort the actives from the non-actives.

For all the models, a 10-fold cross validation was used to train the model on existing DP survival data. Then each C-map gene profile was evaluated through each individual method. From their composite score, a selection was made of 41 predicted actives and tested; 40 were tested in DP survival assay, 29 of which turned out to be true actives with 21 having a DP survival score >200. (Hit rate 72.5%). To follow up on the first successful test, this data was included with a set of earlier data of 80 positive and negative hair growth materials to retrain the model, and then tested 10 predicted actives and 13 predicted non-actives. Of these, 4 predicted actives turned out to be true actives (hit rate 40%) and 2 predicted non-actives turned out to be active (hit rate 85%).

What is claimed is:

1. A method for constructing a data architecture for use in identifying connections between perturbagens and genes associated with one or more cosmetic hair biology conditions and preparing a hair/scalp care composition, comprising:
  (a) providing a gene expression profile for a control human fibroblast cell;
  (b) generating a gene expression profile for a human fibroblast cell exposed to at least one perturbagen by extracting a biological sample from the exposed cell and subjecting the biological sample to microarray analysis via a microarray scanner;
  (c) identifying genes differentially expressed in response to the at least one perturbagen by comparing the gene expression profiles of (a) and (b);

(d) creating an ordered list comprising identifiers representing the differentially expressed genes, wherein the identifiers are ordered according to the differential expression of the genes;
(e) storing the ordered list as a fibroblast instance on at least one computer readable medium; and
(f) constructing a data architecture of stored fibroblast instances by repeating (a) through (e), wherein the at least one perturbagen of step (a) is different for each fibroblast instance;
(g) providing a gene expression profile for a control human keratinocyte cell;
(h) generating a gene expression profile for a human keratinocyte cell exposed to at least one perturbagen by extracting a biological sample from the exposed cell and subjecting the biological sample to microarray analysis via a microarray scanner;
(i) identifying genes differentially expressed in response to the at least one perturbagen by comparing the gene expression profiles of (g) and (h);
(j) creating an ordered list comprising identifiers representing the differentially expressed genes, wherein the identifiers are ordered according to the differential expression of the genes identified in (i);
(k) storing the ordered list created in step (j) as a keratinocyte instance on the at least one computer readable medium;
(l) constructing a data architecture of stored keratinocyte instances by repeating (g) through (k), wherein the at least one perturbagen of step (h) is different for each keratinocyte instance;
(m) querying the data architectures of stored fibroblast and keratinocyte instances with at least one hair biology-relevant gene expression signature, wherein querying comprises comparing the at least one hair biology-relevant gene expression signature to each stored fibroblast and keratinocyte instance, wherein the hair biology-relevant gene expression signature represents genes differentially expressed in association with the at least one hair biology condition;
(n) assigning a connectivity score to each of the instances; and
(o) preparing a hair/scalp care composition comprising at least one perturbagen, wherein the connectivity score of the instance associated with the at least one perturbagen has a negative correlation.

2. A method according to claim 1, comprising using a programmable computer to perform one or more of steps (c), (d), (e) and (f).

3. A method according to claim 1, wherein the ordered list comprises the ordered list of identifiers in association with a numerical ranking for the identifier corresponding to its rank in the ordered list.

4. A method according to claim 1, wherein the biological sample comprises mRNA.

5. A method according to claim 1, wherein the microarray is a global microarray or a specific microarray, wherein the specific microarray comprises oligonucleotides which hybridize to genes corresponding to a gene expression signature for a cellular phenotype.

6. A method according to claim 1, wherein the step of constructing the data architecture of stored fibroblast instances by repeating steps (a) through (e) comprises repeating steps (a) through (e) for between about 50 and about 50,000 instances.

7. A method according to claim 6, wherein the step of constructing the data architecture of stored fibroblast instances comprises repeating steps (a) through (e) for between about 1000 and about 20,000 instances.

8. A method according to claim 1, wherein the at least one perturbagen is a cosmetic agent.

9. A method according to claim 1, wherein each of the different perturbagens is a cosmetic agent.

10. A method according to claim 1, wherein the identifiers are selected from the group consisting of gene names, gene symbols, microarray probe set ID values, and combinations thereof.

11. A method according to claim 1, wherein the ordered list is arranged so that an identifier associated with a most up-regulated gene is positioned at the top of the ordered list and an identifier associated with a most down-regulated gene is positioned at the bottom of the ordered list.

12. A method according to claim 11, wherein the ordered list of each fibroblast and keratinocyte instance is arranged so that an identifier associated with each gene that is not differentially expressed is positioned between the identifier associated with the most up-regulated gene and the identifier associated with the most down-regulated gene.

13. A method according to claim 1, wherein each fibroblast and keratinocyte instance comprises between about 1,000 and about 50,000 identifiers.

14. A method according to claim 1, wherein each fibroblast and keratinocyte instance comprises metadata for the at least one perturbagen associated with the instance.

15. A method according to claim 1, wherein the at least one perturbagen of step (b) is the same as the at least one perturbagen of step (h).

16. A method according to claim 1, wherein the at least one perturbagen is a botanical.

17. A method according to claim 16, wherein the botanical is derived from one or more of a root, stem, bark, leaf, seed, or fruit of a plant.

18. A method according to claim 1, wherein the at least one perturbagen is selected from the group consisting of a vitamin compound, a sugar amine, a phytosterol, hexamidine, a hydroxy acid, a ceramide, an amino acid, and a polyol.

19. A method according to claim 18, wherein the vitamin compound is selected from the group consisting of a vitamin B3 compound, a vitamin B5 compound, a vitamin B6 compound, a vitamin B9 compound, a vitamin A compound, a vitamin C compound, a vitamin E compound, and derivatives and combinations thereof.

20. A method according to claim 18, wherein the vitamin compound is selected from the group consisting of retinol, retinyl esters, niacinamide, folic acid, panthenol, ascorbic acid, tocopherol, and tocopherol acetate.

21. A method according to claim 1, wherein the comparison of the at least one hair biology-relevant gene expression signature to each stored fibroblast and keratinocyte instance is performed by a programmable computer.

22. A method according to claim 1, wherein the at least one hair biology condition is selected from the group consisting of follicular miniaturization (alopecia), dermal papilla activation, hair density modification, chronogenetic alopecia, senile alopecia, hair diameter modification, loss of hair pigmentation, hair thinning, hair loss, fragile hair, curl or lack of curl; and combinations thereof.

23. A method according to claim 1, wherein the at least one hair biology-relevant gene expression signature is constructed by a method comprising (i) identifying genes having up-regulated expression in the at least one hair biology condition when compared to a control; (ii) identifying genes having down-regulated expression in the at least one hair biology condition when compared to a control; (iii) creating one or more gene expression signature lists associated with the at least one hair biology-relevant gene expression signature comprising identifiers corresponding to a plurality of the genes identified in (i) and (ii); and storing the one or more gene expression signature lists on the at least one computer readable medium.

24. A method according to claim 23, wherein the number of genes having up-regulated expression in the at least one hair biology condition is between about 10 and about 400, and the number of genes down-regulated in the at least one hair biology condition is between about 10 and about 400.

25. A method according to claim 24 wherein the identifiers for between about 80% and about 100% of the up-regulated genes are set forth as in Table B and wherein identifiers for between about 80% and about 100% of the down-regulated genes are set forth in Table A.

26. A method according to claim 1, wherein the identifiers representing the genes identified in (i) and (ii) are selected from the group consisting of gene names, gene symbols, and microarray probe set ID values.

27. A method according to claim 23, wherein the one or more gene expression signature lists comprises a first list representing a plurality of the up-regulated genes identified in (i) and a second list representing a plurality of down-regulated genes identified in (ii).

28. A method according to claim 23, wherein at least one hair sample is taken from a human subject exhibiting the at least one hair biology condition, a biological sample is extracted from the hair sample, and a gene expression profile of the at least one hair sample is generated prior to at least one of the steps (i) and (ii).

29. A method according to claim 28, wherein the at least one human subject is between the ages of about 18 and about 80.

30. A method according to claim 28, wherein the hair sample comprises cells from a vertex of a head of the human subject.

31. A method according to claim 1, wherein a plurality of connectivity scores represents a positive correlation and a plurality of the connectivity scores represents a negative correlation.

32. A method according to claim 1, wherein the connectivity score has a value between +2 and −2.

33. A method for constructing a data architecture for use in identifying connections between cosmetic perturbagens and genes associated with cosmetically improving hair biology and preparing a hair/scalp care composition, comprising:
  (a) providing a gene expression profile for a control fibroblast human cell;
  (b) generating a gene expression profile for a human fibroblast cell exposed to at least one perturbagen by extracting a biological sample from the exposed cell and subjecting the biological sample to microarray analysis via a microarray scanner;
  (c) identifying genes differentially expressed in response to at least one perturbagen by comparing the gene expression profiles of (a) and (b);
  (d) creating an ordered list comprising identifiers representing the differentially expressed genes, wherein the identifiers are ordered according to the differential expression of the genes;
  (e) storing the ordered list as a fibroblast instance on at least one computer readable medium;
  (f) constructing a data architecture of stored instances by repeating (a) through (e), wherein the at least one perturbagen of step (b) is different qualitatively or quantitatively for each instance;
  (g) repeating steps (a) through (f) for a control human keratinocyte cell and human keratinocyte cells;
  (h) constructing a data architecture incorporating both the fibroblast and the keratinocyte instances;
  (i) querying the data architecture of stored instances with at least one hair biology relevant gene expression signature, wherein querying comprises comparing the hair biology-relevant gene expression signature to each stored cell instance, wherein the hair biology-relevant expression signature represents genes differentially expressed in a human tissue affected with a cosmetic hair biology condition or genes differentially expressed in cells treated with at least one benchmark agent having known efficacy in treating a cosmetic hair condition;
  (j) assigning a connectivity score to each of the instances; and
  (k) preparing a hair/scalp care composition comprising at least one perturbagen, wherein the connectivity score of the instance associated with the at least one perturbagen has a negative correlation.

34. A method according to claim 33, comprising using a programmable computer to perform one or more steps (c), (d), (e), and (f).

35. A method according to claim 33, wherein the ordered list comprises the ordered list of identifiers in association with a numerical ranking for the identifier corresponding to its rank in the ordered list.

36. A method according to claim 33, wherein the biological sample comprises mRNA.

37. A method according to claim 33, wherein the microarray is a global microarray or a specific microarray, wherein the specific microarray comprises oligonucleotides which hybridize to genes according to a gene expression signature for a cellular phenotype.

38. A method according to claim 33, wherein the step of constructing the data architecture of stored instances by repeating steps (a) through (e) comprises repeating steps (a) through (e) for between about 50 and about 50,000 instances.

39. A method according to claim 33, wherein the step of constructing the data architecture of stored instances comprises repeating steps (a) through (e) for between about 1000 and 20,000 instances.

40. A method according to claim 33, wherein the at least one perturbagen comprises an agent modifying hair follicle cycling.

41. The method of claim 40 wherein modifying hair follicle cycling comprises transitioning dermal papilla cells from a resting telogen stage to a growing anagen stage.

42. The method of claim 33 wherein prior to step (a), induced pluripotent stem cells (IPSC) are induced into the human cell line selected from the group consisting of fibroblast and keratinocyte cell lines.

43. The method according to claim 33 further comprising
  (l) repeating steps (a) through (f) for a control human melanocyte cell and human melanocyte cells and/or repeating steps (a) through (f) for a control human dermal papilla cell and human dermal papilla cells; and
  (m) constructing a data architecture incorporating all instances.

* * * * *